United States Patent
Lynn et al.

(10) Patent No.: US 10,297,348 B2
(45) Date of Patent: *May 21, 2019

(54) PATIENT SAFETY PROCESSOR

(71) Applicant: Lawrence A. Lynn, Columbus, OH (US)

(72) Inventors: Lawrence A. Lynn, Columbus, OH (US); Eric N. Lynn, Villa Ridge, MO (US)

(73) Assignee: Lawrence A. Lynn, Columbus, OH (US)

( * ) Notice: Subject to any disclaimer, the term of this patent is extended or adjusted under 35 U.S.C. 154(b) by 64 days.

This patent is subject to a terminal disclaimer.

(21) Appl. No.: 13/844,212

(22) Filed: Mar. 15, 2013

(65) Prior Publication Data

US 2013/0209068 A1 Aug. 15, 2013
US 2016/0381340 A9 Dec. 29, 2016

Related U.S. Application Data

(63) Continuation of application No. 12/437,417, filed on May 7, 2009, now Pat. No. 9,053,222, and a
(Continued)

(51) Int. Cl.
*H04N 9/87* (2006.01)
*G06F 19/00* (2018.01)
(Continued)

(52) U.S. Cl.
CPC ........... *G16H 50/20* (2018.01); *G06F 19/321* (2013.01); *G06Q 50/22* (2013.01); *G06Q 50/24* (2013.01);
(Continued)

(58) Field of Classification Search
CPC .... G06Q 50/22; G06Q 50/24; G01N 2800/26; A61B 5/412; G16H 50/20; G16H 50/70;
(Continued)

(56) References Cited

U.S. PATENT DOCUMENTS 3,638,640 A 2/1972 Shaw
3,646,606 A 2/1972 Buxton
(Continued)

FOREIGN PATENT DOCUMENTS

DE 2450900 5/1975
EP 0178197 A1 4/1986
(Continued)

OTHER PUBLICATIONS

Author Unknown, FiO$_2$, Wikipedia Encyclopedia, modified Oct. 30, 2007 . . . http://en.wikipedia.org/wiki/FiO2.
(Continued)

*Primary Examiner* — Joy Chng
(74) *Attorney, Agent, or Firm* — Vorys, Sater, Seymour and Pease LLP; Rex W. Miller, II

(57) ABSTRACT

A processor-based system for analyzing physiologic data and medical care is provided wherein the patient data is analyzed to construct images that are representative of a patient's condition. The processor provides a self-modulating analysis, which is responsive to the occurrence of additional data items to increase the information contained in the images. Identifications of modes of physiologic failure by the analysis of the generated images provides for earlier recognition and intervention and improved protocolization of testing and treatment.

31 Claims, 42 Drawing Sheets

Related U.S. Application Data continuation-in-part of application No. 12/437,385, filed on May 7, 2009, now abandoned, and a continuation-in-part of application No. 12/629,407, filed on Dec. 2, 2009, which is a continuation of application No. 10/150,842, filed on May 17, 2002, now Pat. No. 7,758,503, application No. 13/844,212, which is a continuation-in-part of application No. 11/369,355, filed on Mar. 7, 2006, now abandoned, which is a continuation of application No. 10/150,582, filed on May 17, 2002, now Pat. No. 7,081,095, application No. 13/844,212, filed on Mar. 15, 2013, which is a continuation-in-part of application No. 12/152,747, filed on May 16, 2008, now abandoned.

(60) Provisional application No. 61/126,906, filed on May 7, 2008, provisional application No. 61/200,162, filed on Nov. 25, 2008, provisional application No. 60/291,691, filed on May 17, 2001, provisional application No. 60/291,687, filed on May 17, 2001, provisional application No. 60/295,484, filed on Jun. 1, 2001.

(51) Int. Cl.
| | | |
|---|---|---|
| *G06Q 50/22* | (2018.01) | |
| *G06Q 50/24* | (2012.01) | |
| *G16H 15/00* | (2018.01) | |
| *G16H 50/20* | (2018.01) | |
| *G16H 50/50* | (2018.01) | |
| *G16H 50/70* | (2018.01) | |

(52) U.S. Cl.
CPC ............. *G16H 15/00* (2018.01); *G16H 50/50* (2018.01); *G16H 50/70* (2018.01); *H04N 9/87* (2013.01)

(58) Field of Classification Search
CPC ...... G16H 50/50; G16H 15/00; G06F 19/321; H04N 9/87
USPC .......................................................... 705/2, 3
See application file for complete search history.

(56) References Cited

U.S. PATENT DOCUMENTS

| | | |
|---|---|---|
| 3,884,219 A | 5/1975 | Richardson et al. |
| 3,926,177 A | 12/1975 | Hardway et al. |
| 3,999,537 A | 12/1976 | Noiles |
| 4,022,353 A | 5/1977 | Hamlin |
| 4,036,211 A | 7/1977 | Veth et al. |
| 4,141,354 A | 2/1979 | Ismach |
| 4,340,044 A | 7/1982 | Levy et al. |
| 4,696,307 A | 9/1987 | Montgieux |
| 4,714,341 A | 12/1987 | Hamaguri |
| 4,800,495 A | 1/1989 | Smith |
| 4,805,623 A | 2/1989 | Jobis |
| 4,807,631 A | 2/1989 | Hersh et al. |
| 4,838,275 A | 6/1989 | Lee |
| 4,846,195 A | 7/1989 | Alt |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 4,995,400 A | 2/1991 | Boehringer et al. |
| 5,028,787 A | 7/1991 | Rosenthal et al. |
| 5,065,749 A | 11/1991 | Hasebe et al. |
| 5,066,859 A | 11/1991 | Karkar et al. |
| 5,072,737 A | 12/1991 | Goulding |
| 5,084,327 A | 1/1992 | Stengel |
| 5,092,326 A | 3/1992 | Winn et al. |
| 5,094,246 A | 3/1992 | Rusz et al. |
| 5,119,815 A | 6/1992 | Chance |
| 5,122,974 A | 6/1992 | Chance |
| 5,143,078 A | 9/1992 | Mather et al. |
| 5,167,230 A | 12/1992 | Chance |
| 5,190,038 A | 3/1993 | Polson et al. |
| 5,238,001 A | 8/1993 | Gallant et al. |
| 5,246,003 A | 9/1993 | DeLonzor |
| 5,247,931 A | 9/1993 | Norwood |
| 5,253,645 A | 10/1993 | Friedman et al. |
| 5,263,244 A | 11/1993 | Centa et al. |
| 5,269,310 A | 12/1993 | Jones et al. |
| 5,279,295 A | 1/1994 | Martens et al. |
| 5,285,783 A | 2/1994 | Secker |
| 5,297,548 A | 3/1994 | Pologe |
| 5,309,908 A | 5/1994 | Friedman et al. |
| 5,312,454 A | 5/1994 | Roline et al. |
| 5,355,880 A | 10/1994 | Thomas et al. |
| 5,372,136 A | 12/1994 | Steuer et al. |
| 5,385,143 A | 1/1995 | Aoyagi |
| 5,390,666 A | 2/1995 | Kimm et al. |
| 5,390,670 A | 2/1995 | Centa et al. |
| 5,413,099 A | 5/1995 | Schmidt et al. |
| 5,423,327 A | 6/1995 | Clauson et al. |
| 5,469,845 A | 11/1995 | DeLonzor et al. |
| 5,482,036 A | 1/1996 | Diab et al. |
| 5,520,176 A | 5/1996 | Cohen |
| 5,558,086 A | 9/1996 | Smith et al. |
| 5,483,646 A | 10/1996 | Uchikoga |
| 5,553,614 A | 10/1996 | Chance |
| 5,564,417 A | 10/1996 | Chance |
| 5,575,285 A | 11/1996 | Takanashi et al. |
| 5,584,298 A | 12/1996 | Kabal |
| 5,611,337 A | 3/1997 | Bukta |
| 5,619,991 A | 4/1997 | Sloane |
| 5,630,413 A | 5/1997 | Thomas et al. |
| 5,639,617 A | 6/1997 | Bohuon |
| 5,645,059 A | 7/1997 | Fein et al. |
| 5,645,060 A | 7/1997 | Yorkey |
| 5,660,171 A | 8/1997 | Kimm et al. |
| 5,680,857 A | 10/1997 | Pelikan et al. |
| 5,692,503 A | 12/1997 | Keunstner |
| 5,716,384 A | 2/1998 | Snell |
| 5,724,580 A | 3/1998 | Levin et al. |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hok |
| 5,800,348 A | 9/1998 | Kaestle |
| 5,804,370 A | 9/1998 | Romaschin et al. |
| 5,822,544 A | 10/1998 | Chaco et al. |
| 5,830,136 A | 11/1998 | DeLonzor et al. |
| 5,830,139 A | 11/1998 | Abreu |
| 5,831,598 A | 11/1998 | Kauffert et al. |
| 5,840,019 A | 11/1998 | Wirebaugh |
| 5,842,981 A | 12/1998 | Larsen et al. |
| 5,846,190 A | 12/1998 | Woehrle |
| 5,862,802 A | 1/1999 | Bird |
| 5,865,174 A | 2/1999 | Kloeppel |
| 5,871,442 A | 2/1999 | Madarasz et al. |
| 5,873,821 A | 2/1999 | Chance et al. |
| 5,920,263 A | 7/1999 | Huttenhoff et al. |
| 5,931,790 A | 8/1999 | Peel, III |
| 5,935,099 A | 8/1999 | Peterson et al. |
| 5,942,986 A | 8/1999 | Shabot et al. |
| 5,995,855 A | 11/1999 | Kiani et al. |
| 5,995,856 A | 11/1999 | Mannheimer et al. |
| 5,995,859 A | 11/1999 | Takahashi |
| 6,002,952 A | 12/1999 | Diab et al. |
| 6,004,276 A | 12/1999 | Wright et al. |
| 6,011,986 A | 1/2000 | Diab et al. |
| 6,024,699 A | 2/2000 | Surwit et al. |
| 6,050,951 A | 4/2000 | Friedman et al. |
| 6,064,898 A | 5/2000 | Aldrich |
| 6,067,462 A | 5/2000 | Diab et al. |
| 6,067,466 A | 5/2000 | Selker et al. |

(56) References Cited

U.S. PATENT DOCUMENTS

| | | |
|---|---|---|
| 6,070,098 A | 5/2000 | Moore-Ede et al. |
| 6,081,742 A | 6/2000 | Amano et al. |
| 6,083,172 A | 7/2000 | Baker, Jr. et al. |
| 6,088,607 A | 7/2000 | Diab et al. |
| 6,095,984 A | 8/2000 | Amano et al. |
| 6,102,038 A | 8/2000 | DeVries |
| 6,102,870 A | 8/2000 | Edwards |
| 6,120,460 A | 9/2000 | Abreu |
| 6,134,460 A | 10/2000 | Chance |
| 6,141,590 A | 10/2000 | Renirie et al. |
| 6,148,814 A | 11/2000 | Clemmer et al. |
| 6,150,951 A | 11/2000 | Olejniczak |
| 6,151,516 A | 11/2000 | Kiani-Azarbayjany et al. |
| 6,154,667 A | 11/2000 | Miura et al. |
| 6,159,683 A | 12/2000 | Romaschin et al. |
| 6,163,715 A | 12/2000 | Larsen et al. |
| 6,171,258 B1 | 1/2001 | Karakasoglu et al. |
| 6,181,958 B1 | 1/2001 | Steuer et al. |
| 6,181,959 B1 | 1/2001 | Schollermann et al. |
| 6,230,035 B1 | 5/2001 | Aoyagi et al. |
| 6,230,142 B1 | 5/2001 | Benigno et al. |
| 6,230,708 B1 | 5/2001 | Radko |
| 6,266,546 B1 | 7/2001 | Steuer et al. |
| 6,285,895 B1 | 9/2001 | Ristolainen et al. |
| 6,312,393 B1 | 11/2001 | Abreu |
| 6,322,515 B1 | 11/2001 | Goor et al. |
| 6,353,750 B1 | 3/2002 | Kimura et al. |
| 6,363,270 B1 | 3/2002 | Colla et al. |
| 6,364,834 B1 | 4/2002 | Reuss et al. |
| 6,385,589 B1 | 5/2002 | Trusheim et al. |
| 6,393,311 B1 | 5/2002 | Edgar, Jr. et al. |
| 6,397,091 B2 | 5/2002 | Diab et al. |
| 6,397,099 B1 | 5/2002 | Chance |
| 6,398,727 B1 | 6/2002 | Bui et al. |
| 6,411,833 B1 | 6/2002 | Baker, Jr. et al. |
| 6,415,166 B1 | 7/2002 | Van Hoy et al. |
| 6,415,175 B1 | 7/2002 | Conley et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,475,153 B1 | 11/2002 | Khair et al. |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,553,242 B1 | 4/2003 | Sarussi |
| 6,571,622 B2 | 6/2003 | Koch |
| 6,579,242 B2 | 6/2003 | Bui et al. |
| 6,580,086 B1 | 6/2003 | Schultz et al. |
| 6,583,794 B1 | 6/2003 | Wattenberg |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,659,961 B2 | 12/2003 | Robinson |
| 6,662,030 B2 | 12/2003 | Khalil et al. |
| 6,662,032 B1 | 12/2003 | Gavish et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,690,958 B1 | 2/2004 | Walker et al. |
| 6,697,658 B2 | 2/2004 | Al-Ali |
| 6,699,194 B1 | 3/2004 | Diab et al. |
| 6,708,048 B1 | 3/2004 | Chance |
| 6,711,424 B1 | 3/2004 | Fine et al. |
| 6,711,425 B1 | 3/2004 | Reuss et al. |
| 6,714,245 B1 | 3/2004 | Ono |
| 6,721,584 B2 | 4/2004 | Baker, Jr. et al. |
| 6,723,077 B2 | 4/2004 | Pickup et al. |
| 6,731,274 B2 | 5/2004 | Powell |
| 6,738,666 B1 | 5/2004 | Park et al. |
| 6,752,150 B1 | 6/2004 | Remmers et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes |
| 6,801,799 B2 | 10/2004 | Mendelson |
| 6,810,277 B2 | 10/2004 | Edgar, Jr. et al. |
| 6,816,266 B2 | 11/2004 | Varshneya et al. |
| 6,820,618 B2 | 11/2004 | Banner et al. |
| 6,829,496 B2 | 12/2004 | Nagai et al. |
| 6,830,549 B2 | 12/2004 | Bui et al. |
| 6,836,679 B2 | 12/2004 | Baker, Jr. et al. |
| 6,839,581 B1 | 1/2005 | El-Solh et al. |
| 6,850,053 B2 | 2/2005 | Daalmans et al. |
| 6,863,652 B2 | 3/2005 | Huang et al. |
| 6,869,402 B2 | 3/2005 | Arnold |
| 6,873,865 B2 | 3/2005 | Steuer et al. |
| 6,889,153 B2 | 5/2005 | Dietiker |
| 6,898,451 B2 | 5/2005 | Wuori |
| 6,918,878 B2 | 7/2005 | Brodnick |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,963,767 B2 | 11/2005 | Rantala et al. |
| 6,983,178 B2 | 1/2006 | Fine et al. |
| 6,985,762 B2 | 1/2006 | Brashears et al. |
| 6,993,371 B2 | 1/2006 | Kiani et al. |
| 6,994,675 B2 | 2/2006 | Sharrock |
| 6,996,427 B2 | 2/2006 | Ali et al. |
| 7,013,898 B2 | 3/2006 | Rashad et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,034,692 B2 | 4/2006 | Hickle |
| 7,035,679 B2 | 4/2006 | Addison et al. |
| 7,035,697 B1 | 4/2006 | Brown |
| 7,040,315 B1 | 5/2006 | Stromberg |
| 7,044,917 B2 | 5/2006 | Arnold |
| 7,047,056 B2 | 5/2006 | Hannula et al. |
| 7,081,095 B2 | 7/2006 | Lynn et al. |
| 7,118,534 B2 | 10/2006 | Ward et al. |
| 7,127,278 B2 | 10/2006 | Melker et al. |
| 7,139,599 B2 | 11/2006 | Terry |
| 7,161,484 B2 | 1/2007 | Tsoukalis |
| 7,162,306 B2 | 1/2007 | Caby et al. |
| 7,171,269 B1 | 1/2007 | Addison et al. |
| 7,186,217 B2 | 3/2007 | Kawasaki |
| 7,188,621 B2 | 3/2007 | DeVries et al. |
| 7,190,261 B2 | 3/2007 | Al-Ali |
| 7,190,995 B2 | 3/2007 | Chervin et al. |
| 7,209,775 B2 | 4/2007 | Bae et al. |
| 7,218,966 B2 | 5/2007 | Haefner |
| 7,220,220 B2 | 5/2007 | Stubbs et al. |
| 7,222,623 B2 | 5/2007 | DeVries et al. |
| 7,231,240 B2 | 6/2007 | Eda et al. |
| 7,236,811 B2 | 6/2007 | Schmitt |
| 7,239,905 B2 | 7/2007 | Kiani-Azarbayjany et al. |
| 7,252,637 B2 | 8/2007 | Ebner et al. |
| 7,263,395 B2 | 8/2007 | Chan et al. |
| 7,267,652 B2 | 9/2007 | Coyle et al. |
| 7,272,426 B2 | 9/2007 | Schmidt et al. |
| 7,309,314 B2 | 12/2007 | Grant et al. |
| 7,338,447 B2 | 3/2008 | Phillips |
| 7,353,054 B2 | 4/2008 | Kawasaki et al. |
| 7,366,569 B2 | 4/2008 | Belalcazar |
| 7,367,339 B2 | 5/2008 | Hickle |

(56) References Cited

U.S. PATENT DOCUMENTS

| | | | |
|---|---|---|---|
| 7,367,954 B2 | 5/2008 | Starr et al. | |
| 7,370,650 B2 | 5/2008 | Nadjafizadeh et al. | |
| 7,373,193 B2 | 5/2008 | Al-Ali et al. | |
| 7,407,485 B2 | 8/2008 | Huiku | |
| 7,407,486 B2 | 8/2008 | Huiku et al. | |
| 7,421,296 B1 | 9/2008 | Benser et al. | |
| 7,428,520 B2 | 9/2008 | Armstrong et al. | |
| 7,447,541 B2 | 11/2008 | Huiku et al. | |
| 7,460,909 B1 | 12/2008 | Koh et al. | |
| 7,488,293 B2 | 2/2009 | Marchovecchio | |
| 7,499,835 B2 | 3/2009 | Weber | |
| 7,539,537 B2 | 5/2009 | Hickle | |
| 7,544,190 B2 | 6/2009 | Pickup et al. | |
| 7,632,685 B2 | 12/2009 | Ivey et al. | |
| 7,635,337 B2 | 12/2009 | Huika et al. | |
| 7,640,055 B2 | 12/2009 | Geva et al. | |
| 7,645,613 B2 | 1/2010 | Ivey et al. | |
| 7,659,075 B2 | 2/2010 | Bergmann | |
| 7,668,579 B2 | 2/2010 | Lynn | |
| 7,674,230 B2 | 3/2010 | Reisfeld | |
| 7,723,492 B2 | 5/2010 | Bergmann et al. | |
| 7,758,503 B2 | 7/2010 | Lynn et al. | |
| 7,785,262 B2 | 8/2010 | Melker et al. | |
| 7,792,642 B1 | 9/2010 | Neilley et al. | |
| 7,794,406 B2 | 9/2010 | Reisfeld et al. | |
| 7,803,118 B2 | 9/2010 | Reisfeld et al. | |
| 7,803,119 B2 | 9/2010 | Reisfeld | |
| 7,806,832 B2 | 10/2010 | Gallagher et al. | |
| 8,274,360 B2 | 9/2012 | Sampath | |
| 8,275,553 B2 | 9/2012 | Ochs et al. | |
| 8,365,730 B2 | 2/2013 | Baker, Jr. et al. | |
| 8,398,555 B2 | 3/2013 | Ochs et al. | |
| 8,414,488 B2 | 4/2013 | Colman | |
| 8,428,966 B2 | 4/2013 | Green, III | |
| 8,438,041 B2 | 5/2013 | Green, III | |
| 8,439,835 B1 | 5/2013 | McKinley et al. | |
| 8,527,449 B2 | 9/2013 | Gajic et al. | |
| 8,663,107 B2 | 3/2014 | Kiani | |
| 8,666,467 B2 | 3/2014 | Lynn et al. | |
| 8,728,001 B2 | 5/2014 | Lynn | |
| 8,781,753 B2 | 7/2014 | Ivey et al. | |
| 9,042,952 B2 | 5/2015 | Lynn et al. | |
| 2001/0005773 A1 | 6/2001 | Larsen et al. | |
| 2001/0018557 A1 | 8/2001 | Lynn et al. | |
| 2001/0020122 A1 | 9/2001 | Steuer et al. | |
| 2001/0039376 A1 | 11/2001 | Steuer et al. | |
| 2001/0044588 A1 | 11/2001 | Mault | |
| 2001/0044700 A1 | 11/2001 | Kobayashi et al. | |
| 2002/0002327 A1 | 1/2002 | Grant et al. | |
| 2002/0026106 A1 | 2/2002 | Khalil et al. | |
| 2002/0026941 A1 | 3/2002 | Biondi et al. | |
| 2002/0030682 A1* | 3/2002 | Eberlein | A61B 5/0002 345/440 |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0085952 A1 | 7/2002 | Ellingboe | |
| 2002/0091326 A1 | 7/2002 | Hashimoto et al. | |
| 2002/0099273 A1* | 7/2002 | Bocionek | A61B 5/411 600/300 |
| 2002/0111748 A1 | 8/2002 | Kobayashi et al. | |
| 2002/0128544 A1 | 9/2002 | Diab et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0165462 A1 | 11/2002 | Westbrook et al. | |
| 2002/0198443 A1 | 12/2002 | Ting | |
| 2003/0000522 A1 | 1/2003 | Lynn et al. | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0101076 A1 | 5/2003 | Zaleski | |
| 2003/0127097 A1 | 7/2003 | Yurko | |
| 2003/0135127 A1 | 7/2003 | Sackner et al. | |
| 2003/0139687 A1 | 7/2003 | Abreu | |
| 2003/0144584 A1 | 7/2003 | Mendelson | |
| 2003/0150842 A1 | 8/2003 | Mikame | |
| 2003/0158466 A1* | 8/2003 | Lynn | A61B 5/00 600/300 |
| 2003/0181815 A1 | 9/2003 | Ebner et al. | |
| 2003/0194752 A1 | 10/2003 | Anderson et al. | |
| 2003/0220548 A1 | 11/2003 | Schmitt | |
| 2003/0220576 A1 | 11/2003 | Diab | |
| 2003/0228625 A1 | 12/2003 | Toh et al. | |
| 2004/0010188 A1 | 1/2004 | Wasserman | |
| 2004/0039295 A1 | 2/2004 | Olbrich et al. | |
| 2004/0044276 A1 | 3/2004 | Arnold | |
| 2004/0048264 A1 | 3/2004 | Stoughton et al. | |
| 2004/0054270 A1 | 3/2004 | Pewzner et al. | |
| 2004/0064020 A1 | 4/2004 | Diab et al. | |
| 2004/0073098 A1 | 4/2004 | Geva et al. | |
| 2004/0078219 A1 | 4/2004 | Kaylor et al. | |
| 2004/0078228 A1 | 4/2004 | Fitzgerald et al. | |
| 2004/0087846 A1 | 5/2004 | Wasserman | |
| 2004/0087916 A1 | 5/2004 | Pickup | |
| 2004/0096917 A1 | 5/2004 | Ivey et al. | |
| 2004/0097460 A1 | 5/2004 | Ivey et al. | |
| 2004/0106142 A1 | 6/2004 | Ivey et al. | |
| 2004/0107065 A1 | 6/2004 | Al-Ali | |
| 2004/0111014 A1 | 6/2004 | Hickle | |
| 2004/0117204 A1 | 6/2004 | Mazar et al. | |
| 2004/0127779 A1 | 7/2004 | Steuer et al. | |
| 2004/0128163 A1* | 7/2004 | Goodman | G06Q 10/10 705/2 |
| 2004/0157242 A1 | 8/2004 | Ivey et al. | |
| 2004/0158135 A1 | 8/2004 | Baker, Jr. et al. | |
| 2004/0162499 A1 | 8/2004 | Nagai et al. | |
| 2004/0163648 A1 | 8/2004 | Burton | |
| 2004/0170154 A1 | 9/2004 | Carter et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0181134 A1 | 9/2004 | Baker, Jr. et al. | |
| 2004/0181196 A1 | 9/2004 | Pickup et al. | |
| 2004/0183683 A1 | 9/2004 | Funahashi | |
| 2004/0204637 A1 | 10/2004 | Diab et al. | |
| 2004/0230105 A1 | 11/2004 | Geva et al. | |
| 2004/0230106 A1 | 11/2004 | Schmitt et al. | |
| 2004/0249299 A1 | 12/2004 | Cobb | |
| 2004/0254481 A1 | 12/2004 | Brodnick | |
| 2004/0254490 A1 | 12/2004 | Egli | |
| 2005/0001728 A1 | 1/2005 | Appelt et al. | |
| 2005/0017864 A1 | 1/2005 | Tsoukalis | |
| 2005/0027207 A1 | 2/2005 | Westbrook et al. | |
| 2005/0033129 A1 | 2/2005 | Edgar, Jr. et al. | |
| 2005/0043616 A1 | 2/2005 | Chinchoy | |
| 2005/0065556 A1 | 3/2005 | Reghabi et al. | |
| 2005/0070774 A1 | 3/2005 | Addison et al. | |
| 2005/0080323 A1 | 4/2005 | Kato | |
| 2005/0085735 A1 | 4/2005 | Baker, Jr. et al. | |
| 2005/0098178 A1 | 5/2005 | Banner et al. | |
| 2005/0101850 A1 | 5/2005 | Parker | |
| 2005/0109340 A1 | 5/2005 | Tehrani | |
| 2005/0113651 A1 | 5/2005 | Wood et al. | |
| 2005/0113656 A1 | 5/2005 | Chance | |
| 2005/0113709 A1 | 5/2005 | Millet | |
| 2005/0119586 A1 | 6/2005 | Coyle et al. | |
| 2005/0119708 A1 | 6/2005 | Haefner | |
| 2005/0125256 A1 | 6/2005 | Schoenberg et al. | |
| 2005/0143665 A1 | 6/2005 | Huiku et al. | |
| 2005/0154422 A1 | 7/2005 | Band et al. | |
| 2005/0164238 A1 | 7/2005 | Valkirs et al. | |
| 2005/0168722 A1 | 8/2005 | Forstner et al. | |
| 2005/0177034 A1 | 8/2005 | Beaumont | |
| 2005/0181354 A1 | 8/2005 | Estep, III | |
| 2005/0187480 A1 | 8/2005 | Kario et al. | |
| 2005/0192488 A1 | 9/2005 | Bryenton et al. | |
| 2005/0192500 A1 | 9/2005 | Caro et al. | |
| 2005/0203357 A1 | 9/2005 | Debreczeny et al. | |
| 2005/0222503 A1 | 10/2005 | Dunlop et al. | |

(56) References Cited

U.S. PATENT DOCUMENTS

| | | |
|---|---|---|
| 2005/0228248 A1 | 10/2005 | Dietiker |
| 2005/0240091 A1 | 10/2005 | Lynn |
| 2005/0245830 A1 | 11/2005 | Hutchinson |
| 2005/0247311 A1 | 11/2005 | Vacchiano et al. |
| 2005/0251056 A1 | 11/2005 | Gribkov et al. |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0009688 A1 | 1/2006 | Lamego et al. |
| 2006/0009809 A1 | 1/2006 | Marcovecchio et al. |
| 2006/0015021 A1 | 1/2006 | Cheung |
| 2006/0020181 A1 | 1/2006 | Schmitt |
| 2006/0030763 A1 | 2/2006 | Mannheimer et al. |
| 2006/0042631 A1 | 3/2006 | Martin et al. |
| 2006/0052680 A1 | 3/2006 | Diab |
| 2006/0058683 A1 | 3/2006 | Chance |
| 2006/0064024 A1 | 3/2006 | Schnall |
| 2006/0081259 A1 | 4/2006 | Bruggeman et al. |
| 2006/0084854 A1 | 4/2006 | Cho et al. |
| 2006/0137577 A1 | 6/2006 | Chang et al. |
| 2006/0149144 A1 | 7/2006 | Lynn et al. |
| 2006/0155176 A1 | 7/2006 | Ebner et al. |
| 2006/0155206 A1 | 7/2006 | Lynn et al. |
| 2006/0155207 A1 | 7/2006 | Lynn et al. |
| 2006/0157647 A1 | 7/2006 | Siuzdak et al. |
| 2006/0161071 A1 | 7/2006 | Lynn et al. |
| 2006/0167363 A1 | 7/2006 | Osypka et al. |
| 2006/0189872 A1 | 8/2006 | Arnold |
| 2006/0189880 A1 | 8/2006 | Lynn et al. |
| 2006/0195028 A1 | 8/2006 | Hannula et al. |
| 2006/0195041 A1 | 8/2006 | Lynn et al. |
| 2006/0195149 A1 | 8/2006 | Hopper |
| 2006/0200012 A1 | 9/2006 | Mansour et al. |
| 2006/0200016 A1 | 9/2006 | Diab et al. |
| 2006/0217614 A1 | 9/2006 | Takala et al. |
| 2006/0217615 A1 | 9/2006 | Huiku et al. |
| 2006/0217628 A1 | 9/2006 | Huiku |
| 2006/0224058 A1 | 10/2006 | Mannheimer |
| 2006/0235324 A1 | 10/2006 | Lynn |
| 2006/0235726 A1 | 10/2006 | Paraison et al. |
| 2006/0247501 A1 | 11/2006 | Ali |
| 2006/0258921 A1 | 11/2006 | Addison et al. |
| 2006/0271408 A1 | 11/2006 | Rosenfeld et al. |
| 2006/0276695 A9 | 12/2006 | Lynn et al. |
| 2006/0287590 A1 | 12/2006 | McEowen |
| 2007/0004957 A1 | 1/2007 | Hilburg |
| 2007/0010723 A1 | 1/2007 | Uutela et al. |
| 2007/0015976 A1 | 1/2007 | Miesel et al. |
| 2007/0027369 A1 | 2/2007 | Pagnacco et al. |
| 2007/0027375 A1 | 2/2007 | Melker et al. |
| 2007/0073361 A1 | 3/2007 | Goren et al. |
| 2007/0093701 A1 | 4/2007 | Myers et al. |
| 2007/0093721 A1 | 4/2007 | Lynn et al. |
| 2007/0142719 A1 | 6/2007 | Kawasaki et al. |
| 2007/0149860 A1 | 6/2007 | Lynn et al. |
| 2007/0129647 A1 | 7/2007 | Lynn |
| 2007/0179350 A1 | 8/2007 | Nadeau |
| 2007/0179369 A1 | 8/2007 | Baker, Jr. |
| 2007/0184512 A1 | 8/2007 | Ivey et al. |
| 2007/0191688 A1 | 8/2007 | Lynn |
| 2007/0191697 A1 | 8/2007 | Lynn et al. |
| 2007/0203406 A1 | 8/2007 | Anderson et al. |
| 2007/0208269 A1 | 9/2007 | Mumford et al. |
| 2007/0213619 A1 | 9/2007 | Linder |
| 2007/0213620 A1 | 9/2007 | Reisfeld |
| 2007/0213621 A1 | 9/2007 | Reisfeld et al. |
| 2007/0213622 A1 | 9/2007 | Reisfeld |
| 2007/0213624 A1 | 9/2007 | Reisfeld et al. |
| 2007/0225606 A1 | 9/2007 | Naghavi et al. |
| 2007/0225614 A1 | 9/2007 | Naghavi et al. |
| 2007/0238937 A1 | 10/2007 | Chang et al. |
| 2007/0240723 A1 | 10/2007 | Hong et al. |
| 2007/0255146 A1 | 11/2007 | Andrews et al. |
| 2007/0255322 A1 | 11/2007 | Gerber et al. |
| 2007/0282212 A1 | 12/2007 | Sierra et al. |
| 2008/0009689 A1 | 1/2008 | Benaron et al. |
| 2008/0014115 A1 | 1/2008 | Johns |
| 2008/0027368 A1 | 1/2008 | Kollar et al. |
| 2008/0036752 A1 | 2/2008 | Diab et al. |
| 2008/0050829 A1 | 2/2008 | Ivey et al. |
| 2008/0051764 A1 | 2/2008 | Dent et al. |
| 2008/0064965 A1 | 3/2008 | Jay et al. |
| 2008/0066753 A1 | 3/2008 | Martin et al. |
| 2008/0082018 A1 | 4/2008 | Sackner et al. |
| 2008/0114576 A1 | 5/2008 | Jackson et al. |
| 2008/0138832 A1 | 6/2008 | Ivey et al. |
| 2008/0167540 A1 | 7/2008 | Korhonen et al. |
| 2008/0177163 A1 | 7/2008 | Wang et al. |
| 2008/0183058 A1 | 7/2008 | Mannheimer |
| 2008/0183083 A1 | 7/2008 | Markowitz et al. |
| 2008/0188729 A1 | 8/2008 | Sato et al. |
| 2008/0195322 A1 | 8/2008 | Altschuler et al. |
| 2008/0200775 A1 | 8/2008 | Lynn |
| 2008/0200781 A1 | 8/2008 | Van Herpen et al. |
| 2008/0208012 A1 | 8/2008 | Ali |
| 2008/0208618 A1 | 8/2008 | Schoenberg et al. |
| 2008/0235049 A1 | 9/2008 | Morita et al. |
| 2008/0235057 A1 | 9/2008 | Weidenhaupt et al. |
| 2008/0269583 A1 | 10/2008 | Reisfeld |
| 2008/0269626 A1 | 10/2008 | Gallaher et al. |
| 2008/0269832 A1 | 10/2008 | Wong et al. |
| 2008/0275349 A1 | 11/2008 | Halperin et al. |
| 2008/0281168 A1 | 11/2008 | Gibson et al. |
| 2008/0286763 A1 | 11/2008 | Russwurm et al. |
| 2008/0287756 A1 | 11/2008 | Lynn |
| 2008/0305464 A1 | 12/2008 | Lynn |
| 2008/0312533 A1 | 12/2008 | Balberg et al. |
| 2009/0069704 A1 | 3/2009 | MacAdam et al. |
| 2009/0082641 A1 | 3/2009 | Giftakis et al. |
| 2009/0083072 A1 | 3/2009 | Osawa et al. |
| 2009/0143694 A1 | 6/2009 | Krauss |
| 2009/0171169 A1 | 7/2009 | Nagata |
| 2009/0186774 A1 | 7/2009 | Turner et al. |
| 2009/0187082 A1 | 7/2009 | Cuddihy et al. |
| 2009/0281838 A1 | 11/2009 | Lynn et al. |
| 2009/0281839 A1 | 11/2009 | Lynn et al. |
| 2009/0299154 A1 | 12/2009 | Segman |
| 2009/0318775 A1 | 12/2009 | Michelson et al. |
| 2010/0066540 A1 | 3/2010 | Theobald et al. |
| 2010/0070888 A1 | 3/2010 | Watabe et al. |
| 2010/0079292 A1 | 4/2010 | Lynn et al. |
| 2010/0094648 A1 | 4/2010 | Seward |
| 2010/0160171 A1 | 6/2010 | Freishtat |
| 2010/0174161 A1 | 7/2010 | Lynn |
| 2010/0234705 A1 | 9/2010 | Lynn |
| 2010/0261977 A1 | 10/2010 | Seely |
| 2011/0009722 A1 | 1/2011 | Amundson et al. |
| 2011/0009760 A1 | 1/2011 | Zhang et al. |
| 2011/0015501 A1 | 1/2011 | Lynn et al. |
| 2011/0046498 A1 | 2/2011 | Klap et al. |
| 2011/0105350 A1 | 5/2011 | Garrett et al. |
| 2011/0118569 A1 | 5/2011 | Shi et al. |
| 2011/0130671 A1 | 6/2011 | MacQuarrie et al. |
| 2011/0208539 A1 | 8/2011 | Lynn |
| 2012/0053425 A1 | 3/2012 | Michelson et al. |
| 2012/0145152 A1 | 6/2012 | Lain |
| 2012/0165623 A1 | 6/2012 | Lynn et al. |
| 2012/0172247 A1 | 7/2012 | Narimatsu et al. |
| 2012/0197094 A1 | 8/2012 | Zhang et al. |
| 2012/0220845 A1 | 8/2012 | Campbell |
| 2012/0232359 A1 | 9/2012 | Al-Ali et al. |
| 2012/0328594 A1 | 12/2012 | McKenna et al. |
| 2012/0330118 A1 | 12/2012 | Lynn et al. |
| 2013/0052671 A1 | 2/2013 | Grueb et al. |
| 2013/0060110 A1 | 3/2013 | Lynn et al. |
| 2013/0073311 A1 | 3/2013 | Lynn et al. |
| 2013/0124221 A1 | 5/2013 | Lynn |
| 2013/0131993 A1 | 5/2013 | Lynn et al. |
| 2013/0158375 A1 | 6/2013 | Lynn |
| 2013/0209068 A1 | 8/2013 | Lynn |
| 2013/0211214 A1 | 8/2013 | Olsen |
| 2013/0218600 A1 | 8/2013 | Lynn et al. |
| 2013/0254717 A1 | 9/2013 | Al-Ali et al. |
| 2013/0262730 A1 | 10/2013 | Al-Ali et al. |

(56) References Cited

U.S. PATENT DOCUMENTS

| | | |
|---|---|---|
| 2013/0268291 A1 | 10/2013 | Lynn et al. |
| 2013/0274572 A1 | 10/2013 | Al-Ali et al. |
| 2013/0276785 A1 | 10/2013 | Melker |
| 2013/0290011 A1 | 10/2013 | Lynn et al. |
| 2013/0338459 A1 | 12/2013 | Lynn |
| 2014/0152673 A1 | 6/2014 | Lynn et al. |
| 2014/0163897 A1 | 6/2014 | Lynn et al. |
| 2014/0176538 A1 | 6/2014 | Lynn et al. |
| 2014/0176558 A1 | 6/2014 | Lynn et al. |
| 2014/0180722 A1 | 6/2014 | Lynn et al. |

FOREIGN PATENT DOCUMENTS

| | | |
|---|---|---|
| EP | 0459647 B1 | 10/1991 |
| EP | 0615723 | 3/1993 |
| EP | 0666056 A1 | 7/1994 |
| EP | 0392503 B1 | 5/1995 |
| EP | 0684011 A1 | 5/1995 |
| EP | 0700690 B1 | 2/2002 |
| EP | 0759791 B1 | 8/2002 |
| EP | 1529487 A1 | 7/2003 |
| EP | 0934 723 B1 | 9/2004 |
| EP | 1172123 B1 | 10/2004 |
| EP | 0875258 B1 | 11/2004 |
| EP | 1905356 | 9/2007 |
| GB | 1554829 | 2/1978 |
| JP | 63275325 | 11/1988 |
| JP | 05266002 | 3/1992 |
| JP | 05-266002 | 10/1993 |
| JP | 2000-042111 | 2/2000 |
| JP | 2002336207 A | 11/2002 |
| JP | 2004145853 | 5/2004 |
| JP | 2005034472 | 2/2005 |
| JP | 2006519626 | 8/2006 |
| JP | 2007058565 A | 3/2007 |
| JP | 4435681 B2 | 3/2010 |
| KR | 1020020064206 | 8/2002 |
| WO | WO 86/00234 | 1/1986 |
| WO | WO 92/12750 | 8/1992 |
| WO | WO 93/16629 | 9/1993 |
| WO | WO 94/23780 | 10/1994 |
| WO | WO 96/39927 | 12/1996 |
| WO | WO 97/19719 | 6/1997 |
| WO | WO 98/12965 | 4/1998 |
| WO | WO 98/43071 A1 | 10/1998 |
| WO | WO 99/13766 | 3/1999 |
| WO | WO 00/21438 | 4/2000 |
| WO | WO 00/74551 A2 | 12/2000 |
| WO | WO 01/40776 | 6/2001 |
| WO | WO 01/76461 | 10/2001 |
| WO | WO 01/76471 | 10/2001 |
| WO | WO 01/82099 A1 | 11/2001 |
| WO | WO 01/87149 | 11/2001 |
| WO | WO 02/41771 A1 | 5/2002 |
| WO | WO 03/000125 A1 | 1/2003 |
| WO | WO 03/039326 | 5/2003 |
| WO | WO 03/053780 | 7/2003 |
| WO | WO 2004056301 A2 | 7/2004 |
| WO | WO 2004/075746 A2 | 9/2004 |
| WO | WO 2004080300 A1 | 9/2004 |
| WO | WO 2004/105601 A1 | 12/2004 |
| WO | WO 2005/037077 | 4/2005 |
| WO | 2005/056087 A1 | 6/2005 |
| WO | WO 2005/065540 A1 | 7/2005 |
| WO | WO 2005/096931 A1 | 10/2005 |
| WO | WO 2005/110215 A2 | 11/2005 |
| WO | WO 2006/086010 A2 | 8/2006 |
| WO | WO 2006/116469 A2 | 11/2006 |
| WO | WO 2007/013708 | 2/2007 |
| WO | WO 2007/051006 A2 | 5/2007 |
| WO | WO 2007/131064 | 11/2007 |
| WO | WO 2007/131066 | 11/2007 |
| WO | WO 2008/008163 A2 | 1/2008 |
| WO | WO 2008/097411 A1 | 8/2008 |
| WO | WO 2008/117338 A1 | 10/2008 |
| WO | WO 2010/108018 A3 | 9/2010 |

OTHER PUBLICATIONS

Avance Innovating with you, shaping exceptional care, Brochure, GE Healthcare, pp. 8.

Centiva/5 Critical Care Ventilator, Brochure, GE Healthcare, pp. 8.

Cirignotta, Fabio, Cerebral Anoxic Attacks in Sleep Apnea Syndrome, Sleep, 1989, pp. 400-404, vol. 12 No. 5.

Critical Care Therapy and Respiratory Care Section Policy, National Institute of Health, pp. 7.

Curry, J. Paul, Threshold Monitoring, Alarm Fatigue, and the Patterns of Unexpected Hospital Death, APSF Newsletter, Fall 2011, pp. 32-35.

Datex-Phmeda Output Protocols Ohmeda Corn 1.0 Serial Protocol, Brochure, Datex-Ohmeda, Version 1.5, pp. 31.

Davidson Ward, Sally et al., Responses to hypoxia and hypercapnia in infants of substance-abusing mothers, The Journal of Pediatrics, 1992, pp. 704-709, vol. 121 No. 5 Pt. 1.

Diagnostic Apparatus, Bibliographic Data: JP63275325A, Publication Date Nov. 14, 1988, 12 pages.

Horne, Rosemary S.C. et al., Arousal responses and risk factors for sudden infant death syndrome, Sleep Medicine 3, 2002, Supplement, pp. S61-S65.

Horne, Rosemary S.C. et al., Effects of Prematurity on Arousal from Sleep in the Newborn Infant, Pediatric Research, 2000, pp. 468-474, vol. 47 No. 4.

Intensive Care Ventilators, Product Comparison by Healthcare Product Comparison Systems, Inc. published by ECRI, Apr. 2006, 71 pages.

International Application No. PCT/US2009/059102, Written Opinion of the International Searching Authority, dated Apr. 5, 2011.

Litvak, Eugene et al., "Rethinking Rapid Response Teams," JAMA, 2010, vol. 304(12), pp. 1375-1376.

Lung Volumes, Wikipedia, available at http://en.wikipedia.org/wiki/Tidal_volume, printed on Nov. 15, 2007, 4 pages.

Maddox, Ray et al., "Clinical Experience with Patient-Controlled Analgesia Using Continuous Respiratory Monitoring and a Smart Infusion System," Am. J. Health-Syst. Pharm., 2006, vol. 63, pp. 157-164.

McEwen, James et al., Detection of Interruptions in the Breathing Gas of Ventilated Anaesthetized Patients, Canadian Journal of Anaesthology, 1988, vol. 35, No. 6, pp. 549-561.

McKinney, "Alarm fatigue sets off bells, Mass. incident highlights need for protocols check," Modern Healthcare, 2010, vol. 40(15), pp. 14.

Moldenhauer, Kendra et al., "Clinical triggers: an alternative to a rapid response team," 2009, vol. 35(3), pp. 164-174.

Moses, James et al., "The correlation and level of agreement between end-tidal and blood gas pC02 in children with respiratory distress: a retrospective analysis," BMC Pediatrics, 2009, vol. 9(20), 6 pages.

Newman, N.M., Arousal defect: Mechanism of the Suddent Infant Death Syndrome?, Australian Pediatric Journal, 1989, pp. 196-201.

Nguyen, H. Bryant, et al, Severe Sepsis and Septic Shock: Review of the Literature and Emergency Department Management Guidelines, Annals of Emergency Medicine, Jul. 2006, vol. 48, No. 1, pp. 28-55.

Ochroch, Andrew et al., "The impact of continuous pulse oximetry monitoring on intensive care unit admissions from a postsurgical care floor," Anesth Analg, 2006, vol. 1 02(3), pp. 868-875.

Pae, Eung-Kwon et al., Neuroscience Letters 375, 2005, pp. 123-128.

Rivera, Luis, MD et al., Dynamic Ventilatory Characteristics During Weaning in Postoperative Critically Ill Patients, Anesthesia & Analgesia, 1997, vol. 84, pp. 1250-1255.

Saper, Clifford et al., "The Sleep Switch: Hypothalamic Control of Sleep and Wakefulness," Trends in Neurosciences, 2001, vol. 24(12), pp. 726-731.

(56) References Cited

OTHER PUBLICATIONS

Shelley, Kirk, "Photoplethysmography: Beyond the Calculation of Arterial Oxygen Saturation and Heart Rate," The International Anesthesia Research Society, 2010, 30 pages.
Sieker, Herbert et al., "Carbon dioxide intoxication: the clinical syndrome, its etiology and management with particular reference to the use of mechanical respirators," Medicine, 1956, vol. 35(4), pp. 389-423.
Simmons, Daniel et al., "Hyperventilation and respiratory alkalosis as signs of gram-negative bacteremia," JAMA, 1960, vol. 174(18), pp. 2196-2199.
Smith, Gary et al., "Review and performance evaluation of aggregate weighted 'track and trigger' systems," Resuscitation, 2008, vol. 77, pp. 170-179.
Stock, Christine et al., "The PaC02 rate of rise in anesthetized patients with airway obstruction," J. Clin. Anesth., 1989, vol. 1(5), pp. 328-332.
Taenzer, Andreas et al., "Impact of pulse oximetry surveillance on rescue events and intensive care unit transfers: a before-and-after concurrence study," Anesthesiology, 2010, vol. 112(2), pp. 282-287.
Van Lieshout, Johannes et al., "Physical manoeuvres for combating orthostatic dizziness in autonomic failure," The Lancet, 1992, vol. 339, pp. 897-898.
White, David, "Opioid-induced suppression of genioglossal muscle activity: is it clinically important?" J. Physiol., 2009, vol. 587, pp. 3421-3422.
Wiedemann et al., The effect of sedation on pulmonary function Anaesthesist, 1995, vol. 44 Suppl 3, pp. S588-93 (Abstract only).
Younes, Magdy, "Contributions of Upper Airway Mechanics and Control Mechanisms to Severity of Obstructive apnea," Am. J. Respir. Crit. Care Med., 2003, vol. 168, pp. 645-658.
Campbell, Beverly, Arterial Waveforms: Monitoring Changes in Configuration, Hemodynamics, Heart & Lung, May/Jun. 1997, vol. 26, No. 3, pp. 204-214.
Abelson, Harold et al., Structure and Interpretation of Computer Programs, MIT Press, 2nd Edition, 1996, p. 99-107, 113-126.
Agronsky, Dominik, et al., Diagnosing Community-Acquired Pneumonia with a Bayesian Network, AMIA, Inc., 1998, pp. 632-636.
Fry, Donald, et al., The Changing Face of *Staphylococcus aureus*: A Continuing Surgical Challenge, Surgical Infections, 2011, vol. 12, No. 3, pp. 191-203.
International Search Report for International (PCT) Patent Application No. PCT/US2012/065124, dated Mar. 25, 2013, 10 pages.
International Search Report for International (PCT) Patent Application No. PCT/US2012/065129, dated Mar. 23, 2013, 12 pages.
Kreisel, Kristen, et al., USA300 Methicillin-resistant *Staphylococcus aureus* bacteremia and the risk of severe sepsis: is USA300 Methicillin-resistant *Staphylococcus aureus* associated with more severe infections?, Diagnostic Microbiology and Infectious Disease, 2011, vol. 70, pp. 285-290.
Lappin, Emma, et al., Gram-Positive Toxic Shock Syndromes, The Lancet, May 2009, vol. 9, pp. 281-290.
Appeal Brief for U.S. Appl. No. 11/351,961, filed Sep. 24, 2009.
Caines et al: "Overlooking orthostatic hypotension with routine blood-pressure equipment" 1 Lancet The Lancet Limited. London, GB, vol. 352, No. 9126, Aug. 8, 1998 (Aug. 8, 1998), p. 458, DXP004832973, ISSN:0140-6736, the whole document.
Capuano, Terry Ann, et al., Remote Telemetry, Nursing Management, Vo. 26, No. 7, Jul. 1995, p. 26.
Charbonnier et al., "A trend-based alarm system to improve patient monitoring in intensive care units," Control Engineering Practice, Pergamon Press, Oxford, GB, vol. 15, No. 9, May 12, 2007; pp. 1039-1050.
Doctors use 'remote control' to monitor ICU patients, CNN.com. technology>computing, Aug. 21, 2000, http://www.cnn .com/2000/ TEC H/computing/08/21/icu. t_t l.
Earthrowl-Gould, T., et al.; "Chest and abdominal surface motion measurement for continuous monitoring of respiratory function," Proc. Instn Mech Engrs, V215, Part H; pp. 515-520 (2001).

East, Christine E., et al.; "Fetal Oxygen Saturation and Uterine Contractions During Labor," American Journal of Perinatology, vol. 15, No. 6, pp. 345-349 (Jun. 1998).
Examiner's Answer for U.S. Appl. No. 11/351,961, dated Jan. 4, 2010.
Ferrari, A U, et al., Inverse Relationship between heart rate and blood pressure variabilities in rats. Hypertension. Nov. 1987, vol. 10, No. 5, pp. 533-537.
Final Office Action for U.S. Appl. No. 11/351,961, dated Apr. 24, 2009.
Finding Value in Intensive Care, From Afar, The New York Times on the Web, Jul. 27, 1999, www.Visicu.com/ companynews/0799_ nytimes.htm.
Grundy, Betty L., et al., Telemedicine in Critical Care: An Experiment in Health Care Delivery, JACEP, vol. 6, Oct. 1977, pp. 439-444.
Hornero, Roberto, et al.; "Utility of Approximate Entropy From Overnight Pulse Oximetry Data in the Diagnosis of the Obstructive Sleep Apnea Syndrome,"; IEEE Transactions on Biomedical Engineering, vol. 54, No. 1, pp. 107-113, Jan. 2007.
International Preliminary Report on Patentability Including Written Opinion for International (PCT) Patent Application No. PCT/US2009/ 043150, dated Nov. 9, 2010 9 pages.
International Preliminary Report on Patentability including Written Opinion for International (PCT) Patent Application No. PCT/US2009/ 064312, dated May 31, 2011 10 pages.
International Search Report and Written Opinion for application No. PCT/GB2010/001624 dated Dec. 7, 2010.
International Search Report for International (PCT) Patent Application No. PCT/US2009/043150, dated Aug. 4, 2009 2 pages.
International Search Report for International (PCT) Patent Application No. PCT/US2009/064312, dated Feb. 26, 2010 3 pages.
International Search Report, PCT/US2008/002253; dated Jun. 9, 2008.
International Search Report, PCT/US2008/002254, dated Jul. 28, 2008.
Johansson, A.; "Neural network for photoplethysmographic respiratory rate monitoring," Medical & Biological Engineering & Computing, vol. 41, pp. 242-248 (2003).
Johnston, W.S., et al.; "Extracting Breathing Rate information from a Wearable Reflectance Pulse Oximeter Sensor," Proceedings of the 26th Annual International conference of the IEEE EMBS, San Francisco, California; Sep. 1-5, 2004; pp. 5388-5391.
Kaplan, Simon M. and Geraldine Fitzpatrick, Designing Support for Remote Intensive-Care Telehealth Using the Locales Framework, ACM, 1997, pp. 173-184.
Lee, Ho Sung, et al., Remote Patient Monitoring Service through World-Wide Web, Proceedings—19th International Conference-IEEE/EMBS, Oct. 3-Nov. 2, 1997, pp. 928-931.
Levy, Mitchell M., et al., 2001 SCCM/ESICM/ACCP/ATS/SIS International Sepsis Definitions Conference, Critical Care Medicine, 2003, pp. 1250-1256, vol. 31 No. 4.
Mabry, Susan L., et al., Integrated Medical Analysis System, Proceedings of the 1997 Winter Simulation Conference 1997, , pp. 1167-1168.
Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).
Members of the American College of Chest Physicians/Society of Critical Care Medicine Consensus Conference Committee, Definitions for sepsis and organ failure and guidelines for the use of innovative therapies in sepsis, Critical Care Medicine, 1992, pp. 864-874, vol. 20 No. 6.
Miksch, Silvia, Artificial Intelligence for Decision Support: Needs, Possibilities, and Limitations in ICU, 10th Postgraduate Course in Critical Care Medicine A.P.I.C.E. '95, Springer, 1995, pp. 1-11.
Nenov, Valeriy and John Klopp, Remote Access to Neurosurgical CU Physiological Data using the World Wide web, health Care in the Information Age, 1996, pp. 242-249.

(56) References Cited

OTHER PUBLICATIONS

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).
Non-Final Office Action for U.S. Appl. No. 11/351,961, dated Aug. 19, 2008.
Notice of Allowability for U.S. Appl. No. 10/150,582, dated Feb. 13, 2006.
Notice of Allowance for U.S. Appl. No. 11/455,408, dated Jan. 23, 2012 8 pages.
Notice of Allowance for U.S. Appl. No. 11/455,488, dated Aug. 22, 2011 8 pages.
Notice of Allowance for U.S. Appl. No. 11/455,488, dated Nov. 29, 2011 8 pages.
Official Action for Canada Patent Application No. 2,678, 776, dated Feb. 8, 2012.
Official Action for Canada Patent Application No. 2,678,856, dated Feb. 2, 2012 3 pages.
Official Action for U.S. Appl. No. 10/150,582, dated Jun. 20, 2005.
Official Action for U.S. Appl. No. 11/274,960, dated Jun. 8, 2010.
Official Action for U.S. Appl. No. 11/274,960, dated Oct. 20, 2010.
Official Action for U.S. Appl. No. 11/280,559, dated Mar. 21, 2011 13 pages.
Official Action for U.S. Appl. No. 11/280,559, dated Oct. 5, 2011 12 pages.
Official Action for U.S. Appl. No. 11/280,653, dated Dec. 1, 2010 9 pages.
Official Action for U.S. Appl. No. 11/280,653, dated Jun. 13, 2011 8 pages.
Official Action for U.S. Appl. No. 11/280,653, dated Mar. 31, 2010.
Official Action for U.S. Appl. No. 11/351,787, dated Apr. 22, 2011 11 pages.
Official Action for U.S. Appl. No. 11/351,787, dated Nov. 12, 2010.
Official Action for U.S. Appl. No. 11/351,961, dated Apr. 24, 2009.
Official Action for U.S. Appl. No. 11/351,961, dated Aug. 19, 2008.
Official Action for U.S. Appl. No. 11/351,961, dated Jan. 4, 2010.
Official Action for U.S. Appl. No. 11/369,355, dated Aug. 18, 2011 8 pages Restriction Requirement.
Official Action for U.S. Appl. No. 11/369,355, dated Jan. 6, 2012 8 pages.
Official Action for U.S. Appl. No. 11/369,379, dated Jun. 20, 2011 8 pages.
Official Action for U.S. Appl. No. 11/455,408, dated Dec. 27, 2010.
Official Action for U.S. Appl. No. 11/455,408, dated Jul. 27, 2011 6 pages.
Official Action for U.S. Appl. No. 11/455,488, dated Dec. 28, 2010.
Official Action for U.S. Appl. No. 12/437,385, dated Apr. 5, 2011 22 pages.
Official Action for U.S. Appl. No. 12/437,385, dated Nov. 25, 2011 18 pages.
Official Action for U.S. Appl. No. 12/437,417, dated Mar. 4, 2011 24 pages.
Official Action for U.S. Appl. No. 12/839,177, dated Nov. 21, 2011 12 pages.
Perednia, Douglas A., Telemedine Technology and Clinical Applications, JAMA, vol. 6, Feb. 8, 1995, p. 483.
Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.
Remote Monitoring of ICU Patients Lowers Mortality Rates, Complications, Johns Hopkins Newsrelease, Mar. 20, 2001, http://www.newswise.com/articles/2001/3/ICU.JHM.html.
Response to Non-Final Office Action for U.S. Appl. No. 11/351,961, filed Dec. 19, 2008.
Restriction Requirement for U.S. Appl. No. 11/369,355, dated Sep. 2, 2010.
Restriction Requirement for U.S. Appl. No. 11/274,960, dated Feb. 3, 2010.
Restriction Requirement for U.S. Appl. No. 11/280,559, dated Mar. 4, 2010.
Restriction Requirement for U.S. Appl. No. 11/280,559, dated Oct. 18, 2010.
Restriction Requirement for U.S. Appl. No. 11/351,787, dated Jul. 9, 2010.
Restriction Requirement for U.S. Appl. No. 11/369,355, dated Dec. 8, 2010.
Restriction Requirement for U.S. Appl. No. 11/369,379, dated Dec. 27, 2010.
Restriction Requirement for U.S. Appl. No. 11/369,379, dated Sep. 20, 2010.
Restriction Requirement for U.S. Appl. No. 11/455,408, dated Sep. 30, 2010.
Restriction Requirement for U.S. Appl. No. 11/455,488, dated Sep. 16, 2010.
Rosenfeld, M.D., Brian A., FCCM, FCCP, et al., Intensive care unit telemedicine: Alternate paradigm for providing continuous intensive care, Critical Care Medicine, vol. 28, No. 12, 2000 p. 3925.
Seelbach-Gobel, Birgit, et al.; The prediction of fetal acidosis by means of intrapartum fetal pulse oximetry, Am J. Obstet. Gynecol., vol. 180, No. 1, Part 1, pp. 73-81 (1999).
Spigulis, Janis, et al.; "Optical multi-channel sensing of skin blood pulsations," Optical Sensing, Proceedings of SPIE, vol. 5459, pp. 46-53 (2004).
USPTO, U.S. Appl. No. 11/431,686, Amendment and Response to NF Office Action, filed Jun. 21, 2011.
USPTO, U.S. Appl. No. 11/431,686, Final Office Action, dated Oct. 12, 2011.
USPTO, U.S. Appl. No. 11/431,686, NF Office Action, dated Jan. 21, 2011.
USPTO, U.S. Appl. No. 11/431,686, Office Action (Restriction Requirement), dated Sep. 30, 2010.
USPTO, U.S. Appl. No. 11/431,686, Request for Continued Examination and Preliminary Amendment, filed Feb. 29, 2012.
USPTO, U.S. Appl. No. 11/431,686, Response to Restriction Requirement, filed Oct. 29, 2010.
USPTO, U.S. Appl. No. 11/431,686, U.S. Appl. No. 11/431,686, NF Office Action, dated Jan. 21, 2011.
USPTO, U.S. Appl. No. 12/437,385, Amendment and Response to NF Office Action, dated Jan. 15, 2013.
USPTO, U.S. Appl. No. 12/437,385, Amendment and Response to NF Office Action, dated Sep. 6, 2011.
USPTO, U.S. Appl. No. 12/437,385, Final Office Action, dated Nov. 25, 2011.
USPTO, U.S. Appl. No. 12/437,385, NF Office Action, dated Apr. 5, 2011.
USPTO, U.S. Appl. No. 12/437,385, NF Office Action, dated Aug. 17, 2012.
USPTO, U.S. Appl. No. 12/437,385, Request for Continued Examination and Preliminary Amendment, filed Feb. 7, 2012.
USPTO, U.S. Appl. No. 12/437,417, Amendment and Response to NF Office Action, dated Nov. 5, 2012.
USPTO, U.S. Appl. No. 12/437,417, Amendment and Response to NF Office Action, dated Sep. 6, 2011, 13 pages.
USPTO, U.S. Appl. No. 12/437,417, Final Office Action, dated Feb. 14, 2013.
USPTO, U.S. Appl. No. 12/437,417, NF Office Action, dated Aug. 3, 2012.
USPTO, U.S. Appl. No. 12/437,417, Request for Continued Examination and Preliminary Amendment, filed Feb. 29, 2012.
USPTO, U.S. Appl. No. 12/437,417, Final Office Action, dated Nov. 29, 2011.
USPTO, U.S. Appl. No. 12/629,407, Amendment and Response to NF Office Action dated Sep. 25, 2012, filed Feb. 21, 2013.
USPTO, U.S. Appl. No. 12/629,407, NF Office Action, dated Aug. 16, 2012.
USPTO, U.S. Appl. No. 12/629,407, NF Office Action, dated Sep. 25, 2012.
USPTO, U.S. Appl. No. 12/629,407, Response to Requirement for Restriction, filed Sep. 14, 2012.

(56) References Cited

OTHER PUBLICATIONS

Yoon, Gilwon, et al.; Multiple diagnosis based on Photoplethysmography: hematocrit, Sp02, pulse and respiration, Optics in Health Care and Biomedical optics: Diagnostics and Treatment; Proceedings of the SPIE, vol. 4916; pp. 185-188 (2002).

Alaris System, Brochure, Medication Safety System Focused at the Point of Care, Cardinal Health, Alaris Products, pp. 8, 2004.

Alian, Aymen et al., Evaluation of Rapid Response Team Flag-Alert Parameters, Published on www.cardiopulmonarycorp.com/pdf/rapidresponsealert paramers.pdf referenced in 2008, Internet Publication 2010.

Author Unknown, Chapter IV Oxygen Consumption During ADO, Introduction, pp. 40-46, Book Title Unknown, Study published 1980.

Author Unknown, Chapter X Effects of a 6-minute Period of ADO, Introduction, pp. 108-113, Book Title Unknown, Study published 1980.

Author Unknown, Hospital Inpatient Chart, Completed prior to 2011, not published.

Avance Innovating with you, shaping exceptional care, Brochure, GE Healthcare, pp. 8, 2006.

Bartolo, Anton et al., An Arrhythmia Detector and Heart Rate Estimator for Overnight Polysomnography Studies, conditionally accepted for IEEE Transactions, 19 pages, Nov. 3, 2000.

Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company I Sleep Apnea and Narcotic Postoperative Paln . . . http://www.thedoctors.com/risk/bulletins/sleepapnea.asp, 2002: 17:39.

Buckle, Patricia et al., Polysomnography in Acutely Ill Intensive Care Unit Patients, Chest, v. 102 n.1, p. 288 (4), American College of Chest Physicians, Jul. 1992.

Centiva/5 Critical Care Ventilator, Brochure, GE Healthcare, pp. 8, Oct. 2005.

Chi, Time-Series Matrices, University of Minnesota, http://www-users.cs.umn.edu/-echi/papers/infovis97/spread/node13.html, 1997, pp. 1-3.

Critical Care Therapy and Respiratory Care Section Policy, National Institute of Health, pp. 7, revised Mar. 2000.

Daley, Denise M., MD, Beware of All Sedatives in Patients With Sleep Apnea, Anesthesia Patient Safety Foundation Newsletter and posted on the Malpractice company's web site. The Doctors Company, Sleep Apnea and Narcotic Postoperative Pain . . . http://www.thedoctors.com/risk/bulletins/sleepapnea.asp, Letters to the Editor 2002-2003.

Datex-Phmeda Output Protocols Ohmeda Corn 1.0 Serial Protocol, Brochure, Datex-Ohmeda, Version 1.5, pp. 31. Aug. 14, 2001.

Dempsey, Jerome A. et al., Sleep and Breathing State of the Art Review Sleep-Induced Breathing Instability, Sleep, vol. 19, No. 3, pp. 236-247, American Sleep Disorders Association and Sleep Research Society, 1996.

Ferber, Richard et al., Portable Recording in the Assessment of Obstructive Sleep Apnea, ASDA Standards of Practice, American Sleep Disorders Association, vol. 17, No. 4, pp. 378-392, 1610 14th Street, NW, Suite 300, Rochester, MN 55901-2200, USA, 1994.

Fisher, Kyle S., MD, Value of Pulse Oximetry Monitoring on the Ward is Questioned, Anesthesia Patient Safety Foundation Newsletter and posted on the Malpractice company's web site. The Doctors Company I Sleep Apnea and Narcotic Postoperative Pain . . . http://www.thedoctors.com/risk/bulletins/sleepapnea.asp, Fall 2002.

Henderson, L. J. et al., Blood as a Physicochemical System. II, pp. 426-431, Paper, 1924.

Jain, Sanjay S. et al., Perioperative Treatment of Patients with Obstructive Sleep Apnea, Current Opinion Pulmonary Medicine 10, pp. 482-488, 2004.

Kaplan, Joseph et al., Home Pulse Oximetry As a Screening Test for Sleep-Disordered Breathing, Chest, vol. 103, pp. 322S, Northbrook, IL, USA, 1993.

Lynn, Lawrence, Background of Oximetry Utilization for Sleep Apnea Diagnosis, Publication information unknown, Article Written 1994, Not published.

Lynn, Lawrence A. et al., History of Threshold Oximetry, First viewing of Article Apr. 11, 2009, not published.

Lynn, Lawrence A. et al., Piercing the Panacea of Pulse Oximetry, Article Written Jul. 24, 2006, 8 pages, Not published.

Lynn, Lawrence, The Physiologic Parameters Defining the Oximetry Waveform Patterns in Sleep Apnea, Article Written 1994, Not published.

Lynn, Lawrence et al., Patterns of Unexpected In-Hospital Deaths: A Root Cause Analysis, Patient Safety in Surgery, vol. 5, No. 3, pp. 1-25, Feb. 11, 2011.

Final Official Action for U.S. Appl. No. 12/629,407, dated Jul. 17, 2013 14 pages.

Final Office Action for U.S. Appl. No. 13/603,659, dated Sep. 25, 2013, 8 pages, English.

Non-Final Official Action for U.S. Appl. No. 11/369,355, dated Sep. 17, 2013 8 pages, English.

Patil, Ramesh S. et al., Application of an Artificial Intelligence Program to Therapy of High Risk Surgical Patients, New Horizons, vol. 4, No. 4, pp. 541-550, 1996.

Redline, Susan et al., Hypopnea, a Floating Metric: Implications for Prevalence, Morbidity Estimates, and Case Finding, Sleep, vol. 20, No. 12, pp. 1209-1217, 1997.

Ruchala, Joanna B., Chapter 13, Applications of Pulse Oximetry, Book: Design of Pulse Oximeters, pp. 214-236, Oct. 1997.

Sadeh, Avi et al., The Role of Actigraphy in the Evaluation of Sleep Disorders, An American Sleep Disorders Association and Sleep Research Society, Sleep, vol. 18, No. 4, pp. 288-302, 1995.

Scharf, Steven M. et al., Cardiovascular Effects of Periodic Occlusions of the Upper Airways in Dogs, American Review of Respiratory Disease, pp. 321-329, Aug. 1992.

Shneerson J, Obstructive Sleep Apnoea, BMJ, pp. 315-367 (Aug. 9, 1997); http://bmLcom/Shneerson et al. (7104).

Siggaard-Anderson, O et al., Editorial: The Bohr Effect and the Haldane Effect, Publication information unknown, 1973.

Strohl, Kingman P. et al., Physiologic Basis of Therapy for Sleep Apnea, State of Art: Physiologic Basis of Therapy for Sleep Apnea, pp. 791-802, 1986.

Tatevossian, Raymond G. et al. Noninvasive Hemodynamic Monitoring for Early Warning of Adult Respiratory Distress Syndrome in Trama Patients, Journal of Critical Care, vol. 15, No. 4 (December), 2000, pp. 151-159.

Thorpy, Michael et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377, 1994.

Wilkins, Robert L. et al., Egan's Fundamentals of Respiratory Care, Analysis and Monitoring of Gas Exchange, Book, Eighth Edition, Chapter 16, Section III, Capnography/Capnometry During Mechanical Ventilation, pp. 383-389, 2003.

Williams et al., Screening for Sleep Apnea Using Pulse Oximetry and a Clinical Score, Chest, 100/3, Sep. 1991, pp. 631-635.

Apostolopoulou, Eleni et al, Infection Probability Score, Apache II and Karnofsky scoring systems as predictors of bloodstream infection onset in hematology-oncology patients, BMC Infectious Diseases, 2010, vol. 10, No. 135, 8 pages.

Bland, Rd et al., Probability of Survival As a Prognostic and Severity of Illness Score in Critically Ill Surgical Patients, Crit Care Med., Feb. 1985, pp. 91-5, vol. 13, No. 2 (Abstract).

Burykin, Anton et al., Toward optimal display of physiologic status in critical care: I. Recreating bedside displays from archived physiologic data, Journal of Critical Care, 2010 (Article in Press), 9 pages.

Cavallazzi, Md, Rodrigo, Is the Band Count Useful in the Diagnosis of Infection? An Accuracy Study in Critically Ill Patients, Journal of Intensive Care Medicine, 2010, 5 pages.

Finlay, Heather et al., Designing and Testing a Computer-Based Screening System for Transfusion-Related Acute Lung Injury, Am J Clin Pathol, 2005, vol. 124, pp. 601-609.

(56) References Cited

OTHER PUBLICATIONS

Herasevich, Vitaly et al., Designing and testing computer based screening engine for severe sepsis/septic shock, AMIA Annu Symp Proc. Nov. 2008 (Abstract).
Herasevich, Vitaly et al., Enrollment into a time sensitive clinical study in the critical care setting: results from computerized septic shock sniffer implementation, J Am Med Inform Assoc, 2011, vol. 18, pp. 639-644.
Herasevich, Vitaly et al., Limiting ventilator-induced lung injury through individual electronic medical record surveillance, Crit Care Med, 2011, vol. 39, No. 1, pp. 34-39.
Herasevich, Vitaly et al., Validation of an electronic surveillance system for acute lung injury, Intensive Care Med., Jun. 2009, vol. 35, No. 6, pp. 118-1023.
Lu, K, et al., A Mathematical Program to Predict Survival and to Support Initial Therapeutic Decisions for Trauma Patients With Long-Bone and Pelvic Fractures, Injury, Mar. 2007, pp. 318-28.
Mackenzie, I.M.J., The Haemodynamics of Human Septic Shock, Anaesthesia, 2001, vol. 56, pp. 130-144.
Maclean, Lloyd et al., Patterns of Septic Shock in Man—A Detailed Study of 56 Patients, Annals of Surgery, Oct. 1967, vol. 166, No. 4, pp. 543-558.
Marik, Paul et al., The definition of septic shock: implications for treatment, Critical Care and Resuscitation, Mar. 2007, vol. 9, No. 1, Mar. 2007, pp. 101-103.
Marik, Paul, Surviving sepsis: going beyond the guidelines, Annals of Intensive Care, Jun. 7, 2011, 1:17, 6 pages.
Opal, Steven, The Uncertain Value of the Definition for SIRS, Editorial downloaded from www.journal.publications.chestnet.org/ on Nov. 19, 2013, pp. 1442-1443.
Peres Bota, Daliana et al., Infection Probability Score (IPS): A method to help asses the probability of infection in critically ill patients, Crit Care Med, 2003, vol. 31, No. 11, pp. 2579-2584.
Rangel-Frausto Md, M. Sigfrido, The Natural History of the Systemic Inflammatory Response Syndrome (SIRS), JAMA, Jan. 11, 1995, vol. 273, No. 2, pp. 117-123.
Rivers, Emanuel et al., Early Goal-Directed Therapy in the Treatment of Severe Sepsis and Septic Shock, The New England Journal of Medicine, Nov. 8, 2001, vol. 345, No. 19, pp. 1368-1377.
Shoemaker, Wc et al., Hemodynamic and Oxygen Transport Monitoring to Titrate Therapy in Septic Shock, New Horiz., Feb. 1993, pp. 145-59, vol. 1, No. 1 (Abstract).
Shoemaker, Wc et al., Invasive and Noninvasive Haemodynamic Monitoring of Acutely Ill Sepsis and Septic Shock Patients in the Emergency Department, Eur J Emerg Med, Sep. 2000, pp. 169-75, vol. 7, No. 3.
Shoemaker, Wc et al., Pathophysiology of Adult Respiratory Distress Syndrome After Sepsis and Surgical Operations, Crit Care Med., Mar. 1985, pp. 166-72, vol. 13, No. 3 (Abstract).
Shoemaker, Wc et al., Role of Oxygen Debt in the Development of Organ Failure Sepsis, and Death in High-Risk Surgical Patients, Chest, Jul. 1992, pp. 208-215, vol. 102, No. 1.
Shoemaker, Wc et al., Sequence of Physiologic Patterns in Surgical Septic Shock, Crit Care Med, Dec. 1993, pp. 1876-89, vol. 21, No. 12.
Shoemaker, Wc et al., Use of Sequential Physiologic Measurements for Evaluation and Therapy of Uncomplicated Septic Shock, Surgery, Gynecology & Obstetrics, Aug. 1970, pp. 245-254.
Shoemaker, Wc, Cardiorespiratory Patterns in Complicated and Uncomplicated Septic Shock: Physiologic Alterations and Their Therapeutic Implications, Ann. Surg., Jul. 1971, pp. 119-125, vol. 174, No. 1.
Shoemaker, Wc, Circulatory Mechanisms of Shock and Their Mediators, Crit Care Med., Aug. 1987, pp. 787-94, vol. 15, No. 8 (Abstract).
Shoemaker, Wc, Temporal Hemodynamic and Oxygen Transport Patterns in Medical Patients, Chest, Nov. 1993, pp. 1529-1536, vol. 104, No. 5.
Shoemaker, Wc, Temporal Physiologic Patterns of Shock and Circulatory Dysfunction Based on Early Descriptions by Invasive and Noninvasive Monitoring, New Horiz., May 1996, pp. 300-18, vol. 4, No. 2 (Abstract).
Shoemaker, William et al., Role of Physiologic Monitoring in the Intensive Care Unit, Surgery Annual, 1970, pp. 61-81.
Shoemaker, William, Pathophysiologic Basis of Therapy for Shock and Trauma Syndromes: Use of Sequential Cardiorespiratory Measurements to Describe Natural Histories and Evaluate Possible Mechanisms, Seminars in Drug Treatment, Winter 1973, vol. 3, No. 3, pp. 211-229.
Shoemaker, William, Physiologic Mechanisms in Clinical Shock, Adv Exp Med Biol, Oct. 23, 1971, pp. 57-75.
Shoemaker, William, Sequential Hemodynamic Patterns in Various Causes of Shock, Surgery, Gynecology & Obstetrics, Mar. 1971, pp. 411-423.
Simmons, Daniel et al., Hyperventilation and Respiratory Alkalosis as Signs of Gram-Negative Bacteremia, JAMA, Dec. 31, 1960, vol. 174, No. 18, pp. 2196-2199.
Simmons, Richard, The Role of Central Nervous System in Septic Shock, Annals of Surgery, Feb. 1968, vol. 167, No. 2, pp. 158-167.
Sun, Dong et al., The Natural History of the Systemic Inflammatory Response Syndrome and the Evaluation of SIRS Criteria as a Predictor of Severity in Patients Hospitalized through Emergency Services, 1999, vol. 48, No. 1; pp. 28-37.
Velmahos, George et al., Endpoints of Resuscitation of Critically Injured Patients: Normal or Supranormal?, Annals of Surgery, 2000, pp. 409-418, vol. 232, No. 3.
Herasevich et al., Designing and testing computer based screening engine for severe sepsis/septic shock, AMIA 2008 Symposium Proceedings, p. 864.
Herasevich et al., Enrollment into a time sensitive clinical study in the critical care setting: results from computerized septic shock sniffer implementation, J Am Med Inform Assoc. 2011, vol. 18, pp. 639-644.
Fawcett, Tom, ROC Graphs: Notes and Practical Considerations for Data Mining Researchers, Hewlett-Packard Company, 2003, 28 pages.
Guven et al., Diagnostic Value of Procalcitonin Levels as an Early Indicator of Sepsis, Am JEmerg Med, 2002m pp. 202-206, vol. 20
Haumptman et al., Evaluation of the Sensitivity and Specificity of Diagnostic Criteria for Sepsis in Dogs, Veterinary Surgery, 1997, pp. 393-379, vol. 26.
International Search Report for International (PCT) Patent Application No. PCT/US2012/065124, dated July 23, 2015, 6 pages.
Rao, Singiresu, Engineering Optimization Theory: Advantages of Random Search Methods, 2009, pp. 314-317.
PCT—International Preliminary Report on Patentability, for PCT application No. PCT/US2014/019530; dated Sep. 1, 2015; 8 Pages.
PCT—International Preliminary Report on Patentability, for PCT application No. PCT/US2014/019556; dated Sep. 1, 2015; 9 Pages.
PCT—International Preliminary Report on Patentability, for PCT application No. PCT/US2014/019572; dated Sep. 1, 2015; 6 Pages.
PCT—International Preliminary Report on Patentability, for PCT application No. PCT/US2014/019577; dated Sep. 1, 2015; 8 Pages.
PCT—International Preliminary Report on Patentability, for PCT application No. PCT/US2014/019637; dated Sep. 1, 2015; 8 Pages.
PCT—International Preliminary Report on Patentability, for PCT application No. PCT/US2014/019442; dated Sep. 1, 2015; 6 Pages.
PCT—International Preliminary Report on Patentability, for PCT application No. PCT/US2014/019582; dated Sep. 1, 2015; 7 Pages.
PCT—International Preliminary Report on Patentability, for PCT application No. PCT/US2014/019587; dated Sep. 1, 2015; 6 Pages.
PCT—International Preliminary Report on Patentability, for PCT application No. PCT/US2014/019625; dated Sep. 1, 2015; 15 Pages.
Non-Final Office Action issued in U.S. Appl. No. 12/629,407, dated Oct. 2, 2015, 19 Pages.
Stenhouse C, Coates S, Tivey M, Allsop P, Parker T. Prospective evaluation of a Modified Early Warning Score to aid earlier detection of patients developing critical illness on a general surgical ward. State of the Art Meeting, Intensive Care Society, London, Dec. 1999.

(56) References Cited

OTHER PUBLICATIONS

Non-Final Office Action for U.S. Appl. No. 13/392,827, dated Mar. 27, 2015, 18 pages.
Non-Final Office Action for U.S. Appl. No. 13/677,295, dated Apr. 8, 2015, 15 pages.
Non-Final Office Action for U.S. Appl. No. 13/844,381, dated Apr. 9, 2015, 21 pages.
Non-Final Office Action for U.S. Appl. No. 13/844,404, dated Apr. 9, 2015, 18 pages.
Non-Final Office Action for U.S. Appl. No. 13/843,481, dated Apr. 9, 2015, 19 pages.
Final Office Action for U.S. Appl. No. 12/437,385, dated May 14, 2015, 31 pages.
Non-Final Office Action for U.S. Appl. No. 12/777,171, dated Mar. 5, 2015, 12 pages.
Non-Final Office Action for U.S. Appl. No. 14/193,757, dated May 8, 2015, 15 pages.
Non-Final Office Action for U.S. Appl. No. 14/193,829, dated May 22, 2015, 17 pages.
Graham, et al., "Monitor Alarm Fatigue: Standardzing Use of Physiological Monitors and Decreasing Nuisance Alarms," American Journal of Critical Care, Jan. 2010, vol. 19, No. 1, pp. 28-35.
Claise, Brian, "Alarm Fatigue and Its Management Have Become Serious Healthcare Safety Issues," Critical response Systems, Inc., 2011-2014, Document 14-077, Version 1.1, pp. 1-4.
Sendelbach, et al., "Alarm Fatigue—A Patient Safety Concern," AACN Advanced Critical Care, vol. 24, No. 4, pp. 378-386.
Dec. 20, 2016 (US) Final Office Action—U.S. Appl. No. 14/528,645.
May 12, 2016 (US) Final Office Action—U.S. Appl. No. 12/629,407.
Richard J. Allen and Timothy C. Elston; "From Physics to Pharmacology?"; Department of Pharmacology, University of North Carolina at Chapel Hill, Chapel Hill, NC, US; Reports on Progress on Physics; Institute of Physics Publishing; vol. 74, No. 1; Dec. 3, 2010; pp. 1-19; stacks.iop.org/RoPP/74/016601.
Sergey M. Zuev, et al.; "Sepsis Progression and Outcome: A Dynamical Model"; Theoretical Biology and Medical Modelling, Biomed Central, Ltd.; London, GB; vol. 3, No. 1; Feb. 15, 2006; pp. 1-15; http://tbiomed.com/content/3/1/8.

\* cited by examiner

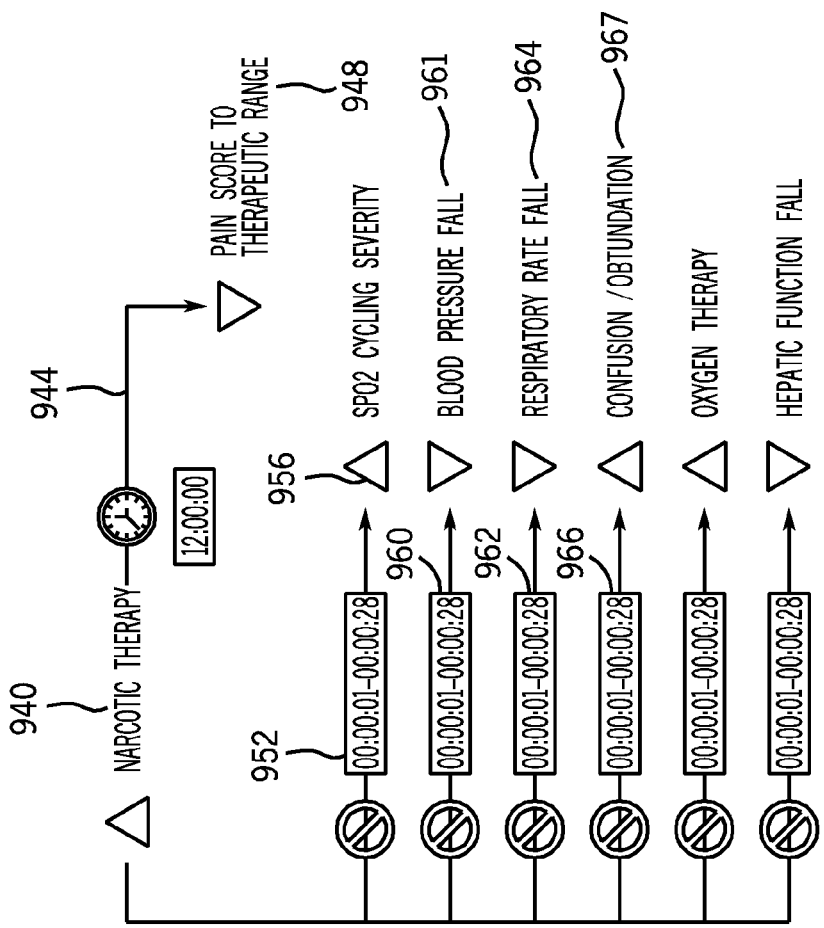
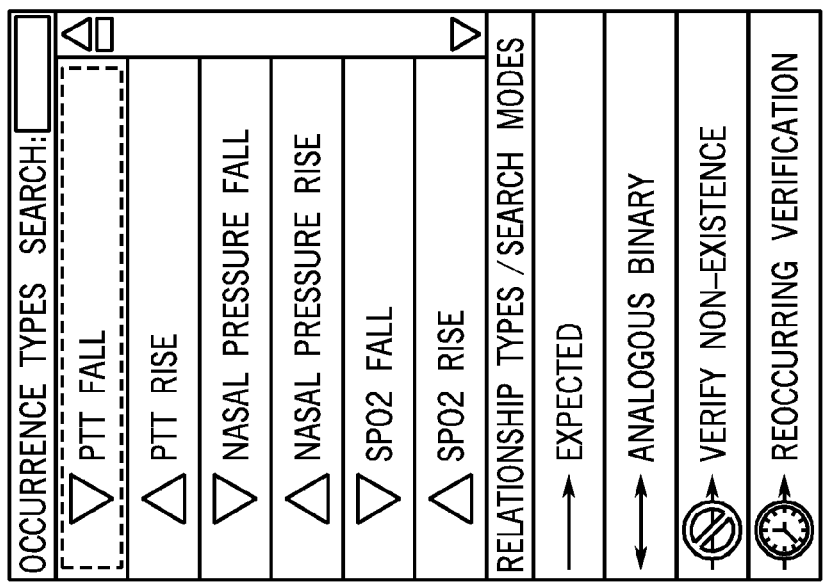
FIG. 13

PATIENT SAFETY PROCESSOR

CROSS-REFERENCE TO RELATED APPLICATIONS

This application is a continuation of U.S. patent application Ser. No. 12/437,417 filed May 7, 2009, which claims the benefit of U.S. Provisional Application No. 61/126,906, filed May 8, 2008 and this application also claims the benefit of U.S. Provisional Application No. 61/200,162, filed Nov. 25, 2008, the disclosures of which are hereby incorporated by reference in their entirety for all purposes. This application is a continuation-in-part of U.S. patent application Ser. No. 12/437,385 filed May 7, 2009 entitled "Medical Failure Pattern Search Engine" the disclosure of which is hereby incorporated by reference in its entirety for all purposes. This application is also a continuation in part of U.S. patent application Ser. No. 12/629,407 entitled "Microprocessor System for the Analysis of Physiologic and Financial Datasets," filed Dec. 2, 2009 which is a continuation of U.S. patent application Ser. No. 10/150,842, entitled "Microprocessor System for the Analysis of Physiologic and Financial Datasets," filed May 17, 2002, now U.S. Pat. No. 7,758,503, the disclosure of which is hereby incorporated by reference in its entirety for all purposes, which claims the benefit of U.S. Provisional Application Ser. No. 60/291,687 filed May 17, 2001, the contents of which are hereby incorporated herein by reference and U.S. Provisional Application Ser. No. 60/291,691, filed on May 17, 2001. This application is also a continuation in part of U.S. patent application Ser. No. 11/369,355, entitled "Centralized hospital monitoring system for automatically detecting upper airway instability and for preventing and aborting adverse drug reactions", filed Mar. 7, 2006, which is a continuation of U.S. patent application Ser. No. 10/150,582 entitled "Centralized hospital monitoring system for automatically detecting upper airway instability and for preventing and aborting adverse drug reactions," filed May 17, 2002 now U.S. Pat. No. 7,081,095, which claims the benefit of U.S. Provisional Patent Application Ser. Nos. 60/291,691 and 60/291,687, both filed May 17, 2001 and U.S. Provisional Patent Application Ser. No. 60/295,484 filed Jun. 1, 2001, the disclosures and contents of which are incorporated by reference as if completely disclosed herein. This application is also a continuation-in-part and claims priority to U.S. patent application Ser. No. 12/152,747 entitled "Pulse Oximetry Relational Alarm System for Early Recognition of Instability and Catastrophic Occurrences," filed May 16, 2008, the disclosure of which is hereby incorporated by reference in its entirety and for all purposes.

BACKGROUND

The present disclosure relates systems and methods for detecting and monitoring patient conditions in clinical medicine settings.

Patient care in a hospital setting involves a complex management process because healthcare workers address multiple patient issues simultaneously. Decisions about patient priority and care made by the healthcare workers are subjective to some degree and may vary depending on the level of expertise and experience of each person involved in patient care. In addition, patients' complaints and symptoms are often complex, because a disease process may have its own associated complications, and a disease may also affect other concurrent patient conditions. Patients may also bring with them a degree of subjectivity in describing their symptoms, which may generate both variable indications of clinical conditions.

Uncontrolled complexity is a cause of large numbers unnecessary death in hospitals. Unfortunately hundreds of common but subtle modes of failure which lead to complications and death can potentially occur with every patient in the hospital. However, present hospital patient monitoring devices are entirely insufficient relative this level of complexity. There is an acute need for a quantum advance in patient data processing which is capable of managing the actual pathophysiologic complexity present. Without such technology vast numbers of unnecessary deaths can be expected to continue in hospitals, unabated and worldwide.

One common example of the challenges involved in detecting complex patient conditions, is undetected septic shock. Whether or not a given patient with an infection progresses to shock often depends on a complex relationship of patient-specific physiologic responses to immunologic and inflammatory perturbation as well as the physiologic state of the patient at the onset and during the perturbation and the timeliness and adequacy of intervention (e.g. antibiotics and/or fluid). These factors interact to define the dynamic state of the patient. This level of complexity, evolving as a "silent" mechanism of death on a busy hospital ward, represents a major threat to patients worldwide.

BRIEF DESCRIPTION OF THE DRAWINGS

Advantages of the present disclosure may become apparent upon reading the following detailed description and upon reference to the drawings in which:

FIG. 13 is a third view of the user interface model of the convergence editor specifically depicting a binary diagram within the convergence editor that pertains to the monitoring narcotic therapy;

DETAILED DESCRIPTION

Figure 1:
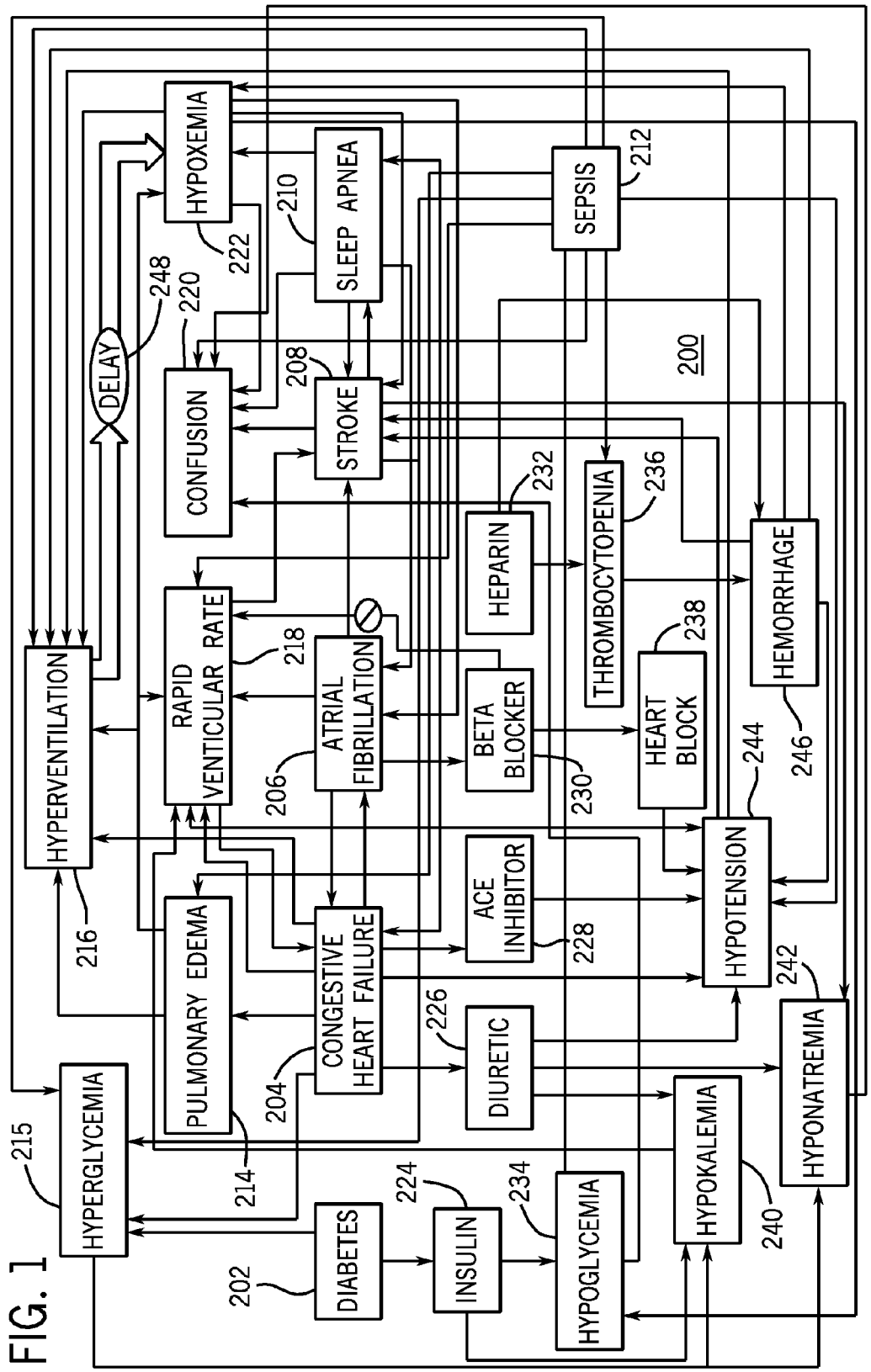
FIG. 1 is an example of a component diagram of a patient demonstrating the overlapping patient complexities that may be used to construct relational binaries and images for detection.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure provides systems and methods for diagnosis, monitoring, and treatment of certain clinical conditions. A processor-based system may characterize and quantify patient physiological conditions by analyzing data relating the patient. In one embodiment, a database of is converted into a format which is favorable for searching and/or analysis of complex relational patterns of trends and variations. One such format is a time series matrix which itself may be formatted to generate an image or moving image of the abnormal components of the time-series matrix that may be further processed into operator-interpretable data.

In one embodiment the time-series matrix constructed by the processor may include a plurality of (e.g., hundreds or thousands) of individual time-series each including different chemical, electrical, mechanical, and/or state related parametric and/or non-parametric values of an individual patient. In one embodiment, data derived from the patient is organized into a comprehensive set of time series each aligned along a single time axis. Each individual time series is two-dimensional with one dimension being time but there are no other limits on second dimensions so that the matrix may have thousands of other dimensions in addition its unifying time dimension. For example the dimensions may include derivatives and frequency measures or calculations of values, calculated or measured relationship between a pluralities of values, time relationships between a plurality of values to name a few. In a few more examples, the dimensions may be further defined by a instantaneous magnitude value, a moving window derived averaged magnitude value, an instantaneous slope of any of the measured or calculated values, and moving window average of the slope of any of the measured values, an acceleration value or area related value, a peak or nadir value, a difference value, a recovery value, a threshold breach, a threshold approximation, a statistical parameter or value, a derivative value, a trend value, frequency domain derived value, to name a few.

One embodiment provides visibility into the complete matrix of patient data by direct search of a hospital's global and/or centralized medical records which may be automatic on a scheduled regular basis, continuous, triggered, or manual basis. Direct search allows rapid access to information relevant to the time and relationships involved complex failure cascade images or other patterns searched for, including outputting an identification of the patient exhibiting the image. The output can comprise a display located at the nurses station or another location and can include direct notification of the patient (as through a pager or phone attached to the patient, nurse or physician (which may be is capable of presenting the image for review). The detection therefore can occur at the central database repository at a central location for the hospital, hospital system, a region, or the entire world, with the provision of direct notification to the hospital, the caregiver, or the patient him or herself.

In one embodiment, for manual searching and/or for preparing the automatic search process a health worker or researcher is presented with a single search box in which the name of a condition, pattern or other occurrence can be entered. The health worker or researcher can then direct the patient safety processor to execute the search. Search results are presented in a paged display allowing for rapid scan. With each "hit" is presented a link to navigate into a screen of data time-relevant to the "hit" and data relevant to the occurrences that constitute the hit. This may include time series displays, occurrence stream displays, patient data, data with regard to the definition of the occurrence and/or constituent occurrences to name a few. A few of the characteristics of the search which can be used to narrow the view of the condition, pattern or other occurrence are listed below. The processor may be programmed to navigate the search using these characteristics. These will be discussed in more detail in the subsequent disclosure.

Time relevance—the understanding of the relationships within the specified occurrence provides the information to display a series of time spans based on the overall evolution of the occurrence within the organism. One embodiment of the patient safety processor search provides rapid switch between these time horizons to provide both a macro and micro-view of the evolving pattern Data relevance—using the definition of the specified occurrence one embodiment of the patient safety processor search system may display the channels of data relevant to the occurrence. These channels of data include channels in which related occurrence appear and also channels in which occurrences do not appear that would be expected. The relevant data set is closely related to the time relevance and therefore is coordinated with the time relevant horizons.

Statistical relevance—One embodiment, using the statistical information, gathered, for example, from local sources and optionally from centralized image data, the statistical relevance of the occurrence may be provided. If the data is real-time data then probable paths of evolution may be presented as well as alternative channels of data that can be executed to further identify the occurrence in question.

Meta-relevance—combining the statistical information with the meta-system of all possible patterns/images the patient safety processor may indicate alternative interpretations of the data, candidate occurrences as well as "what-if" scenarios in which the health worker or researcher indicates certain data points (lab results, etc.) as suspect or provides "best guesses" on missing data.

The health worker or researcher may include filters in the search—such as time horizons, patient populations, geographic locations or occurrence categories to name a few. Occurrence topologies may be created to assist in the filtering. These filters may be pre-defined to provide typical focus areas or may be defined by the health care worker. Advanced Boolean combinations may be provided as well as simpler mechanisms.

Search results may be aggregated by specific levels of granularity (e.g. patient, patient stay, geographical location to name a few). If data is aggregated then the health-care, once a "hit" has been selected, can choose a single occurrence from the aggregation or can choose to see a multi-occurrence display (e.g. within a patient stay).

Further, an aggregation may be selected and then searched within. In this way the health-care worker can iteratively narrow her search until a specific occurrence or occurrence group is selected for display.

The health worker may navigate out of an occurrence or occurrence group display back into the search results. Search or simple time/data selection may provide entry, into the matrix. Once the matrix has been entered the processor display may center (if desired) on a particular occurrence. The relationships maintained within the processor for this occurrence may provide a wide range of navigation. The health care worker may choose to navigate down into the constituent elements of the occurrence. At each level, the display may be configured to the desired relevance. The health care worker is thereby provided with one alternative mechanism of essentially "zooming in" on a particular aspect of the image. The health care worker may also choose to "zoom out" by navigating up to an occurrence (or occurrences) to which the current occurrence is a constituent part. In an example detected fall event in bicarbonate may comprise the occurrence from which manual or automatic navigation zooms out to view an entire sepsis cascade of which it is a part. The higher view may show a high-level image evolution. Lateral movement may occur not only by simple panning (e.g. sliding forward/backward in time) but also by navigating to the next similar occurrence or the next stage of image evolution within the current occurrence. Navigation may also be through the meta-data. This allows the health worker to navigate to similar images to the ones that actually have been identified. These images can be super-imposed for comparison. For example, the health care worker may request to see images that are statistically known to be in the evolution path of the current image. By navigating to expected (but not yet realized) evolution paths the health care worker can anticipate the development of perturbation and see expected reactions to treatment.

Further, within an occurrence or occurrence group display the health care worker or researcher will be presented with opportunities to search based on elements within the display. For example, if an image contains a specific event, the health-care worker may search for other occurrences of that event within a timeframe or other search horizon (e.g. related to a specific physician).

The spin-off search may be modified in one or more ways from the element from which the search was constructed. For example, the health care worker may select a threshold violation and indicate search, but allow a slightly higher or lower threshold. Or, as another example, a binary may be selected but the requirement of the time between occurrences may be relaxed.

In effect, search permeates the patient safety processor system allowing for any element or meta-element to become the launch-point for a patient safety processor search. In this context the health worker or researcher can rapidly follow his or her intuition regarding the nature and evolution of a condition of interest allowing the patient safety processor to provide substantially immediate aggregations of data in views relevant to the relationships within the focus data, the overall statistical relationships in the overall available body of research and the intuition of the current health worker. The processor can be programmed to automatically search using one or more (or another type) of narrowing characteristics. For example the processor could be programmed to, upon the detection of a trend rise in ventilation of a given patient, search for other trends, breaches, events, or images in time relevance to the detected rise on and to determine if an image (such as a cascade) or an event (such as a drug infusion or a fall in bicarbonate) is present and where in combination with the rise in ventilation a new image is detected.

The individual time series of the matrix may extend the entire length of the matrix for example as the weight of the patient or ejection fraction of the left ventricle of a patient or may be transient, as for example with a single injection of an IV narcotic or may be intermittent, as with a time series of the peak (recovery) $SPO_2$ values within sleep apnea clusters. In one embodiment the individual time series are linked to each other by processing to convert the raw time series into time series of events (such as objects by the process of objectification) but another method may be used. Linkage by event processing and/or objectification produces a comprehensive (potentially omni-dimensional) objectified matrix of times series of data relating to a patient, extending along a central common time axis with extensive cross-linkages. series that are not time series (for example a series of frequencies of a parameter detected at a single point in time) may also be objectified, but in this case this type of series extends perpendicular to the time axis of the matrix at the time (or window of time) of the occurrence of that series, series which are not time series have the same time designation for the entire series and, like time series, they may be linked with any other time series or other series in the matrix.

In one embodiment events, relational events, and aggregated events are defined to construct images of physiologic failure and care. Identifications of modes of physiologic failure and care by the analysis of the images provides for earlier recognition and intervention and improved protocolization of testing and treatment. A processing network provides for the development of extensive archives of images of physiologic failure and care to provide for processed integration of the international experience into the image recognition protocols to enhance and accelerate real-time physiologic image recognition and to improve the cost effectiveness of testing and treatment including those hospitals in remote and/or less well served communities.

One embodiment includes a real-time processing method for searching for and detecting physiologic occurrences, physiologic failure and/or care having steps of: (1) converting medical records into at least one time series matrix of a particular configuration suitable for imaging (for example the configuration may be a 2 or more dimensional spatial configuration, and/or a 2 or more dimensional temporal configuration, and/or 2 or more dimensional frequency configuration, and/or another configuration suitable for imaging.); (2) imaging the matrix to detect at least one image indicative of physiologic occurrences, physiologic failure, and/or care (which can for example include a sepsis cascade pattern, a sepsis shock pattern, a drug reaction pattern, to name a few); and (3) taking action based on the detection of the image which can for example, include outputting an indication (which can be an alarm) of the image and/or the likely cause of the image.

In one embodiment the time series matrix is processed (and this processing may be provided as part of the construction of the time series matrix to generate and time series matrix of events. In an embodiment these events are objects (such as objects having a relational hierarchy by the process of time-series objectification) thereby rendering an objectified time series matrix. The raw time series matrix and/or the time series matrix of events and/or the objectified time series matrix may be rendered in a particular configuration such as a particular default digital spatial and/or temporal and/or frequency and/or statistical configuration (to name a few), and then digitally imaged and the image characterized by known digital image recognition methods to detect a pattern and/or a plurality of patterns. These image patterns may be defined along the configuration of the matrix by selections of the user, by methods of digital image recognition, by statistical processing, as by neural net processing or by other methods as for example the methods described and/or listed in U.S. patent application Ser. No. 11/351,449 of the present inventors, the entire disclosure of which is hereby incorporated by reference for all purposes as if completely disclosed herein.

One embodiment includes a real-time processing method for detecting physiologic occurrences, physiologic failure and/or care having steps of: (1) converting medical records into at least one time series matrix of a particular configuration suitable for imaging; processing the matrix to render an matrix of time series of events (such as an objectified time series matrix (for example the configuration of the objectified time series matrix may be a 2 or more dimensional spatial configuration, and/or a 2 or more dimensional temporal configuration, and/or 2 or more dimensional frequency configuration, and/or another configuration suitable for imaging.); (2) imaging the time series matrix of events to detect at least one image indicative of physiologic occurrences, physiologic failure, and/or care (which can for example include a sepsis cascade pattern, a sepsis shock pattern, a drug reaction pattern, to name a few); and (3) taking action based on the detection of the image which can for example, include outputting an indication (which can be an alarm) of the image and/or the likely cause of the image. Steps one, two and three, can be combined so that the time series matrix is built and objectified simultaneously or the time series are objectified and/or imaged and then the matrix is built and the matrix is then objectified and/or imaged. A default configuration of the raw time series matrix may be displayed directly with the images detected in raw form along the default configuration (as may be over-read by physicians or nurses). Alternatively, or in combination, another default configuration may be displayed for the user with the matrix presented in a processed (such as objectified) form with the detected images being highlighted or represented or replaced as icons, motion pictures, or other visual images. In another embodiment the detected images are reprocessed to simplify them and these reprocessed images may be digitally imaged to detect larger and more complex images. In this way the images themselves (much like the objects in the matrix) may have an inheritance hierarchy which reduces the complexity of the digital image recognition of the larger, complex and prolonged images.

One embodiment includes a real-time processing method having steps of: (1) converting medical records into a predetermined format for searching, as for example at least one time series matrix; (2) defining events such as objects (which can be relational events) along the time series matrix; (3) defining patterns including combinations of events, (4) using a processing search engine, searching for the events and/or the patterns and detecting at least one complex pattern or image (which can for example include a sepsis cascade pattern, a sepsis shock pattern, a drug reaction pattern, to name a few); and (4) taking action based on the detection which can for example, include outputting an indication (which can be an alarm) of the pattern(s) and/or the likely cause of the patterns.

While an embodiment event identification and processing using objectification of time series matrices presently contemplated there are many alternative processing methods which can be incorporated to define events or occurrences, such as pertubations, trends, variations, or threshold violations, to name a few along the time series and along the time series matrix to be identified by a waveform search engine (such as the imaging processor). For example the time series matrix or the "event, trend, or pertubation processed or formatted" (such as objectified) time series matrix may be rendered in a particular configuration such as a spatial configuration, and then imaged and the image characterized by image recognition methods to detect a pattern. These image patterns may be defined along the configuration of the matrix by statistical processing, as by neural net processing or other methods. Also the events, objects, or and/or images may be processed using a wide range of search engine types and may be incorporated into larger computer search engines.

Events may be defined by a wide range of methods, for example, by objectification, by probabilistic discovery, by neural net processing, by peak and trough detection, adaptively, by objectification, by a specific rules set, or by a single or combination of signal processing and/or characterization methods in the time domain and/or the frequency domain and/or by other methods.

According to one embodiment, provided herein is a processing method and system for characterizing and quantifying complex layered non-linear systems such as physiologic systems, using a matching layered processing architecture, termed an "objectified time series matrix." Although the objectified time series matrix is applicable to a wide range of signal processing environments, in an example, the matrix is applied to organize, control, characterize and quantify substantially all aspects the electronic medical records (EMR) of a patient and is employed as a real-time patient safety processor. Here, the matrix is including hundreds or thousands of parallel and, in some cases, perpendicular series (and of segments of parallel time and perpendicular series) derived from the EMR which are programmatically bonded together in a manner to produce an embodiment which may provide real time programmatic images which organize the complexity of the evolving processes indicative of the global and regional state of health and disease.

In one embodiment such a matrix is including hundreds or thousands of individual time-series each including different chemical, electrical, mechanical, and/or state related parametric and/or non-parametric values of an individual patient. In one embodiment all data derived from the patient is organized into a comprehensive set of time series each aligned along a single time axis. Each individual time series is two-dimensional with one dimension being time but there are no other limits on second dimensions so that the matrix may have thousands of other dimensions in addition its unifying time dimension. For example the dimensions may include derivatives and frequency measures or calculations of values, calculated or measured relationship between a pluralities of values, time relationships between a plurality of values to name a few. In a few more examples, the dimensions may be further defined by a instantaneous magnitude value, a moving window derived averaged magnitude value, an instantaneous slope of any of the measured or calculated values, and moving window average of the slope of any of the measured values, an acceleration value or area related value, a peak or nadir value, a difference value, a recovery value, to name a few. The individual time series of the matrix may extend the entire length of the matrix for example as the weight of the patient or ejection fraction of the left ventricle of a patient or may be transient, as for example with a single injection of a IV narcotic or may be intermittent, as with a time series of the peak (recovery) $SPO_2$ values within sleep apnea clusters. In one embodiment the individual time series are linked to each other by objectification but other methods may also be used. Linkage by objectification produces a comprehensive (potentially omni-dimensional) matrix of times series of data relating to a patient, extending along a central common time axis with extensive cross-linkages. series that are not time series (for example a series of frequencies of a parameter detected at a single point in time) may also be objectified but in this case this type of series extends perpendicular to the time axis of the matrix at the time (or window of time) of the occurrence of that series, series which are not time series have the same time designation for the entire series and, like time series, they may be linked with any other time series or other series in the matrix.

Also provided herein is an objectified time series matrix of patient related signals. A comprehensive matrix derived from a complex patient would appear relatively opaque when viewed with hundreds or even thousands of parallel, objectified time series with various objectified linkages. Provided herein is a processing system and method for imaging the objectified matrix of patient signals to render motion pictures of physiologic failure. According to one embodiment, the construction of a matrix of time series for the organization and analysis of non-linear systems is accomplished by: (1) generating a large set of time-series of data relating to the nonlinear system; (2) converting the datasets into parallel time series; (3) identifying occurrences along and between the time series; (4) aggregating the occurrences into a real-time hierarchal data matrix; and (5) analyzing specific nonlinear processes using the data matrix.

According to one embodiment, the construction of an objectified matrix of time series for the organization and analysis of non-linear systems is accomplished by: (1) generating a large set of time-series of data relating to the nonlinear system; (2) converting the datasets into parallel time series; (3) objectifying the time series; (4) identifying occurrences along and between the objects along the objectified time series; (5) aggregating the occurrences into an image including a real-time hierarchal data matrix of linked objects; and (6) comparing the image to other images and/or to other values or outcomes, or images to determine the significance of the image.

One set of steps applied in building and using a time series matrix of patient related signals to detect physiologic failure includes: (1) conversion of the data set of the electronic medical records into time series sets, (2) linking at least a portion of the series sets; (3) defining controllable micro-domains along and between the series sets; (4) analyzing these micro-domains for occurrences, which may for example be a primary or relational perturbation having a specific primary or relational slope, amplitude, polarity, state, acceleration, frequency, pattern, value, or other characteristic to name a few; (5) aggregating the occurrences rendering at least a programmatic image of the aggregated occurrences; (6) comparing the image to stored images indicative of disease; (7) taking action based on the detected image; and (8) outputting an indication based on the detected image.

In one embodiment all data relating to a given patient are converted into time series, parallel in time but not necessarily all comprehensively covering the complete time span evaluated. The objectified time series matrix is constructed by adding each new occurrence in a manner, which defines an inheritance-based hierarchy of ascending complexity. The objectified matrix is progressively built to transform the electronic medical records into a highly organized data structure from which may be derived real-time motion pictures of physiologic condition, which allows early detection and intervention.

According to one embodiment, a patient safety processor including an objectified time series matrix is provided by: (1) generating a large set of time-series of data of a patient including at least data relating to the physiologic state and/or care of a patient; (2) converting the datasets, including at least the monitored datasets and laboratory datasets into parallel time series; (3) objectifying the parallel time series; (4) converting the objectified time-series into micro-domains; (5) identifying occurrences along and between the micro-domains; (6) aggregating the occurrences into a real-time hierarchal patient safety data matrix for the generation of motion pictures of the organized occurrences; and (7) recognizing and interpreting along the motion pictures, specific pathophysiologic processes or other adverse processes defined by the motion picture.

According to one embodiment, a patient safety processor including an objectified time series matrix is provided by: (1) generating a large set of time-series of data of a patient including at least data relating to the physiologic state and/or care of a patient; (2) converting the datasets, including at least the monitored datasets and laboratory datasets into parallel time series; (3) objectifying the parallel time series; (4) placing the objectified time series into an objectified time series matrix; (5) converting the objectified time-series into micro-domains; identifying occurrences along and between the micro-domains; placing each stream of identified occurrences back into the objectified time series matrix so as to progressively and iteratively increase the objectified time series; analyzing the completed objective time series matrix for the identification of motion pictures of the organized occurrences; and recognizing and interpreting along the motion pictures, specific pathophysiologic processes or other adverse processes defined by the motion picture.

According to one embodiment, a Patient safety processor (patient safety processor) including a time series matrix is provided by: (1) generating a large set of time-series of data of a patient including at least data relating to the physiologic state and/or care of a patient; (2) converting the datasets, including at least the monitored datasets and laboratory datasets into parallel time series; (3) identifying relational patterns along a plurality of time series which is indicative of failure cascade such as, for example, a sepsis cascade, a pulmonary embolism cascade, a metabolic cascade, and a microcirculatory cascade to name a few; (4) identifying occurrences such as, for example, inflammatory occurrences, metabolic occurrences, volumetric occurrences, hemodynamic occurrences, therapy occurrences, hematologic occurrences, respiratory occurrences (to name a few), and the timing of the occurrences which relationally or collectively are indicative of at least one failure cascade such as, for example, a sepsis cascade, a pulmonary embolism cascade, a metabolic cascade; and (5) identifying and outputting an indication of the cascade, the timing and type of the occurrences along the cascade, and length of the cascade.

According to one embodiment, a patient safety processor including an objectified time series matrix is provided by: (1) generating a large set of time-series of data of a patient including at least data relating to the physiologic state and/or care of a patient; (2) converting the datasets, including at least the monitored datasets and laboratory datasets into parallel time series; (3) objectifying the parallel time series; (4) placing the objectified time series into an objectified time series matrix; identifying occurrences such as, for example, inflammatory occurrences, metabolic occurrences, volumetric occurrences, hemodynamic occurrences, therapy occurrences, hematologic occurrences, respiratory occurrences (to name a few), and the timing of the occurrences which relationally or collectively are indicative of at least one failure cascade such as, for example, a sepsis cascade, a pulmonary embolism cascade, a metabolic cascade; (5) identify and output an indication of the cascade, the timing and type of the occurrences along the cascade, and length of the cascade.

According to one embodiment, a patient safety processor may generate a time series matrix for the early detection of septic shock or the pre-septic shock state by: (1) generating a large set of time-series of data of a patient including at least data relating to the physiologic state and/or care of a patient; (2) converting the datasets, including at least the monitored datasets and laboratory datasets into parallel time series; (3) identifying occurrences such as, for example, inflammatory occurrences, metabolic occurrences, volumetric occurrences, hemodynamic occurrences, therapy occurrences, hematologic occurrences, respiratory occurrences (to name a few), and the timing of the occurrences which relationally or collectively are indicative of the septic shock or pre-septic shock failure cascade; (4) identify and output an indication of the septic shock or pre-septic shock failure cascade; (5) identify and output the relational timing of the inflammatory occurrence, the hemodynamic occurrence, and the respiratory occurrence along the cascade; (6) identify and output length of the cascade; and (7) quantify the cascade as the cascade evolves and output a time series of the severity of the cascade.

According to one embodiment, the process of moving from a massive set of time-series data to the recognition of, and interpretation of, a motion picture indicative of a patient's comprehensive state of physiologic failure and treatment includes the isolation, from the global domain of data, individual sets of micro-domains in which the complexity is manageable enough for human researchers and/or software agents directed by human researchers to define and characterize specific properties and relationships (occurrences) along and between the micro-domains which are perceived to be, may be determined to be (and/or are statistically verified to be) associated with clinical conditions. The Patient Safety matrix is then built by combining the occurrences. This process of matrix building from different micro domains is repeated over and over to build an extensive matrix which is including occurrences ordered into relational timed images having an inheritance based hierarchy. The motion picture is a timed aggregation of those images from the matrix. The motion pictures range from isolated adverse occurrences to simple physiologic failures and finally to catastrophic pathophysiologic cascades. The global "motion picture" output of the patient safety processor is a comprehensive flow of the detected images in combination as they evolve.

One embodiment of the present techniques provides a system and method for the characterization, investigation, and analysis of the complex environment of non linear relational signals (such as physiologic signals) through the repeated and layered use of micro-domains, which, provides a mechanism such that the micro-domains may be modeled by a human researcher with an expert understanding of the physiological and systemic relationships to render detected images which are added to the objectified matrix. One embodiment provides a mechanism by which both the scope and the variables available within the micro-domains that exist within a set of physiological signals may be identified, modeled, analyzed, characterized, compared and statistically investigated. In this embodiment, the process follows four basic steps: (1) Establish the type and scope of a candidate micro-domain; (2) Calculate and characterize all or various relationships, sub-elements, values, variables, properties within the candidate micro-domain; (3) Refine the scope of the candidate micro-domain given the newly understood relationships, sub-elements, values, variables and properties; and (4) Determine whether the candidate micro-domain meets criteria to be specified as a true occurrence of the micro-domain type considered.

Once micro-domains are established as objects within an object stream, the micro-domains themselves become available to be aggregated to establish scope. In other words, the scope of a micro-domain may be defined as a set of durations (and/or points) along a time series, the aggregation of other micro-domains or the combination of the two. In one embodiment this 4-step process provides symmetry of scale across levels of the analysis by which the patient safety processor uses the same approach of analysis at each level of pre-objectified and objectified data—starting with raw pre-objectified time series and going up.

Alternatively, the data from the objectified time series matrix may be converted into images, such as moving pictures. In one embodiment, data from the electronic medical records and patient monitors are used to generate graphical displays, which may include moving pictures of the patient condition. In an embodiment, such moving pictures, or animated displays, may be referred to as "motion pictures of physiologic condition" (MPPC). Provided herein is a processing system and method for generating real-time MPPC of clinical data. The data and/or images may also be analyzed to detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate the MPPC. In addition, the MPPC may also include a graphical representation of any treatment applied in association with the clinical condition.

Once the image or moving image (i.e. an image that includes more data over time as the patient monitoring progresses) MPPC of the patient condition has been generated, this image may be further processed to create an operator-interpretable indicator to assist in patient diagnosis and/or treatment. For example, the image may be directly compared to a database of similar images taken from patients with clinically confirmed diagnoses. The database image or composite of multiple images with the greatest similarity to the generated image may indicate the correct diagnosis for the patient. For example, if the generated moving image, particularly as the image progresses over time, has the greatest similarity to a database image indicating, for example, ""septic shock cascade", "inflammation failure", "pulmonary thromboembolic cascade", "hemorrhagic failure cascade" to name a few, a processor may generate a text or other indicator to a healthcare provider indicating such a diagnosis. The processor may also indicate that additional tests should be ordered to confirm the diagnosis. The processor may also indicate and/or provide orders for specific treatments in light of the diagnosis. In an embodiment, a moving image may be indicative of two or more clinical conditions. The processor may indicate tests that may rule out one or more of such conditions. In addition, over time, one condition may be determined by the processor to be more likely while additional time-series data may also rule out another condition.

These database images may be formed from retrospective clinical data. In an embodiment, the images may be analyzed for similarity by any suitable technique, including image registration. In embodiments, the matches may be made by image similarity measures that include cross-correlation, mutual information, sum of squared intensity differences, and ratio image uniformity. In an embodiment, the individual time-series objects that make up the image may be processed as a group for similarity to other groups of time-series objects associated with a particular diagnosis or clinical condition. The Motion Picture of Physiologic Condition (MPPC) may, for example, include abnormal and/or perturbed components and in particular "Motion Pictures of Physiologic Failure" (MPPF) of the physiologic system and of exogenous forces relating to that system. Provided herein is a processing system and method for generating real-time MPPCs of healthcare signals and processing those images to timely detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate and then recognize motion pictures of physiologic failures and of the treatment applied in association with the failures.

Also provided herein is a processor and processing method for the automatic generation and/or analysis of the images of physiologic and/or clinical condition and the characterization and aggregation of the image components of complex dynamic systems, such as physiologic systems and medical care systems. The processing system may generate real-time MPPC of healthcare signals and processing those images to timely detect perturbations, aggregate and cascading perturbations, perturbation relationships, physiologic responses to perturbations, treatments associated with the perturbations, physiologic responses to the treatments, physiologic failures, testing failures, treatment failures, and communication failures to generate and then recognize motion pictures of physiologic failures and of the treatment applied in association with the failures. According to one embodiment, a processor first renders parallel time-series from each of a plurality of sensors and testing sources, which are applied to broadly monitor the dynamic system for failure. In an example, a processor programmed with instructions for time series objectification of patient data detects patterns along the parallel times-series, converts these patterns into time series of discrete objects, then organizes these objects into discrete relational objects (such as binary objects, or relational binaries, derived of relational object pairs). The processor then organizes the relational binaries to render a unifying programmatic image of the physiologic system and the care provided. The processor then automatically recognizes objects in the image components and may be able to perform analysis on the images.

One embodiment may include a patient safety processor having a single processor or a combination of processors programmed to generate time series objects, a relational binaries, moving images, patient safety images, and/or patient safety visualizations. The patient safety processor outputs images of the patient's physiologic system and medical care. In an embodiment, the processor includes processing functions for time series objectification, relational binary processing, and an imaging processing. In an alternative embodiment, the patient safety processor combines multiple processing mechanisms (e.g., time series objectification, relational binary processing, and imaging processing) into a single matrix construction processor.

According to an embodiment, perturbations detected by the processor are converted to image components that may be used to generate a moving image. In an embodiment, an MPPC may be representative of a "motion picture of physiological failure" (MPPF) when a failure image becomes progressively more complete and recognizable by the processor as each additional failure image component is added. One embodiment may involve building a dynamic real-time image of disease, injury, and/or drug reactions, the care provided, and the expense associated with that care. The image is initially associated with initial image components including one or more minor perturbations, which may for example be caused by circulation of one or more toxic, acidic, and/or immunogenic material of endogenous or exogenous origin. At first these perturbations, such as toxins, inflammatory and/or thrombogenic mediators, may induce and/or cause only minor changes in cell permeability, ion flux, or hydrogen ion elevation, and trigger various minor physiologic perturbations and responses each of which may produce an image component. The measurements of various mediators, ions, biologic profiles, as well as standard blood tests, and the outputs of vital sign monitors may begin to vary as a function of these early physiologic perturbations and responses, and it is these variations that enlarge the group of image components from which the larger image is derived. Early in the process, each of these alterations in permeability, cell injury, mediator production, and physiologic perturbations, when considered in isolation, are often minor. However, collectively they may represent the early manifestations of a nascent and evolving moving image of a serious clinical condition.

According to one embodiment, each perturbation is programmatically organized to form an image component of the MPPC. Many of these detected images components may be isolated because they are related to a benign process, and the image may self-extinguish or may not develop into an image associated with a clinical condition involving intervention or an MPPC. Yet, as noted above, others may represent the first image components of an early moving image. Provided herein are systems and methods for the detection of the early image components of an evolving moving image to provide timely detection of physiologic failures before these failure progresses to shock (including, for example, hypovolemic, obstructive, septic, toxic, cardiogenic, hypoxic, and/or hypercarbic shock.) In one embodiment, it is advantageous to detect the early image components of the moving image before shock develops to improve the prognosis for the patient and to apply goal-directed therapy while clinical intervention is still beneficial.

According to one embodiment, a patient safety processor constructs a programmatic MPPC, which is used for dynamic, motion picture responsive, protocolization of care. This motion picture is comprehensive, including not only the events including a single or few parameters such as a the heart rate, but also other parameters that may include, for example: the slope and pattern of the heart rate, the slope and patterns of the systolic pressure variation, the slope and patterns respiration rate, the slope and patterns $SPO_2$, the slope and patterns ventilation-oximetry index, the slope and patterns drug and fluid infusion rate, the slope and patterns blood pressure, the slope and patterns of the Neutrophil count, and the slope and patterns of inflammatory and/or thrombotic markers, and various other blood, urine and/or exhaled gas test to name a few. The signals from all of these sources may be converted to time-series and may, for example, be physiologic signals, therapy signals, laboratory signals, or historical signals, which may be objectified, as by an objectification processor, to produce the discrete programmatic objects (events). According to one embodiment, the processor detects a first discrete event that includes a pattern or value of at least one medical signal, and a second discrete event that includes a second pattern or value of at least one medical signal, the processor then aggregates at least the first event and the second event to produce a first relational object, the processor further detects a third event that includes a pattern or value of at least one medical signal, and a fourth event that includes a second pattern or value of at least one medical signal, the processor then aggregates at least the third event and the fourth event to produce a second relational object. The first relational object and the second relational object are then aggregated to produce a first image component. Additional images are built accordingly and the image components are then aggregated according to the time of occurrence to derive the moving image and care.

In an example, the pulse related components of the typical motion picture of sepsis failure cascade would include occurrences such as early rise in heart rate, rise in pulse amplitude, and rise in slope of the pulse upstroke (as measured at the finger tip) in combination and typically proceeded by a brisk rise in inflammatory markers. In contrast the typical motion picture of occult hemorrhagic failure cascade (as for example due to heparin related retroperitoneal hemorrhage) would include occurrences of an early rise in heart rate, a fall in pulse amplitude, and a fall in slope of the pulse upstroke (as measured at the finger tip) and a rise in the respiratory related pulse pressure variation and a fall in hemoglobin. According to one embodiment, all of these occurrences along the image of an occult hemorrhagic failure cascade can all be derived from a multi wavelength pulse oximeter.

According to an embodiment, a relational binary processor is provided that divides detected variations into discrete alpha events and beta events, which are combined by the relational binary processor to construct the relational events which are termed relational binaries. These relational binaries are aggregated according to timing, frequency, and/or spatial relationship to construct images. These images are then further aggregated according to timing, frequency and/or spatial relationship to construct and progressively build MPPC (from which visual images or electronic representations may be derived as desired). These MPPC are often moving images of catastrophic cascading failures, thereby allowing more reliable detection to allow timely rescue of the patient.

The signals may be chemical or physiologic measurements, as provided by patient monitors, recorded in the electronic medical record, and/or may be biomarkers specifically ordered, either automatically by the processor or manually by the clinician to indicate the potential presence of the sepsis (as those, for example, disclosed in U.S. patent application Ser. Nos. 10/704,899, 11/647,689). The presence and/or concentration of such markers may be presented in the context of the MPPC with the timed positioning relative to the others parameters, which then allows the relevance of the biomarker to be much more readily identified. According to an embodiment, the temporal and relational pattern of inflammatory markers and temporal and relational patterns of contemporaneously measured or associated physiologic parameters are aggregated to produce a progressively enlarging MPPC of an evolving patient condition.

Therefore, to achieve the detection of various pre-shock states as well as earlier detection of failures, one embodiment detects early variations and aggregates them to provide an MPPC to dynamically present expanding failure cascades of pre-shock and shock states. This allows separation of expanding images from the smaller and less expansive image components having benign characteristics, and further allows separation of the images of minor isolated failures from failures that progress to generate an expanding MPPC heralding the potential for transition to one of the shock states. Each group of images as well as the complete MPPC and care may be analyzed for the purpose of assessing patient care in a hospital, a ward, or under the care of a given healthcare worker.

The occurrence of a large number of images indicating non cascading failures which self extinguish may be indicative of an unstable patient population or poor health care delivery. In the alternative, a large number of cascading failures are indicative of risk of injury. The MPPC and the images may be used to determine if that is due to the patient population or the quality of the care.

One embodiment detects failure cascades along with the determination of the specific fundamental perturbations, or treatments, or lack of treatments that occur early in a failure cascade. Specific fundamental failures are detected before they progresses to complex failures and particularly before they progresses to the pre-shock or shock state. Furthermore, the processor builds an image derived of the relational perturbations and treatments as the cascade expands. According to one embodiment, each time series is processed to separate expected events from unexpected events. The unexpected and/or abnormal events are then aggregated further to repetitively generate relational events, images and finally the MPPC which includes a motion picture of the cascade (if present) as well as the treatment applied in association with the cascade. This MPPC is further processed to allow the detection of the probable cause or causes of the occurrence of the moving failure images well as the images of the MPPC as it evolves thereby allowing detection of the nature and cause of the failure cascade.

As noted above according to one embodiment, an analysis is provided wherein the fundamental components of the analytic process include a basic relational variable that includes a plurality of events. In a contemplated embodiment, the basic relational variable is that includes two events (a relational pair) and this is called a relational binary. In one embodiment, the relational binaries are initially selected by the users as from a menu (or by a drag and drop interface) of relational binaries and/or of events from which the user builds the desired object binaries the binaries are then used as by drag and drop to build the definition of images for detection. This may be performed by, for example, by national or regional expert groups, or by specific departments in a hospital, or by an individual physician to provide custom management. This may also be automatically performed by the processor (as, for example, through the investigation of a large number of historical data sets that have been comprehensively analyzed and categorized according to outcomes. The objectified time series matrix and/or the MPPC may be may be outputted in various interactive, hierarchical, and relational formats for review and automatic or manual adjustment. The MPPC may detect a wide range of failures, such as physiologic failures, treatment occurrence failures indicating the absence of expected treatment in relation to a given perturbation, testing occurrence failures indicating the absence of expected testing in relation to a given perturbation, treatment response failures indicating the absence of the expected correction of perturbation or the occurrence of a new potentially complicating perturbation in relation to a given treatment and/or dose.

The processor combines the complex data of the electronic medical record into a single motion picture of perturbations, treatments, physiologic responses, diagnostic testing, recoveries, diagnoses, missing data, patient locations, and/or other datasets. Dynamic images are generated of relational variations of a set of time series associated with a complex system to generate a real time motion picture of a failure of the system and/or of forces applied to the system. According to one embodiment, the patient safety processor automatically outputs a unified timeline, for example, derived of detected images of a given type. According to another embodiment, the processor, upon detecting a failure cascade, may present and highlight the evolving MPPC in real time on an outputted display of an image diagram for the physician to review. The portion of the motion picture, which has already been completed, may be reviewed backward and forward to review in a single summary snap shot view.

Many physiologic failures such as, for example septic shock, pulmonary embolism, congestive heart failure, respiratory arrest due to narcotics in the presence of sleep apnea, thrombotic thrombocytopenia purpura (TTP), hemorrhage due to anticoagulation, respiratory failure due to bronchospasm, and adult respiratory distress syndrome, but not limited to these clinical conditions, begin with one or two non-specific perturbation(s). Physiologic failure is commonly a relational expansion, often beginning with a fundamental physiologic perturbation at a single focal point in time. In fact, this initial perturbation is often completely masked once the cascade has progressed past a certain point. In such cases, testing or monitoring for the single perturbation may not be useful for making a diagnosis. In many cascading clinical conditions, the first perturbation(s) of the cascade may often only be detected in retrospect after the cascade has further progressed when the first perturbation(s) is no longer present. This provides a basis for optimizing the detection of the first point(s) by real-time imaging of the cascade as it develops and then examining the image to determine the first perturbation(s).

While a pattern of a single time series provides a larger image of a dynamic process than a single value or range, such a pattern is still only a tiny image fragment of the process. The determination of thresholds and even the detection of various patterns of perturbations include incomplete analysis, which will inevitably allow an unacceptable rate of progression to catastrophic failure. Even in situations wherein a measurement or test may seem definitive as a stand-alone test, action or conclusions based on a single value (or an average of a plurality of values) will have a reasonable probability of being incorrect. Consider, for example, a single measured spot $SPO_2$ value of 94. This value is largely meaningless without knowing if the $SPO_2$ is rising, falling, or cycling. Yet this infinitesimal image fragment of a patient's complex physiologic system is used everyday in hospitals to determine care. Furthermore, even if the pattern of the $SPO_2$ is known (for example the $SPO_2$ has been stable at about 94 for at least 12 hours) this is an incomplete image, which is largely useless and, in fact, a potentially misleading piece of information. Without knowing the relational pattern of the minute ventilation during the related time interval of the measured $SPO_2$ pattern, the healthcare worker may be lulled into a false sense of security even as the patient is dying of septic shock or heart failure.

Furthermore, an alarm or interpretive output which is based on a programmatic image of both the patterns of both the $SPO_2$ and the related minute ventilation without additional relational elements of the image, such as, for example, the associated pattern of the white blood cell count, temperature, pulse, blood pressure, microbiologic values, and medications will be incomplete leaving too much synthesis for the healthcare worker. In another example, consider the detection of a pattern of a sustained rise in pulse or respiration rate. Each such pattern represents a tiny fragment of the present physiologic state and each pattern may be benign or alternatively may be an early image component of a much larger dynamic process of failure often associated with an evolving failure cascade. The difference between a benign or pathologic rise in pulse or respiration rate cannot be determined with this tiny image alone and often cannot even be known at the time of the onset of the rise. Therefore a tree diagram protocol with a branch based on a rising pulse or rising respiration rate adds a great degree of programmatic complexity with a high risk that the protocol will precede down the wrong pathway. An incomplete analysis of the physiologic system will often cause the healthcare worker to generate a large amount of investigation, testing, analysis and evaluation that is not necessary and therefore increases the cost of overall care. Further, these false paths of treatment and evaluation may distract the care worker from the determining the actual operative failure modes.

Prior to shock, a patient's physiologic system is perturbed by both disease and treatment. A given treatment provided to correct a perturbation might reduce the perturbation, have no effect on the perturbation, exacerbate the perturbation, cause another perturbation and/or make another perturbation worse or better. To determine which effect a treatment is having and to assure that this determination of treatment effect is complete, it is necessary to collect and, just as importantly, as provided by one embodiment, organize and analyze large amounts of relational data in a timely manner.

Another problem is that, within present hospital systems the healthcare worker is forced to do a great deal of archeology (digging, isolating, identifying, etc.) before synthesis may be effectively completed. For this reason, the synthesis of information by the healthcare worker is often not executed in a manner, which allows immediate searching, filtering, re-analysis, etc. This friction combined with the typical workload of healthcare workers limits the number and range of high-level scenarios, which may be investigated. Also the healthcare worker may, because of lack of available organized data and time, execute decisions without a complete set of synthesized information and worse, may not realize that this is the case.

For these reasons, even with conventional electronic medical record embedded protocols, patients remain subject to a range of failures across a broad range of failure modes based on the complexity of their individual condition and the complexity of the environment facing the care giver. In fact, because failures often overlap, one protocol may reduce the risk of one failure while increasing the risk of another. For example, oxygen given to treat hypoxemia under one protocol may delay the detection of pulmonary embolism by stabilizing the $SPO_2$ and hiding the early signs of impending shock from the healthcare worker.

Because so many confounding and overlapping occurrences can be present, the time series objectification processor, the relational binary processor and imaging processor execute multiple iterations of analysis and refinement. In one embodiment this analysis would begins with a phase one execution in which each processor in order (time series, relational binary, and imaging) operates on the specified set of time series inputs storing the interim analysis results in memory and/or in the patient safety image database. After this has been completed, the patient safety processor may execute phase two preferably in the same order providing each processor with the original time series data as well as the full analysis from the previous phase(s). This second phase may refine the analysis in terms of the first phase analysis. This process may contain as many phases as required for complete refinement of the analysis.

In one embodiment, each phase uses the same definition sets (event definition set, binary definition set, image definition set), but determines which property evaluations, rules and constraints are available per phase. The order of time series is determined to maximize the availability of constraints. If a rule and/or constraint cannot be enforced in the current phase then it is ignored allowing for a relaxed set of rules to be executed and a greater number of objects to be identified. With each subsequent phase additional rules and constraints are applied as they become enforceable until all rules and constraints have been applied and all properties have been calculated, evaluated and assigned.

As an example, if an oximeter supplies a time series for oximetry and motion artifact, the multiphase analysis will allow the rule to reject an event on the existence of motion artifact unless the motion artifact is determined to present a particular density, pattern, frequency, magnitude, and/or have a relationship (as for example occurring at substantially the same time) with an arousal or other event or image. The definition of an arousal (an image) is created in terms of oximetry relational binaries and pulse events. Since the definition of an oximetry event depends on the existence of a higher-level object of which it will be an element, the patient safety processor recognizes that a single-phase approach will be inadequate and sets up a two-phase approach. Within the first phase the times series objectification processor creates oximetry events without the artifact constraint and the relational binary processor and image processor execute with the expanded set of oximetry events. In phase two, the results of phase one are available to the processors and the times series objectification processor may evaluate the complete rule.

If the processor determines that motion artifact of a particular density, pattern, frequency, and/or magnitude exists in relation to the point of time in which an oximetry event would be created the processor may query the phase one analysis for the given time window to determine whether an arousal exists. If an arousal does exist, then the motion artifact may be eliminated as rejecting the event and the analysis may continue as before. If an arousal does not exist, then the oximetry event may be rejected and, as the analysis continues, any higher-level objects that were dependent on the existence of that event will fail to be created. In one example, a micro-arousal (an image) may be defined as occurring when a new onset of motion occurs at a time when motion is not dense and near the end of a desaturation event and wherein the motion is temporally associated with a recovery from the desaturation. In addition the image of the micro-arousal may include a positive reciprocation of the in slope of the ascending portion of the pulse waveform, a positive reciprocation of the heart rate, a positive reciprocation of the pulse amplitude, to name a few events, binaries and/or images which may be included.

In an alternate embodiment, each phase has a specific group of definition sets (event definition set, binary definition set, and image definition set), which are constrained by the inputs of the phase. Within the multiphase approach of analysis the definition of events, relational binaries and images may be defined in terms of a related time series (e.g. an artifact indication stream), a derived/transformed time series (e.g. a time series derived from a calculation from two or more time series) and/or higher-level elements from a previous phase. In an alternative embodiment, post-processing phases are designed to refine resultant analysis. In this embodiment, rules are applied after the analysis to alter elements if they meet certain criteria. The patient safety processor would be supplied with a post-analysis rule set for identifying elements that should be added, altered or deleted. Using the above example, the event definition set used by the time series objectification processor will not include the constraint with reference to the motion artifact. Rather, the post-analysis rule set would include the rule to remove all events if motion artifact is found at the same time and the event is not part of an arousal. The post-processing execution would look for all events that meet this rule and mark them for removal. After all post-processing criteria have been evaluated the patient safety processor would begin the process of analysis alteration. In this embodiment, as well as other embodiments, each object provides the functionality to determine all objects upon which it is dependent down to the event level. In one embodiment, this functionality is accomplished through a recursive database procedure. Once all dependent elements are identified, each will be evaluated as to the action to take. For example, a relational binary will be removed if an event is removed, but a cycling relational binary may or may not be removed with the removal of a single event.

In an alternative embodiment, the construction of the objectified time series matrix is accomplished by a single matrix construction processor consuming two inputs—a set of raw time series and an occurrence definition set. In this embodiment, occurrence definition, including sub-elements of definitions, would contain explicit dependency requirements for construction. Dependencies would be defined in terms of raw time series required, occurrence stream required, and/or the specific sub-elements within the specified time series and/or occurrence streams. Each occurrence definition would include a potential occurrence stream which may be added to the matrix. The matrix construction processor would examine each occurrence definition iteratively and in succession to determine whether the dependencies for the specified occurrence are available for analysis. If all dependencies are available then the matrix construction processor executes the necessary analysis to identify, qualify and completely construct all occurrences associated with the given occurrence definition. The resultant occurrences, if any, are aggregated into an occurrence stream and added into the matrix.

For example, an oxygen rise event may be defined as an occurrence with a dependency only on the existence of a raw oximetry time series. In this case, the matrix construction processor would be free to construct the oxygen rise occurrence stream and place it into the matrix as soon as a raw oximetry time series is added to the matrix. Once the oxygen rise occurrence stream has been placed into the matrix any occurrence definitions that are dependent on the oxygen rise occurrence (for example the oxygen reciprocation occurrence) may become available for construction. To provide additional flexibility within this embodiment, construction may be broken into the 4 stages described above: (1) type and Scope establishment; (2) property, relationship and sub-element creation; (3) Scope refinement; and (4) Occurrence qualification.

During the first stage a candidate occurrence is created. In one exemplary embodiment candidate occurrences are aggregated into stream s and placed into the matrix. Occurrence are not marked as qualified (e.g. true) occurrences until stage 4 of construction has been completed for the given occurrence definition. Construction may be interrupted between and within the stages as described above. If the dependencies required to accomplish stage 1 is available but the dependencies for stage 2 are not available, the matrix construction processor will proceed with stage 1 of construction but leave the subsequent stages for later processing. In one embodiment, candidate occurrences may be used within stage 1 construction of other occurrence definitions. In this embodiment, the matrix construction processor identifies all occurrences as being in one of four possible states: candidate, qualified, disqualified and suspect. Candidate occurrences are occurrences that have completed stage 1 but not stage 4 of construction. Qualified occurrences are occurrences that have met all the requirements specified in stage 4 of construction. Disqualified occurrences passed stage 1 but either explicitly failed stage 4 of construction or was one of its required sub-elements or scope objects was later determined to be disqualified or altered in such a way to fail scope requirements and/or qualification. Finally, suspect occurrences are occurrences that have passed stage 1 but one or more of its dependent sub-elements or scope objects has been determined to be disqualified or altered in such a way that further analysis may reveal it will fail scope requirements and/or qualification. The inclusion of the suspect state allows for flexible analysis execution in cases where candidate occurrences have been used by other occurrences to establish scope. In the case that the candidate occurrence is found to be disqualified, the matrix construction processor marks all occurrences which were dependent on the candidate occurrence as suspect. Suspect occurrences may be subsequently analyzed to determine whether the disqualification of the associated candidate occurrence (or alteration of a property on which the parent depended) does in fact disqualify the parent occurrence. This embodiment has several advantages, including the maintenance of a complete set of dependencies for occurrences, occurrence properties, relationships and sub-elements provides for additional information within the patient safety console. For example, if the patient safety console displays an index (for example, an instability index), the availability of the dependency tree allows the user to examine what elements go into the evaluation of the index and from which properties, relationships and sub-elements they were derived. In addition, evolutionary states of analysis may be persisted and analyzed by researchers and/or the patient safety processor to further understand the relationships within the resultant MPPC. Disqualified occurrences may be evaluated for research purposes and especially during the construction of occurrence definitions. Disqualified occurrences may be identified as "near misses" such that the researcher or the automated process within the patient safety processor may evaluate the result of changes within the occurrence definitions. The independent and iterative nature of the analysis approach along with the persistence of interim states lends itself to parallel, concurrent and/or distributed processing of the matrix. In other words, matrix construction may be executed within multiple threads of execution on multiple processors within a single machine or by any number of independent machines.

As discussed, according to one embodiment, the relational binary processor generates relational binaries. Such relational binaries are including an alpha occurrence object and a beta occurrence object. An early step in this process includes the defining the relational binaries by the user or by the processor. To define a relational binary, first, the alpha occurrence may be defined (as by the user or adaptively). The alpha occurrence may be, for example, an event defined both in terms of its channel and the object along the channel. In a contemplated embodiment, the objects along each channel are defined by characteristics (such as the slope, amplitude, or other features defining the object including as discussed in the aforementioned patent applications). As well, a beta occurrence defined as, for example, an event in terms of its channel and its characteristics. Alpha and beta occurrences may be events, other relational binaries, images, repeating images or pattern images to name a few.

The definition of events within the patient safety processor depends on the time series mode and type. The patient safety processor supports two time series modes: numeric and non-numeric. For each mode, there are several time series types. For the numeric mode, the patient safety processor supports several types that specify the type of data point that may be stored within the time series. Numeric types include integer, floating point, double precision, decimal, positive integers to name a few. Non-numeric types include Boolean, domain and freeform string to name a few. With numeric time series directional events may be defined in terms of characteristics of the segment including magnitude, duration, and slope to name a few. Threshold violations also may be identified as an event. With non-numeric types events may be defined as either a state matching event or a state transition event. directional events may also be defined in terms of best-fit or least-squared linear regression approach, by an imaging approach, a polarity defining approach, to name a few.

With state matching events a set of values may be defined (either by the identification of individual values or by a pattern-matching mechanism such as a regular expression) and optionally a minimum and maximum duration may be selected. An event may be said to have occurred if and when and for the length of time that the "points" within the time series match the target set for at least the specified minimum duration (if any) and for no greater than the specified maximum duration (if any).

State transition events may be defined by selecting two sets of values (either by the identification of individual values or by a pattern-matching mechanism such as a regular expression). An event may be said to have occurred if and when a first "point" is in the first set defined and the next subsequent point is in the second set defined. The patient safety processor provides for a unary "not" operator to handle two important specific cases of state transition. The researcher may define the first set specifically and then define the second set as being "not" the first set. In this way, an event may be created when a "point" is in the first set and the next subsequent point is in not in the first set. This is a specific type of state transition called a leaving state event. Similarly the second set may be specifically defined and the first set may be defined as "not" the second set. In this way, an event may be created when a "point" is not in the second set and the next subsequent point is in the second set. This is a specific type of state transition called an entering state event.

Alternatively, state transition events may be defined by specifying a state flow diagram or state machine definition and the beginning and end state for the transition. In this type of event, the transitional states are maintained as part of the state transition event as well as the order in which they occurred. Events may be individually defined with a statistical approach rather than an absolute or relative approach with any or all of the characteristics used for the definition. For example, a directional event may be defined as a deviation from previous (or subsequent) trends within a selected window of time. The comparison set may be the stream within which the event potentially exists or it may be a designated group of stream s (e.g. a group designated as "normal"), a randomly selected group or the entire set of stream s of the specified type available. This deviation may only consider sets already analyzed and sections only before a fixed or moving point in time (as in a real time analysis or simulated real time analysis) or may use all sets and times available. In an alternative embodiment, the search for deviation may be applied with reference to a definitive object or set of definitive objects selected by the processor or by an expert.

Both alpha and beta occurrences may also be defined in terms of the relationship of its characteristics to the characteristics of the candidate correlating occurrence (i.e. the alpha for the beta or the beta for the alpha). In one embodiment the user may define the relational objects, (as by using a drag and drop designer), by selecting the channel or stream (which defines the time series type), and by selecting the occurrences which meet specified range of criteria, and by identifying the timed relationship (such as the time interval) of the beta occurrence in relation to at least a portion of the preceding alpha occurrence, and/or by identifying the spatial relationships and/or frequency relationships of one occurrence to the other occurrence. may In the most fundamental relational binary, the event binary, the alpha and beta occurrences are events identified by the time series objectification processor, for example such as a time series objectification processor in U.S. patent application Ser. No. 11/280,559 and U.S. Pat. No. 7,081,095, the disclosures of which are hereby incorporated by reference in their entirety for all purposes as if completely disclosed herein. The relational binary processor then aggregates the relational binaries according to their time of occurrence and/or to specific criteria for aggregation set by the user or processor to derive images and the images are aggregated according to their time of occurrence to derive the MPPC and care derived of events and patterns across hundreds of parallel time series. In a sense, the relational binaries and events become the discrete "pixels" from which MPPC of a patient's physiologic system are constructed by the patient safety processor.

According to one embodiment, the patient safety processor may be also programmed to organize the events and relational binaries into larger aggregate factorable objects, which may also be constructed as a unified object timeline rather than a motion picture. Each aggregate factorable object may include a specific aggregation of events and relational binaries objects. In some aggregate factorable objects, the individual relational binary and event objects occur in a specific sequence or range of sequences (which may be overlapping) and the objects have a specific temporal relationship (or range of temporal relationships) with respect to each other. One specific type of object timeline may be specified as simply a grouped set. In another example, relational binaries are ordered in specified sequence in which the event and relational binaries objects were detected thereby defining the object timeline.

According to one embodiment, objects of specified types may also be combined derived to render a "unified patient timeline" which may be a simple summary of the patient's physiologic system and care. The MPPC and care provides the information at more comprehensive level. Both may be configured to provide further simplified summarization or image detail revealing drill down. The unified patient timeline may for example, represents an instance of at least one factorable aggregate object derived from a plurality of parallel time series into a single time-series or time line, often of relational binary objects of a specific type or plurality of types. In one instance the unified patient timeline and/or the MPPC and care may be constructed to be a life long time line and/or motion picture, which preferably may be recorded whenever signals are available, such as during a hospitalization or when connected to a home monitor or when blood testing is made. The beginning of the motion picture or time line may be defined by the time of the earliest date of data (which may be derived from archived patient data) the unified patient timeline does not end until a patient dies. segments of the timeline (or motion picture) may be separated for examination by location of the patient such as a hospitalization segment, or by actions taken to treat the patient, such as a peri-operative segment, or by events relating to altered patients states such as the segment immediately preceding death or while sleeping. According to one embodiment, an object nomenclature may be provided which designates the timed and sequence relationships of the binary objects and events of a plurality the parallel patient related time series, thereby converting a large plurality of datasets into this single time series of factorable objects, which may be readily outputted interpretable through application of a succinct nomenclature.

In one embodiment, the physician may mark a test result or other data point as mistaken or anomalous. In this case the processor splits the analysis into two—the working analysis (which removes or alters the test result or other data point) and a background analysis (which maintains the original data). The processor may run scenarios in which the original test result stays in effect to determine if conditions occur that might have been expected from the "so-called" anomalous test. The background will not affect the working analysis but notification may be generated if a correlation of events is found in a sufficiently suggestive pattern to warrant a consideration that the original test results may not have been mistaken and, in fact, would account for conditions that do not fit the current working state (e.g. the state with the test results removed). Background analyses may be deleted according to time (e.g. after a certain amount of time in which no correlation to following events is found) or at the request of the user or system operator (e.g. to reduce resource requirements).

In another example the processor may be programmed to generate more frequent testing binaries to confirm or exclude an apparently evolving image. In this way the processor is trying to look as far forward as possible with additional testing to confirm the motion picture of a particular failure as early as possible so that the delay associated with waiting for the detection of a failure cascade as by various traditional threshold breaches is eliminated.

In an example, as part of assuring that the future image is complete, the testing binaries are designated such that the addition of certain drugs (the alpha event) into the image, may cause automatic orders for testing to monitor for complications related to the drug (the beta event) if selected events, binaries, and/or images are present. In an example, if the physician orders heparin, a testing binary may be generated and added to the image, which includes automatic order for a platelet count every 48 hours. According to one embodiment, the time series objectification processor is objectifying the time series of platelet counts to detect a least one fall event (as for example defined by a negative slope and/or a magnitude of fall and/or a threshold fall), if a fall event is detected a divergent binary is generated and a marker indicating a fall is added to the image along the platelet count time series, the processor may generate more frequent platelet testing binaries, to confirm the presence of these divergent binaries in the image. If multiple divergent binaries are detected then the processor may generate different types of testing binaries wherein the alpha event is the fall in platelet count. This may trigger a cascade of testing binaries such as, for example, wherein the alpha event is a binary including a heparin treatment and a fall in platelet count and the beta event is, for example, a platelet factor IV assay and/or another assay. In this way, using the imaging processor, the delay associated with waiting for an absolute or relative threshold drop in the platelet count is not required but rather the slope of the platelet count, the presence or absence of prior heparin therapy, the patient's risk of bleeding or thrombosis, may all be included in the image to trigger the automatic measurement of additional testing. In addition the image of cascade as it evolves may trigger additional testing binaries (as for hepatic function tests, as required to determine the safety of Argatoban, a medication which may be ordered if the images are consistent with heparin induced thrombocytopenia). Here the advantage of having these binaries and images as part of a MPPCF is evident, because the processor will be examining the images of the motion picture for other causes of the fall in platelet count which may include cascades indicating TTP as will be discussed and/or occult hemorrhage to name a few.

One embodiment programmatically images the parallel physiologic time series to render a relational pyramid of data with the top of the pyramid representing data at the highest level of analysis and abstraction while data moves down through layers of analysis, the bottom layer being the raw data stream s. The healthcare worker may investigate the pyramid in the following ways to name a few: (1) Drilldown—the care worker may navigate into the details of the data and the rationale of the analysis (i.e. both the conditions that exist and the rules by which the analysis has arrived at its conclusion); and (2) Aspects—view ports into the system which emphasize certain elements/conditions and de-emphasize (and/or filter out) other elements/conditions). These two examples above may be used together allowing the healthcare worker to navigate through the relational pyramid vertically (drilldown through levels of analysis) and horizontally (through filters/aspects).

In one embodiment the relational pyramid may be manipulated by the healthcare worker and/or researcher to consider hypothetical scenarios or scenarios based on the rejection of certain test results or events which may be considered in error, anomalous or otherwise inaccurate. Alternate pyramids may be stored in whole or as differential images. Alternate pyramids may be compared against the working pyramid to understand the results of the altered data.

In one embodiment, the processor will automatically consider alternate pyramids under certain conditions—such as the existence of perturbation for which no precursors may be identified. The sudden existence of perturbation or of divergence may, by considering the range of possible precursors, suggest anomalous conditions: inaccurate diagnosis, faulty monitoring equipment, labeling mistakes, the failure of a patient to take medication as prescribed, to name a few. According to one aspect, the values and/or patterns of the blood tests such as the inflammatory mediators is/are compared to the image(s) of physiologic perturbation or to the pattern(s) or values of at least one physiologic parameter, such as the pulse rate, respiration rate, and/or ventilation oximetry index to name a few. Upon the detection of an apparent relationship, the processor may automatically order a sufficing number of sequential blood tests to confirm that the pattern of the parameter is convergent with the pattern of the blood test thereby providing strong supporting evidence, reinforcing redundant evidence, that the physiologic parameter and the mediator have a common physiologic failure based linkage, such as the failure of sepsis for example. One embodiment extends that analysis to incorporate specialized inflammatory mediators into the moving picture of failure so that comprehensive comparison of the marker or indicator to the image of the physiologic parameters and treatment may be provided. One embodiment generates dynamic images of relational variations of a set of time series associated with a complex system to generate a real time motion picture of a failure of the system and/or of forces applied to the system and condenses the complex data of the EMR into a single motion picture of perturbations, treatments, physiologic responses, diagnostic testing, recoveries, diagnoses, missing data, patient locations, and/or other datasets and further provides treatment, and/or testing, alarms, notifications, diagnosis, and/or orders based on the motion pictures.

One embodiment provides a system and method for programmatic characterization of a plurality of related complex and dynamic processes, which; converts patterns along a plurality of parallel times series derived from each of the process into discrete objects, organizes these discrete objects into relational objects, and, organizes the relational objects to render a unifying programmatic image of a complex and dynamic process, and then, applies expert systems to automatically recognize images or image portions, or the specific motion pictures which are indicative of at least one failure of the complex processes and/or provides a relational object image generating and processing system to provide characterization and quantification of physiologic systems by generating an organized analytic construct defined by a time series matrix of relational objects.

Although the number of potential modes of failure is very high in any hospital environment, the occurrence of certain modes of failure is reasonably likely under a given set of circumstances in the hospital. A failure mode diagram illustrating common modes of failure given a combination of a group of diseases is shown in FIG. 1. The number of potential failures may be very large (in the hundreds) for a given patient in a hospital setting and the nurse or physician is often expected to monitor many such patients on the floor while timely detecting the failures such that the nurse is expected to timely detect even a single failure from as many as a thousand failures which may occur among the patients under his or her care. For this reason, processor based failure imaging and detection is desirable.

FIG. 1 illustrates a complexity diagram 200 of an example of a patient on a medical hospital ward. The diagram 200 demonstrates the level of complexity that may be modeled into moving images as provided herein to determine the nature of and origin of perturbations within this level of complexity. The diagram 200 is one type of failure mode diagram which may be constructed by an expert panel and then used according to one embodiment to facilitate the construction of the various components the moving images provided herein, including the events, relational binaries, and image components. The failure image component diagram 200 includes a number of overlapping diseases present for this single patient including diabetes 202, congestive heart failure 204, arterial fibrillation 206, stroke 208, sleep apnea 210 and sepsis 212. The diseases may induce physiologic failures, such as a divergent rise in ventilation 216, a rapid ventricular rate 218, pulmonary edema 214, and fall in oxygen saturation (hypoxemia) 222. Furthermore the treatments are potentially associated with medication failures such as a high threshold breach of the partial thromboplastin time (PTT) or a low threshold breach of the glucose (hypoglycemia) 234. Additionally, the administration of a treatment (for example, insulin 224, a diuretic 226, an ACE inhibitor 228, a beta blocker 230 and/or heparin 232) to a patient may lead to additional physiologic failures (for example, a fall in platelet count (thrombocytopenia) 236, the occurrence of heart block 238, a fall in serum potassium (hypokalemia) 240, a fall in serum sodium (hyponatremia) 242, a fall in blood pressure (hypotension) 244. In one embodiment, a single patient may have early high blood glucose (hyperglycemia) 215 followed by later low blood glucose (hypoglycemia) 234. As shown, the interrelationship of progression of multiple diseases, the patient symptoms, and multiple treatments may lead to treatment delay 248 or confusion 220.

Figure 2:
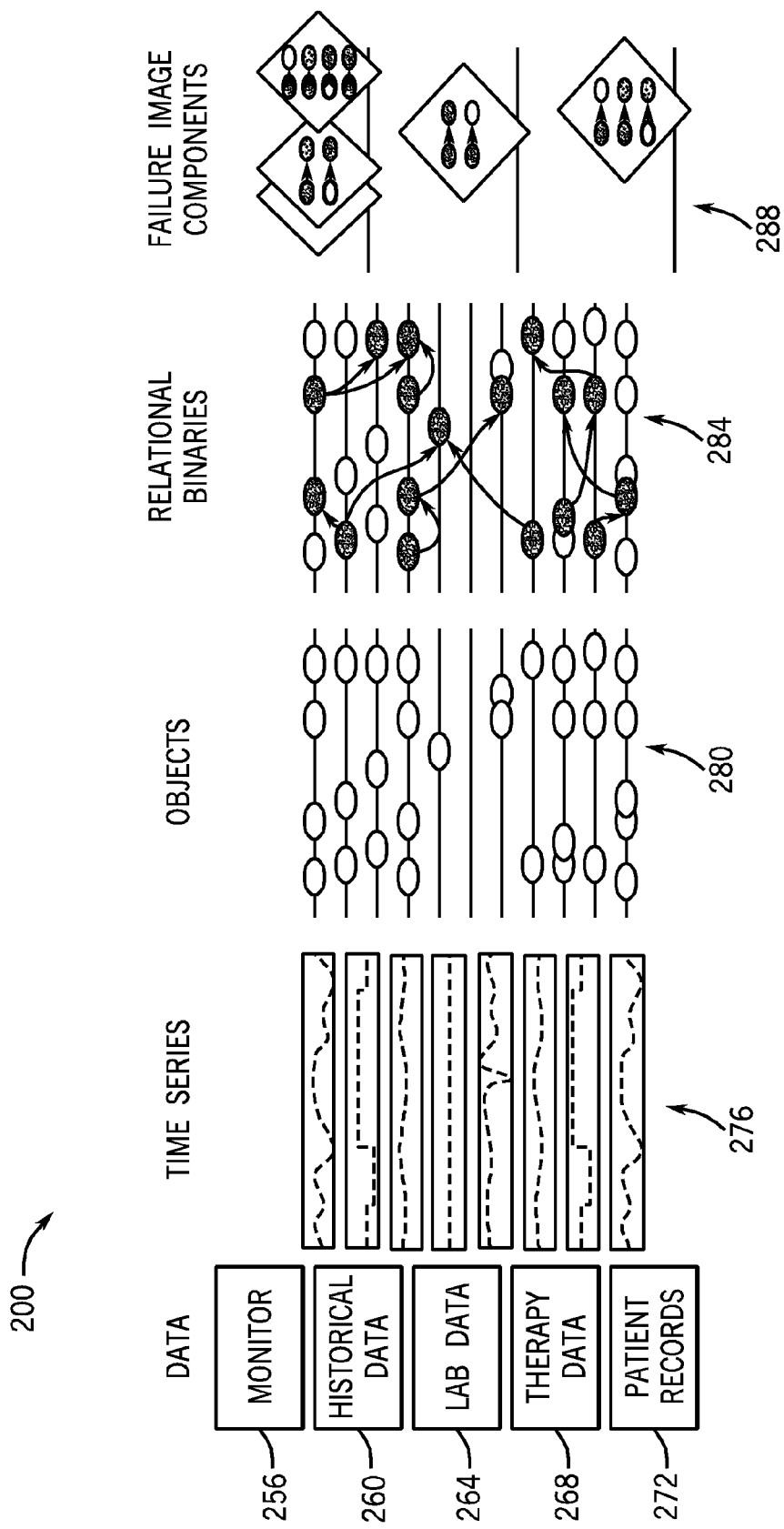
FIG. 2 is a diagram depicting the levels of analysis in accordance with an example of a embodiment.

FIG. 2 depicts an overview of the flow of analysis for modeling complex patient physiological condition in one embodiment. A wide range sources may provide inputs to the modeling. For example, patient monitors 256, patient records 272, historical patient data 260, lab results 264 and therapy data 268 may provide the raw data input into the analysis stream. These inputs are converted to a set of parallel time series 276. Patterns and threshold violations along this plurality of parallel time series identified, coalesced, synthesized and organized into discrete objects forming object stream s 280 within each channel. These discrete objects are analyzed to identify known relational patterns into instances of relational binaries 284. In one embodiment, expert systems then further refine the analysis by organizing and synthesizing these relational binaries into a set of failure images 288, which as an aggregate whole make up a unified programmatic image of the complex and dynamic state of a patient and/or a patient population.

Figure 3A:
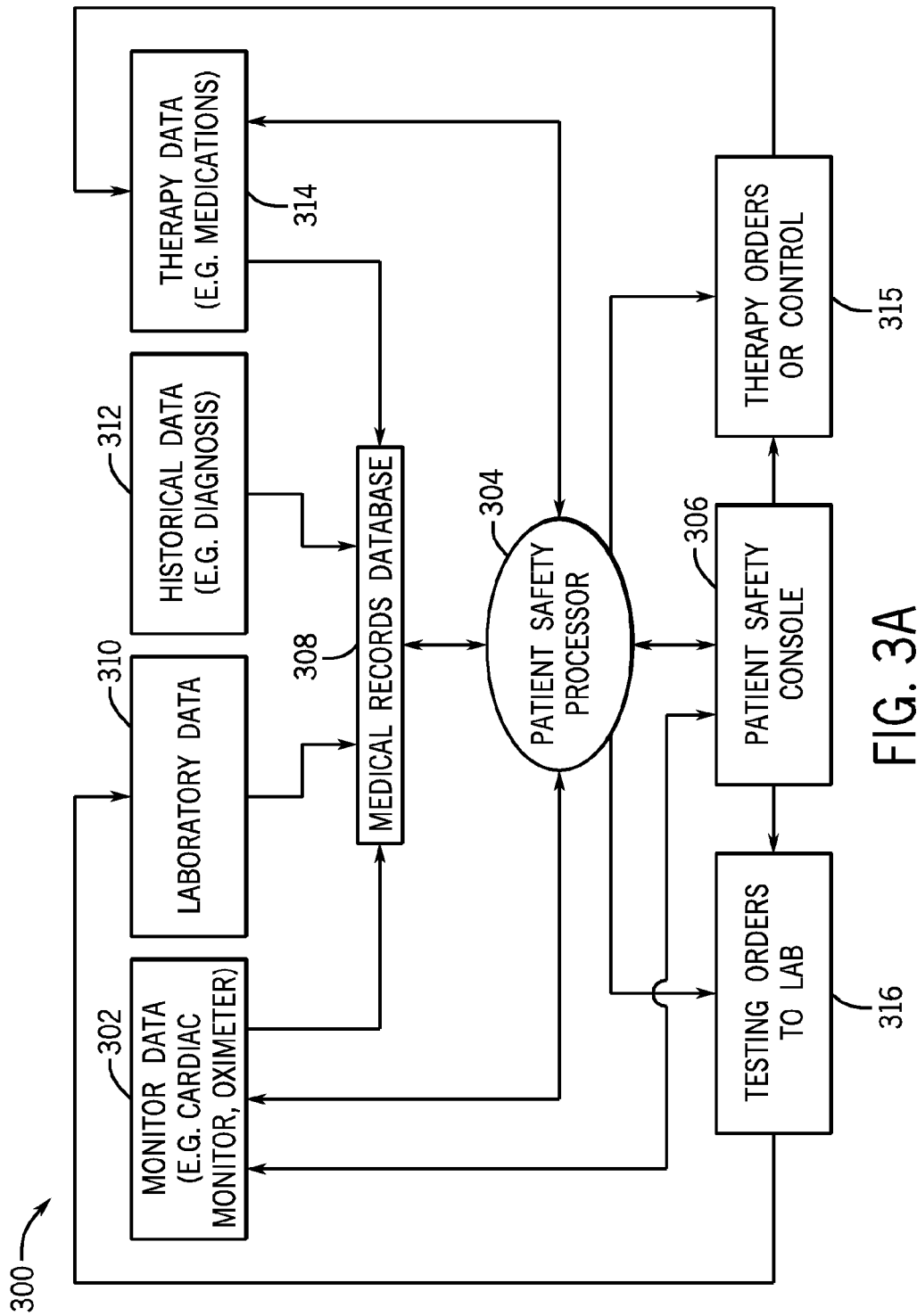
FIG. 3A is a data flow diagram in accordance with an example of a embodiment.
Figure 3B:
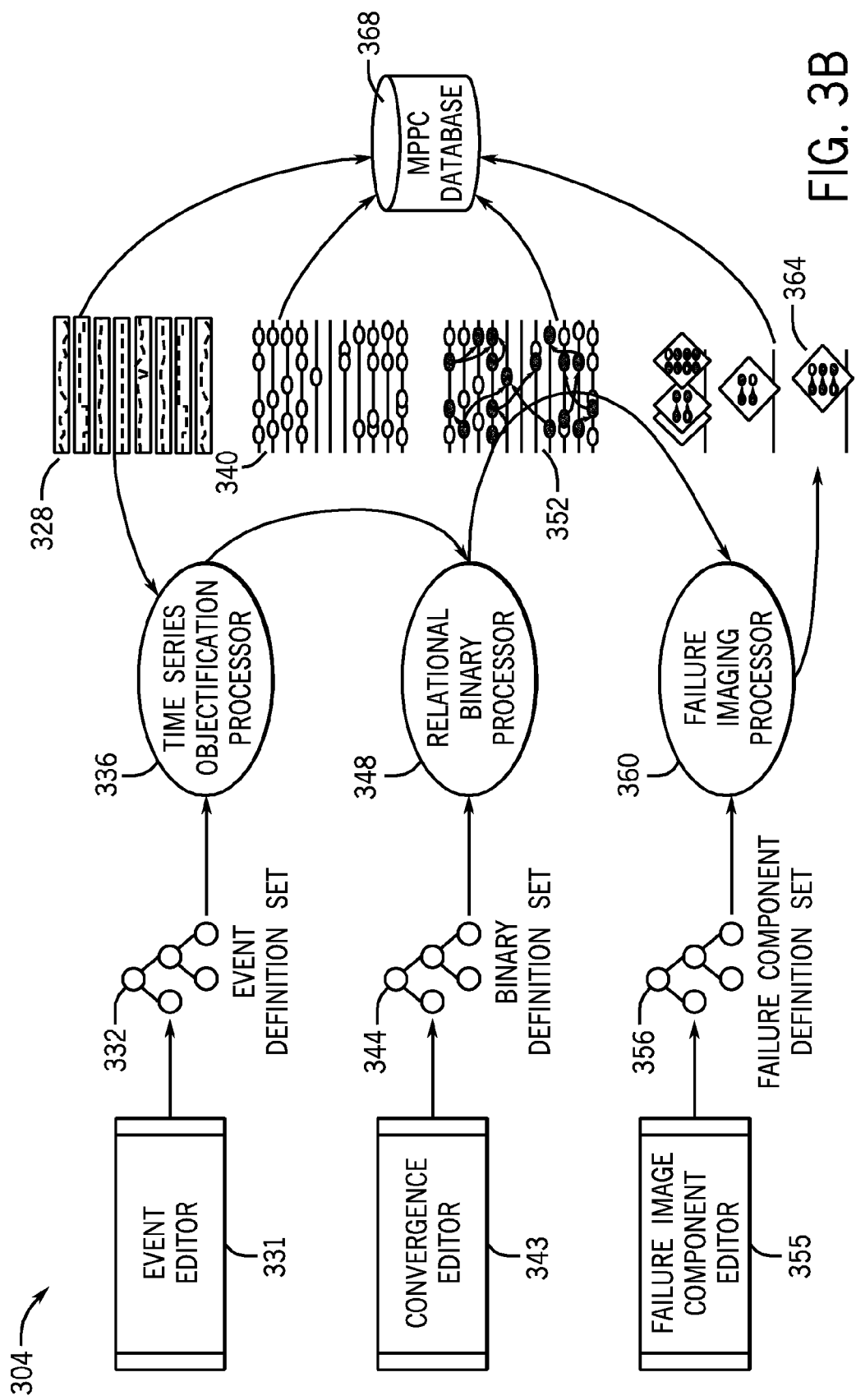
FIG. 3B is a diagram of an example of a system in accordance with an example of a embodiment.
Figure 3C:
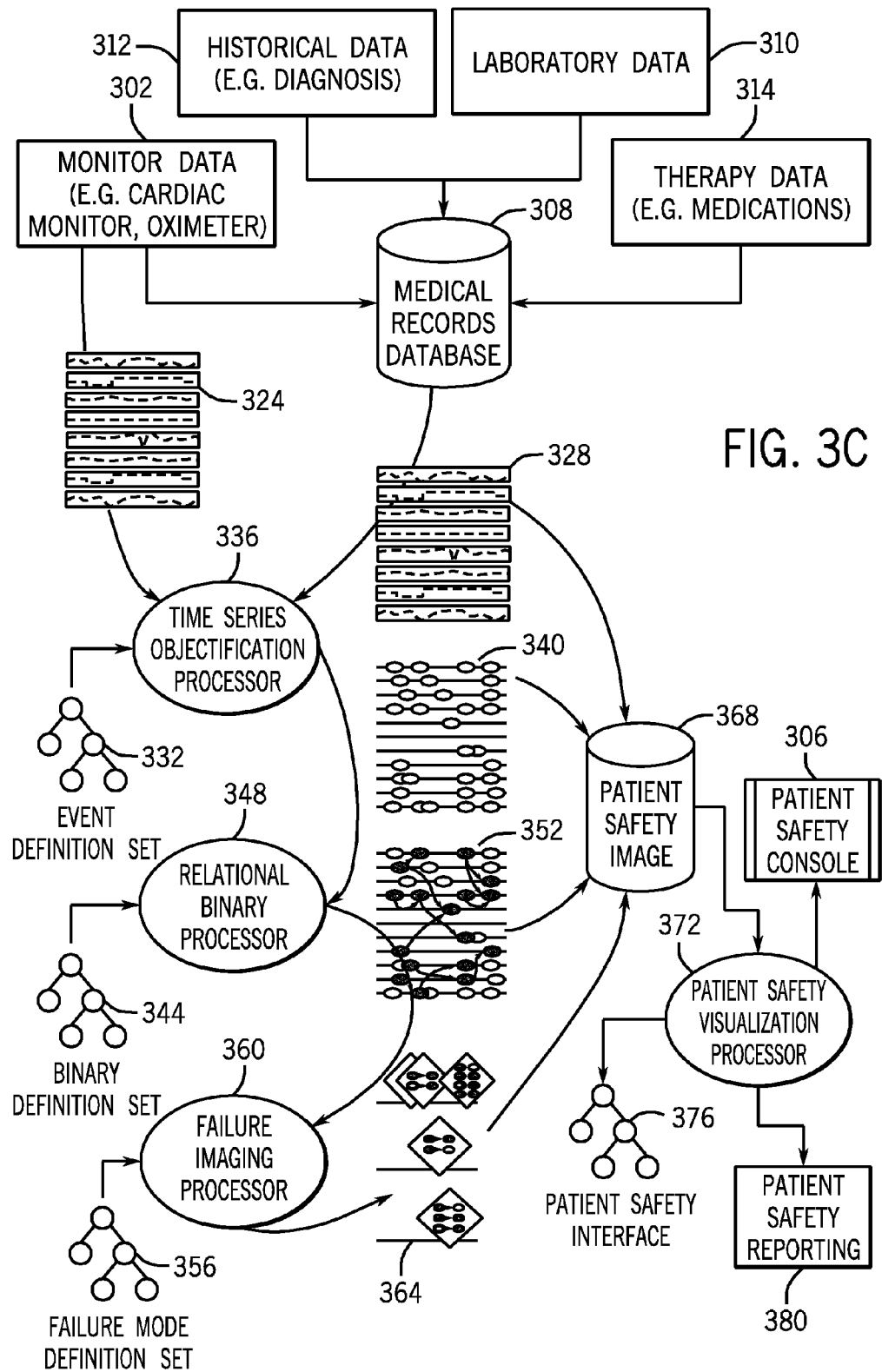
FIG. 3C is a data and action flow diagram in accordance with an example of a embodiment.

FIG. 2 depicts the flow of analysis 240 from raw data to the aggregate of images, while FIG. 3A and FIG. 3B includes some of the data stores, data flow, processors and output mechanisms within the exemplary embodiment. FIG. 3A depicts another data flow of one embodiment. The data management system 300 includes a monitor 302, a patient safety processor 304 that may include, for example, time series objectification processor 336, relational binary processor 348, and failure imaging processor 360. Alternatively, processors 336, 348, and 360 or instructions for performing the processing steps of time series objectification, relational binary processing, and/or failure image processing may be located on one or more additional processing components in communication with processor 304 that are part of the system 300. The processor 304 is adapted to provide output of the analysis to a device 306, which provides an interface for a healthcare worker. The data flow involves inputs from a wide range of sources (302, 304, 308, 310, 312, 314). As shown, the inputs may be sent to a processor 304 that may direct further action for the patient, including testing orders 316, indicators to the healthcare provider that may be displayed on a console or device 306, and therapy orders 315. Accordingly, the healthcare worker may use the device 306 to control and oversee the entire hospitalization process. In one exemplary embodiment, the processor 304 may be used to drive the device 306. The processor 304 may be adapted to constantly process all of the real-time data of all of the patients regardless of the status of the viewing console and to automatically send testing orders 316 and/or therapy orders 315 based on the analysis of the images derived from the processor 304, as will be discussed.

The data management system 300 may include one or more processor-based components, such as general purpose or application-specific computers. In addition to the processor-based components, the data management system 300 may include various memory and/or storage components including magnetic and optical mass storage devices and/or internal memory, such as RAM chips. The memory and/or storage components may be used for storing programs and routines for performing the techniques described herein that are executed by the processor 304 or by associated components of the data management system 300. Alternatively, the programs and routines may be stored on a computer accessible storage medium and/or memory remote from the data management system 300 but accessible by network and/or communication interfaces present on the computer.

The data management system 300 may also include various input/output (I/O) interfaces, as well as various network or communication interfaces. The various I/O interfaces may allow communication with user interface devices, such as a display, keyboard, mouse, and printer that may be used for viewing and inputting configuration information and/or for operating the system 300. The various network and communication interfaces may allow connection to both local and wide area intranets and storage networks as well as the Internet. The various I/O and communication interfaces may utilize wires, lines, or suitable wireless interfaces, as appropriate or desired.

In one embodiment, the device 306 is turned on as for continuous viewing (with a notification) by the processor 304 when images are indicative of a significant potential failure and/or cascade process or at a point wherein the patient's risk class exceeds a threshold value. The risk class may, for example, be derived as a function of a calculated instability index or a detected instability index pattern and/or detected failures. The instability index may be, for example, a confidence metric correlated with a matched image. For example, when an MPPC has a high likelihood of being associated with a serious condition, the instability index may be high. The instability index may be a numeric index, a color or graphic indicator, and/or an audio or text message.

In accordance with an embodiment, the device 306 includes an interactive screen displaying items, such as one or more working diagnoses, differential diagnosis, parameters derived from patients including laboratory parameters, monitored parameters, and subjective parameters (e.g., sedation scale, confusion scale, or pain scale) or the like. In an embodiment, the term "parameter" herein may refer to an absolute or relative data point or set, a pattern, or a deviation, a range of such data points or sets, a pattern of such data, a relationship along a single set of data and/or or between a plurality of sets of data, and/or patterns of data. The data may be an objective data type or subjective data type and may be directly and/or indirectly derived or historical in origin. In addition various outputs from the failure imaging processor 360 (FIG. 3B) may be displayed. According to on embodiment, the processor 304 may provide data for display present on the device 306 or through a report (either electronic or paper) or within an electronic representation that may provide an interface to external systems.

The data management system 300 further includes a medical records database 308 including laboratory data 310, historical data (e.g., diagnosis) 312 and therapy data (e.g., medications) 314. The medical records database 308 is coupled to the processor 304 and to the monitor 302 so that those systems may have access the data stored in the medical records database 308. The processor 304 may include a component or direct link to the centralized patient medical record, which contains real time data and receives data input from all hospital sources. Thus, a database containing substantially all of the components relating to the patient available to the hospital may be directly accessible to the processor 304 in real time to allow the embedded relational processor render relational binaries, and construct and detect failure image components which include these data from varied sources.

In accordance with an embodiment, the processor 304 is adapted to comprehensively engage the medical records database 308. As discussed further below, the processor 304 may be programmed to provide for formal, automatic simultaneous engagement, of physiologic failure image components, medication failure image components, testing failure image components, aggregate failure image components as derived from the relational processor and to render them in a timeline for viewing.

The processor 304 may be adapted to provide an immediate review of all failure image components and to take action based on the detection of specific failure image components. The processor 304 may be capable of responding faster and more reliably than the healthcare worker because it may be adapted to constantly monitor the evolving failure image components form the earliest onset of the first divergent binary. The processor 304 may therefore detect failure image component cascades, which originate from single divergent binaries, which might easily be undetected by the healthcare worker until it is too late. The processor 304 may also be programmed to alarm on divergent or null binaries upon which no action has been taken or upon which the action has not corrected the evolving divergent binary or failure image component. For example, in a scenario in which the processor 304 has been updated by the nurse that a blood culture has been obtained, the presence of a null binary may be generated indicating testing failure image component if after a pre-selected time the result is not available to the processor 304 whereas the presence of a divergent binary indicative of a physiologic failure image component may be detected if the culture is positive. If testing failure image component is detected the processor 304 notifies the lab of the apparent delay. The notification is an alpha event and a receipt response to that notification is a true beta event. Therefore the failure of the lab to indicate receipt may cause the occurrence of a divergent binary, which may trigger the notification of the nurse in the same manner until a convergent binary concludes the sequence. If on the other hand, a physiologic failure image component is detected (the culture is positive), the processor 304 notifies the nurse again in the same binary generating fashion.

While a positive blood culture is the beta event of the culture testing binary, it is the alpha event for another group of testing binaries such that the initial divergent testing binary may cause the processor to assure acquisition of a complete blood count, a comprehensive metabolic profile, increased frequency of blood pressure and pulse measurements, ventilation indexing oximetry and other testing as programmed into the processor 304 in response to the specific divergent binary detected (in this case a positive blood culture). These new testing binaries may generate unexpected beta events (such as a low blood pressure, a high pulse, or high ventilation to oximetry index) and these beta events may thereby define a new set of divergent physiologic binaries. This new set of divergent binaries (in aggregation) may be sufficient to meet the pre-selected criteria of an aggregate failure image component suggestive of early septic shock, which diagnostic consideration now includes an alpha event to a plurality of new binaries which have been programmed into the processor to assure timely and proper monitoring, timely proper patient location, and timely proper diagnostic testing, and timely and proper intervention in the event of the detection of this type of aggregate failure image component. In addition, the beta events of the divergent physiologic binaries which included the aggregate failure image component now become alpha events for new physiologic binaries wherein the beta event of each of the new binaries includes the return of each these values back to a normal range within a pre-selected time period (thereby assuring, that the aggregate failure image component is corrected timely, if possible). In additional, the positive blood culture is also the alpha event for a treatment binary such that the processor 304 may be expecting to see the correct antibiotic in response to positive blood culture administered within a pre-selected time interval. If this does not occur a divergent binary indicating treatment failure may be identified and assured nurse notification may proceed by the binary building method previously discussed.

According to one embodiment, in response to the detection of any significant divergent physiologic binary, the device 306 may be programmed to prevent the failure of notification by building a set notification binaries, which must end with convergence. The device 306 may also be programmed to prevent failure to timely treat by building a set of treatment binaries, which must end with convergence. Further, the device 306 may be programmed to prevent failure test by building a set of testing binaries, which must end with convergence. The device 306 may also be programmed to detect associated physiologic failure image components by identifying divergent physiologic binaries in associated with the initially discovered divergent binaries.

According to one embodiment, the processor 304 includes an associated, connected and/or embedded eventing system. In this eventing subsystem, users may designate actions to be initiated or data to be recorded when a specific occurrence is identified. This eventing system may interface with other internal or external systems including notification systems, workflow systems, asynchronous communication systems, reporting systems, decision support systems, dashboards, data warehousing and/or data mining systems to name a few.

According to one embodiment the relational processor is self-modulating and provides an automatically expanding analysis, which is rapidly responsive to the occurrence of even a minor failure image component. The analytic activity of the processing system is capable of multidimensional growth and diminishment in direct response to the magnitude and number of failure image components detected. In this regard, the processor 304 upon the occurrence of a physiologic failure image component may generate a cascade of notification, testing, treatment, and physiologic binaries even if that failure image component includes only a single physiologic divergent binary. The beta event of the physiologic binary may include the alpha event of each of a new generation of notification, testing, treatment, and physiologic binaries. Each of these new binaries also have a beta event, each which may induce the formation of other binaries wherein the beta event includes the alpha of another binary of the same or another type. A spontaneously growing cascade of binaries thereby evolves toward assuring timely notification, timely testing, and timely restoration of physiologic stability.

A rapidly expanding, cascade of these types of divergent binaries indicates evolving patient instability of the patient or poor performance of the healthcare system. An analysis (as by objectified pattern recognition or statistical analysis) of the timed patterns of the types and sequence of the divergent binaries may allow the determination of poor health or poor responsiveness of the healthcare worker is causing the cascade to be propagated. As health is restored, and provided the healthcare workers are timely responsive, the binary cascade may automatically diminish and the various failure image components may no longer be detected. The outputs of the relational binary object processor therefore provides a self modulating processing system which may be readily used and further analyzed to track the health of a single patient, or the patients on a given floor, or the patients hospital wide. The outputs of the object binary processor also provides a self modulating processing system indicative of the quality of healthcare delivery provided to a given patient, on a given floor, or hospital wide.

The processor 304 may be applied to other complex dynamic data sets other than medical data wherein a self-modulating relational analysis and control would be useful. The processor 304 has utility for the data mining, for example in association with the processing of archived datasets to identify the failure image component process from the initial spark (the first divergent binary) to extensive system failure. The processing of archived datasets provides the opportunity to review the automatic modulation of the binary cascades which are derived of various failures and to facilitate the construction of dynamic failure image component diagrams for complex processes in the hospital, as well as in industrial processing such as the food, chemical, or pharmaceutical processing. The processor may be programmed such that the user may select each alpha event and allow the processor to detect, offer, and/or derive events and relational binaries, which have specified temporal, frequency, or spatial relationships with the selected event object. Alternatively the processor 304 may be programmed to construct its own set of convergent object binaries with a learning dataset by processing the outputs of healthy individuals and then the processor may be used to detect divergent binaries when applied to patients by identifying the lack of the expected beta events (which were defined by the learning dataset). Sensitivity for cascading (the initiation of further processing based on the detection of a divergence or a failure image component) may be adjusted by modifying the sensitivity for trueness of the beta event or by modifying the criteria such as slope, or magnitude of the objects during the objectification process. This provides a high degree of flexibility in defining sensitivity to the designation of a binary as divergent and this therefore allows a high degree of control over the sensitivity to cascade initiation, propagation, and extinguishment. Cascades may be modular or divergent or failure image component specific. A modular group of cascades may be selectable from a menu and then each one in the group modified as desired.

As shown in FIG. 3B, the processor 304 may include instructions for any number of processing functions. As shown the processor 304 may include an event editor 331 (creates event definitions 332), a convergence editor 343 (creates binary definitions sets 344), and a failure image component 355 (creates failure components 356). The event definitions 332, binary definitions 344, and failure components 356, may be used an inputs for the time series objectification processor 336, the relational binary processor 348, and the failure imaging processor 360. The time series objectification Processor 336 is programmed, with the rules and parameters provided by the event definition set 332, to convert parallel time series (324, 328) of the electronic medical record 320. The relational binary processor 348 then, with the rules and parameters provided by the binary definition set, processes the object stream s 340 to generate stream s and cascades of relational binaries 352. Further then, the failure imaging processor 360, with the rules and parameters provided by the Failure image component definition set 356, synthesizes the relational binaries, and in some cases isolated objects from the object stream, into one or more images 364. The output of each of these three processors (336, 348 and 360) as well as the original time series upon which they were applied is stored in an MPPC database 368. In an example, the processor 304 may be programmed so that detection of one or more events, binaries, image components or detection of a specific MPPC, may cause the processor to take action such as provide an outbound notification of the detection, orders for testing or treatment, or direct control signals to a treatment and/or testing device to change, cease or initiate testing and/or treatment.

According to one embodiment, the relational binary processor 348 and the time series objectification processor 336 may adapt to the output of each other to modify the analysis. For example, the detection of an event, a reciprocation, an incomplete reciprocation or other objects or patterns by the time series objectification processor 336 may cause an adjustment to the cascade responsive to the detection of a divergence. Alternatively or in combination the criteria for designation of a wave segment as an event object within the time series objectification processor 336 (for example the slope criteria for identifying a fall event object of serum sodium) may also be adjusted based on the presence of a specific alpha event. In an example, when an alpha event including a diagnosis of cerebral vascular infarction (CVA) is detected, this may cause the time series objectification processor 336 to reduce the absolute slope (less negative slope) for designating a fall event object of serum sodium, which, is preferably one of the betas in such patients. By automatically reducing the absolute slope for the designation of the beta event the alpha diagnosis of cerebral vascular infarction is adjusting the sensitivity of the diagnostic process allowing automatic and dynamic adjustment upon the occurrence and detection of different physiologic vulnerabilities. In this example, the increase in sensitivity for detection of a fall event object in serum sodium (which, combined with the alpha that includes a CVA diagnosis) would include a divergent binary), which may trigger a diagnostic cascade for close monitoring of the serum sodium and/or the evaluation of additional laboratory studies and/or the reduction of free water delivery. This is desirable due to the unique vulnerability faced by patients with CVA as a function of the potential for inappropriate increase in antidiuretic hormone due to the CVA.

Since the relational binary definitions within the binary definition set 344 may be individually defined and refined by processing large populations of historical data, correlations may be verified, rather than being simply proposed and maintained as a function of consensus or expert opinion. In one embodiment, cascades originated by criteria for divergence provided by an expert, which untimely lead to extinguishment without intervention may be automatically adapted to either change the sensitivity for the detection of the divergent beta or to change the cascade resulting for the divergent binary. In another example, cascades originated by criteria provided by an expert which continue self propagate and expand despite timely action and without progression of the physiologic divergence may be automatically adapted to either change the sensitivity for the detection of the divergent beta or to change the cascade resulting for the divergent binary. The sensitively and specificity may be further enhanced because the system may be applied to archived training data sets wherein the outcomes are known so the magnitude and direction of the cascades may be compared to the desired magnitude and direction of the cascades and adjusted accordingly. With applied archived datasets the application of auto-adaptive adjustment in event criteria, divergence criteria, or cascade generation may be applied until the cascades proceed without premature auto extinguishment and excessive propagation. Furthermore the system may be applied to hypotheticals on the missing data to allow determination as to how they might affect incomplete (null) binaries.

According to one embodiment the processors, including the time series objectification processor 336, the relational binary processor 348 and failure imaging processor 360, may output the results of their analysis into the MPPC Database 368. The MPPC Database 368 contains the time series 328 on which the analysis was performed as well as the results of analysis including the event stream s 340, the relational pairs 352, the aggregate failures 364 as well as aggregations, relationships and alternative images of these elements. In one embodiment, the metadata rule-sets (both primary and alternative and/or temporarily overridden or altered elements) are persisted as XML (event definition set 332, binary definition set 344, Failure image component definition set 356) in the patient safety image database 368.

According to one embodiment, a processor is programmed to render sequential time series components (which may be discrete and/or succinct) and which may be subsequently linked other sequential time series components along and across parallel time series to produce a comprehensive relational image of physiologic failure and for patient care. These components may be rendered by methods defining polarity reversal or inflection points, state changes, by imaging methods to detect pattern components (for example subsequent to time series rendering into a particular format for example), and/or by another method for defining and/or programmatically "packaging" events, image components, and/or occurrences for relational imaging and analysis. According to one embodiment "time series objectification" is employed for this purpose. Time series objectification may be rendered by a time series objectification processor 336, an embodiment of which is discussed below. In one embodiment, time series objectification is the process of converting a set of time series into a stream of sequential discreet elements or objects such that substantially the entire time series of data is converted to a time series of objects in a relational hierarchy of ascending complexity. In another embodiment these objects are created by identifying boundaries within the time series based on the values of the points within the time series (for example threshold violation and/or state match to name a few) and/or the relationship between these points (for example polarity reversal, inflection point, state transition to name a few) using a set of rules based on an understanding of phenomena within the system from which the time series are derived or which are learned adaptively. The discrete objects which are created represent and characterize an occurrence providing a time location and a set of properties derived from the aggregated data within the boundary defined. These objects are differentiated by location and the properties derived and therefore individual objects can be qualified and the stream of objects can be searched against. Further, the conversion to discrete objects provides for the identification, qualification and searchability of relationships between elements. Relationships can be converted into aggregations and/or hierarchy of elements within which properties can be derived from components of an aggregation/hierarchy to the aggregation/hierarchy itself and/or from the hierarchy/aggregation to the participating components.

A time series objectification processor 336 may for example, contain instructions as provided in U.S. patent application Ser. Nos. 11/280,559, and 11/351,449 the specifications of which are incorporated by reference herein in their entirety for all purposes. Accordingly, such processors may function by constructing a time series matrix including of substantially all of the parameters derived during the process of the hospitalization and then objectify each time series in the matrix to produce an objectified time series matrix. The time series which include the matrix may, for example, include objective measured values, drug dosing, infusion rates, and subjective clinical scores to name a few. At least some of the time series may be provided as a step function. For example, time series of the weights, serum sodium values, $SPO_2$, ventilation volume or rate, heart rate, pulse amplitude, pulse slope, drug infusion dose, sedation score, pain score, stupor score, working diagnoses, an instability score, a severity of illness score, to name a few, may all be included.

The objectification processor can define objects by a wide range of methods which may be programmatic and/or image based or by another method of defining objects. In an embodiment, a time series objectification processor applies a linear and/or iterative dipole slope approach to the recognition of waveform events, as for example respiratory or oxygen saturation events. For example, the events associated with airway collapse and recovery are generally precipitous and unipolar, for this reason the linear method suffices for the recognition and characterization of these nonlinear waves. However, the iterative dipole slope approach is particularly versatile and may be used in situations whereby the user would like an option to select the automatically identification of a specific range of nonlinear or more complex waves. Using the iterative dipole slope method, the user may select specific consecutive sets of points from reference cases along a waveform as by sliding the pointer over a specific waveform region. Alternatively, the user may draw the desired target waveform on a scaled grid. The user may also input or draw range limits thereby specifying an object or set of objects for the microprocessor to recognize along the remainder of the waveform or along other waveforms. Alternatively, the processor may automatically select a set of objects based on pre-selected criteria that may be empirically determined. Since the iterative dipole process output may be shape-dependent (including frequency and amplitude) but is not necessarily point dependent, it is highly suited to function as a versatile and discretionary engine for performing waveform pattern searches. In accordance with embodiments, the waveform may be searched by selecting and applying objects to function as Boolean operators to search a waveform. The user may specify whether these objects should be in the same order. Recognized object sequences along the waveform may be scored to choose the degree of match with the selected range. If desired, (as for research analysis of waveform behavior) anomalies within objects or occurring in one or more of a plurality of simultaneously processed tracings may be identified and stored for analysis.

After the process of objectification and further processing of the time series matrix (e.g., generated from object stream s 340) the images are transferred to the patient safety visualization processor 372 which presents and highlights the detected MPPC on an outputted display or patient safety console 306 or through a patient safety report 380 (either electronic or paper) or within an electronic representation as an interface 376 (for example the European Data Format (EDF)) which may provide an interface to external systems. In one embodiment, the aggregation of data, analysis and metadata provide the source of data for the patient safety visualization processor 372. In one embodiment, the Patient Safety Visualization Process 372 provides a visualization of a patient's condition in a comprehensive grouping defined by rows of timelines of specific signals and/or grouping and/or categories of signals and/or signals. In one embodiment the global state of each row is represented by color in a spectrum with a different color moving from stability to failure (for example, Sustained Stability [deep blue], Stability [light blue], convergence [green], Perturbation [yellow], Divergence [orange], Null [black], Failure [red], Cascading Failure [bright red]). In another embodiment colored arrows, icons, blinking or highlighted text, and/or other visual representations along each time line represent these states.

In one embodiment the patient safety visualization processor 372 represents the patient condition as a set of pixel stream s moving from left to right to show evolution of condition over time. The processor provides the navigation backward and forward in time as well as up and down through levels of analysis within the patient safety image database 368. In this embodiment the levels of analysis may be, for example:
time series—Unanalyzed data stream s in the form of time series
events and Perturbation—events, state matches, state transitions and threshold violations characterized within their respective channels as to whether they represent clearly defined perturbation according to the event definition set 332
Systemic Response—convergent, divergent and null binaries representing the relationships between events, state matches, state transitions, threshold violations, perturbations and expected elements according to the binary definition set 344
Failure—Failure images that have been identified within a single patient
System Failure—Failure images within a specific category (such as the respiratory system) representing images of failure that have been identified within a single patient
Failure Patterns—Trends of failure and failure images within patient population or a specific region, such as a specific hospital ward for example.

In one embodiment the patient safety visualization processor 372 composes an image on computer monitor (the patient safety console 306), which may be composed by a series of pixels oriented horizontally representing data and analysis stream s. These pixel stream s may be stacked vertically with the position on the x-axis representing a specific point in time. The processor provides for the movement of the pixel stream s horizontally to provide a pan through time.

Each pixel stream may be composed of a set of pixels, which indicate the state of the data and/or analysis at the specified point in time. The pixel has a state (e.g. represented by color) and granularity (the length of time it represents [for example 1 minute]). The size of the view as well as the selected span of time determines the granularity of the pixel. In the contemplated embodiment, the pixel is displayed by the highest level of instability found within the time span represented by the single pixel within the pixel stream. Further, each pixel has a level of abstraction, which determines which objects from the patient safety image database 368 contribute to its state. The contributing objects are shown below by level of analysis:
time series—Data points within the channel (e.g. oxygen Saturation Values)
events and Perturbation—events and threshold violations
Systemic Response—Relational binaries
Failure—Failure images
Failure Patterns—Failure trends and correlations.

In one embodiment, groups of pixel stream s are stacked vertically to create a patient safety visualization. Patient safety visualizations may be composed of pixel stream s of different patients or of data and analysis stream s within a single patient. Patient safety images provide the ability of the care worker to filter the analysis quickly to identify problem areas or areas of a specific nature. Sorting may be provided highlight emerging failure cascades or other pattern failures. In an embodiment patient safety images may be composed of different levels of analysis displayed on the patient safety console 384 at the same time correlated by time. The use of mixed-analysis level visualizations provides the care worker with the ability to quickly understand the relationship between the lower levels of data (e.g. incomplete recovery within oximetry) and the higher levels of analysis (e.g. the identification of narcotic-induced ventilation instability).

In an embodiment the patient safety console 384 provides the user the ability to trace a failure condition back to the earliest events associated with the failure to provide a visual display of a failure cascade. Alternatively, individual events and threshold violations may be selected to identify which higher-level objects in which they played a part. In other words, low-level events may be traced forward to understand their relationship within evolving patient instability. This tracing may be accomplished in many ways. For example, the processor 304 may exploit the fact that Alpha events of a relational binary are often the Beta event of a preceding relational binary. This chain of relational binaries provides a powerful tool of analysis. The patient safety visualization processor provides the ability to isolate these binary Chains showing their origin, evolution and resolution.

Alternatively, and in concert, the processor 304 may use the trend of probabilistic momentum. In one embodiment, visualizations may be filtered by the existence and character of binary Chains or a recognizable trend of Probabilistic Momentum. In one embodiment, and if selected by configuration, the patient safety visualization processor provides the ability to navigate into the metadata models at any point within the visualization. event, convergence and image Diagrams or other occurrence definition Visualizations are accessible from objects, which were composed using specified elements within these diagrams within the event definition set 332, binary definition set 344 and image definition set 356. Navigation into the metadata models provides expert care workers and researchers the ability to further understand and/or alter the analysis.

The patient safety console 384 presents a complex set of data and analysis that meets the immediate need of the busy care worker. In one embodiment, analysis at the highest levels may be collapsed into a single pixel stream or group of pixel stream s per patient that provides a simple representation of the evolution of overall patient safety. Within and from that pixel stream the care worker may drill down into the most complex displays: multiple levels of analysis, binary Chains, trends of Probabilistic Momentum and metadata models to name a few. Alternatively this drill down may be provided by for example mouse over, touch screen, or may appear automatically when the processor detects certain adverse patterns or thresholds.

In one embodiment, the object stream visualization focuses on the relationships and cascading of the onset of perturbation within the patient. This is an alternate, and complimentary, view to the pixel stream s described above which focus to a greater extent on the state of discrete elements within the system at various levels of analysis. These two visualizations may be used in parallel and/or provide navigation between them. In the contemplated embodiment, the object stream visualization represents events and threshold violations as icons along a time series in which the icon is placed at the first point in time in which the event or threshold violation occurred. Icons indicate their character by color, size and decorations. The basic icon is an arrow pointing either up or down (as in FIG. 15A). An up arrow indicates a positive movement, which triggered an event whereas the down arrow indicates a negative movement. Boolean changes will be indicated as an up arrow when moving from false to true and a down arrow when moving from true to false. state matches are indicated as an up arrow during match. state transitions are indicated as an up arrow when moving into the state indicated and a down arrow when moving out of the state indicated. threshold violations are indicated as an up arrow if the threshold violation is defined in terms of "greater than" and a down arrow if the threshold violation is defined in terms of "less than". The thickness and/or color of the arrow may be used to indicate the extent of movement.

Decorations on the arrow may be presented to provide visual cues as to the nature of the event. A line underneath the head of the arrow indicates that the event that occurred was a threshold violation. A circle around the arrow (see 979 of FIG. 15A) may be used to indicate that the event was the result of a action or test ordered by the processor 304. Decorations and/or matching colors and/or flashings may be used to indicate a relationship warning by the processor, as in the warning of the potential relationship between the low platelet count and the medication clopidogrel in FIG. 18.

In one embodiment, the patient safety visualization processor will provide automated visual navigation for a specified period of time and/or specified images. This automated visual navigation acts as an analysis-driven video playback of the selected period of time. The healthcare worker selects "Play" and allows the patient safety visualization processor to move visually through the evolution of a specified condition. The healthcare worker may choose navigation movements including "Play", "Pause", "Fast-Forward", "Rewind", "Skip Forward", "Skip Backward", to name a few. In the contemplated embodiment, during Play mode the patient safety visualization processor moves at different speeds through the automated visualization depending on the severity of the condition being displayed. If the time series being displayed have little perturbation (or little perturbation related to the specified failure cascade) the processor will move very quickly through time (i.e. from left to right). When an area of interest, as determined by the processor, comes into vision the patient safety visualization processor will slow the movement from left to right. Further, the patient safety visualization processor will highlight elements that indicate, clarify and specify the evolution and/or cascade of failure as well as their relationships with other elements. The patient safety visualization processor will further display translucent pop-up panels that provide further textual and/or visualization elements to describe the current view and elements within the current view. At any point, the healthcare worker may "Pause" the automated visual navigation to review the displayed data and/or drill into what has been displayed.

In a complimentary embodiment, the healthcare worker may select from a summary view a time span to review and also indicate sections of the time span for which they are interested. The patient safety visualization processor will slow for the areas selected that are of interest and will increase the textual and visualization display appropriately for the highlighted sections. In one embodiment the patient safety visualization processor chooses the object stream s to display and may include or remove stream s as they become important in the video navigation. The healthcare worker may choose to include additional stream s or to "pin" stream s so as to make them always available in the video navigation. missing stream s are also indicated. The patient safety visualization processor may further indicate to the healthcare worker the time required for automated visual navigation (e.g. "Standard visual navigation will require 2 minutes and 37 seconds").

The patient safety visualization processor will include audio and visual elements corresponding to and synchronized with the time series data along with time series data if video and audio feeds are available. In the contemplated embodiment, healthcare workers may include audio and/or video comments into the data stream s to communicate and collaborate regarding elements displayed within the patient safety visualization processor. The patient safety visualization processor may be directed to include all or a specified subset (e.g. "Include Comments from Doctor X") of these elements within the automated visual navigation or may be directed simply to indicate their presence such that the healthcare worker may invoke them as needed.

In one embodiment, the patient safety visualization processor may "record" an automated visual navigation session into a non-interactive video format which may be viewed on standard video equipment, with streaming technology or in a standard media player such that automated visual navigation sessions may be shared with healthcare workers who do not have access to the patient safety image database or the patient safety visualization processor (e.g. as an attachment to an e-mail or accessed from a video-enabled phone).

Figure 4:
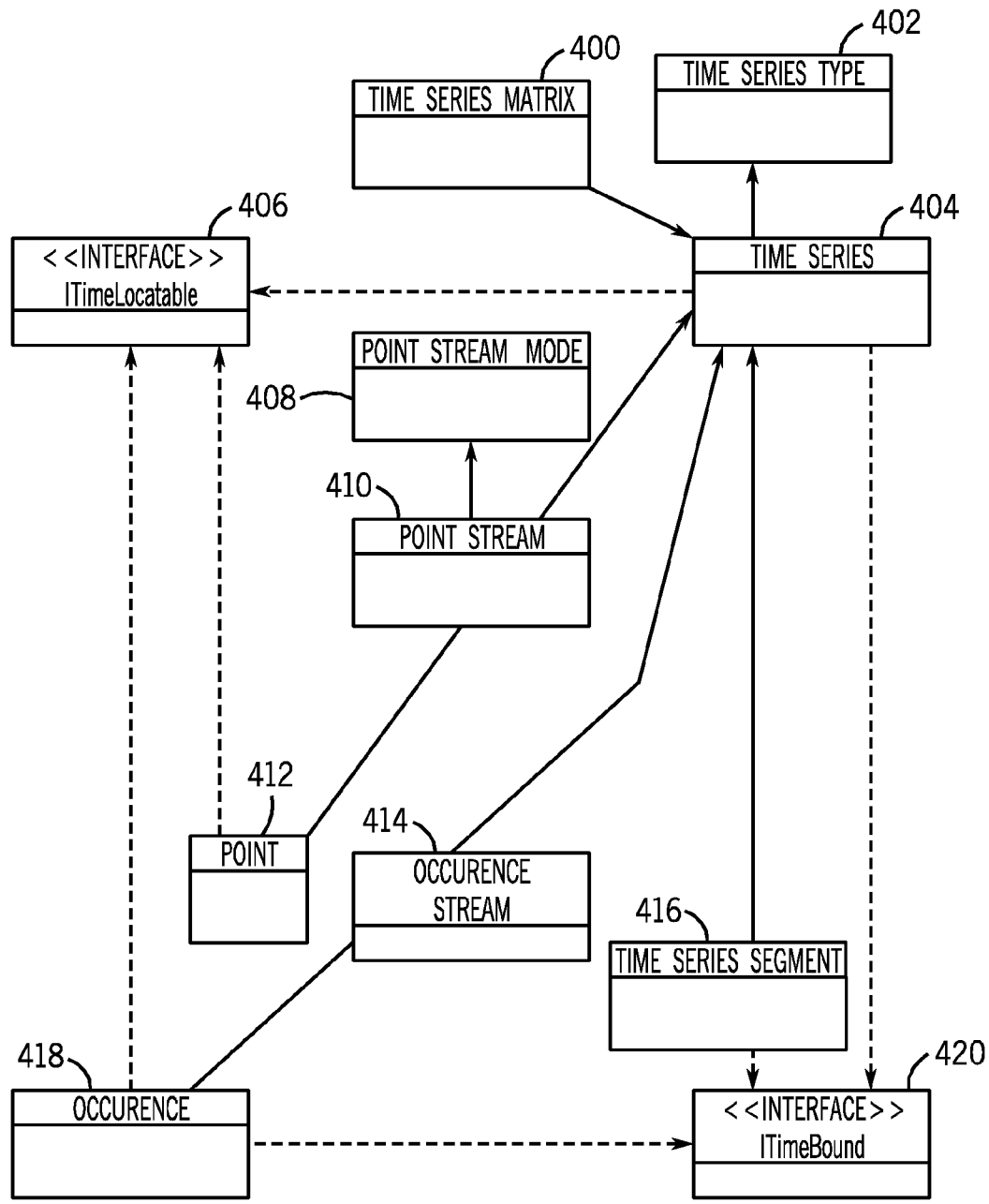
FIG. 4 is an example of a UML static diagram of a time series matrix within one embodiment of a relational binary processor.

FIG. 4 depicts a UML static diagram of the time series matrix within one embodiment of the processor 304. According to the depicted embodiment the most basic time-related element within the processor 304 is a point 412. A point 412 is the value of a signal at a particular instance in time. A point does not have duration, but is locatable in time (implements the interface time locatable 406). Points may be aggregated into an ordered collection within a point stream 410 which is a type of time series 404. Point streams 410 are often referred to as signals. Point streams 410 have two modes 408: numeric and non-numeric. Numeric streams include points values that are integer, floating point, double precision, decimal, positive integers to name a few. Non-numeric point stream modes include point values that are Boolean, domain and freeform string to name a few. Point streams 410 may be continuous or non-continuous. Continuous point stream s have a single sample rate and the points contained therein are equidistant apart in time. Non-continuous point stream s may have any distance between the points in the stream and include a time with each point in the stream point streams 410 represent one kind of time series 404, occurrence stream s 414 represent another. An occurrence 418 is an object representing a happening within time. An occurrence 418 (as show in FIG. 5) may be an event, a relational binary, an image, a repeating occurrence or a pattern occurrence to name a few. An occurrence is locatable in time (implements the interface time locatable 406) but also spans time and therefore has a start time and end time (implemented with a time bound 420 interface). occurrences 418 may be aggregated into a stream ordered by time called an occurrence stream 414. Occurrence stream s may always be converted into a Boolean point stream 410 by creating points with the value "True" for all points in the span in which an occurrence exists and "False" for all points in which an occurrence does not exist.

Having a flexible time series 404 supports the construction of the time series objectification matrix. For example raw signals from monitoring equipment may be contained within numeric point stream 410 whereas complex micro-domains such as images may be stored in occurrence stream s 414. Both of these stream s may be treated similarly as a time series 404. The time series matrix 400 is simply an aggregation of supplied and derived time series 404. The fact that all elements within the streams are time locatable gives the matrix the parallelism that allows time relationships to be identified and aggregated into the scope of an occurrence 418.

Each time series 404 has a single type (time series type 402). For signals this may be defined as the signal type (e.g. oximetry, EKG). The matrix 400 may contain many time series of the same type. For occurrence stream s the time series type is defined by the occurrence definition associated with the definition (e.g. oximetry fall event, Narcotic Induced Instability image). A time series may be broken up into sub-spans called time series segments 416. Both the time series 404 itself and all associated time series segments 416 are time bound 420 (e.g. have a start and end time).

Figure 5:
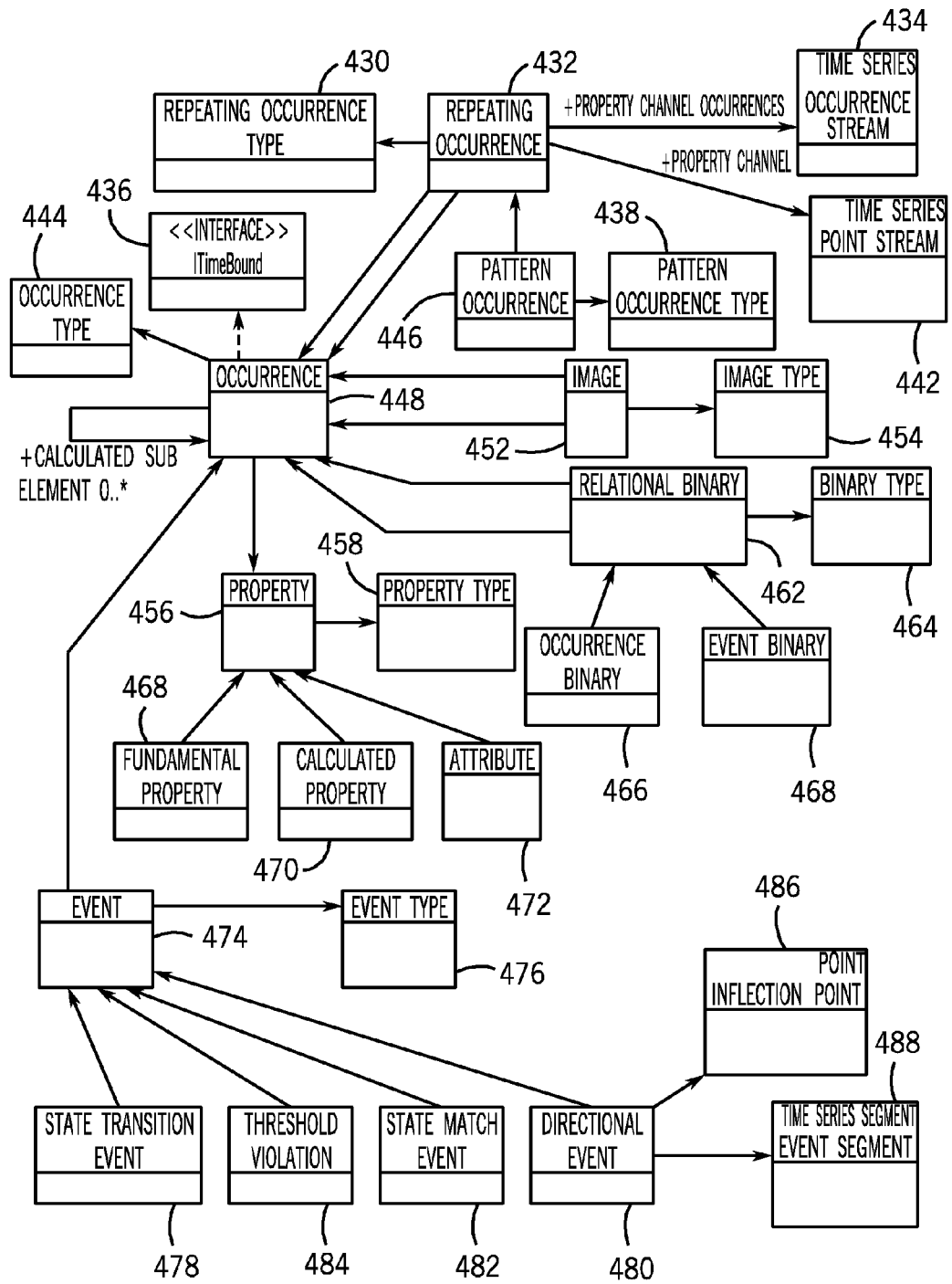
FIG. 5 is an example of a UML static diagram of a subset of classes within a patient safety processor specifically defining a subset of the resultant occurrences and related elements from an analysis.

FIG. 5 is a UML static diagram that depicts, according to one embodiment, a model of the occurrences that may be resultant from a matrix Construction process. Recall from FIG. 4 that the time series matrix 400 is constructed of two types of time series 404—point streams 410 and occurrence stream s 414. FIG. 5 focuses on the fundamental element of the latter of these two—the occurrence 448. Note that the occurrence on FIG. 4 418 and the occurrence on FIG. 5 448 are two views of the same class. The occurrence class 448 is an abstract class (meaning that it is a conceptual class from which other classes are derived and which when instantiated must be sub-classed). The occurrence 448 object represents a happening in time. FIG. 5 depicts several subclasses of occurrence 448 which the processor 304 may identify and create during the matrix creation process. The simplest of these subclasses is the event 474. An event 474 is an occurrence within a single point stream. events 474 are further subclassed into 4 types: directional event 480, threshold violation 484, state match event 482 and state transition event 478. directional events 480 represent an identified unipolar pattern within a point stream 408. threshold violations 484 represent the existence of a breach of some specified, calculated or derived limit within an associated point stream. state match events 482 represent time in which the value within the point stream matched at least one element in a set or fell within a domain defined by a set definition mechanism. A state transition event 478 represents the change from one state to another as defined by points matching an initial set and subsequent points matching a second set either by matching a value or by falling within a domain defined by a set definition mechanism. Alternatively, state transition events 478 may be defined by specifying a state flow diagram or state machine definition and the beginning and end state for the transition.

The processor 304 defines an isolated event as an event identified independent of a relational binary, in other words, an event that does not belong to any relational binary. In an example of a embodiment, a range of events may be defined within a single definition. Range-based definitions allow the user to define all but one parameter within the event definition. For that final parameter, rather than a single value or expression, the user is allowed to define a set of value ranges in which the final parameter may fall. For each range provided, the type of event is specified. In this way a set of related events may be defined.

The processor 304 employs a multistage approach to the identification, creation and refinement of event objects. An initial set of criteria is used to establish the time location of a time series segment, which is established as an event candidate with a specific start and end time within a single point stream. Once this time series segment has been established it becomes a micro-domain within which further properties and elements may be derived. For example, within events established on a numeric time series that are specific to a unipolar trend of data (e.g. directional events 480), the processor 304 will further refine the trend by looking for smaller changes in the trend. The processor 304 calls points of change within the trend Inflection points 486. Once inflection points are determined then the event is broken up into smaller segments called event segments 488. In one embodiment Inflection points 486 are derived in three ways:

1. At each point within the candidate event, the slope difference between the preceding and subsequent dipole is measured. If the absolute value of this difference meets a specific threshold then the point examined is designated as an Inflection point 486.
2. Moving through the candidate event, the processor 304 establishes an initial slope as the slope of the first dipole within the candidate event. The processor 304 then creates a series of evaluation event segments using an increasing number of dipoles (first two, then three and so on) within the candidate event. For each of these evaluation segments the slope is calculated. If the absolute value of the difference between the initial slope and the evaluation segment slope meets a specified threshold then the processor 304 determines that an inflection point has occurred within the evaluation segment. Then the evaluation segment is examined at each point (starting with the second point) calculating the absolute value of the difference between the slope of the segment before the point and the slope of the segment after the point. When this difference is greater than 50% of the threshold used to establish the existence of an Inflection point 486 then the point being examined is determined as the Inflection point 486 and a segment is created from the beginning of the candidate event to this point. Once this inflection point has been established then the first dipole after that point becomes the initial slope to be evaluated against and the process begins again until the end of the candidate event is reached at which, if any inflection points were found, the final segment is added as an event segment.
3. Finally the slope of each dipole may be placed into a time series and that time series examined looking for state transition events 478. Each point at which a state transition occurs is established as an inflection point and the intervening dipoles are aggregated as event segments. For example, within oximetry the researcher may establish two slope ranges—slow descent and rapid descent. The processor 304 will walk the dipole stream looking for a point at which the previous and subsequent dipoles fall into the two different ranges.

When this occurs, the processor 304 would designate the point as an inflection point (designated as "Change from slow descent to rapid descent") and the event segments created would be characterized "Slow Descent" and "Rapid Descent".

The creation of sub-objects (e.g. inflection points and event segments) within an event provides a wide array of elements against which the definition of the event may be refined. For example, the researcher may decide to create an event type 476, which must include a "Slow Descent" segment followed by a "Rapid Descent" segment. The researcher may choose to remove the "Slow Descent" portion of the candidate event from the final event, or split the candidate event into two separate events. Alternatively, the researcher may not choose to use these elements and their properties as part of the criteria (e.g. used to accept or reject) but may use them to characterize the event (as per, for example, the assigning of attributes described below).

For each event 474 there is an event type 476 which identifies the type of micro-domain which has been created. The event type is associated with the definition used to identify, construct and qualify the event. For example, a researcher may create an oximetry Rise event as an event type 476 which defines a positive directional event 480 within the oximetry point stream. The definition for the event (depicted in FIG. 8a) provides the parameters which the processor 304 uses to search for, construct and qualify an oximetry Rise event. The event type 476 provides the researcher a way to specify a particular pattern which then may be associated with other more complex occurrences (e.g. an image). In this way the event type 476 provides an abstraction which simplifies the reference to a particular pattern. The term type is used this way throughout the UML diagrams as the reference to a particular definition. The type, therefore, provides the link between the instance of a pattern (or other object) and the definition of a pattern (or other object).

Another subclass of occurrence 448, within this embodiment, is the relational binary 462. The relational binary comes in two subclasses: occurrence binary 466 and event binary 468. The relational binary is depicted more completely on FIG. 6. The binary type 464 expresses the specific binary pattern found as defined in the uniquely associated binary definition (See FIG. 8B). Another subclass of occurrence 448, within this embodiment, is the image 452. The image 452 represents an aggregation of one or more occurrences 448. The image type 454 expresses the specific occurrence pattern found as defined in the uniquely associated image definition (See FIG. 8C).

During matrix construction, the processor 304, by default, aggregates and analyzes repeating objects. The processor 304, after identifying an occurrence, reviews the object stream for other occurrences proximate within the associated stream s. By default, the processor 304 looks for repeating occurrences 432 (e.g. occurrences of the same occurrence mode (e.g. relational binary) and occurrence type (e.g. oxygen reciprocation)). Each occurrence type definition specifies a minimum recurrence count as well as a recurrence threshold time span by which the processor 304 may determine whether or not to aggregate occurrences of the same type into a repeating occurrence object. In one embodiment, the recurrence threshold may be specified either as a fixed time span or as a series of time spans depending on the state of the aggregation process. For example, the definition may include an initial recurrence threshold (a maximum time span allowed between the first and second occurrence) and a subsequent recurrence threshold (a maximum time span allowed between any subsequent two occurrences). In one embodiment, this threshold may be a function (e.g. the time being increased incrementally by the number of occurrences that have already been aggregated).

Figure 27:
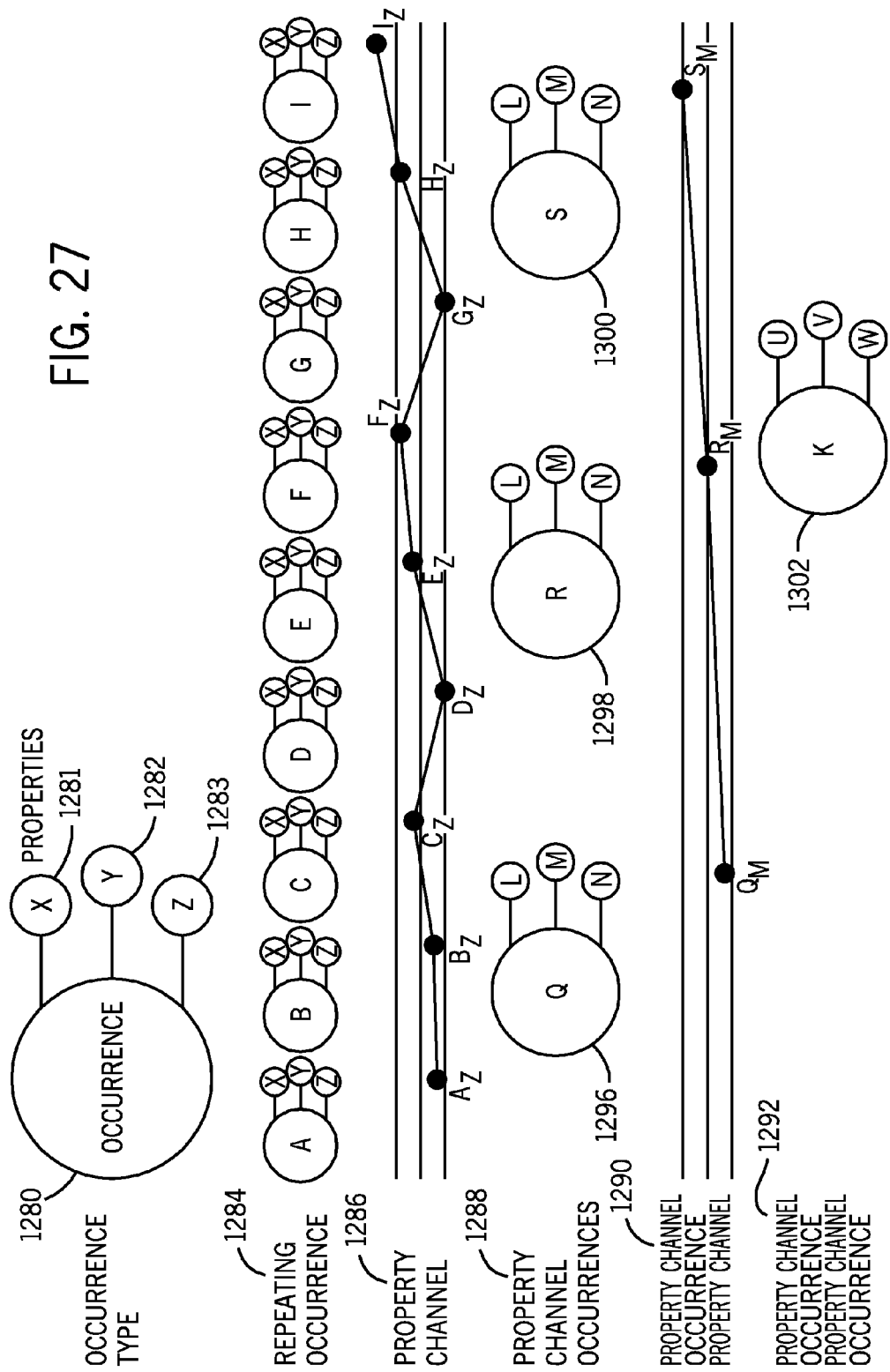
FIG. 27 is a diagram depicting the generation of property channels within a repeating occurrence micro-domain.

Once the processor 304 has identified a repeating occurrence 432 and has aggregated occurrences within this object, the processor 304 will create a point stream 442 for all properties of the specific type of occurrence being aggregated called a property channel 442. FIG. 27 provides a diagram to illustrate the role of property channels 442 within a repeating occurrence 432. For example, consider when the processor 304 is searching for a specific occurrence 1280 which is an oxygen fall event. If the processor 304 has aggregated 9 fall events into a repeating occurrence 1284 then a property channel 1286 (442 in FIG. 5) will be created of the slope of the fall events within the aggregation. In FIG. 27, the circles (1281, 1282, and 1283) attached to the occurrence 1280 represent properties of the occurrence. In this case, the property channel 1286 (442 in FIG. 5) will have 10 points (shown as $A_z$ through $I_z$) with each point representing the magnitude of one fall event within the repeating occurrence 1284 (432 in FIG. 5). In another example, the nadirs of the oxygen reciprocation would constitute a property channel 442.

These property channels 442 are attached to the repeating occurrence 432 and may be accessed through the repeating occurrence 432 object. Further, these property channels may be analyzed through the time series objectification processor, the relational binary processor and the Imaging Processor to create occurrences within and between the property channels and/or between occurrences within the property channels and other point streams or occurrence streams in the system. For example, in FIG. 27 the points in the property channel 1286 (which represent the magnitude of fall events (the property designated as 'Z' 1283) within the repeating occurrence 1284 of fall events) when aggregated into a property channel create dipoles that have slope. Within this point stream we may see that these points may be broken up into unidirectional segments. The first segment ($A_z$, $B_z$, $C_z$) has a positive slope indicating that the magnitude of the fall event within the repeating occurrence 1284 is trending to be larger. These three points may be aggregated into an event depicted as occurrence Q 1296. This occurrence will have its own properties (depicted as the attached circles L, M and N) according to the event definition of this occurrence channel. The second segment ($C_z$, $D_z$) does not qualify as an event (because of duration requirements, for example). The third segment ($D_z$, $E_z$, $F_z$) does meet criteria and forms a second event depicted as occurrence R 1298. The fourth segment ($F_z$, $G_z$) does not meet event criteria. The fifth segment ($G_z$, $H_z$, $I_z$) meets criteria and forms a third event depicted as occurrence S 1300. Since these events identified in the context of a property channel 1286 of a repeating occurrence 1284 are occurrences in their own right, they are aggregated into an occurrence channel 1288. Further, as in the example depicted, occurrences that repeat may be aggregated into repeating occurrences. So occurrences Q, R and S (1296, 1298 and 1300) may be aggregated into a repeating occurrence and the properties of the events may form a property channel 1290 which may be analyzed to find events (as event K 1302 constructed from points $Q_M$, $R_M$, $S_M$) which may be aggregated into occurrence channels 1291. In other words, the process may be recursively applied.

One species of repeating occurrence 432 is cycling. Cycling is a specific type of repeating occurrence in which there is a repeating occurrence 4332 of a relational binary 462 made up of a perturbation event is followed by an event returning the system to normal. A repeating occurrence 432 with a property moving in a specific direction is called a trending recurrence. A trending recurrence is a specific type of repeating occurrence 432. repeating occurrences 432 may be trending in more than one property. The relationship between occurrences within a repeating occurrence supplies additional properties, which are placed in a point stream and analyzed. For example, the time between occurrences is tracked. As an example, consider 9 fall events that are aggregated into a repeating occurrence 432. In this case a property channel 442 of 8 points will be created of the time spans between the occurrences within the aggregation.

The processor 304 may not create a definition for each repeating occurrence. A definition may be constructed from the minimum recurrence count and recurrent thresholds supplied within the occurrence type definitions. The processor 304 allows repeating occurrence definitions to be created to add additional criteria to the identification process and/or to add calculated properties and/or attributes to the repeating occurrence 432. In these cases where a specific definition is created, the researcher must indicate whether the user-defined definition replaces the default definition, or is to be identified in addition to the default definition. In this way, the researcher may identify any number of specific types of repeating occurrences 432 for a single occurrence type 444 (e.g. oxygen fall event).

The researcher may also select to suppress repetition for any occurrence type 444 causing the processor 304 to ignore repeating occurrences 432 for the specified occurrence type 444. A repeating occurrence 432 is itself an occurrence and therefore may repeat. Recurrent repeating occurrences (which in themselves are simply repeating occurrences 432 of repeating occurrences 432) will create property channels for the properties of the repeating occurrences 432 contained within. For example, the number of occurrences within a repeating occurrence will be aggregated into a property channel 442. As with the repeating occurrence 432, the Recurrent repeating occurrence does not require a definition, but the researcher may provide a definition to add additional criteria and/or specify calculated properties and/or attributes. repeating occurrences 432 and Recurrent repeating occurrences may be elements of an image 452. In particular, the processor 304 recognizes a particular type of image designated a deviation image. In a deviation image a repeating occurrence 432 is followed by a specific image or set of images that represent a deviation from an established cyclic phenomenon. narcotic-induced ventilation instability is one such deviation image. In this case, the physiologic response to an oxygen desaturation event has set up a repeating occurrence 432 of convergent oxygen reciprocation binaries. If this repeating occurrence 432 is followed by a narcotic therapy event and then a divergent oxygen reciprocation binary the processor 304 will identify the narcotic-induced ventilation instability deviation image. In one embodiment, deviation images include additional fundamental properties including the point of deviation—the time at which the repeating occurrence ended.

repeating occurrences 432 may be identified for any occurrence types including images 452, therefore many repeating patterns of occurrence may be addressed with this mechanism. For example, if A and B are images, then the pattern ABABAB may be identified as the repeating occurrence of an image defined as AB. Patterns that are more complicated than simple repetition are addressed in the processor 304 with the pattern occurrence 446. The pattern occurrence 446 defines a pattern in terms of other occurrences. Researchers first define the set of occurrence types which will be used at least once in the pattern and define each a mnemonic. For example, the researcher may choose 3 images and assign them the mnemonics A, B and C. Mnemonics are alphanumeric representations of occurrences used as a reference to an occurrence type. Once the set of occurrence types has been selected and mnemonics assigned the researcher may define the pattern in terms of the mnemonics separating them with brackets. For example, the researcher may define a pattern as [A][B][A][C][A][B][A]. In one embodiment, a pattern occurrence 446 may have a set of patterns, any of which, if matched, will cause a pattern occurrence to be created. pattern occurrences 446 are defined as a subclass of repeating occurrence 432 and therefore have property channels 442 in the same way that repeating occurrences 432 have property channels 442, but, since the members of the pattern occurrence 446 are of different types, the property channels are only created for properties that match within the pattern occurrence. For example, in the example above (with the pattern [A][B][A][C][A][B][A]), there will be property channels 442 containing 7 points for properties that exist in A, B and C. For properties that exist only in A and B, there will be property channels with 6 points. pattern occurrences 446 are occurrences themselves and therefore the processor 304 will automatically identify repeating pattern occurrences as described above.

When the processor 304 identifies an occurrence 448 (or candidate occurrence) the aggregation of all elements within that occurrence becomes a micro-domain. Relationships, properties and elements within this micro-domain have meaning because they exist within the specific context of the occurrence. The processor 304 provides for mechanisms to exploit this fact and to allow the researcher to specify properties that reflect the new meaning of properties and the relationship between elements within the micro-domain of a specific occurrence type 444. When an occurrence 448 is identified it has a set of properties 456 or values that the processor 304 identifies, calculates and/or assigns. There are three types of properties 456—fundamental properties 468, calculated properties 470 and attributes 472. Fundamental properties 468 are defined by the processor 304 depending on the occurrence mode and the nature of the associated point stream or occurrence stream. For example, all occurrences have the fundamental properties of start time, end time and duration to name a few. As another example, all occurrences that are events 474 on a numeric point stream have a magnitude and slope to name a few. As another example, repeating occurrences 432 have a member count and mean separation duration to name a few.

Calculated properties 470 and attributes 472 are properties 456 that have an expression-based definition. The processor 304 uses this mechanism to refine processor 304-specific occurrence objects and elements (as an example Inflection points 486). The researcher is also able to define these properties and store these definitions with the occurrence definition (See FIG. 7A). The results of these expressions are attached to the occurrence 448 and available within the matrix.

Figure 6:
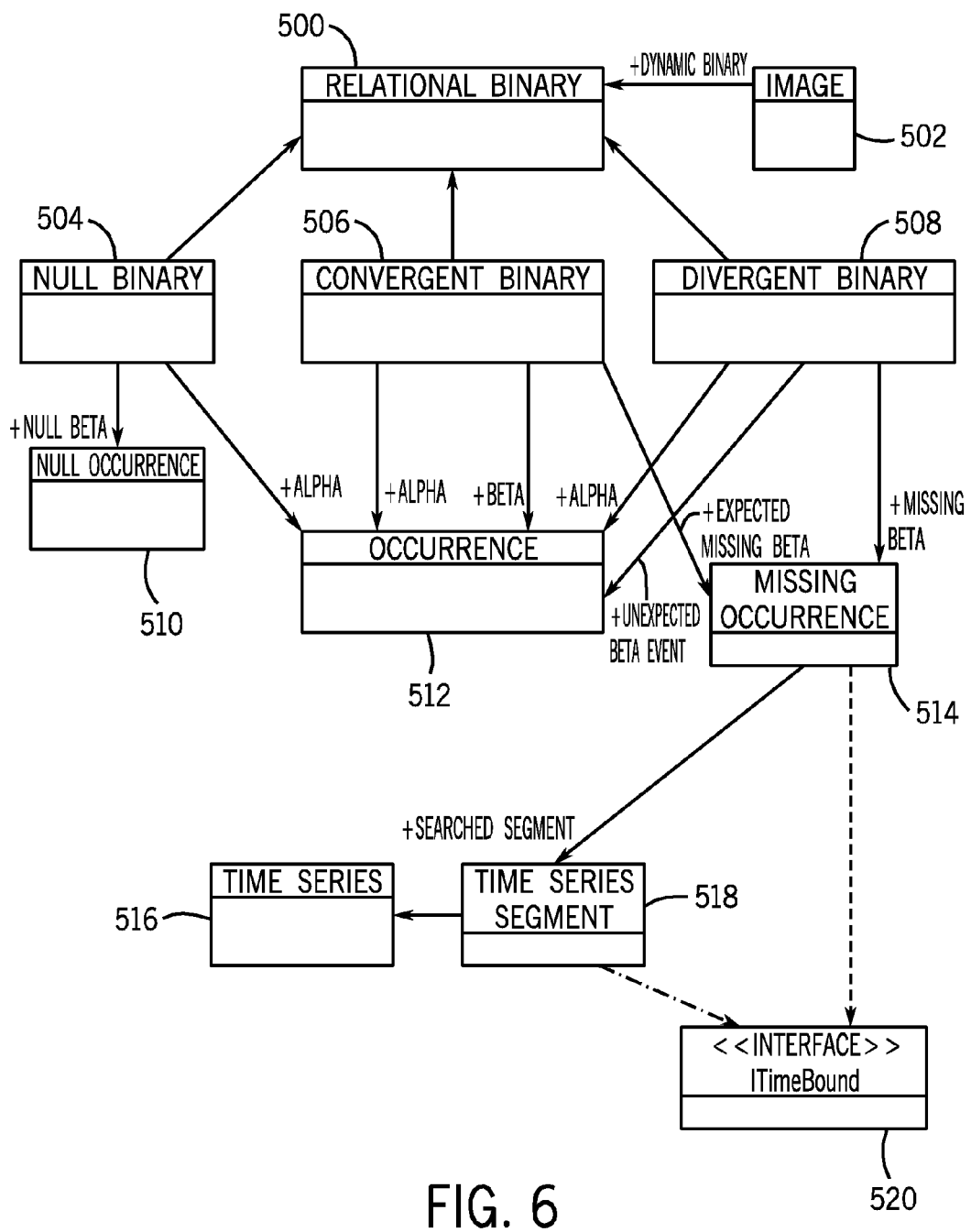
FIG. 6 is an example of a UML static diagram of a subset of classes within a patient safety processor specifically modeling the binaries resultant from an analysis.

FIG. 6 depicts a UML static diagram of a subset of classes within the processor 304 specifically modeling the relational binaries resultant from an analysis. may According to one embodiment, there are three subclasses of relational binaries 500; the convergent binary 506, the divergent binary 508 and a null binary 504. (Although others relational binaries may be provided). These three subclasses do not represent three different types of binaries with different binary definitions, but rather the 3 forms (call binary Mode) that a binary created from a single binary definition may take.

In summary the three modes are described as follows:
1. convergent binary—the mode in which the Alpha and Beta occurrences were identified as expected
2. divergent binary—the mode in which the Alpha occurrence was identified but the Beta element was not found as expected
3. null binary—the mode in which the Alpha occurrence was identified but the time series (or set of time series) in which the Beta element was specified is missing, corrupted or otherwise unavailable.

The three modes are described below in more detail. A convergent binary 506 represents a relational binary wherein the processor 304 has identified the Beta occurrence which has been defined as having an expected relationship to the Alpha occurrence. A convergent binary 506 may have either a true occurrence 512 or a missing occurrence 514 as a beta depending on what has been specified as the expected condition. If a true occurrence 512 was specified in the relational binary definition (See FIG. 8*b*) then the associated convergent binary 506 may have a true occurrence 512 as a Beta. If a missing occurrence 514 was specified then the associated convergent binary 506 may have a missing occurrence 514 as a Beta. The class structure therefore allows for zero or one occurrence 512 and zero or one missing occurrence 514. In a presently contemplated embodiment a convergent binary 506 may not contain two Beta occurrences (missing or True).

divergent binaries 508 represent a pair of occurrences identified in a relationship that contradicts the expected relationship as described in the binary definition. Therefore a divergent binary 508 may have either a true occurrence 512 or a missing occurrence 514 as a Beta depending on what has been specified as the expected condition. If a True occurrence 512 was specified in the binary definition then the associated divergent binary 508 may have a missing occurrence 514 as a Beta. If a missing occurrence 514 was specified then the associated divergent binary 508 may have a True occurrence 512 as a Beta. The class structure therefore allows for zero or one occurrence 512 and zero or one missing occurrence 514. According to one embodiment, a divergent binary 508 may not contain two Beta occurrences.

Null binaries 504 represent the existence of a condition in which an alpha occurrence was identified but the data stream (or stream s) from which the expected beta event is to be derived is unavailable to the processor 304. A missing occurrence 514 is associated with a set of time series segments 518 that represents the areas within the matrix that was searched for the occurrence described as expected in the binary definition. Null occurrences 510 are not associated with time series segments 518 because at least one time series to which they would have been attached or the relevant section of that time series is unavailable or corrupted. The processor 304 will convert null binaries 504 to convergent 506 or divergent 508 binaries as new time series or time series segments become available and analysis is executed. An occurrence 512 may be the Beta occurrence of a first relational binary 500 and the Alpha occurrence of a second relational binary 500.

In one embodiment occurrence stream s are stored as divergent binary streams and convergent binary streams. In the alternative or in combination, all such stream s or a portion of specific stream s or a grouping of stream s filtered for severity of divergence (for example) may be aggregated and rendered for periodic viewing wherein, for example, the temporal relationships of for example divergent binaries or of the occurring images are easily recognized or specifically indicated.

To further clarify this structure it may be useful to describe the order of operation within an example of a embodiment of the processor 304 as it constructs the analysis according to one embodiment.
1. The processor 304 selects a relational binary type for which the dependencies have been shown to be available; then
2. The time series that are associated with the relational binary definition are iterated through to match any identified occurrences 512 with candidate Alpha occurrences (as defined in the specified binary definition). A single occurrence 512 may match any number of Alpha occurrence definitions and each one is considered a candidate Alpha occurrence.
   a. For each candidate Alpha occurrence, the specified search region is examined for the expected Beta occurrence
      i. If any of the time series in which the expected Beta occurrence is unavailable or corrupted
         1. A null binary 504 is created (along with its associated Null occurrence 510)
   b. If the expected Beta is located and the specified conditions obtain
      i. A convergent occurrence 506 is created
   c. If the expected Beta is not located or the specified conditions do not obtain
      i. A divergent binary is created 508

The actual relationship between the alpha and beta events, which include the object binaries, is not necessarily defined by cause and effect (which may not be known with complete certainty) but is rather defined by the pattern relationship such as a temporal, spatial, and/or frequency relationship of the occurrences, or simply by their prior designation as a relational pair. For example, the actual relationship between the alpha and beta occurrences including a given relational binary could be a cause and effect, two effects resulting from an unmonitored cause, a relationship between two monitoring technologies measuring the same physiological phenomenon, an expected compensatory response, or a pathologic response, to name a few. Once the general association has been captured within the binary then the relationship between the occurrences within the binary is examined to determine if the relationship meets the requirements for the determination of a higher level of relationship (e.g. cause and effect, compensatory response to name a few). Though the focus of FIG. 6 is relational binaries 500, it also depicts the structure of images 502. The processor 304 creates images by aggregating dynamic binaries 500.

Specifically, the search for an image may be reduced to successive searches for occurrence binaries. An image is defined by a set of occurrences and their relationships within the image. Two sets of occurrence sets are defined—Sequenced and Non-Sequenced. Sequenced occurrences are defined with a time relationship to at least one other occurrence within the image. Non-Sequenced occurrences are defined only with a time relationship to the span of the overall image. (See FIG. 8*c* for a complete description of the definition).

The process of searching for an image starts with making sure that all of the constituent occurrences types have already been processed for construction and the resultant occurrence stream s have been placed into the matrix. At this point the overall search region (a single patient stay, for example) is reviews to gather the counts of the constituent occurrences within the region. If any of the required occurrences has a count of zero within the target region then the search for the specific image type may be abandoned. (In an alternative embodiment, the processor 304 continues to construct the image as much as possible so as to store "Near Miss" images for research or analysis purposes.) Next the Sequenced set of occurrences is processed first. Sequenced occurrences have a specified time relationship to at least one other occurrence type within the image and therefore may easily be aggregated into dynamic binaries 500. For example, if three occurrence types are specified as A, B and C; A is defined as preceding B and B is defined as preceding C then the processor 304 may aggregate this set of 3 occurrence types into 2 dynamic binaries to search for. The first dynamic binary is created by choosing A as the Alpha occurrence and B as an expected Beta occurrence. This dynamic binary is searched for within the target region and the resultant dynamic occurrence stream is placed back into the matrix. Once the [A→B] dynamic binary has been processed, then the second dynamic binary may be created as a binary having the dynamic [A→B] binary as the Alpha and the C occurrence type as the Beta (described as [[A→B]→C]. If only the time relationship has been specified between the constituent sequenced occurrences (as opposed to, say specific related properties within the created micro-domain), then the order of the dynamic aggregation of binaries is not required to follow the sequence. In other words, the processor 304 may, for performance or other reasons, choose to aggregate B and C first as [B→C] and then aggregate A as [A→[B→C]]. Since the process of searching for binary occurrence is equivalent for searching for a single occurrence (when only the time relationship is specified) then the results are the same. In this way, any number of sequenced occurrence types may be processed to find their existence within the target time region.

non-sequenced occurrence types are searched somewhat differently because of their unstructured nature. First the occurrence counts of all specified non-sequenced occurrence types are placed into a set and sorted from least to greatest as far as their count within the target region. In an example of a embodiment the processor 304 begins with the least count occurrences and proceeds through greater count occurrences to maximize performance. For each occurrence type within the non-sequenced set a dynamic binary is created first with the resultant occurrence created by aggregating all of the Sequenced occurrence types (as [A→[B→C]] in the above example) and then with all of the other Non-Sequenced occurrence types. Continuing the example above, if two Non-Sequenced occurrence types are specified D and E, then the following set of dynamic binaries would be created and processed: [D→[A→[B→C]]], [D→E], and [E→[A→[B→C]]]), [E→D]. In certain cases, the reverse dynamic binaries (both [D→E] and [E→D] are not required.

An image may also specify that a specific occurrence must not be found proximate to the rest of the image. In this case processor 304 will use the verify non-existence relationship within the dynamic binaries created. If multiple occurrences of a dynamic binary are found during the image identification process the processor 304 will select which of the occurrences to include into the image. (In one embodiment, pruned constituent occurrences are stored for research or analysis purposes.) The selection may be directed by researcher specifications so as to minimize time relationships within the image or may be directed to maximize the overall span of the image 434. Dependencies may also be a factor. For example, if a more proximate occurrence being selected destroys a dynamic binary required for image completion the processor 304 may select a different occurrence to be maintained though it is less proximate. This decision may be directed by the researcher according to the nature of the micro-domain and its relationship to physiological forces.

Occurrence stream s created from dynamic binary types will be maintained within the matrix if the target image is found. If the target image is not found, the processor 304 may be configured to remove the dynamic binary occurrence stream s since they are relevant only within the context of the given image micro-domain. image Identification is completed if and when all of the dynamic binaries that are created generate occurrences that match the required time relationships. When this occurs the constituent occurrences are aggregated into a micro-domain establishing the scope of the image. At this point further stages of construction may proceed to generate properties, relationship and sub-elements, refine scope and finally to qualify the image to see if it is a true image or a disqualified candidate.

Figure 7A:
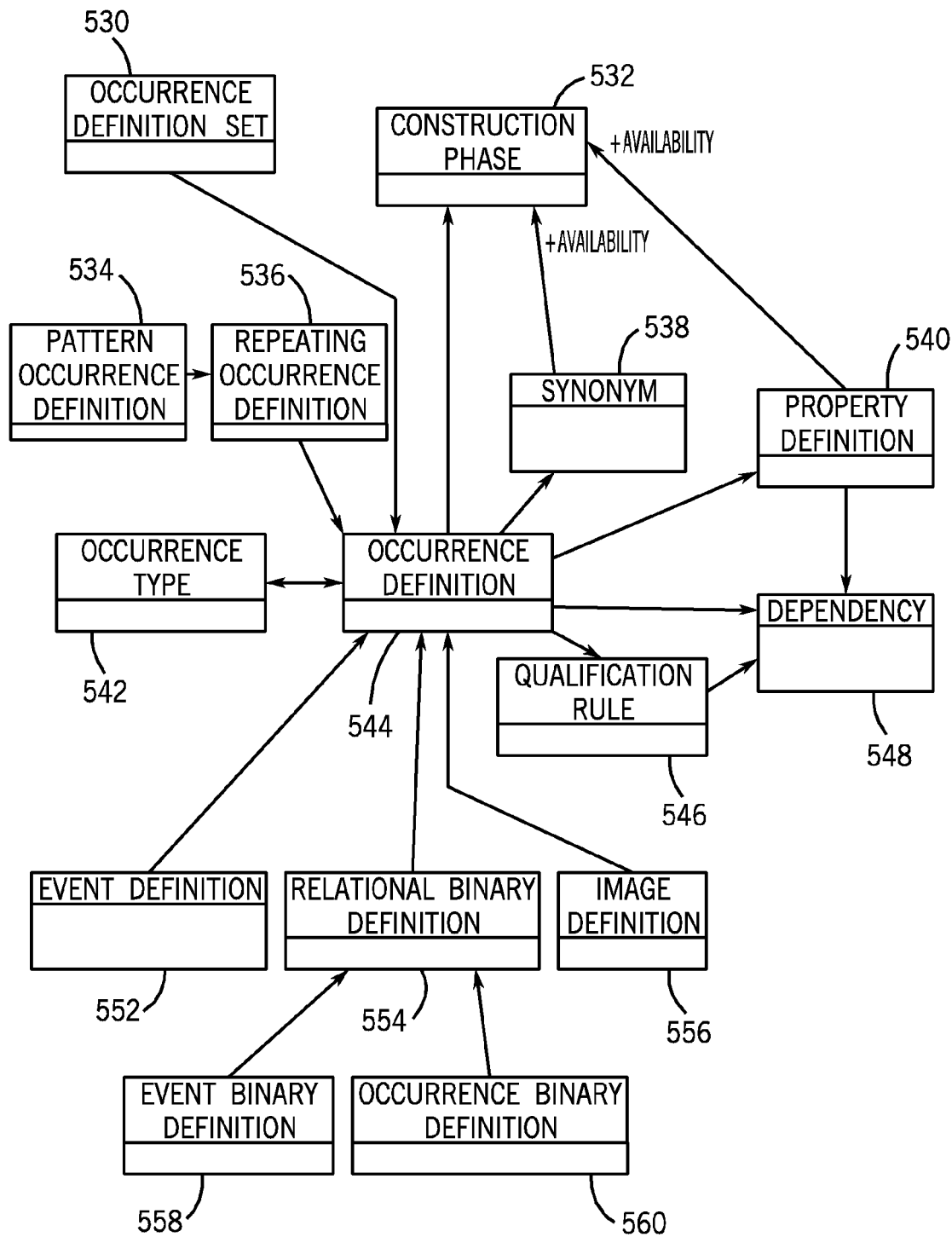
FIG. 7A is a UML static diagram of a subset of classes within the patient safety processor specifically modeling the an occurrence definition set used by the patient safety processor to identify, construct and qualify occurrences.

FIG. 7A is a UML static diagram depicting a subset of classes within the processor 304 specifically modeling the occurrence definition set 530 used by the processor 304 to identify, construct and qualify occurrences. An occurrence definition set 530 is an aggregation of occurrence definitions 544. In one exemplary embodiment, the processor 304 applies an occurrence definition set to a set of raw point streams to create the objectified time-series matrix. An occurrence definition 544 is metadata used to identify, construct and qualify an occurrence within the matrix. Once an occurrence has been created it is linked through its occurrence type 542 to the specific occurrence definition from which it was created. Every occurrence definition contains four aggregations of sub-elements: property definitions 540, Synonyms 538, Qualification Rules 546 and Dependencies 548. properties definitions 540 provide the ability, once a micro-domain scope has been established, to refine, quantify, highlight and further express the nature of the micro-domain. There are three types of properties: fundamental properties, calculated properties and attributes (as described in FIG. 5). Fundamental properties are defined by the processor 304 and may or may not have an explicit definition in the occurrence definition set. Calculated properties and attributes will have a definition in the occurrence definition set associated with a specific occurrence type.

In one embodiment, a researcher may specify an inheritance relationship between occurrence types. With this mechanism, all of the properties associated with the parent occurrence type will be defined in the child type. In this way, an "Is-A" relationship may be established. Calculated properties definitions are a type of property definition 540 defined with a name and an expression. The expression may contain references to any number of other properties 456 (Fundamental properties, Calculated properties or attributes). This mechanism may be used simply to rename certain fundamental properties within the context of the occurrence definition 544. For example, if a binary type called an oxygen reciprocation binary is defined as a fall event (Alpha) and a Rise event (Beta), then the oxygen reciprocation binary may include a calculated property called Magnitude Ratio which is defined as "=Alpha.Magnitude/Beta.Magnitude". The processor 304 verifies submitted expressions for validity. Calculated properties have access within their expressions to a set of functions. Functions available include mathematical functions (Absolute Value, Square Root, to name a few), aggregation functions (Mean, Count, Sum, to name a few) and relational conversion functions (Relative To, time Span From, to name a few) to name a few.

In one embodiment, to assist with cross-channel expressions the processor 304 provides functions and values that may be included in these expressions. The Relative To function provides the ability to derive a percentage relative to a target element. Further, the processor 304 allows evaluations relative to the ranges of associated time series. This value is called Normalized and has a specific function. The processor 304 and researcher may create additional properties called attributes using an attribute definition. attributes are properties that are assigned based on condition being true. attribute definitions have three parts: Conditional Expression, attribute Name and Value Expression. If the Conditional Expression is found to be true then the Value Expression is evaluated and the result is assigned to the property with the name provided in the attribute Name. The Value Expression is of the same format as the calculated property expression. The Conditional Expression uses the format of the calculated property expression but also requires at least one Boolean operator (.e.g. "alpha.Magnitude>4) or property.

In an alternative embodiment, Calculated properties and attributes may be defined and/or assigned with an embedded programming language (e.g. a scripting language). In one embodiment, to assist with expressions, the processor 304 provides a mechanism to define Synonyms 538 within the occurrence definition 544. Both elements and properties may be defined as a Synonym. For example an oxygen reciprocation binary may contain a Synonym called Recovery which is defined as "=Beta" and another Synonym may be called desaturation and be defined as "=Alpha". Synonyms are simply symbolic replacements for use within expressions, conditions and search criteria. The processor 304 will pre-process all expressions to replace synonyms before evaluation. For example, now the Magnitude Ratio above could be defined as "=Recovery Magnitude/desaturation.Magnitude". In one embodiment each occurrence must go through a qualification stage to determine its veracity as an occurrence of the type specified. This qualification process uses Qualification Rules 546 that are attached to the occurrence definition. In one embodiment the subsequent stage of qualification is accomplished through a rule set applied to the properties within the candidate occurrence. In an alternative embodiment, the candidate is run through a series of preservation and rejection tests. Preservation and rejection tests may be designated as absolute (e.g. if this state obtains, reject the candidate with no further evaluation) or may be aggregated into a set of overrides. In the second case the rules are created in the format: "Preserve if X unless Y" and/or "Reject if M unless N" where X,Y,M and N may represent any Boolean expression over the occurrence candidate's properties.

In the contemplated embodiment, the processor 304 maintains (or is able to derive) the Dependency 548 of all occurrence definitions 544, property definitions 540 and Qualification Rules 548. This dependency works down to the Fundamental property level. The processor 304 may then, given these dependencies, determine whether certain Fundamental properties, Calculated properties and/or attributes may be left unevaluated or their evaluation delayed. For example, if an attribute is created by the researcher but not used (directly or indirectly) then the processor 304 will leave the attribute unevaluated. If at some future time, for example during display by the patient safety visualization processor, this attribute is requested then the processor 304 will execute evaluation. The management of dependencies also allows for caching strategies in which the processor 304 stores the results of evaluation during execution and/or persistence, but may accurately recognize the need for re-evaluation if any of the dependent properties have been changed. Further, within the instance of an occurrence, not only are the dependencies well understood, but the values of each element within the dependencies are known. Given this fact, the researcher or care worker may drill down into occurrence instances to understand both the metadata and data dependencies of the selected occurrence. For example, within a oxygen Cluster (for example, defined as a repeating occurrence of oxygen reciprocation binaries), the caseworker may see not only the value of a specified property (for example, an instability index), the structure of calculation that created the property and the specific occurrences and the values of their properties that participated in the final value.

Finally, an occurrence definition is associated with a set of ordered Construction Phases 532. Elements within the occurrence definition 544 may be associated with a specific Construction Phase to indicate to the processor 304 when it is appropriate to identify, create or evaluate the sub-element. For example, if constituent occurrence types are marked with the Construction Phase "Scope", then the marked occurrence types are required for establishing the occurrence as a candidate occurrence. If they are marked with a subsequent phase then the constituent occurrence is added after scoping to refine the scope. properties marked with a specific Scope are not evaluated until the specified phase is being executed. Qualification Rules are automatically considered in the Qualification Construction Phase.

Occurrence definitions 544 are subclassed into a set of definitions classes that represent the type of patterns that the processor 304 may search for. Specifically, occurrence definition 544 is subclassed into event definition 552, relational binary definition 554, image definition 556 and repeating occurrence definition 536. The repeating occurrence definition is further subclassed into pattern occurrence definition. The relational binary definition is subclassed into event binary definition and occurrence binary definition (for more detail see FIG. 8B). The event definition is further subclassed as well (see FIG. 8A).

Figure 7B:
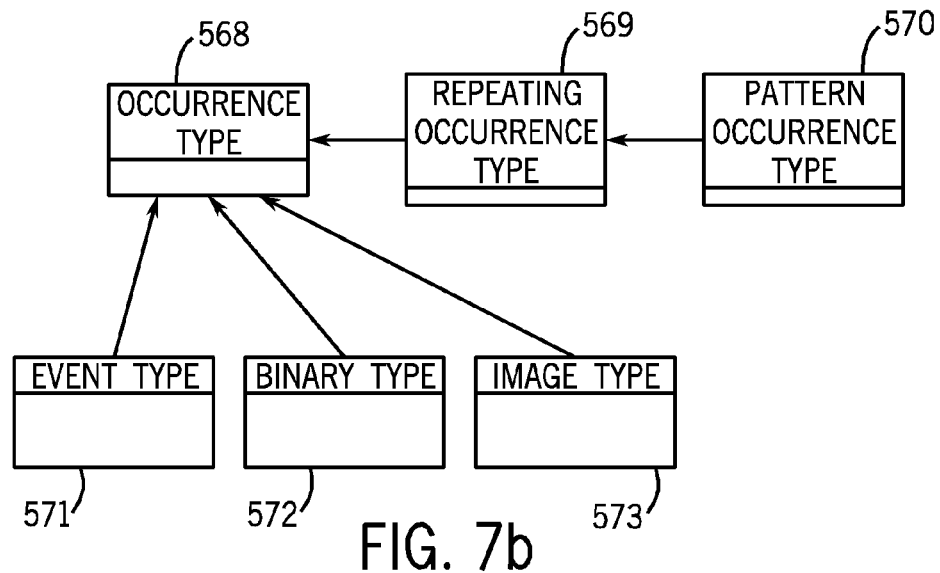
FIG. 7B is a UML static diagram of a subset of classes within the patient safety processor specifically modeling the an occurrence types used to link created occurrences with their definition.
Figure 8A:
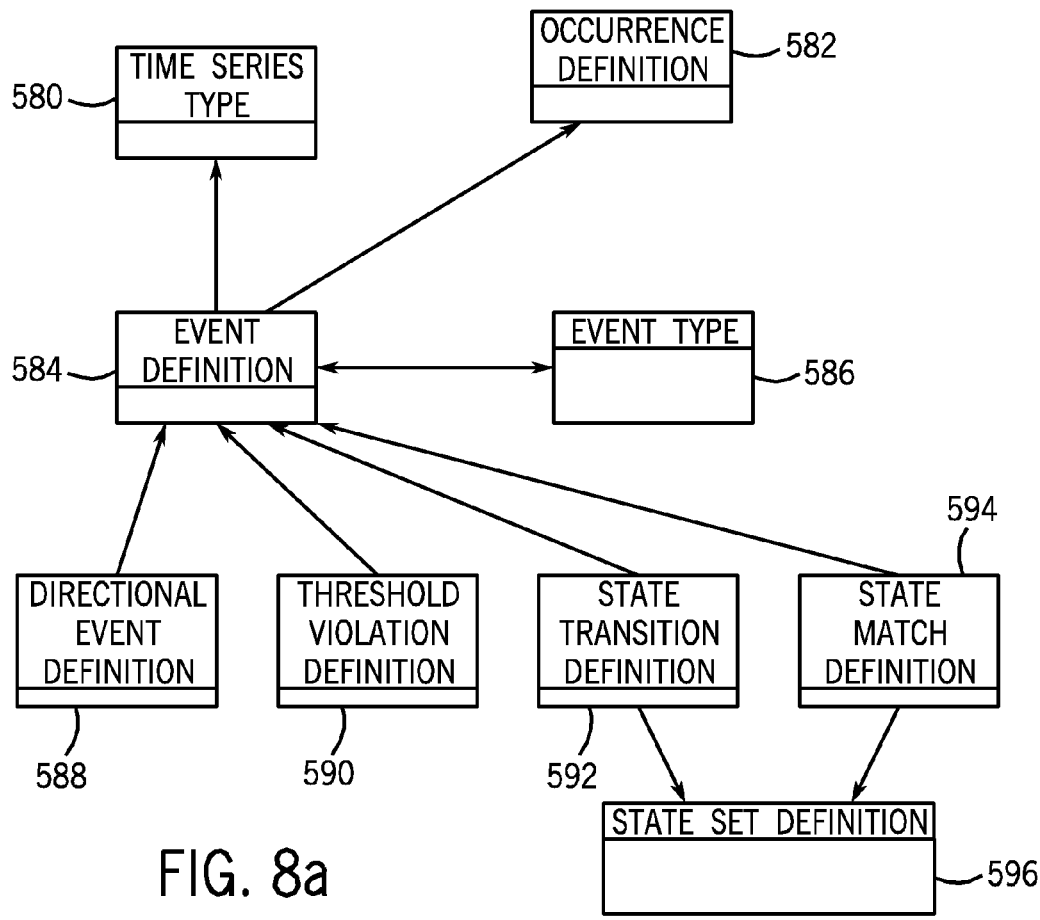
FIG. 8A is a UML static diagram of a subset of classes within the patient safety processor specifically modeling the an occurrence definition set used by the patient safety processor to identify, construct and qualify events.

FIG. 7B depicts a model of the occurrence types 568 within the processor 304. There are 5 primary occurrence types: event type 571, binary type 572, image type 573, repeating occurrence type 569 and pattern occurrence type. For more description of the types as they relate to occurrences within the matrix see FIG. 5 and FIG. 6. For more descriptions of the types as the relate to occurrence definitions within the occurrence definition set see FIGS. 7A, 8A, 8B and 8C. FIG. 8A shows a subset of the occurrence definition set as it relates to the event definitions. In one embodiment, the classes described here represent the event definition set used by the time series objectification processor to create the event streams.

An event definition 584 is a subclass of an occurrence definition 582 and each event definition is associated with a unique event type 586. event subclasses are described in detail in the text associated with FIG. 5. The definitions of each of these event subclasses are contained within the directional event definition 588, threshold violation definition 590, state transition definition 592, and state match definition 594 respectively. state transition definitions 592 and state match definitions use state sets and therefore contain state set definitions 596 which provide the parameters, lists, expressions or other mechanisms for defining a distinct aggregations of states. events are occurrences that happen within a single time series and therefore the event definition 584 is associated with a single time series type 580.

Figure 8B:
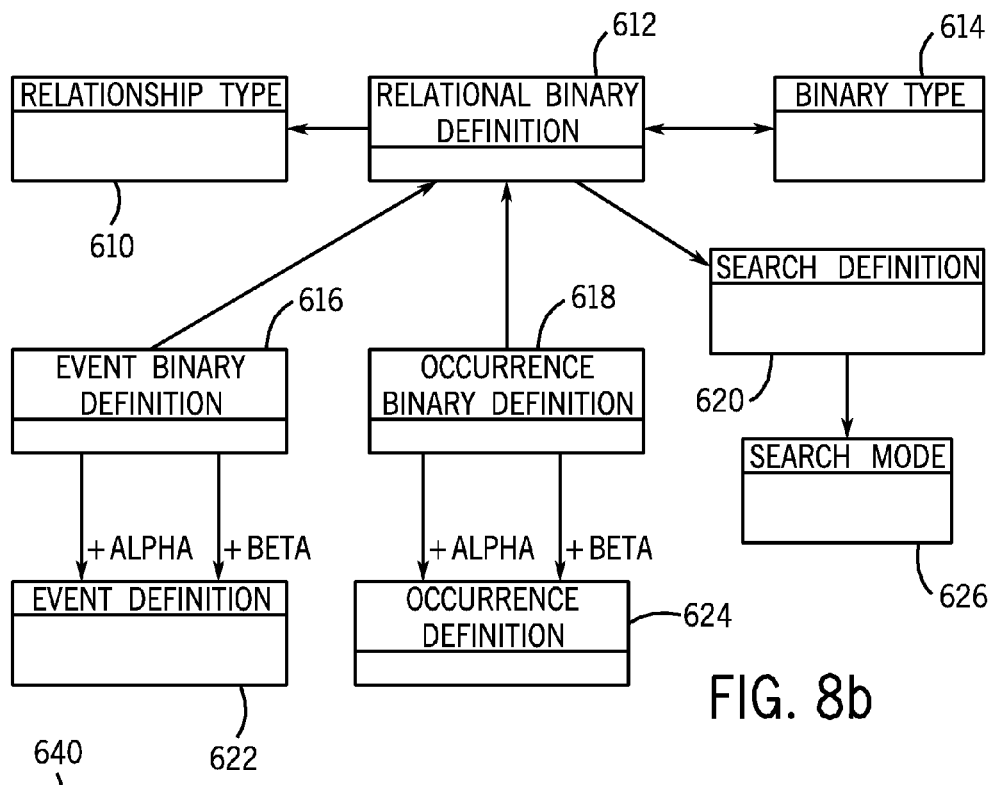
FIG. 8B is a UML static diagram of a subset of classes within the patient safety processor specifically modeling the an occurrence definition set used by the patient safety processor to identify, construct and qualify relational binaries.

FIG. 8B shows a subset of the occurrence definition set as it relates to the binary definitions. In one embodiment, the classes described here represent the binary definition set used by the Relational Processor to create the convergence analysis. A relational binary definition 612 represents the parameters used to identify a relational binary. In one exemplary embodiment, a relational binary definition 612 is made up of four key elements—the binary type 614, the Search definition 620 and the definitions of the Alpha and the expected Beta.

There are two subclasses of relational binaries—event binaries and occurrence binaries. The event binary definition 616 requires that the Alpha and Beta are events and therefore uses event definitions 622 whereas the occurrence binary may use an occurrence definition 624 as Alpha and Beta. relational binaries that are between an event and an occurrence will be an occurrence binary since an event is a subclass of occurrence. A Search definition 620 includes parameters, expressions and other descriptions to tell the processor 304 the relative time series segment(s) to search for the Beta event or occurrence. The Search Mode 626 indicates different types of searches including Expected, Verify Non-Existence and Reoccurring Verification. A Search definition 620 must have at least one Search Mode 626 but may have more that are used in combination (e.g. a Reoccurring Verification of Non-Existence). For each relational binary, the relationships may be further defined to select a more specific Relationship type 610 (or to match one of a set of relationships), for example cause and effect, subordination to name a few. The relational binary definition may optionally include rules for the indication of a specific Relationship type. In an alternative embodiment the selection of the Relationship type is implemented through the attribute mechanism.

Figure 9:
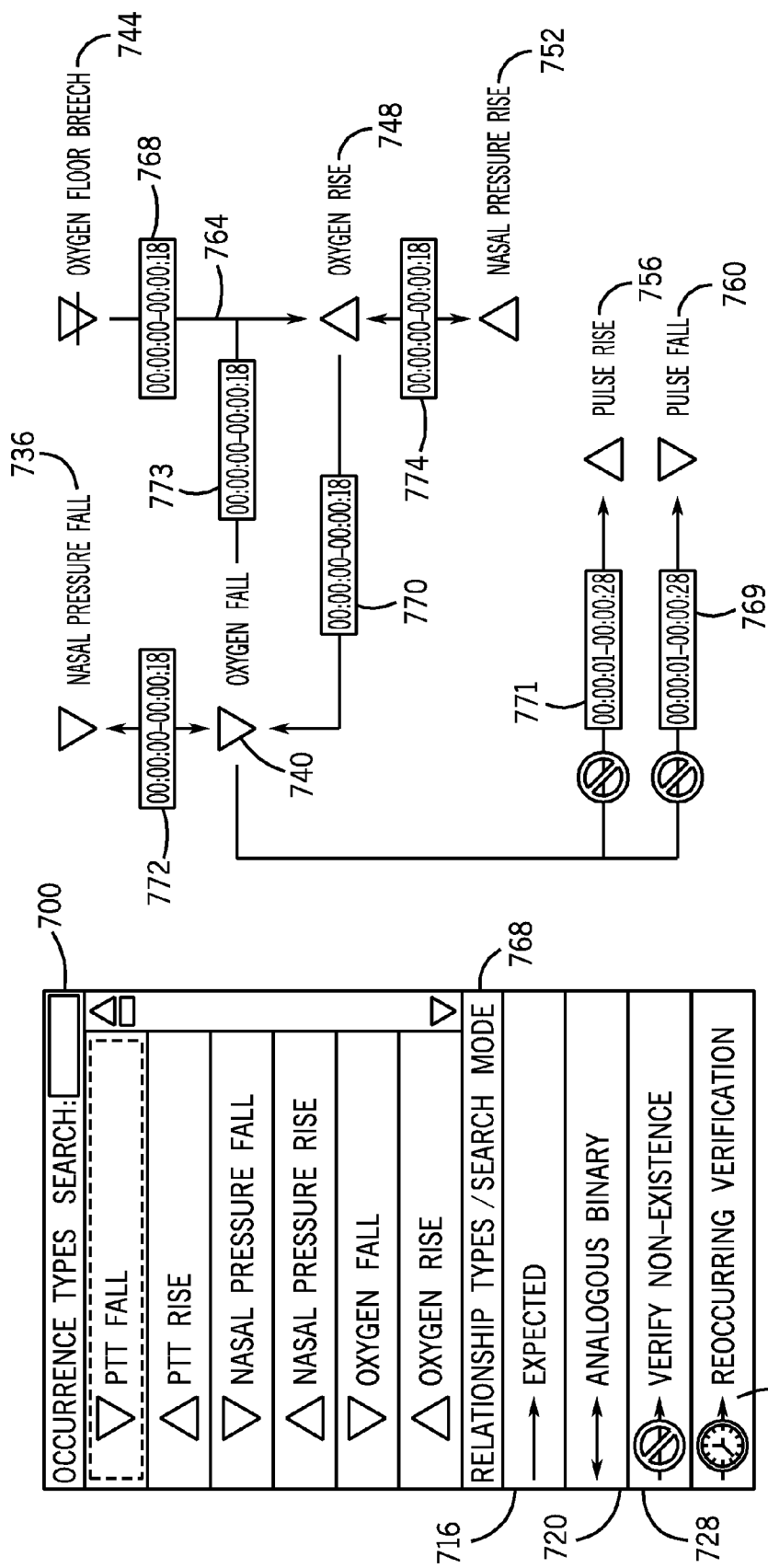
FIG. 9 is a user interface model of the convergence editor that may be used to visually construct and persist the binary definition set depicting a binary diagram within the convergence editor that pertains to the monitoring of sleep apnea.

This structure may best be understood within the context of the User Interface modeled in FIG. 9. FIG. 9 shows a set of event binaries. Each pair of events (e.g. 744, 748), which has a connecting relationship (e.g. 764), represents a single event binary definition 616. The connecting line between the two events represents the Search Mode 626 (of FIG. 8b). Search Modes include: Expected 716, Analogous binary 720, Verify Non-Existence 728, and Reoccurring Verification 732 to name a few. The Search Mode 626 determines the type and frequency of search that may occur when the candidate Alpha event is identified. For example, the Reoccurring Verification 732 type may generate multiple relational binaries for a single candidate Alpha occurrence because it directs the relational binary processor to search for the Expected occurrence with a specified frequency, generating relational binaries at each interval. In the contemplated embodiment some binary Search Modes may be used in combination (e.g. Reoccurring Verification 732 and Verify Non-Existence 728).

The box containing a pair of time offsets (e.g. 768) represents the Search definition 620. This definition contains the Start and End time offsets from the end point of the Alpha occurrence for which the Beta occurrence should be searched in the target Beta time series. Finally the icons represent the Alpha and Beta event types. These types reference a unique definition which provides the parameters with which the relational binary processor may search the identified time series segment(s) for the existence of a pattern. Further, criteria is contained within the binary definition itself based on the micro-domain established by a candidate aggregation of an alpha and beta paired by the spacial requirements alone. These criteria, established by the researcher or automatically determined by the processor 304 (as per guided image discovery described below), may utilize all of the properties (including Fundamental properties, Calculated properties and attributes described below to name a few) of the candidate binary to accept or reject the binary as a true representative of the specified binary type.

Figure 8C:
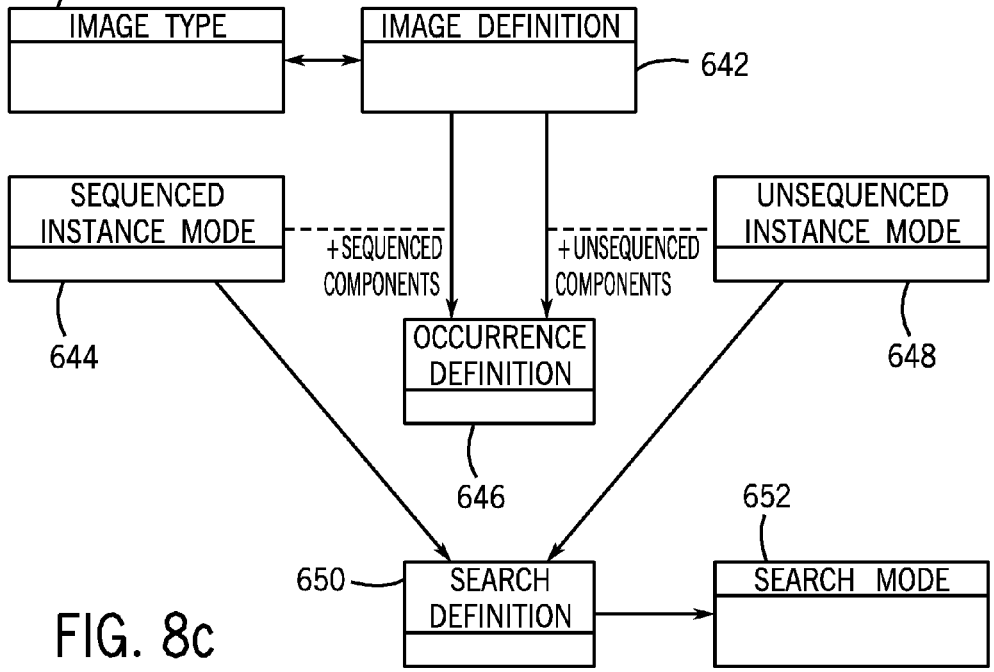
FIG. 8C is a UML static diagram of a subset of classes within the patient safety processor specifically modeling the an occurrence definition set used by the patient safety processor to identify, construct and qualify images.

FIG. 8c shows a subset of the occurrence definition set as it relates to the image definitions. In one embodiment, the classes described here represent the image definition set used by the image processor to create the image analysis. An image definition 642 represents the set of element definitions and their relationships, which allow the image processor to determine whether the pattern of elements meets the criteria of the specified image. This Structure of FIG. 8c may best be understood within the context of the User Interface in FIG. 10. Each diagram represents a single image definition 642. If a specific sequence of elements is required to identify the image then the sequence is specified with connectors and time offsets (e.g. 812, 824, 816, 828, and 820). Each icon represents an occurrence type which may be used to identify a single occurrence definition 646. image elements may include an Instance Mode (644 and 648) which indicates the Mode of the specific instance to be found. For example if the occurrence is a binary then the Mode indicates whether the binary should be a convergent, divergent or null binary. Within FIG. 10, the mode is specified by in a parenthetical description at the end of the occurrence type name. Icons may represent any occurrence type—event types, binary types, image types, repeating occurrence types or pattern occurrence types. occurrence types are listed 815 and available for selection, drag-and-drop. Relationships, as with the binary editor are available 833 to establish the relationship and/or search mode between sequenced elements.

FIG. 9 shows an embodiment of a convergence editor, which, in one embodiment, provides the ability for the creation, and modification of a binary definition set, which may be used by the relational binary processor to create the convergence analysis. A binary definition set may be represented as a convergence model—a visual representation of the object instances shown in FIG. 8b. The user interface includes a design surface 764 and an element toolbox 700, which allows for the drag-and-drop creation and manipulation of a subset of the convergence model called a binary diagram. The aggregation of all binary diagrams created with a single name constitutes the entire convergence model and may be, in one embodiment, persisted as a binary definition set in the relational database, in an XML file, a model or in DSL artifacts (either textual or visual) to name a few. Breaking a convergence model into binary diagrams allows for multiple views into the model. These views are not mutually exclusive (i.e. the same binary definition may be represented in multiple diagrams) and therefore provide views into model at various levels of complexity and points of reference.

FIG. 9 provides a reference example to describe the elements within the convergence editor and the relationship to the elements in FIG. 8b. convergence Element Toolbox 700 presents the visual elements which may be added to the design surface and therefore to the binary diagram. The icons represent occurrence types that may be added. The Relationships 768 section of the toolbox 700 presents a set of lines, which may be used to connect two events to create a relational binary. The line chosen determines the Search Mode 626. Search Modes include: Expected 716, Analogous binary 720, Verify Non-Existence 728, and Reoccurring Verification 732. The visual icon attached to the line cues the user to its mode. The Search Mode 626 determines the type and frequency of search that may occur when the candidate Alpha occurrence is identified. For example, the Reoccurring Verification type 732 may generate multiple binaries for a single candidate Alpha occurrence because it directs the relational binary processor to search for the Beta occurrence with a specified frequency, generating binaries at each interval. Some Search Modes may be used in combination (e.g. Reoccurring Verification 732 and Verify Non-Existence 724).

Each relationship added to the design surface 764 must have at least one time interval provided (e.g. 768) which represents the Search definition 620 for the relational binary definition 612. Each relationship may be directional. The line includes an arrow end-style on the end that represents the Beta definition, either a Beta event definition 622 or a Beta occurrence definition 624. The end without an arrow represents the Alpha definition, either the Alpha event definition 622 or the Alpha occurrence definition 624. Within FIG. 9, all of the binaries defined are event binaries.

Each pair of events, which has a connecting relationship, represents a single event binary definition 616. In the above figure, the following seven binaries:
1. An Analogous binary between Nasal Pressure fall and oxygen fall (736, 772, 740)
2. An Expected binary between oxygen fall and oxygen rise (740, 773, 748)
3. An Expected binary between oxygen Floor Breech threshold violation and oxygen rise (744, 768, 748)
4. An Expected binary between oxygen rise and oxygen fall (748, 770, 740)
5. An Analogous binary between oxygen rise and Nasal Pressure Rise (748, 774, 752)
6. A Verify Non-Existence binary between oxygen fall and Pulse Rise (740, 771, 756)
7. A Verify Non-Existence binary between oxygen fall and Pulse fall (740, 769, 760)

This diagram does not represent all of the relationships of each of these events. It is an example of a subset view into the overall convergence model with a focus on sleep apnea. Relationships and elements may be removed from this diagram without removing them from the entire model (i.e. the editor distinguishes between "Remove" which removes the element from the diagram but not the model and "Delete" which removes the element from the diagram and the model [including all other diagrams]). A diagram may be constructed that shows all of the events and relationships, but it would likely be so large and complex as to be unreadable.

The editor will check the diagram for validity before persistence or at the user's request. For example, a relationship without a Beta occurrence would invalidate a diagram. An invalid diagram may invalidate the convergence model. It is contemplated that a convergence model cannot be persisted into a binary definition set. The editor allows for an invalid state to provide flexibility during diagram construction. Further, if the target binary definition set is associated with image definition sets that are available to the editor, the editor may warn of conflicts with associated models by changes to the diagram. Depending on editor settings, these changes are disallowed, or the changes may be propagated into the images. Each diagram element may be manipulated in a more detailed way through property editors associated with the element type and access to the occurrence property Subsystem described below. The property editors provide access to all editable properties of the associated definition objects such that the editor is sufficient to construct a complete binary definition set. The editor provides for adding text, notes, lines and other visual elements to the diagram to increase human readability and to communicate between users. These additional visual elements have no affect on the binary definition set.

Figure 10:
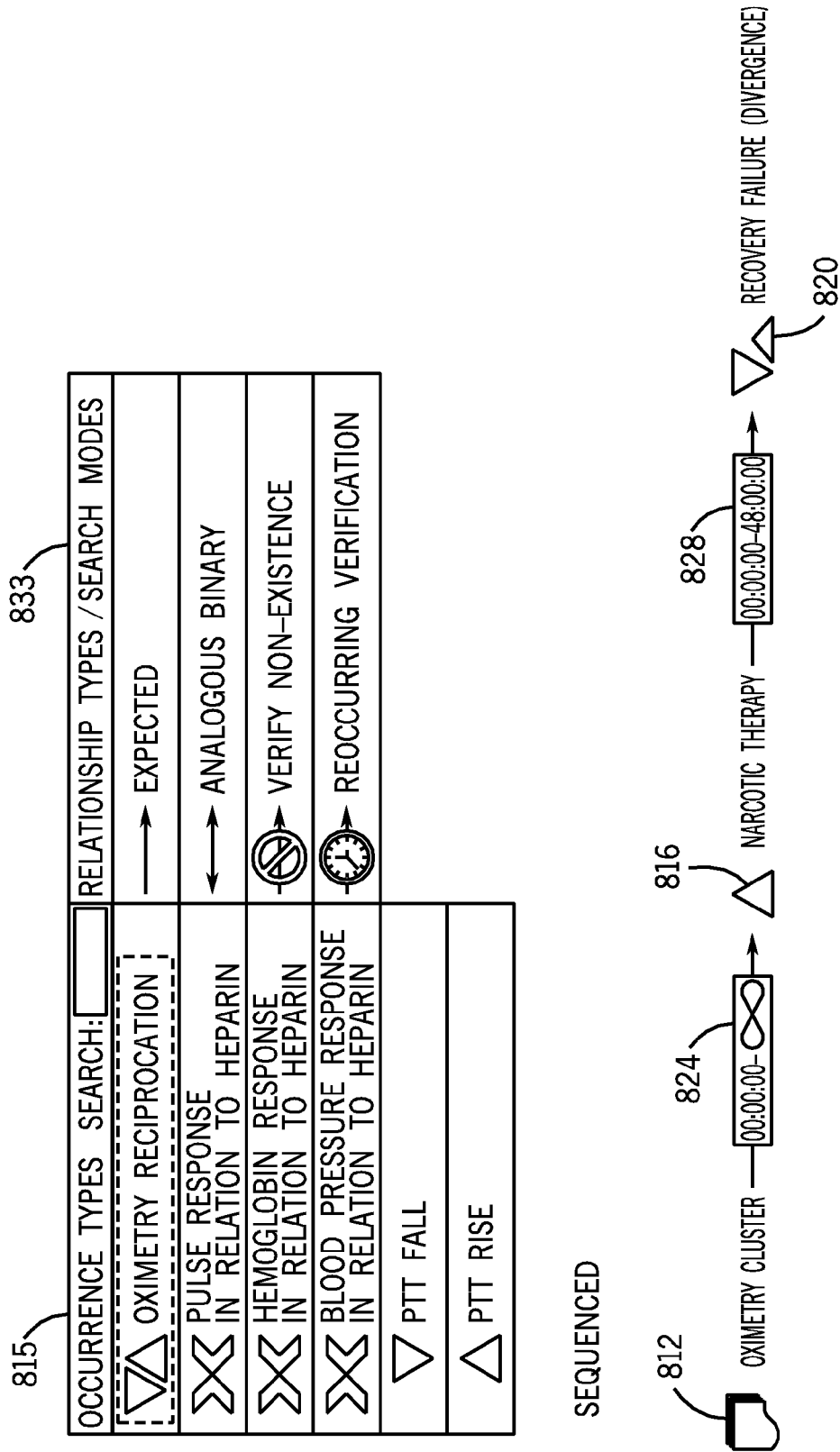
FIG. 10 is a user interface model of the image editor that may be used to visually construct and persist the image definition set depicting a image diagram within the image editor that defines narcotic-induced ventilation instability.

FIG. 10 shows an embodiment of the image editor that provides the ability for the creation and modification of an image definition set, which will be used by the image processor, in coordination with a binary definition set, to create a convergence analysis. A image definition set may be represented as an image diagram—a visual representation of the object instances shown in FIG. 8. The user interface includes a design surface 832 and an element toolbox 780, which allows for the drag-and-drop creation and manipulation of a subset of the image called an image diagram. The aggregation of all image diagrams created with a single name constitutes the entire image model and may be persisted as an image definition set in the relational database, in an XML file, a model or DSL artifact (either textual or visual) to name a few. As with the convergence model, image diagrams are views into the model that provide visualizations at various levels of complexity and points of reference.

FIG. 10 provides a reference example to describe the elements within the image editor and the relationship to the elements in FIG. 8C. The box on the left is the occurrence type Selection Box 815 which presents the visual elements which may be added to the design surface 832 and therefore to the image diagram. The design surface is split into two sections—Sequenced and Non-Sequenced. If there are only elements in one or the other then only the one section is show (as in FIG. 10 in which there are only Sequenced occurrence types specified). occurrence types dropped into the Sequenced section require a relationship in time and therefore require that a relationship be specified between them (e.g. 824). The Relationships Selection Box 833 presents a set of lines, which may be used to connect two occurrence types. Each relationship added to the design surface must have a time interval provided (e.g. 828) which represents the Search definition 642 associated with the Sequenced Instance Mode 644. Each relationship is directional indicating precedence in the sequence. may Zero or more sequences may be specified, but if an element is placed in the Sequenced section it must be part of a sequence. Elements placed in the Non-Sequenced section cannot have relationships. Only existence is specified within an overlapping Span of Influence (defined below). The image diagram differs from the binary diagram in that the diagram itself represents an entity—the image definition 650—and is not simply a collection of other entities (e.g. binaries in the case of the binary editor). Removing elements changes the definition of when a image will be identified. All elements added to the image diagram represent an "And" relationship for identification purposes (i.e. all elements and sequences must exist for the image to be identified). In one embodiment, to create "Or" scenarios, multiple image diagrams are created with variation representing the "Or" combinations. An image may include any combination and number of occurrence types. The editor may check the diagram for validity before persistence or at the user's request. The editor allows for an invalid state to provide flexibility during diagram construction. Each diagram element may be manipulated in a more detailed way through property editors associated with the element type. The property editors provide access to all editable properties of the associated definition objects such that the editor is sufficient to construct a complete image definition set.

The spatial configuration (in time) of the occurrences are preferably satisfied to create a candidate image. Once a candidate image is established, the processor 304 may use this set of objects as a micro-domain to establish all of the properties using the occurrence property Subsystem (described below). The properties derived within this micro-domain may then be used to refine the definition of an image, to more specifically characterize the image or be used in the decision to accept or reject the candidate image as a true (i.e. qualified) image. The image editor may be used to enter into the occurrence property Subsystem to further define calculated properties and attributes (defined below) of the image. The editor provides for adding text, notes, lines and other visual elements to the diagram to increase human readability and to communicate between users. These additional visual elements have no affect on the image definition set.

Figure 11:
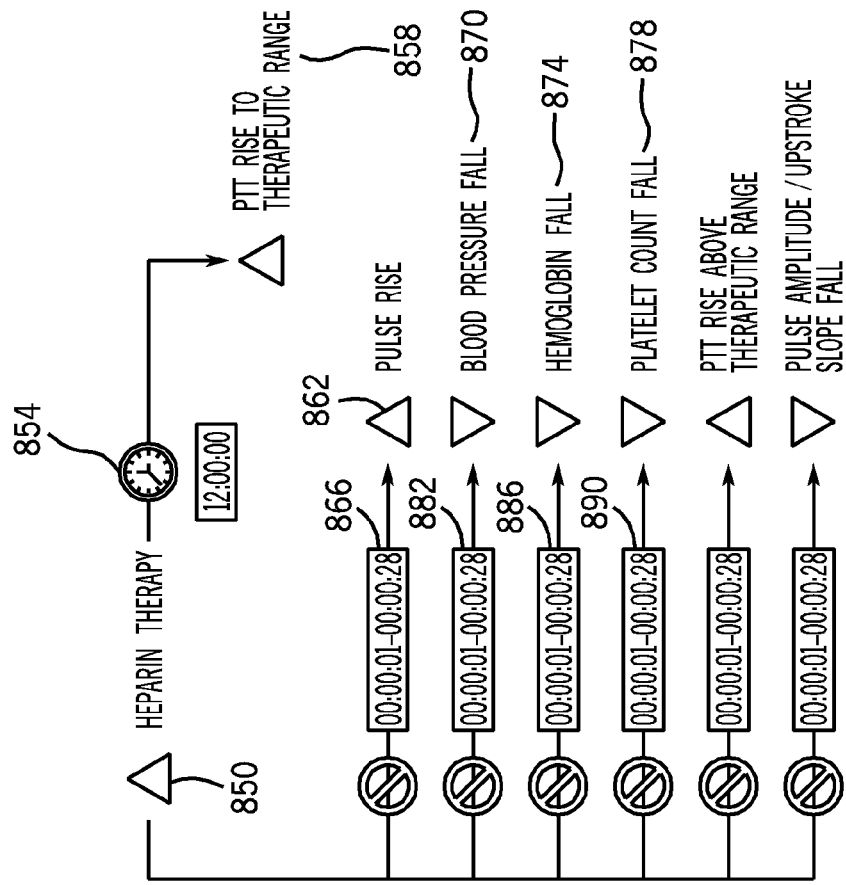
FIG. 11 is an additional view of the user interface model of the convergence editor specifically depicting a binary diagram within the convergence editor that pertains to the monitoring heparin therapy.
Figure 12:
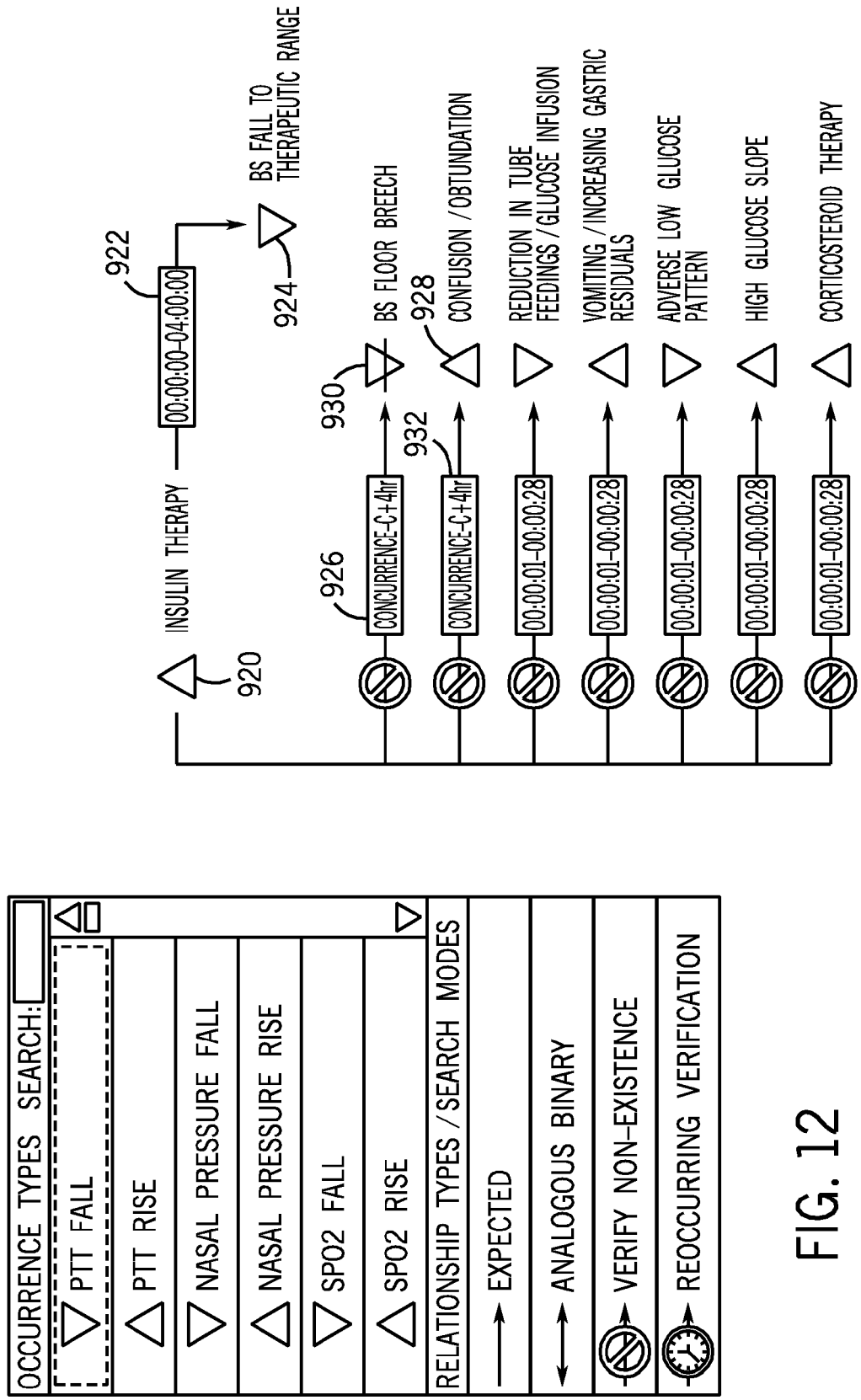
FIG. 12 is an additional view of the user interface model of the convergence editor specifically depicting a binary diagram within the convergence editor that pertains to the monitoring insulin therapy.

FIG. 11 provides an additional example of a binary diagram referring to heparin therapy in which the following binary definitions are specified:
 1. A Reoccurring Verification binary 854 between heparin therapy 850 and PTT Rise to Therapeutic Range 858.
 2. A Verify Non-Existence binary 866 between heparin therapy 850 and Pulse Rise 862.
 3. A Verify Non-Existence binary 882 between heparin therapy 850 and Blood Pressure fall 870.
 4. A Verify Non-Existence binary 886 between heparin therapy 850 and Hemoglobin fall 874.
 5. A Verify Non-Existence binary 890 between heparin therapy 850 and Platelet Count fall 878.
 6. and other examples FIG. 12 provides an additional example of a binary diagram referring to insulin therapy in which the following binary definitions are specified:
 1. An Expected binary 922 between insulin therapy 920 and Blood Sugar fall 924 To Therapeutic Range.
 2. A Verify Non-Existence binary 926 between insulin therapy 920 and Blood Sugar Breech 930.
 3. A Verify Non-Existence binary 926 between insulin therapy 920 and Confusion 928.

FIG. 13 provides an additional example of a binary diagram referring to narcotic therapy in which the following binary definitions are specified:
 1. A Reoccurring Verification binary 944 between narcotic therapy 940 and Pain Score fall To Therapeutic Range (948)
 2. A Verify Non-Existence binary 952 between narcotic therapy 940 and SPO$_2$ cycling 956.
 3. A Verify Non-Existence binary 960 between narcotic therapy 940 and Blood Pressure fall 961.
 4. A Verify Non-Existence binary 962 between narcotic therapy 940 and Respiratory Rate fall 964.
 5. A Verify Non-Existence binary 966 between narcotic therapy 940 and Confusion 967.

Figure 14:
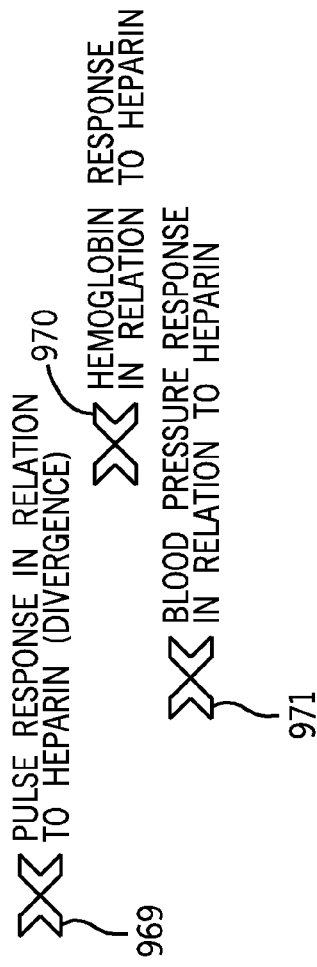
FIG. 14 is a user interface model of the image editor that may be used to visually construct and persist the image definition set showing an image diagram within the image editor that defines heparin-induced hemorrhage.

FIG. 14 provides an additional example of the image editor in which three non-sequenced binaries (969, 970, and 971) are defined as sufficient to identify possible Heparin-Associated Hemorrhage.

Figure 15A:
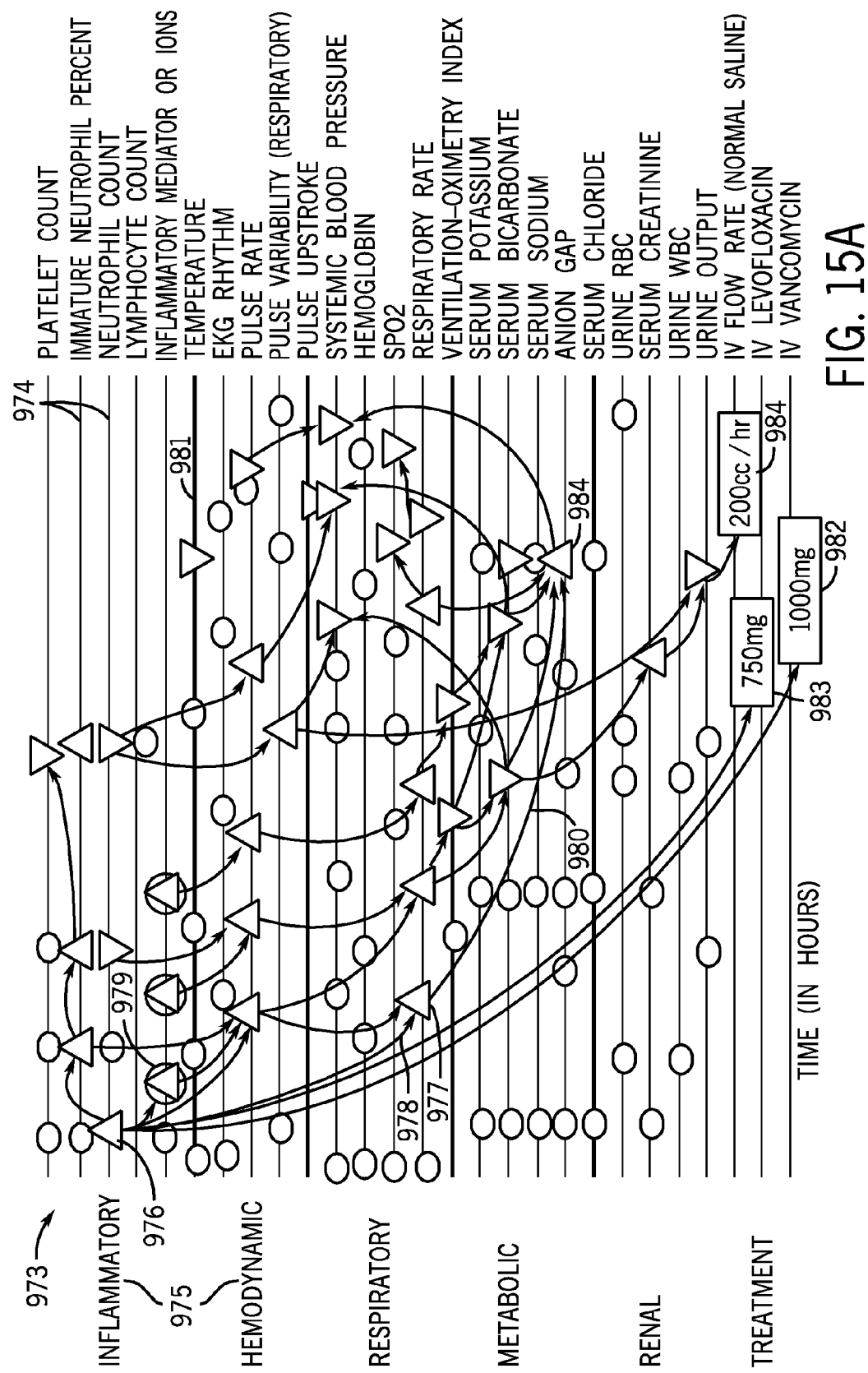
FIG. 15A is an image frame with a plurality of timelines organized into groupings, which shows an image of an expanding cascade of septic shock.

FIG. 15A shows an image frame 973 of a patient's physiologic system and care and demonstrates one exemplary image according to one embodiment as generated by the image processor. The image shown is indicative of dynamic progression from an image suggestive of stability to an image suggestive of a cascade of septic shock. The image displays objectified events, which met criteria as up and down arrows indicating whether they are, rise events or fall events respectively. Minor time series variations (such as detected minor rises or falls typical of signal noise, which fail to meet criteria by the objectification processor as events) are represented on each time-line as open circles along parallel time lines. (The visualization of such variations may be turned on or off as desired.) The detected events are combined with other events to form binaries which are then combined to produce an image of relational patterns including aggregate binaries and individual events defining the dynamic state of the patient's physiological system and of the medical care applied to the physiologic system during the time interval of each respective image Within the complete image, smaller images aggregate to produce the larger image of failure (in this case, of septic shock).

Since FIG. 15A is a late "time lapsed" frame of a MPPC, which has exhibited many earlier frames, wherein the processor 304 suggested that confidence of septic shock was high. The figure is readily understood by the representations of rise events or fall events as up-arrowheads and down-arrowheads respectively on each time line 974, each of which is labeled on the left. The timelines 974 are grouped into categories 975 designated on the right. The first event detected within the time interval of the image is a perturbation event—a rise event of the Neutrophil count 976 shown by the upward pointing arrowhead on the Neutrophil timeline. This perturbation event is combined by the relational processor to a second perturbation event—a rise in respiratory rate 977 also shown by an upward arrowhead, to generate the first relational binary 978 (combined in the figure by the arrow connecting 976 and 977). (While the respiratory (tidal or ventilation rate) may be used the respiratory amplitude (tidal or ventilation amplitude) may alternatively be used or a mathematical combination of both may be used to generate a time series and/or a derivative of the tidal curve (in one example the slope and amplitude, the area under the peak to peak and/or the area above the nadir to nadir) may be used. time series of all of these may be incorporated into the matrix for at risk patients or the time series may include only one or two but expanded to include derivatives retrospectively and prospectively upon the detection of a pattern or image or upon the identification of risk factors. In one embodiment the respiratory time series are monitored using a nasal cannula whereas in another they are monitored using a sound sensor placed on an airway or chest. Both the rate of the tidal sounds and the amplitude of the tidal sound and the length of the tidal sounds in each cycle can be used to provide an indication of tidal amplitude. Early termination of tidal sounds (especially inspiration) before the next breath suggests that the tidal amplitude is not high. The duration of the tidal sounds and the tidal sound amplitude can be used in a manner analogous to the duration and amplitude of the nasal thermister temperature in a single direction.) Each subsequent perturbation in the image is designated by its timeline and arrowhead. An arrowhead with a circle around it designates perturbations determined by testing automatically ordered by the processor 304 in response to the detection of a particular image. In an example the rise event in inflammatory mediators or indicators 979 was ordered by the processor 304 to better define the inflammation portion of the image which was somewhat obscured because the early images demonstrated a rise in neutrophil count, a rise in pulse, and a rise in respiration rate but with a normal temperature. Since this ambiguous image must be better defined to decide care, testing for inflammatory mediators/indicators is automatically ordered by the processor to better complete the image.

Using these basic designations the image of FIG. 15A becomes self-explanatory and FIG. 15A reveals a clear image frame (a time lapsed snap shot) late an MPPC including perturbations of inflammation, followed by a hemodynamic perturbations, followed closely by respiratory perturbations, and then renal perturbations in an expanding and linked cascade 980. Note that the initial rise in Neutrophil count 976, the first detected perturbation event, will have completely disappeared later in the cascade such that frames late in a failure process are best viewed with the sufficient scale to observe the onset of the cascade 980. Note the image shows a complete lack of any events along the temperature timeline 981. Without the Patient safety processor, the lack of a fever could easily fool a healthcare worker who may think of fever as a reliable indicator for the early detection of sepsis. Note however that the processor 304 is programmed to recognize that it has rendered an incomplete image and the processor 304 seeks to complete the image by ordering testing for inflammatory mediator 979. This testing serves as a "surrogate images" for a rise in temperature thereby establishing that the entire image does in fact exhibit an early component of inflammation.

Two drug treatments are evident in the image, the antibiotics Vancomycin 982, designated by its dose on the time line, and Levofloxacin 983, similarly designated. Also a rise in IV fluids in the form of normal saline 984 is indicated. All of these treatments come late after the image has long been indicative of a high probability of sepsis. (This delay, which may be detected in real-time by the patient safety processor, suggests poor and ineffective care, which has ignored or otherwise been poorly responsive to the patient safety processor. The processor may be programmed to provide an indication of the quality of the care provided. time lines, which include the care worker or ward may be provided so that delays may be linked to particular locations or care workers.)

Figure 19:
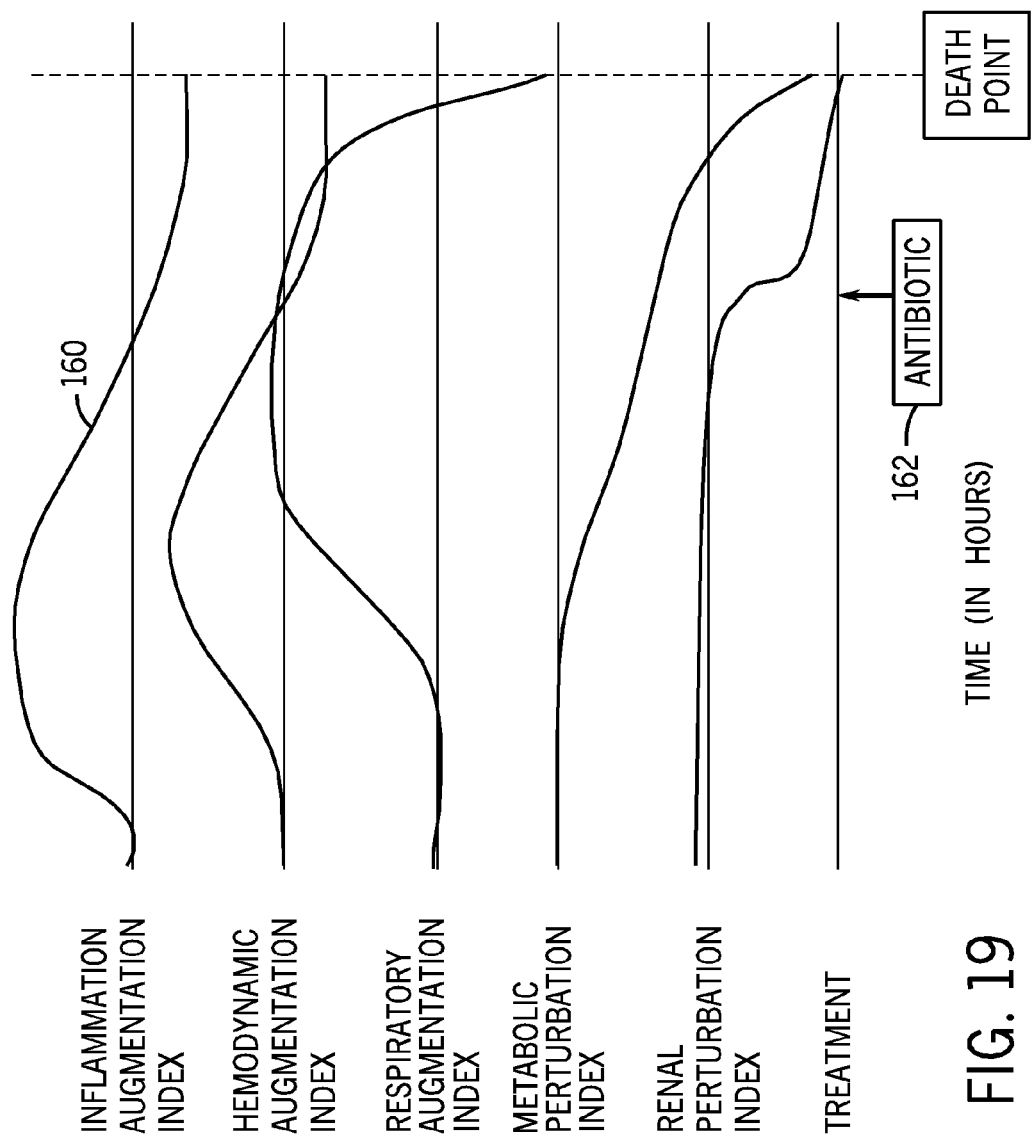
FIG. 19 shows overview image of perturbation onset and progression as derived from the time lapsed MPPC of FIG. 15A wherein the perturbations in each grouping are incorporated into an aggregate index along a single smoothed time series for each group.

The image of the progressive cascade 980 shows the drug treatments components 982, 983 of the image are too late because they appear within the image very late along the cascade 980. The late portions of the image of the cascade 980 also include a very ominous beta including a rise in anion gap 985. The addition of this new image provides a mature image of cascade 980, which is now strongly indicative of a stage of septic shock. Other image views may be for example; specific expanded portions of the time lines, specific expanded views of images (or other occurrences) along the timeline portions, specific groupings of the timelines, overviews of perturbation progression from group to group (an example of this is shown in FIG. 19), to name a few.

Figure 15B:
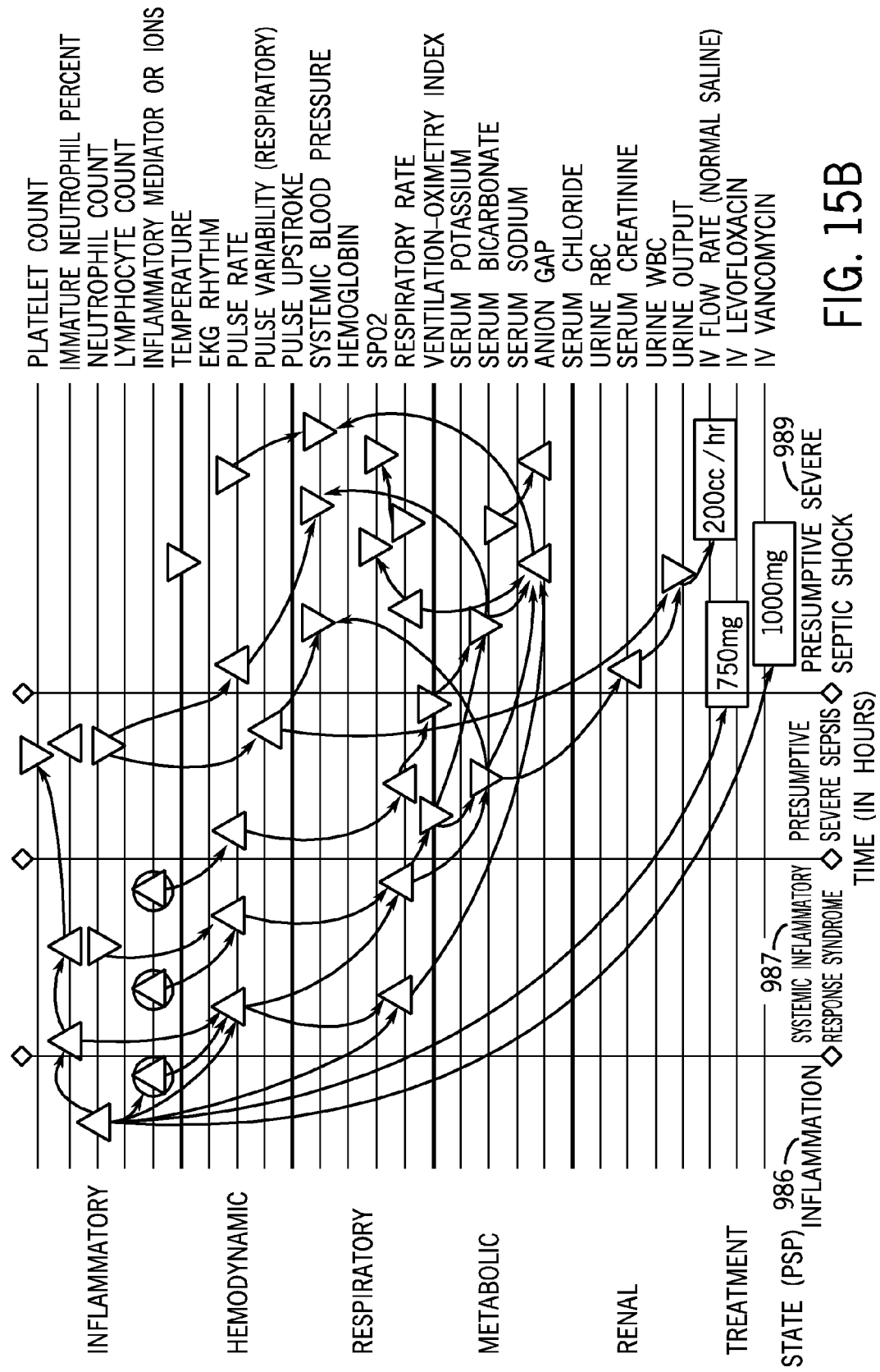
FIG. 15B is an image frame with a plurality of timelines organized into groupings, which shows a image of an expanding cascade of septic shock with portions of the image being separated into sequential states.

FIG. 15B is the image frame of FIG. 15A with portions of the image being separated into sequential states of inflammation 986, systemic inflammatory response syndrome 987, presumptive severe sepsis 988, and presumptive severe septic shock 989.

Figure 15C:
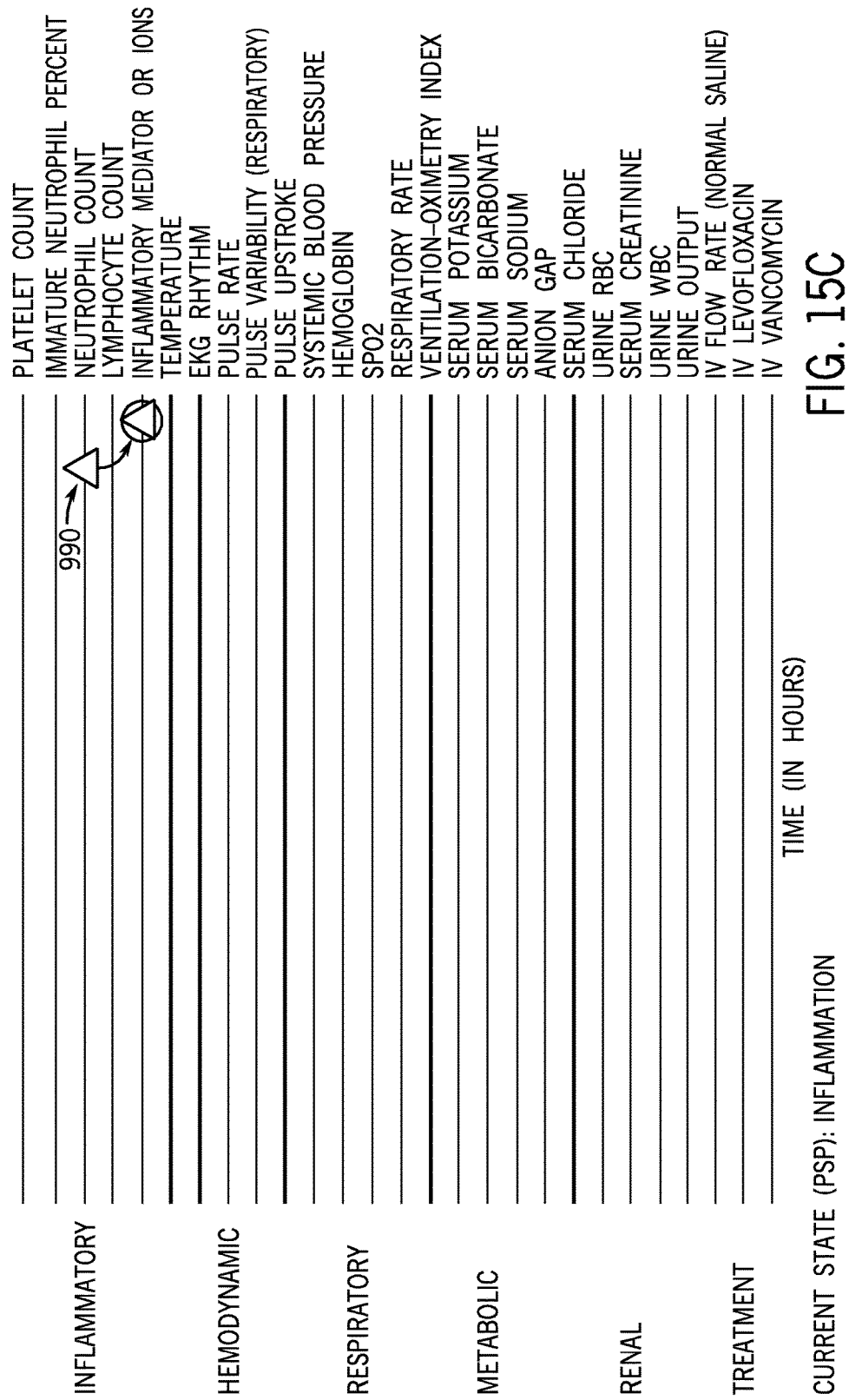
FIG. 15C is a image frame with a plurality of timelines organized into groupings, showing an image of an expanding cascade of severe septic shock an early image of septic shock as presented in real time to demonstrate that there is little in these first perturbations to warn of the impending deadly cascade.

FIG. 15C is an early image frame from real time imaging of the process in FIG. 15. The first "spark", a rise in Neutrophil count 990 evident in this image, is entirely non-specific despite the fact that it, in retrospect, heralds the onset of septic shock, completely disappears by the time this motion picture has reached the point illustrated in FIG. 15D focused testing, more frequent CBC testing, and/or more frequent vital sign measurement to determine the significance of this rise in Neutrophil count may be suggested or ordered by the processor to expand the image to more quickly move toward a more specific image.

Figure 15D:
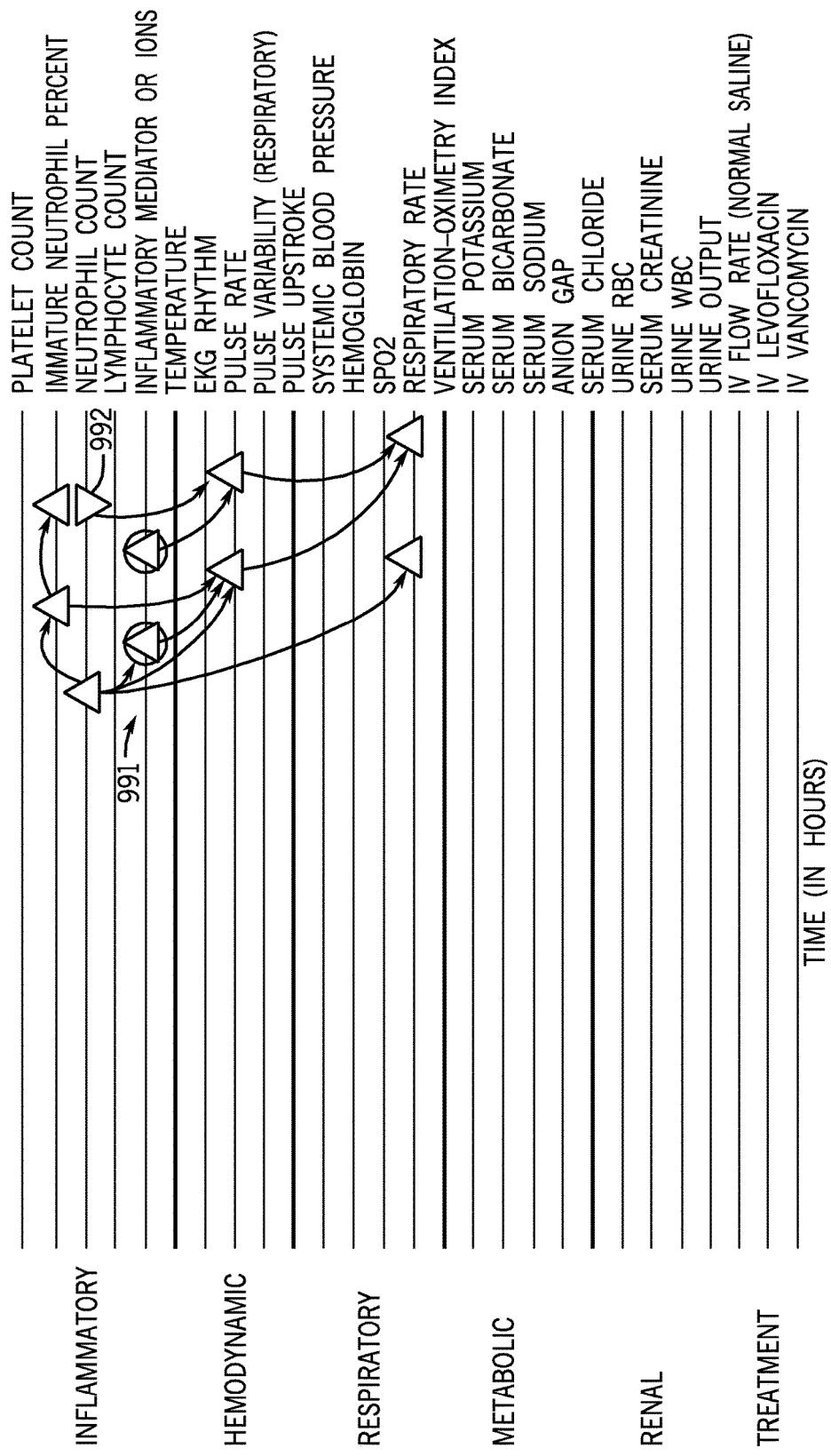
FIG. 15D is an image frame that shows an image of a failure cascade severe septic shock as presented in real time to demonstrate the early image of inflammatory, hemodynamic, and respiratory augmentation, with early immune failure.

FIG. 15D is an image frame from real time imaging of the process in FIG. 15. This frame demonstrates early images of inflammatory, hemodynamic, and respiratory augmentation 991 combined with early immune failure 992.

Figure 15E:
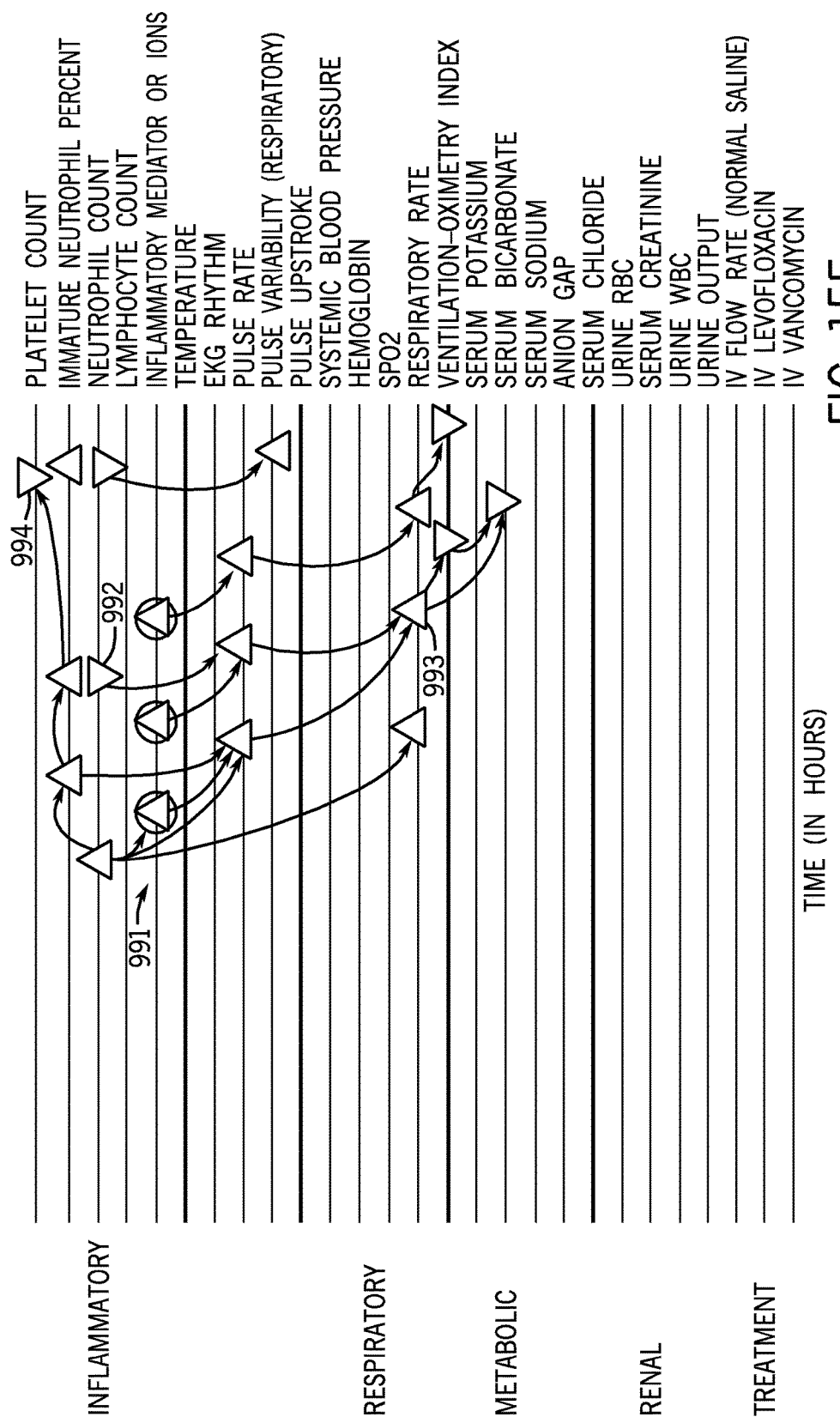
FIG. 15E is an image frame that shows an image of a failure cascade of severe septic shock as presented in real time to demonstrate the image of inflammatory, hemodynamic, and respiratory augmentation, with immune failure, but now with evidence of decline in respiratory gas exchange and fall in platelet count.

FIG. 15E is an image frame from real time imaging of the process in FIG. 15A This frame demonstrates demonstrate the images of inflammatory, hemodynamic, and respiratory augmentation 991, with immune failure 992, but now with images indicative of a decline in respiratory gas exchange 993 and fall in platelet count 994.

Figure 15F:
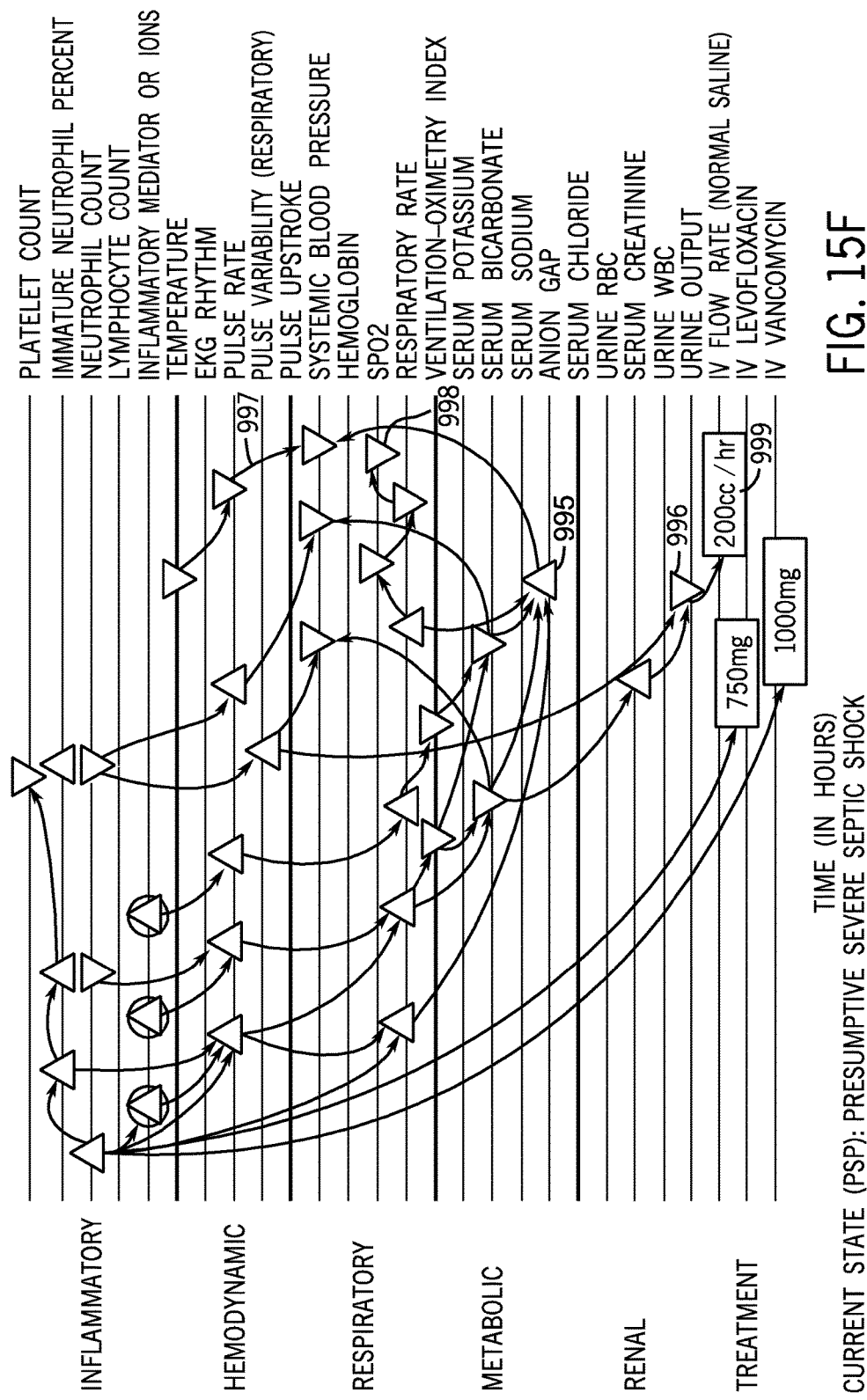
FIG. 15F is an image frame that shows an image of an advanced cascade of severe septic shock as presented in real time to demonstrate progression to metabolic failure, renal failure, hemodynamic failure, and respiratory failure.

FIG. 15F is an image frame of FIG. 15A to demonstrate that the image of now shows expansion of the image of the failure cascade from the frame in FIG. 15E to now include the images of metabolic failure 995, renal failure 996, hemodynamic failure 997 and respiratory failure 998. This is the point wherein rescue begins in many patients monitored by today's EMR and monitoring systems. The introduction of fluid resuscitation 999 at this late frame of the image means that the fluid will likely have little effect on progression of the image.

Figure 16:
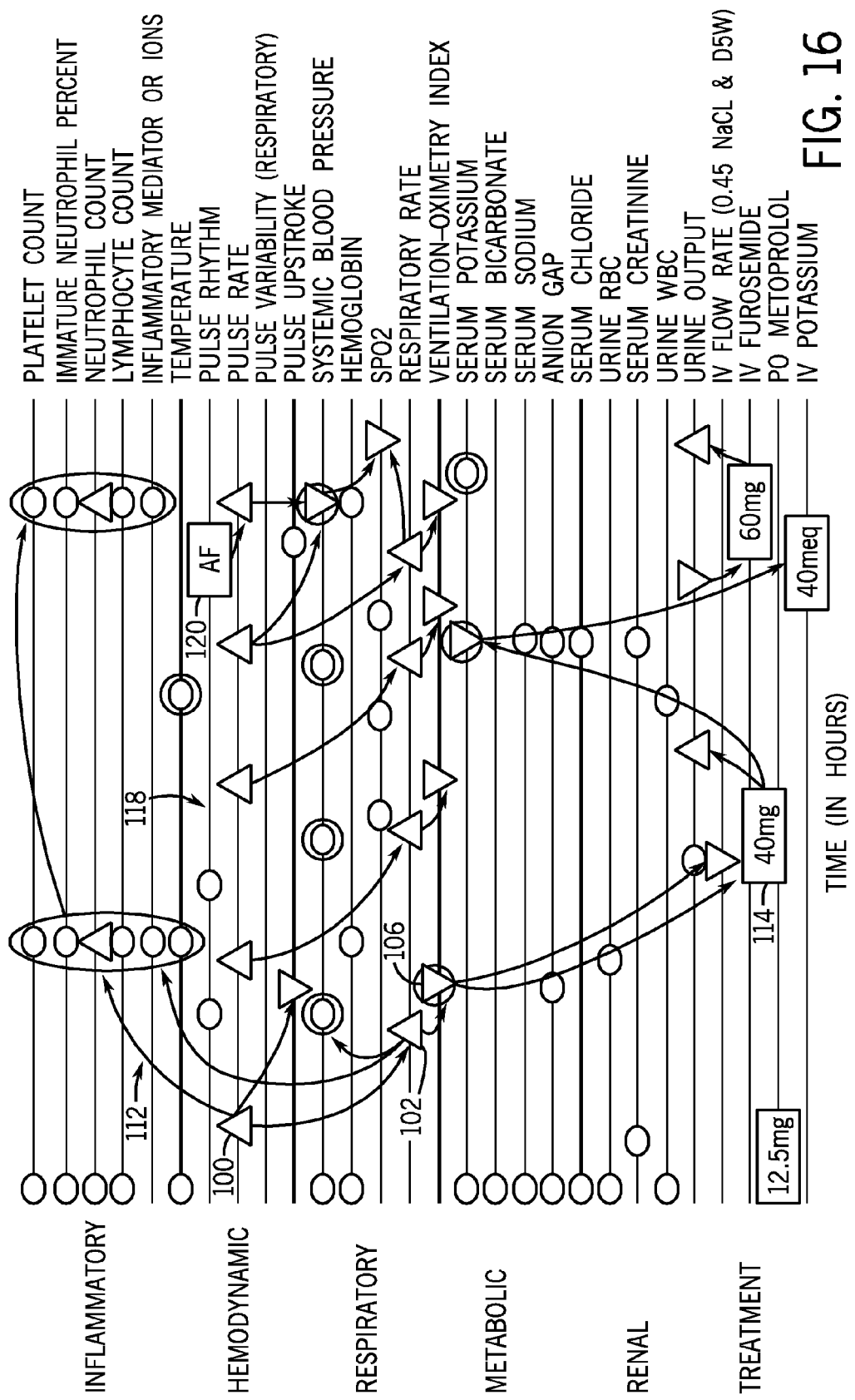
FIG. 16 is a general image including a plurality of timelines organized into groupings, which shows a image of congestive heart failure.

FIG. 16 shows a time lapsed image frame of the failure cascade of congestive heart failure. Note the first perturbation event detected by the processor is hemodynamic (a rise event in pulse rate 100), rather than inflammatory as in FIG. 15A. Then the next detected perturbation event is respiratory, a rise in respiratory rate 102 which combined with the rise in pulse 100 produces the first relational binary 104. Note also there is a fall in the ventilation indexed oximetry value 106 producing a second relational binary 108 with the rise in respiratory rate 102. The rise in respiration rate 102 is the beta event of the first relational binary 104 and the alpha event of the second relational binary 108. Together these two joined relational binaries form an image 110, which may be followed back to the initial onset of the image of the nascent congestive heart failure cascade 112. Treatments including furosemide 114 and metoprolol 116 are initiated fairly close to the onset of the image of the nascent cascade 112 but are not effective in preventing subsequent occurrence of an image of a progressive cascade 118. This image of a progressive cascade 118 is constrained by the both the components and length of the MPPC. The Patient safety processor upon detection of this image may search for the fundamental cause of the cascade progression, as by automatically ordering cardiac enzymes (not shown), and other tests if the safety committee of the hospital desires this type of testing proactivity in this setting. Note the cascade 118 includes the development of atrial fibrillation 120 and subsequent further deterioration.

Figure 17:
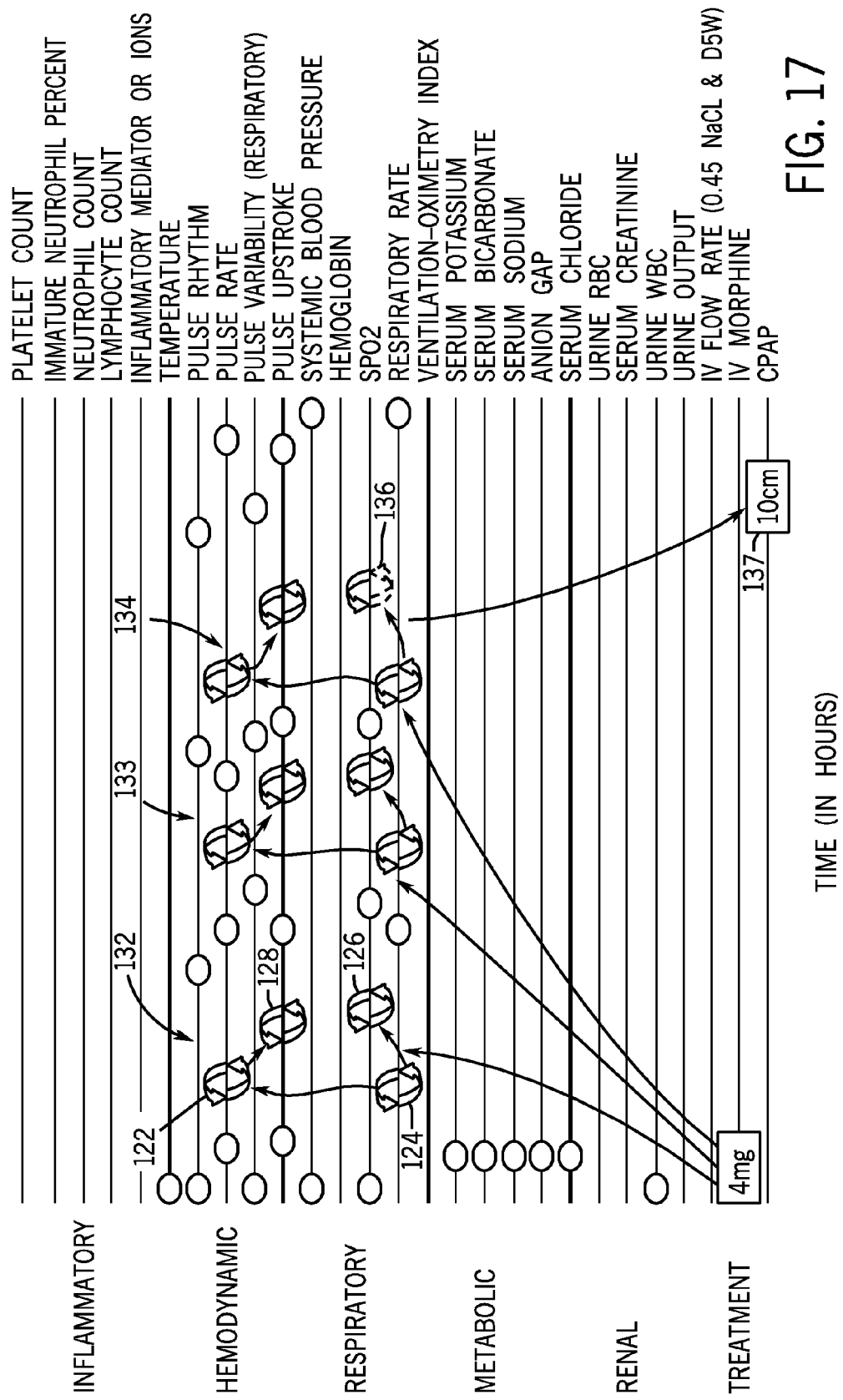
FIG. 17 is a general image including a plurality of timelines organized into groupings, which shows a image of sleep apnea.

FIG. 17 shows an image frame of sleep apnea. Note the first perturbation events occur in a group including a repeating occurrence of events within the pulse channel 122, respiratory channel 124, $SPO_2$ 126, and pulse upstroke channel 128. These occur after the initiation of a narcotic dose of 3 mg IV 130. The aggregated images showing cycling, a specific species of repeating occurrence, 132 then repeats to produce second such images 133 and third such images 134. The $SPO_2$ cycle 135 portion of the third images showing cycling 134 becomes more severe with recovery failure 136. CPAP treatment 137 is given timely and no further narcotic is given. Note, in this case, there is no image of an expanding cascade or progressively declining respiratory rate or declining $SPO_2$ to indicate life-threatening narcotic induced sustained hypoventilation. On later review as in morning report or with teaching rounds the entire MPPC, which contain this frame, may be reviewed by moving along a fast framed image to better visualize the subtleties of the progression. Furthermore the physician or nursing group may drill down to see that actual time series (as, for example, by right clicking on the $SPO_2$ repeating occurrence symbol 137). The decision as to whether or not the treatment in this case rendered timely care may be assessed. In an example, the physicians in the session may petition the patient safety committee to adjust the processor 304 to provide a recommendation for earlier automatic RT department notification, along with the nurse notification when images such as those defined in the early portion of this motion picture are present. In this way the Patient safety processor becomes an integral part of the continuous quality improvement actions of the hospital system with the goal being to move treatment and testing leftward into the earliest frame, which provides sufficient image support for the treatment or testing. The goal is to a continuing move toward earlier treatment of the source of the early perturbations before the cascade develops. According to one aspect, the processor 304 is integrated into the continuous quality improvement process and the processor 304 becomes an integral part of the hospitals quality improvement committee meetings and a major source of hospital wide as well as focused analysis and a mechanism to rapidly institutionalize quality improvement focused change.

Figure 18:
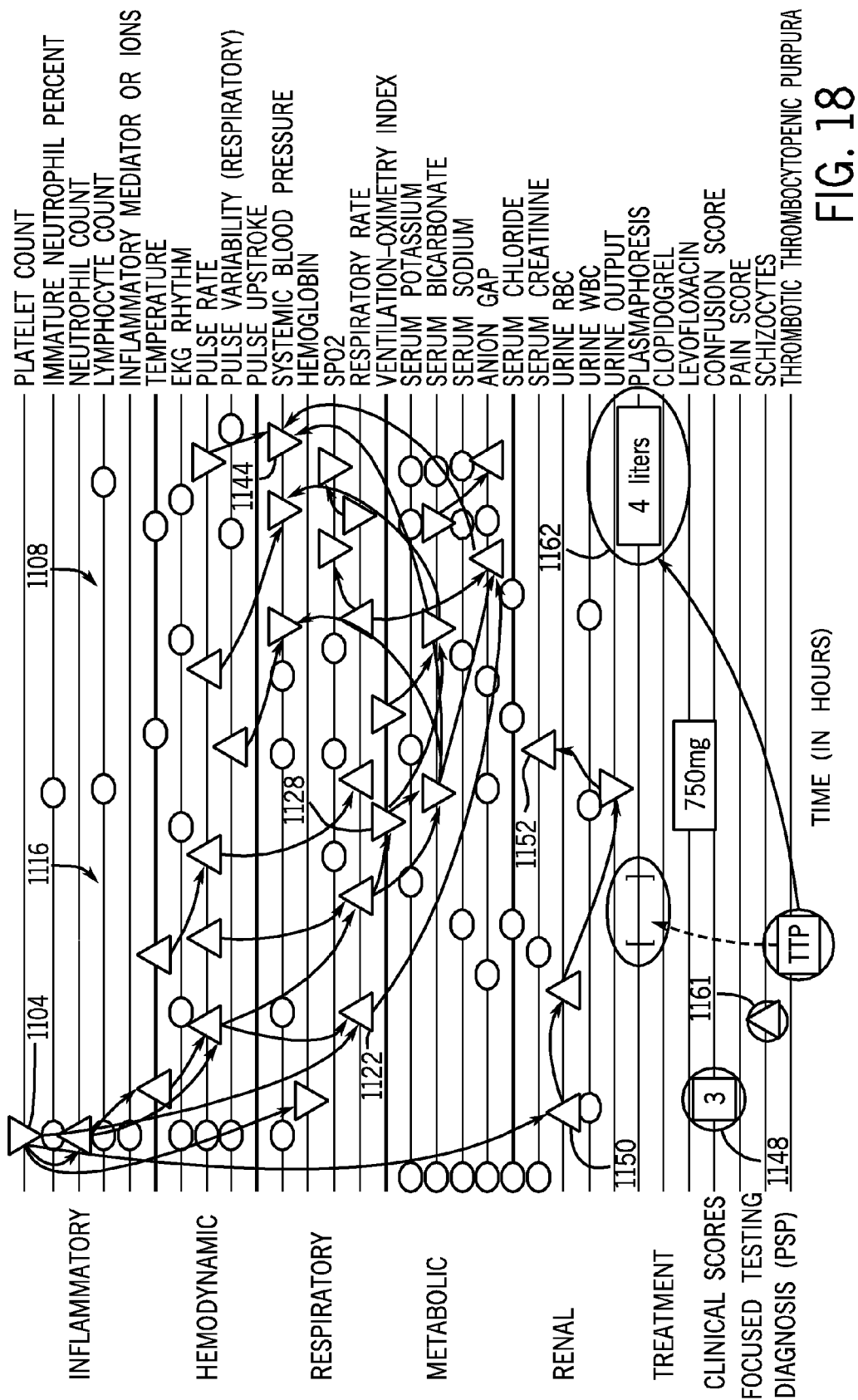
FIG. 18 is a general image including a plurality of timelines organized into groupings, which shows a image of thrombotic thrombocytopenic purpura.

FIG. 18 shows an image frame indicative of a high confidence of thrombotic thrombocytopenic purpura (TTP) a rare thrombotic and inflammatory condition that mimics the image of septic shock. TTP may be caused by the inhibition of ADAMTS enzyme by autoantibodies but this disease may also be rarely triggered by the very common drug clopidogrel. TTP often occurs within 2 weeks of drug initiation and may result in complications if not detected.

Unfortunately, TTP shares many of systemic response features of the very common disorder of sepsis (FIG. 15), which also causes thrombocytopenia. Since sepsis is a much more common condition, misdiagnosis of sepsis in the presence of TTP is a high possibility; furthermore, as with most pathophysiologic failures, both processes may coexist in a single patient along with other related conditions such as systemic lupus erythematosis and pancreatitis. Despite the fact that the moving images of failure in TTP and sepsis are similar, misdiagnosis of sepsis in the presence of TTP may be serious since TTP may not respond to antibiotic treatment.

Since TTP is associated with the accumulation of large multimers of Von Willebrand factor which damaging red blood cells and induce extensive micro vessel thrombosis producing confusion, renal failure and microangiopathic anemia which is associated with sentinel schizocytes which may be detected in the peripheral smear of blood (if the diagnosis is suspected and the test is ordered). Thrombocytopenia, renal failure, and hematuria may appear earlier in this process than with sepsis but these early findings are only an "image clue" and does not differentiate the two moving images. The decision to diagnosis a rare condition instead of a common one on the basis of a clue is a dangerous human tendency and a pitfall, which may result in patient complications. Alternatively the decision to diagnosis a common condition despite the clue because as the trite medical student saying goes "common condition occurs commonly" is equally dangerous. Indeed it is tragic that patient have to die because of such trite and oversimplified thinking. However it is the nature of many humans often approaches the analysis of overwhelming complexity with unknowingly capricious, summary judgment. This combined with the overlapping complexity of disease and healthcare is one of the most important reasons that comprehensive real-time physiologic and care rendering by the generation of digital MPPC and care is important.

The MPPC suggestive of TTP may be generated by the processor, with the processor indicating a image consistent with the possibility of sepsis and/or TTP and other less likely conditions such as an acute vasculidity. The processor may output non-specific characterizations of the image such as "image consistent with a life threatening acute or sub-acute thrombotic and inflammatory augmentation" and may present a differential diagnosis of the processes, which may generate such an image.

Also, as for example upon the detection of a threshold frame or frames, automatically order the peripheral smear, blood cultures, urine cultures, sputum cultures, Chest X-Ray, ANA, pancreatic enzymes, renal sediment, and ANCA study to enlarge and fill in the gaps of the image as rapidly as possible. It is the hospital experts who will ultimately decide the cost effective balance of ordering these tests as defined by the position the tests are ordered along the cascade. If desired the reports from the Chest X-Ray may include a section which will appear as a time series (as for example a step function). The radiologist in the interpretation (and in comparison with the last test and the last number selected by the last reading radiologist) may enter an indication of pulmonary infiltrate, pulmonary edema, and the like and may indicate a value between 1 and 5 which may result in a step change of the processor 304 from the last test. In this way the results of studies such as Chest X-Rays and other such interpreted tests become a source for dynamic time series rendering and incorporation into the imaging process. This will also provide an objective tool for comparing subjective quantification between radiologists and between various testing modalities in relation to the actual MPPC thereby identifying radiologists who are not generating reasonably reproducible or comparable subjective quantification in relation to themselves, others or the MPPC. In an example if a radiologist consistently calls the level of pulmonary edema a 1 or 2 in patients who have MPPCs consistent with of acute severe CHF and acute severe pulmonary edema or if the radiologists quantification consistently fails to follow or predict the clinical course then instruction can be provided or in the alternatively it can be recognized by the processor 304 that the input from that specific radiologist is not useful in further defining the images along the processor 304.

The presence of an image including images defining a failure cascade 1108 including inflammatory-hemodynamic respiratory-augmentation 1116 with an early fall in platelet count 1104, a fall in the Ventilation oximetry Index (VIO) 144, a fall or threshold value of hemoglobin 1144, an rise or threshold value of a confusion score 1148, and/or a rise or threshold value of red blood cells in the urine 1150, and/or a rise or threshold value of Creatinine 1152. Together the combination of images produces a MPPC suggestive of the possibility of TTP and/or sepsis and/or other less common processes. For example, if the patient had just received blood it would suggest a possible transfusion reaction.

It is not as important for the processor 304 to make the diagnosis as it is for the processor 304 to indicate to the healthcare worker the gravity of the image, a differential diagnosis as suggested by the image, and the general type and/or physiologic description of failure cascade present, and perhaps a notification that the detection by the processor 304 of this type of image requires prompt notification of the attending physician and transfer to ICU. If the image has insufficient binaries because results are not available to define enough beta components to define the presence of the image suggestive of TTP with a sufficient confidence level to take action, the unavailable tests are ordered upon the detection of the partial image in an attempt to complete the image. Note in FIG. 18, the detection of the images suggestive of the possible presence of a complete MPPC of TTP triggered the test for Schizocytes 1161 in an attempt to complete the TTP image. The detection of a threshold value step function, and/or rise in schizocytes combined with the rest of the image triggers the warning of the potential presence of TTP. In FIG. 18 reflects poor care because the action based on the processor 304's order for plasmaphoresis 1162 is physically carried out too late. This delay is automatically detected as is the outcome and the processor may be configured to provide an automatic report of variance to the quality improvement department of the hospital.

In this case, failure to rescue is not preempted because of human delay in physically following the orders of the processor 304. The delay in carrying out the order is determined by the processor 304 and the processor 304 may be programmed to up-indicate the warning upon increasing delay. To prevent this delay, the processor 304 may be programmed notify another station if action is not taken in response to detection of various evolving images such as the one in FIG. 18. These may be decided for example by the hospital quality improvement committees or by individual physicians or nurses if desired so that the processor 304 improves over time and may be adjusted to compensate for the diligence of the healthcare worker. The patient receives Levofloxacin early to cover the possibility of sepsis as the image was also consistent with sepsis and the healthcare workers decided to empirically treat for sepsis (albeit with somewhat limited antibiotic coverage). However, the cascade proceeds despite antibiotic therapy. Since a cascade is an image and the relationship of the cascade, its growth, and its features and its timing within an MPPC in relation to the dose, timing, and type of treatment also forms part of the MPPC, these relationships may be automatically assessed by the processor in real-time to determine if treatment is effective. The hospital safety committee or infectious disease committee may decide whether or not to reprogram the processor 304 to make antibiotic suggestions based on various ranges of images before the results of cultures are known.

FIG. 19 shows an overview image of perturbation onset and progression as derived from the time lapsed MPPC of FIG. 15A wherein the perturbations in each grouping are incorporated into an aggregate index along a single smoothed time series for each group. Note this is a typical progression of sepsis with initial involvement of the inflammatory group 160 then each other group is involved in progression. Note the late timing of the treatment 162 is particularly evident in this summary view derived from the more complex images.

Rather than or in combination with an index, if desired the processor may be programmed to provide an indication of the severity and number of the aggregate perturbations in each group. These may be for example designated by many enlarging or colored arrows, other icons, and/or timed instability scores, to name a few. Many such options may be included so that the user may define his or her preference to visualize the sequence and patterns of cascade progression across groups.

A range of expert and pattern recognition systems may be applied to analyze the images and the images generated by the image processor. These include the image Identification Processor. In one embodiment the image Identification Processor works with the image editor which allows the user to select the images for detection using for example a from a drag and drop interface. In an embodiment the drag and drop interface provides for the discretionary selection of, for example, the time-series type to be selected, then occurrences are selected on each time-series type in order and the ranges of relative positions and orders occurrences is selected. In this example, the image editor allows customization of the desired ranges for the components of the images (and therefore the ranges of the images themselves) to be selected as well as the response of the image Identification Processor to the detection of a given image and/or images. The image editor may allow for selecting the ranges of timing and order of the occurrences to generate a specific output such as a proposed diagnosis, warning, order for more testing or imitation or termination of treatment. The image Identification Processor may also be adaptive such that a physician inputs the diagnosis present, such as for example septic shock, with a given image. The physician may also capture a given image or set of images into the image editor to then select ranges about the occurrences within the image which also would have indicated the presence of septic shock so that the adaptive image processor may learn more quickly.

FIGS. 15, 16, 17, 18 and 20 represent a 2 dimensional "time lapsed" snapshot view four MPPC after they have proceeded to advance states. This view also provides an alternate user interface for the creation and editing of the image definition set. Researchers may use an image editor to create and manipulate image models such as those examples depicted in FIGS. 15, 16, 17 and 18.

Figure 20:
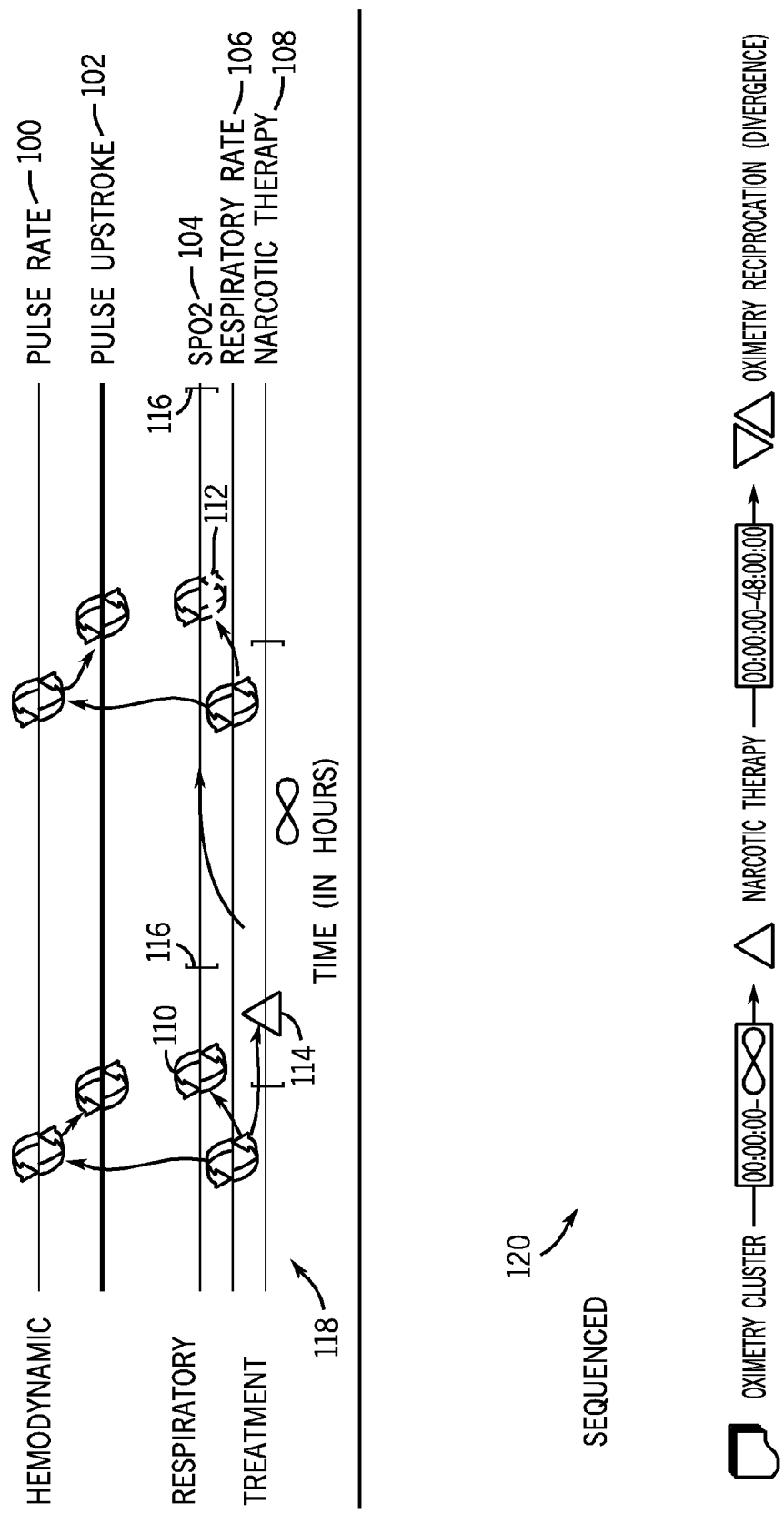
FIG. 20 is a split screen diagram of a drag and drop interface for constructing combined physiologic and treatment images for subsequent detection by the patient safety processor showing the construction of a motion picture indicative of narcotic associated recovery failure in the presence of sleep apnea.

In one embodiment researchers work from the top down to define images. Researchers begin by selecting a set of channels in which they want to "paint" the image. FIG. 20 depicts the image editor being used to "paint" the narcotic-induced ventilation instability image. channels (100, 102, 104, 106, 108) may be ordered in any number of ways, by sorting, categorizing or by simple drag-and-drop selection of location within the image editor. channels may be duplicated (e.g. 100, 102, 104, 106) to expand the image so that the relationships may be defined in a non-overlapping way for complex definitions that define multiple relationships. The image editor maintains the relationships within and between defined elements within the channels regardless of their vertical location within the editor. Researchers then select a channel and the image editor presents a set of occurrences that are available which apply to the given channel. Researchers may select any of these elements and drop them on channel. Also, the researcher may create a new element at any point within a channel (for example using a right-click menu editor). Locations within the editor indicate relative locations in time between selected and/or created elements. If an occurrence which spans multiple channels is dropped on a location, the image editor determines the additional channels to be added. The location of the corresponding event is determined as the midpoint of the search window definition. The entire window is shown as a set of parenthesis 116 indicating the range of the search window relative to the corresponding event, in this case a treatment event with an IV narcotic 114. Search windows are shown only within the beta channel of the relational binary and the event itself is show within the midpoint of the search window. If an event is both a beta and an alpha event the search window displayed is around the event is specific to the event when it is participating as a beta event. Search windows may be suppressed within the editor and/or shown only within the relational binary currently selected due to the fact that a single event may be the beta of any number of binaries. Individual events may be dropped onto a channel or created on a channel. New event types may be defined within the image editor. Events may be connected with a drag-and-drop selection or with an alpha and beta click selection, for example to define new event binary types.

The image editor creates and modifies image definition sets. Furthermore, the image editor works in concert with both the convergence editor and the event editor to create and modify the binary and event definition sets. In one embodiment (shown in FIG. 20), the definition of image is accomplished with a split-screen view showing the image editor in the top pane 118 while the image definition editor is in the lower pane 120 showing an alternative type of image diagram. These two models are completely synchronized with changes in one immediately reflecting the change in the other.

In one embodiment researchers work from the bottom up to define failures from a set of time series. Researchers may begin with a set of actual time series from patients diagnosed with known failures, with a set of time series generated by the processor to simulate certain conditions or a set of time series simulating no perturbation at all within a patient. This set of time series may be designated as immutable (for example with the set of actual time series) or may be edited to provide a sample of the patterns being defined. Researchers may select portions of the time series, which the image editor then will analyze to provide candidate event definitions. Alternatively the researcher may select parameters to define an event and the time series displayed will indicate the results of that definition overlaid on top of the time series to provide visual guidance to the researcher. Once the researcher completes the definition of an event the image editor will compare that definition with other definitions within the same channel. If similar patterns are found the researcher is alerted and allowed to create a new event type or select one of the event types already selected. If the event is a relational event, the researcher may select a corresponding event from which relational parameters may be defined and experimented with or the researcher may simply define a function (e.g. >2xRelative Magnitude). Once an event has been fully defined then the researcher may choose to relate the event to another event within the image or to a search window within the image (e.g. to indicate a missing or null event). The researcher may indicate that a processor-ordered event as the beta of a relational binary. Groups of events and relational binaries or any other occurrence may then be selected to define a images. images already defined within the image definition set are highlighted such that they may be included into the image the researcher is working with or the researcher may simply select to alter its definition. Access into the occurrence property Subsystem is available and the expression editors included indicate immediate results with respect to the current image or other occurrences selected. This allows the image editor to work on all aspects of the image including scope definition, qualification rules to name a few.

In one embodiment, the image editor may be presented with a large collection of time series sets provided with the indication of the presence or absence of a particular known image. The image editor creates a set of candidate definition sets refining them to create the right specificity and sensitively to match the sample set. Once the best-fit definition sets are created, a second large collection of times series sets are provided with the indication of the presence or absence of a particular known image. The image editor first uses the candidate definition set, determining sensitivity and specificity, and then refines the definition set to be better suited if possible to both the first and the second collection of sample data. This process may be executed iteratively until a best-fit set of definition sets is created or the process is deemed not to be asymptotic and is abandoned.

In one embodiment the image may be "played" or executed by the image editor as an MPPC to provide further time-specific markers. A default execution of an image is "played" by placing all events as specified in their default (e.g. midpoint) location within their respective search windows as defined by the image definition. A sample result of this is displayed in FIG. 15B. Once the image is played vertical markers are placed within the timeline as in FIG. 15B to indicate progressive states within an evolving image. In this way, the image definition may be provided the specifications by which the image state may be identified and displayed within the Patient Safety Monitor. FIGS. 15C,15D,15E and 15F show the 4 views of an image evolving within the Patient Safety Monitor over time. The Patient safety processor identifies one or more of the diseases, disorders, or cascades which are most consistent with the present state of the image and displays it at the bottom of the monitor (along with differential diagnosis if desired).

In an alternate and/or complimentary embodiment, the image editor provides the ability to split the execution of an image into multiple intermediate and/or end states. Each different branch within the image definition may be defined as a state within an image or a different, albeit related, image. Trees of related images may be composed to provide alternative evolutions of failure within the image definition.

Figure 22:
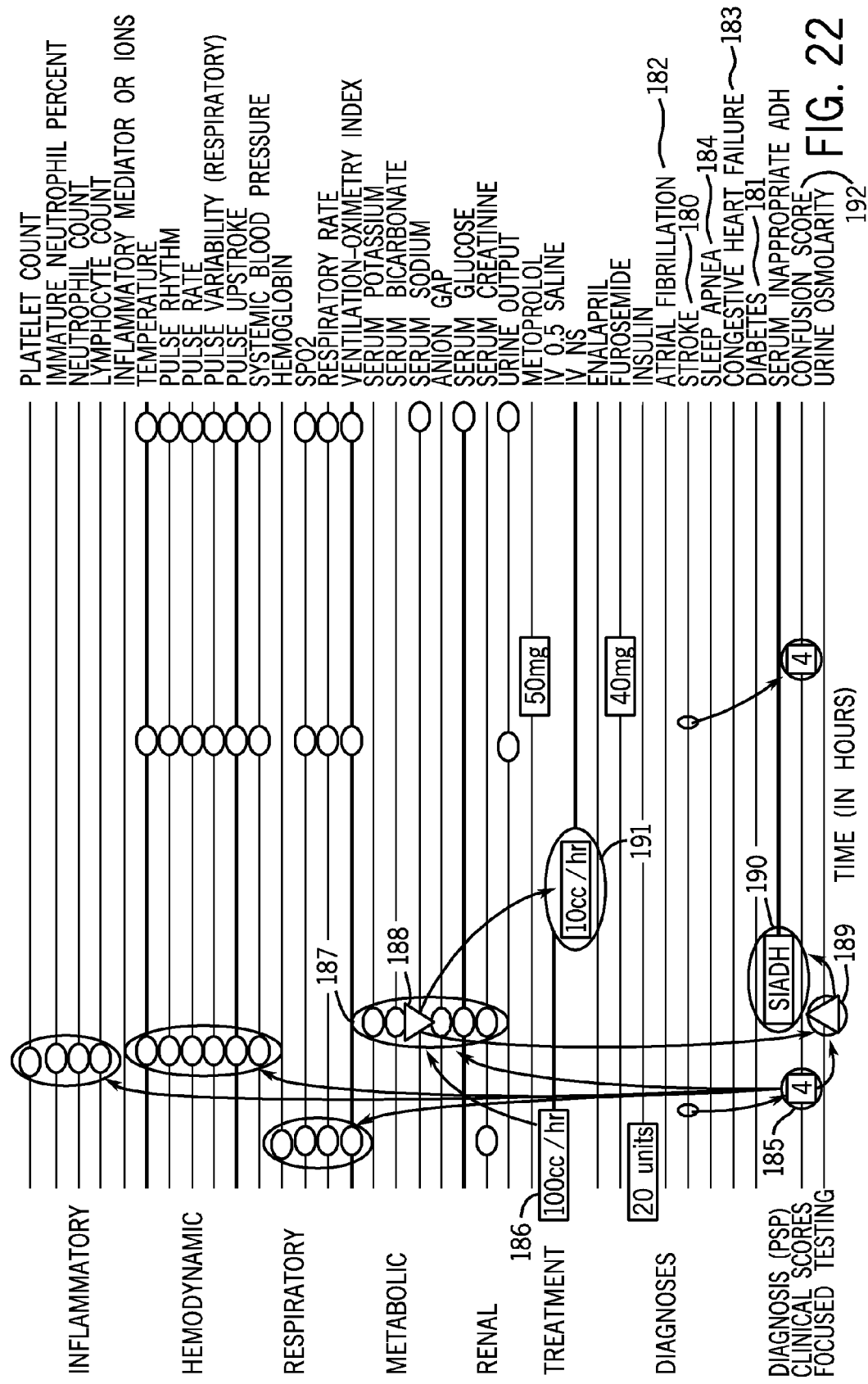
FIG. 22 is a general image including a plurality of timelines from the patient illustrated in FIG. 1, which shows a image of excessive secretion of serum inappropriate antidiuretic hormone (SIADH) induced fall in hyponatremia and confusion.

FIG. 22 is a frame from a time lapsed motion image including a plurality of timelines from the patient illustrated by the dotted lines in the failure mode diagram of FIG. 1. In this image the patient who has experienced a stroke has now developed a condition associated with serum inappropriate antidiuretic hormone (SIADH), which induces an induced fall in serum sodium and confusion. On detection of the elevated confusion score processor 304 examines the pathways for confusion (see some example in FIG. 1) and does not find a low SPO$_2$ low or high respiratory rate, a high ventilation oximetry index, or a rising inflammatory (although not shown here, in addition to systemic inflammation (for example due to sepsis) the processor 304 may also check for focal inflammation such as intra cavitary inflammation of the bladder as a cause of the confusion. The search for a metabolic occurrence is positive with the detection of hyponatremia. This of course does not mean that this is the cause (and the processor 304 will warn that the stroke may still be the direct cause) but the processor 304 cannot make the common mistake that the stroke is the cause and stop there.

The case presented in FIG. 22 is similar to a recent case, which was evaluated in consultation by one of the present inventors. To show how this type of problem happens every day in the hospital and to particularly to demonstrate the long unfulfilled need, the history of that case will be discussed in greater detail.

The patient presented with an acute stroke but was recovering and alert. Then he slowly began to develop confusion and less alertness. As the stroke was large the nurses and physicians managing the case thought that the patient's confusion and obtundation was due to brain swelling and called the family in to adjust code status. For this reason the family consulted one of the present inventors. The patient SPO$_2$ and ventilation rate were normal, he had no signs of sepsis and because of recently normal electrolytes the attending physicians did not think that a metabolic cause for the confusion was a reasonable option. In other words they misdiagnosed the pathophysiologic failure pathway (illustrated on the failure mode diagram 200 of FIG. 1) and they thought the pathophysiologic pathway was following the direct connecting line 170 between stroke 208 and confusion 220 as shown in the failure mode diagram 200 in FIG. 1. However, prior to the onset of the confusion the patient was receiving 0.5 NS in spite of the fact that that he was eating and drinking. Repeat serum sodium confirmed a fall in sodium and SIADH was confirmed with additional testing. Cautious correction of his sodium resulted in rapid recovery and resolution of the confusion and obtundation. This might be considered a straightforward case in isolation but it shows how easy it is to go down the wrong path when managing many complex patients while trying to remember how alert and active such patient were the previous day. Subtle symptoms sneak up on healthcare workers and delay detection of life threatening failures.

Since the stroke caused the SIADH (which cased the fall in serum sodium) the actual modes of failure were significantly different than suspected by the hospitalist in this case. The actual failure followed to path 171 from the stroke 208 to the hyponatremia 242 and then followed the path 172 from the hyponatremia 242 to the confusion 220. In this case the patient survived the missed diagnosis but he experienced several extra days unnecessary days in the hospital because of delay in detection and treatment of this failure.

Now referring to FIG. 22 note that this image is derived from a patient with the failure mode diagram of FIG. 1 having a timeline for a stroke 180, diabetes 181, atrial fibrillation 182, a history of congestive heart failure 183, and sleep apnea 184. These correspond to the failure mode diagram of FIG. 1 illustrating potential relationships between stroke 208, diabetes 202, atrial fibrillation 206, congestive heart failure 204, and sleep apnea 210. Note that in FIG. 20 the Patient safety processor is ordering routine confusion scores 192 because of the timeline 180 indicating a stroke. The detection of an increase in confusion 185 or the presence of hypotonic saline administration 186 to a patient with a stroke timeline 180 automatically triggers a measure of electrolytes and glucose 187 and upon the detection of a fall in serum sodium 188 the processor orders a urine osmolarity 189 and indicates a high probability of SIADH 190 and recommends an adjustment in fluid therapy 191.

Here the problem is simple but the early signs of failure were at first subtle at a time when intervention would have prevented the increased length of stay later the pathways of failure were confused leading to further delay and considerable family since they were told the incorrect diagnosis. In this case the nurses and physicians may have been busy or may have been inexperienced or simply not familiar with the subtle decline in mutation, which may attend the development of SIADH in a stroke patient. The reason subtly findings are missed is myriad. Note also, in defense of the healthcare team, as illustrated in the failure mode diagram of FIG. 1, this is simply one failure and there are very many potential failures for this complex patient and all the nurse and physicians are caring for many such patients. Furthermore, in this case the serum sodium was nearly normal when the low sodium was finally detected so many physicians would not think the level was sufficiently low to cause these symptoms or warrant intervention. However, the sodium had dropped from a high normal to just below normal and in patient with brain edema the magnitude of the fall in serum sodium may be more significant than the absolute value and this variation in vulnerability from patient to patient and within the same patient depending on coexisting disorders, diseases, and medications are not concepts which are easily grasped by some healthcare workers who have observed patients with very low serum sodium values without any change in mentation. This illustrates the value of generating and recognizing a moving picture of the failure and care. The Patient safety processor does not need to see a threshold breach because it is looking at the entire failure and care image over time and, it is programmed to recognize that this image indicates vulnerability to a fall in serum sodium, even a fall which does not go below threshold. The Patient safety processor provides the advantage of continued vigilance and continuous consideration of all of the potential physiologic failures, which are consistent with the images.

According to one aspect of the present embodiment failure mode diagrams, such as the one in FIG. 1, may be used to construct images by applying the cascading binary relationships between diseases, treatments, and perturbations to construct images and image ranges using the image editor. According to one embodiment a failure mode diagram designer is derived for use, for example, by each hospital department or by hospital expert groups to generate failure mode diagrams which relate to their patient populations. In one embodiment of the failure mode diagram designer, a drag and drop tool is provided for entering and/or selecting diagnosis, treatment, complications of disease, complications of treatment, actions of treatment, outputs of monitor, and erroneous outputs and/or failures of monitors (to name a few). The failure mode diagram may include icons for the drag and drop editor. The failure mode diagram may be built in an interactive programming environment which allows the reader to quickly zoom in on any region and the explore and visualize the diagram by diagnosis, complications, drug, treatment, and the like. In this way the interactive effects of any drug can be instantly visualized in relation to its potentially positive or negative effects in different disease states and different failures. This failure mode diagram can be used to assist in the programming of the processor 304 and the processor 304 can provide outputs in the form of highlights along the failure mode diagram to indicate the potential failures detected. In this regard FIG. 1 and FIG. 22 are two exemplary outputs of the processor 304 but they are also exemplary views of editors, which can be deployed to program the processor 304 for failure mode detection.

Figure 21:
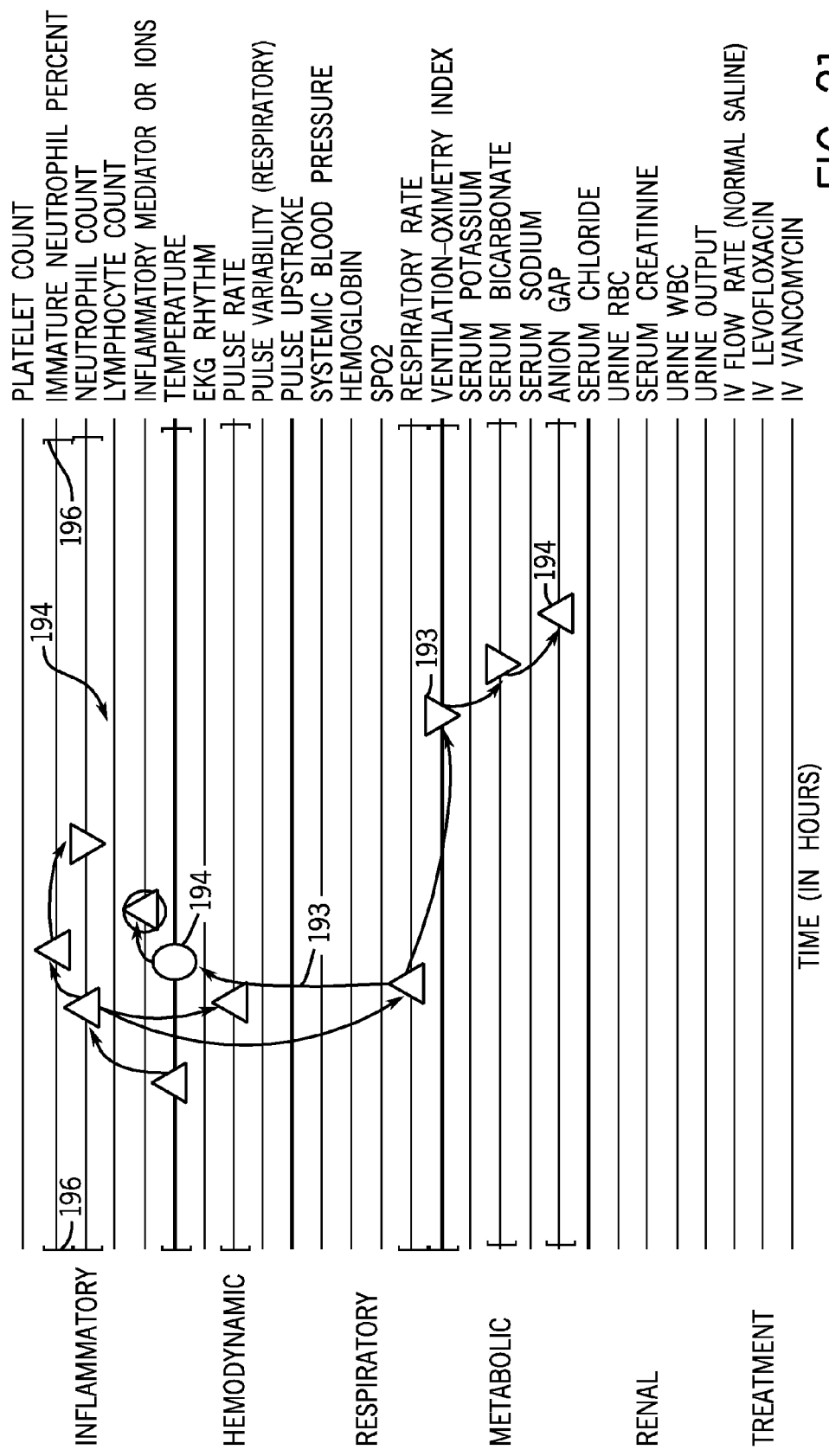
FIG. 21 is an image frame of a image editor for constructing a MPPC for recognition by the Patient safety processor consistent with presumptive severe sepsis.

FIG. 21 is an image frame of an image editor for constructing working within a range of the MPPC for the recognition by the Patient safety processor of images and other occurrences associated with a specified condition. In this case the image shown is consistent with and indicative of presumptive severe sepsis. Note the inflammatory/hemodynamic/respiratory augmentation 192 is followed in the image by a fall in VIO 193 and metabolic failure with a rise in anion gap 194. Note that if the inflammatory/hemodynamic/respiratory augmentation 192 is unassociated with a rise in temperature (a null binary 193 is identified), inflammatory markers 195 are ordered to confirm the presence of the inflammatory component of the image. The typical sequence of binaries is shown but the parentheses 196 indicate that in these events may occur in any order. The processor 304 may provide greater confidence if the order is as shown and lesser confidence if the order is different that shown. As noted images may overlap such that patient with preexisting hemodynamic instability may become septic, for this reason, in this case the order is not deemed pivotal. However, for some images the order of events may provide much greater specificity (in which case the parenthesis is adjusting accordingly). At first the image editor may be set to be more liberal and then adjusted as hospital experience and the quality improvement department dictates.

The patient safety processor is not constrained by these definitions during analysis in an absolute way, but rather compares actual data to a plurality of images and image states to find best-fit matches. The patient safety processor will indicate all possible images and image states ranked by level of confidence. For example the patient safety processor may indicate that a MPPC is consistent the Systemic Inflammatory Response Syndrome with a high degree of confidence and early septic shock with a medium degree of confidence and that TTP (and other potential alternatives) or overlapping failure modes are remotely possible in view of the image and remain to be excluded. The physician may be asked if it is desired to order the focused testing to exclude these remote alternatives or overlaps and/or the processor may be programmed to automatically add this testing based on a specific range of images (as defined, for example, using the drag-and-drop editor discussed previously).

The identification of failure within the patient safety processor is not the single selection of a failure mode or a failure state, but the ranking of a set of images with regard to their fit within the data presented. The identification of multiple images is not simply the selection of alternatives. Multiple failures may, in fact, exist and be interacting with each other. Early states of some images may be very similar, or in fact exactly the same, as the early stages of other images or of a combination of images. The patient safety processor provides the analysis and visualizations that allow the health worker to understand the current state of the patient (and patient environment) in terms of possible future states—alternatives and candidate overlaps—along with confidence levels as to their specification. Further, the Patient safety monitor allows the health care worker to query the patient safety processor with regards to confidence levels and, in particular, the comparative confidence level between two images and/or image states. For example, the confidence level for sepsis is low with the frame shown in FIG. 15B whereas it is intermediate for frame in FIG. 15C and high form all later frames. These confidence levels along with the action desired may be programmed into the processor 304 in advance by specialty groups, hospital safety committees, and/or may be customized and "tuned" by individual physicians and or may be applied adaptively by the processor by comparing the entered new diagnosis with the present image and recoding that image as indication of that state. In the adaptive mode the processor may be programmed to ask "is this image indicative of a failure process defined by this newly entered diagnosis and, if so, please specify the first event, binary or image which in retrospect was part of this specific failure process."

In one embodiment, the patient safety processor may be trained by a pathophysiological engine (such as a human simulator as are known in the art) for the creation of failure and response images. Given a specified event definition set and binary definition set the Patent Safety Processor provides a dynamic image derived from the input of the pathophysiologic engine and the Processor is instructed as to the nature of the images so that when these images are detected in the future they are recognized. In one embodiment a human simulator is connected to the processor 304 to provide an improved teaching tool for healthcare workers. Researchers may select to be presented with a normal, unperturbed patient with various conditions. Once a dynamic image of the patient is displayed researchers may introduce perturbation into the pathophysiological engine, which will result in new dynamic images from the Patient safety processor. For example, a research may select relationships presented according to a convergence and toggle them to divergence. Also, random divergence may be configured into the system. Divergence with respect to a single or a set of response system(s) may be specified to model the breakdown of systemic response. Divergence may be configure globally or for a specific timeframe indicating that systemic response fails, or is delayed. In this way both perturbation and failure of systemic response may be selectively introduced to create images. These images may be persisted to be further edited within the image editor or other tool. The researcher may select several different variations and save them as failures and/or failure states. These failures and/or failure states may be persisted within a image definition set to be used by the image processor. Further, resultant images may be compared with actual patient data to refine image, binary and event definition sets.

Alternately or in combination, according to one embodiment, an MPPC may be carried from the processor 304 to the processor driving the human simulator so that healthcare workers may observe the reanimation of the MPPC of the processor 304 either as a digital animation or as a reanimation derived from output of a human manikin.

One utilization of the embodiment, which combines the pathophysiological engine to the processor 304, is to model treatment protocols. The engine may output expected or unexpected parameters (divergence) in response to treatment and the image output of the processor 304 may be observed, and/or recorded for protocol modeling. Further, using the ability to introduce divergence, allows processed protocols or other protocols to be verified for reasonable redundancy to cover failures of systemic response.

Figure 23:
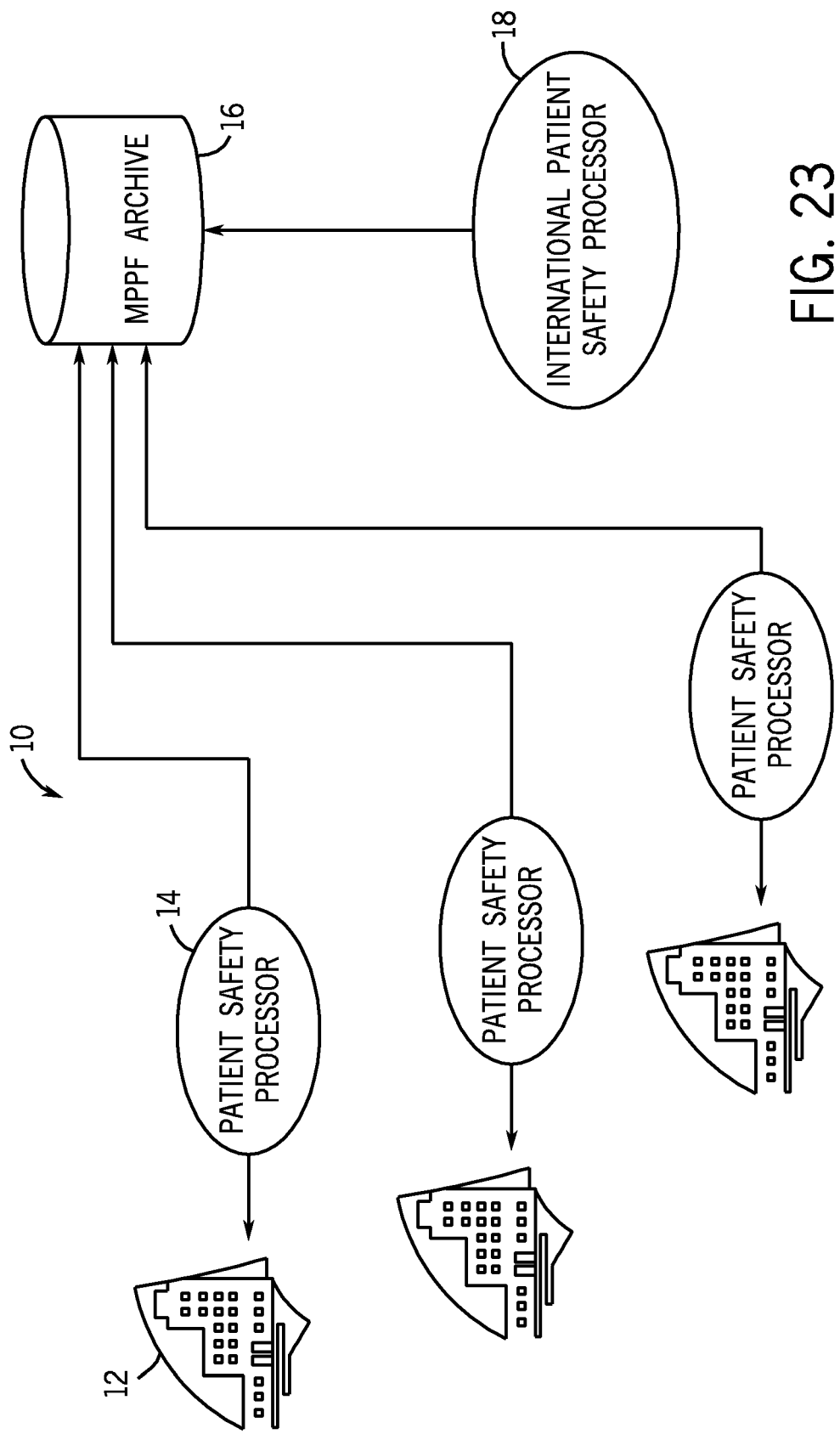
FIG. 23 is a diagram of the patient safety processor network for archiving and cataloging images.

One of the problems with conventional diagnostic process is that, even with diligence, the time to detection of the cause of a complex process is a direct function of care worker experience. One of the present inventors, a trained critical care physician, has over many years managed perhaps several hundred septic shock patients and for this reason he learned to visualize the complex cascades embodied in FIG. 15 in when reviewing the patients chart in consultation. However, this is not an easy task and requires vast experience. Yet during this time the number of TTP cases evaluated by this physician was low. Therefore even the most experienced physicians have only limited experience with uncommon disease cascades. To solve this problem, as shown in FIG. 23, a patient safety processor international network 10 in each hospital 12 is connected to its own processor 14 and each processor 14 is connected to a central MPPC archive 16. The MPPCs from each processor 14 are uploaded to the central MPPC archive 16 from each hospital. The central MPPC archive is connected to the international processor 18, which serves to process the MPPC from the central MPPC archive 16 and to improve MPPC recognition and to develop new image and failure mode recognition and treatment protocols. MPPC from a hospital processor 14, which are classified, as associated with an objectively known case, such as a MPPC suggestive of pulmonary embolism including a positive pulmonary angiogram are applied to build an objectively defined MPPC database to further build the scope and specificity of the MPPC of pulmonary embolism. In the alternative MPPC which are classified as associated with an subjective final diagnosis, such as a MPPC suggestive of SLE induced alveolar hemorrhage, for example, (followed by a opinion of a consensus group that this was the final diagnosis) is added to the subjectively defined MPPC database case database to further build the scope and specificity of the MPPC of SLE induced alveolar hemorrhage. In this way a massive database may be derived from MPPC and images, which are components of MPPC, derived from the worldwide management of disease. International testing and treatment protocols based on the real-time MPPC detection may be developed which may potentially set a minimum standard of detection of catastrophic events even in rural hospitals with a few beds, in urban hospitals which are poorly staffed, and in environments wherein physician and nurse experience may be very low. New protocols may be derived and uploaded to these hospitals for their discretionary use as analysis of the MPPC results in response to older protocols or new or additional treatment outside the protocols reveals potential for improvement. The approach has the potential to provide improved surveillance of drug reactions and efficacy, after, for example the introduction of a new drug into a protocol, which may be an experimental protocol. missing portion of the MPPC may also be identified to support the development of new tests, which fill in the gaps or perhaps reduce the number of tests required to define cause(s) of the failure. Cost comparison of different testing and treatment protocols may be performed.

The bandwidth of the MPPC is defined by the number of tests, historic data, and treatments et al. which include the MPPC. When potentially treacherous images of perturbation are identified along the MPPC the Patient safety processor is programmed to quickly broaden the bandwidth to investigate the alternative causes. This is important because the longer the duration an undetected failure mode the greater the increase in cost and mortality because complications develop with widen the cascade and make salvage more expensive and difficult.

A narrow bandwidth (fewer tests and/or simpler tests per unit of time) is, on the other hand, (without considering the cost of allowing a longer duration of failure) less expensive than a broader bandwidth. The "effective bandwidth" includes those components of the bandwidth, which actually contribute to characterize the factors actively defining the images, which are components of the MPPC. Poorly conceived testing and treatment increases the bandwidth and the medical cost but may not increase the effective bandwidth. The goal of the processor 304 is to increase the effective bandwidth as rapidly as possible without broadening the bandwidth inordinately. The ideal system monitors with a few monitors and tests but uses these as sentinels, increasing the number of monitors and tests automatically if specified occurrences are identified or failure cascades begin.

Therefore, one function of the present invention provide a mechanism to automatically increase the effective bandwidth of the MPPC at any time (for example at 2 AM in a rural hospital), to optimally shorten the duration of failure without the application of a continuously wide and expensive bandwidth. One optimal mechanism to broaden bandwidth is with improved testing, such as focused tests, which have a high sensitivity and specificity for a specific failure mode. The MPPC archive 16 of the patient safety processor Network 10 may be examined for opportunities to increase the motion picture bandwidth and achieving a balanced mechanism for mortality and cost reduction by shortening the duration of failure through earlier detection and improved treatment response.

The use of smaller bandwidths of monitoring and testing combined with the ability to auto adjust to a wider bandwidth upon detection of events, binaries, images, repeating occurrences and patterned occurrences reduces cost, and allows application to a larger populations of patients for the same or less cost. The occurrences, which precede physiologic failure, are recorded and this relationship is monitored by the interaction processor 304 via the network. If a relationship of physiologic failure to these specific occurrences is identified, the processor further examines the MPPC for these now sentinel occurrences, which, if obtained earlier using a wider testing bandwidth, might have provided a more diagnostic image earlier. These test are then added to the processor 304 as automatically ordered upon the detection of the in the sentinel occurrences. If a test or set of tests fails to provide additional image detection or quantification, which is not provided by another cheaper or less invasive test or set of tests, then the test or set of test is not used. In this way the processor 304 is auto adaptive, learning to optimize the processing of the MPPC by eliminating unnecessary or redundant testing and by adding testing which allows earlier detection of failure thereby reducing cost as a function of facilitating timely prevention of cascade development or prevention.

This same approach, using the adaptive processor 304 communicating with one or more centralized processor 304s over the national or international network to continuously or intermittently adjust and improve the testing components of the MPPC may also be applied to the treatment components of the MPPC to determine evidence that a given treatment had a measurable effect (positive or negative) on the MPPC. Treatment components include, for example, drugs, fluids, nutrition, surgical treatments, inhaled gas treatments, pressure treatments, rehabilitation, exercise, positioning, splinting, to name a few. The MPPC provides the images of the treatment relationships, including relationships related to timing of the treatment order, treatment delivery, treatment dose or procedure, the pattern of the individual treatment dose, the pattern of dose administration over time, the method of administration, and other images for comparison with the images of the rest of the MPPC. New treatments such as new drugs, different doses, different procedures, and/or the elimination of a treatment may be applied using the processor 304 to determine, as by the application of statistical comparison, the effect of the new drug on the MPPC in relation to the MPPC without the drug or treatment. In one embodiment, this is determined by the centralized processor 304, which then adjusts the protocol to produce the most favorable treatment regimen as determined by the processor 304 (and after approval by the physician group overseeing the processor 304). Locally at each hospital they may choose to accept or refuse the uploaded change from the centralized processor 304. In either case the subsequent MPPC of the refusing hospital may be compared by the processor 304 to the MPPC of those hospitals which accepted the uploaded changes into their processor 304 to determine if the change indeed had a positive, negative, or no impact on MPPC (including the expense components of the MPPC).

The use of one or more centralized processor 304s in communication with local processor 304s through a national or international Patient Safety Processing Network allows local healthcare delivery systems, hospitals, and even different floors to use different testing and treatment protocols. This diversification is a great strength of the system because the centralized processor has a very wide range of alternative MPPCs to choose from in selecting, what it, (and the overseeing physician experts of the centralized processor 304 if desired) determines is the optimal treatment and testing protocols from the diverse sets of MPPCs (which include a divers set of treatment and testing images).

As discussed, according to one embodiment, the patient safety processing network includes a set of local processor 304 located at hospital ward or unit. The Local processor 304 under the direction of the healthcare workers at that location. This allows the local healthcare workers to control the treatment and testing protocols, and variation of the testing bandwidth, deployed for the patient under their control. The local attending physicians individually or as a group as well as the hospital pharmacists and nurses may prescribe these protocols though the use of the Local processor 304. The local processor 304 records worker(s) (for example as a step time series or non-numeric time series in which a state transition event occurs when the physician, or nurse for example assumes responsibility and a different state transition event occurs when he or she is replaced by another. Alternatively, and possibly in combination, a state match event may be used to indicate the duration for which the physician or nurse was on duty. Those caring for the patient are therefore part of the Motion Picture of Physiological Condition (MPPC). Protocols may be decided by a group or by an individual physician caring for the patient. The extent to which a particular healthcare worker or group is statistically or otherwise associated with favorable or unfavorable MPPC may be assessed by the processor. The protocol choices for the local processor 304 may be made through the use of pre prepared MPPC protocols as previously discussed.

The local processor 304 may recognize the physician time-series and adjust the protocols and MPPC to match those selected by this physician. The physician may override the processor 304 and, if this occurs, this override includes at least one event and includes a new time series until the override is withdrawn. The extent to which a particular override is statistically or otherwise associated with favorable or unfavorable MPPC may be assessed by the Hospital processor 304, The Hospital Group processor 304, or the International processor 304. These may provide modifications in future protocols, and even provide incorporation of the modification of the override or the prevention of this type of override according to the MPPC associated with the override.

The local processor 304 throughout the hospital communicate with a central "Hospital processor 304" which is preferably under direction of the quality improvement committee and the hospital experts in each field. The Hospital processor 304 communicates with all the Local processor 304s and may be used to upload treatment/and or testing and/or bandwidth adjustment protocols and or comparison MPPC, which have been agreed upon for application hospital-wide to the local processor 304s.

Each Hospital processor 304 communicates with (and may be controlled by) central Organization processor 304. The healthcare "Organization processor 304" allows standardization of the hospital protocols through the Hospital processor 304s under its control to set minimum safety treatment and testing standards and may be controlled by a centralized quality assurance group with expert representatives from all of the hospitals. Since the individuals caring for the patient represent at least one time series and the ward represents at least one time series and the hospital represents at least one time series and the organization represents at least one time series. The MMPP at the Organization processor 304 therefore includes all of these caseworker and location time series for each patient. Alternatively, or in combination, if the Patient is wearing a monitored GPS unit, this may include a location time series, which provides continuous real time location as part of the MMPP. (The processor 304s may compare with the entered locations to the GPS location to produce a confirmatory binary.)

One embodiment demonstrates an example of how a new set of time series derived from a new test or testing device may be evaluated for cost effectiveness. In this example, a pulse oximetry reflectance probe is mounted (as by hat or headband or other fixation device one or both eyes to the patient's head) and the probe is wirelessly or otherwise connected to pulse oximeter and the local processor 304 (as by Bluetooth for example). The transmitter may be mounted in the probe, or in or on the headband, hat, or behind the ear (for example, in the position of a hearing aid if desired). A position sensor may also be provided mounted on the patient. A maneuver such as a change in body position from supine to standing may be detected and included as a state transition or state match event by the processor 304 and a fall of a component of the photoplethysmographic pulse (indicative of the perfusion of the capillary bed distribution of the supra-orbital artery, a distal branch of the internal carotid) in relation to a maneuver to produce a divergent binary. In this way the flow of the capillary bed above the eye in relation to a standing maneuver becomes a surrogate marker of other capillary beds supplied from the internal carotidin relation to a standing maneuver. Real time perfusion may be compared with that of the ear, fingertip, or the pulse pressure (as by an invasive arterial line for example) to identify disparate in perfusion in one or both of the internal carotid distribution. The local processor 304 processes the MPPC with these as additional time-series. The local processor 304 uploads the MPPC to the Hospital processor 304, and the Hospital processor 304, Organizational processor 304, and/or International processor 304 where the MPPCs may be evaluated using the patient safety comparison processor to determine if, after adjusting for disparities in the MPPCs as a function of co morbidities and the like, the MPPCs which includes orthostatic reductions in supraorbital perfusion (in combination with therapy or corrective action to reduce falls upon the detection) is associated with a statistically significant decrease in the number of falls in the hospital. These time series may be automatically added (by automatically ordering the intermittent or continuous supra-orbital monitoring used the study) to increase the testing bandwidth when it is detected that the MPPC of a given patient is similar to those of the study population (for example as by type of surgery, age, co morbidities, or other events or images) where the addition of those processed time-series data had a positive impact on outcome. If one the other hand disparate hypo-perfusion above one eye is identified ultrasound evaluation for carotid disease may be ordered by the processor 304 and the result added as an event.

All the Organization processor 304s (or Hospital processor 304s if the hospital is not under a central organization) are preferably connected to an International processor 304. The International processor 304 is preferably controlled by a healthcare information corporation, such as Google or Microsoft, which maintains the International processor 304 and the network as part of a centralized repository of electronic medical records for example Health Vault™ by Microsoft). Each subordinate processor 304 (below the international processor 304) is capable of operating independent of the processor 304 Network so extensive redundancy, lack of subordinate dependency, and therefore greater safety against network failure is built into the processor 304 Network.

This processor 304 Network structure allows a wide range of minimum standards to be set by each government and allows the monitoring of the effects across the range of minimum standards to determine relative cost and benefit of individual standards.

Any domain-specific processor 304 will preferably include a patient safety comparison processor (PSCP) which compares the MPPC and all occurrences within the MPPC, such as events, binaries, images, and cascades, to other MPPCs and all of the occurrences of the other MPPCs to identify statistical differences between the MPPC which are associated with improved or adverse expenditure, outcome, length of stay, morbidity, mortality, resource consumption, and/or complications to name a few.

One advantage of the processor 304 is that the objects of the MPPC are discrete and are therefore readily incorporated into statistical software components of the PSCP. Specifically the processor 304 provides the ability to positively identify the existence of an occurrence within a patient's set of stream s given a specific occurrence definition and search window of time. In the contemplated embodiment, the process of identifying any of these occurrences is accomplished through a polymorphic image identification method. The unified method of searching and/or identification according to this embodiment, allows the incorporation of a range of statistical tools thereby providing access to the functionality of a wide array of statistical approaches and methodologies, as are well known in the art, for identifying differences in discrete time related data collections.

The PSCP provides further optimization through basic occurrence query capabilities. For example, a query may be crafted to include a specific occurrence, the domain (e g Local, Hospital, Organizational, International), and a set of conditions. The result set would provide patients along with the time spans in which the specified occurrence obtained. Aggregations of result sets provide an indication of the percentage of identification within the specified population (e.g. 434 (0.003%) patients within the specified domain (~2.3 Million) meeting the conditions (234,046) were identified as having the specified occurrence).

The objects also include organized collections of an ascending hierarchy of complexity and the organized collections, which may be compared statistically at each ascending level of complexity to identify associated differences. In one embodiment the PSCP divides the MPPCs into groups having a least a portion of substantially the same images. For example a grouping may be derived having substantially the same initial sepsis cascade picture and similar co morbidities and age and sex but different physicians, hospitals and/or treatments. Differences in length, progression, compilations and mortality associated with the cascade may be identified and statistically compared with the differences in physicians, hospitals, treatments, testing, and/or treatment timing.

In one embodiment, the processor 304 is supported by an Online Transaction Process (OLTP) system to optimize data inclusion and relational management and image identification while the PSCP includes an associated Online Analytical Processing (OLAP) database optimized for the data mining with regard to occurrence presence and analysis within large populations. occurrence identification within a patient provides a primary measure while dimensions are established for time, patient characteristics, personnel, etc. The multidimensional data environment allows for the inclusions of dimensions as data is available and/or determined as providing important data segmentation. Hierarchies (e.g. domain hierarchies, personnel hierarchies) are included to "roll up" aggregations.

When a particular testing, treatment, bandwidth variation, ward location, or hospital location is identified as statistically associated with improved outcome, then the International processor 304 may offer, as for download, new protocols which incorporate those identified particulars into the Hospital processor 304*s* and/or Organization processor 304*s* for their consideration. New medication or treatments may be assessed in this way with blinding accommodated by the processor 304 such that the time series of the experimental medication is labeled with an experimental code.

In one embodiment, the PSCP applies a top down approach to statistical analysis of objects wherein an expert or panel of experts at any level from the ward to the international level, defines the statistical comparisons, which they desire. This may be performed by a Probability Assessment Studio, for example as by drag and drop of occurrences (selecting relational timing ranges for the objects), such as events, binaries, images, etc. into a first window and then drag and drop of occurrences also selecting relational timing ranges for these objects such as a blood culture result, a diagnosis, a medication, a combination of medication and another object, to name a few. The processor may then provide the statistical comparison indicating the statistical relationship of the compared objects.

In one embodiment, the Probability Assessment Studio indicates Near Misses and their percentages as well as the probability of hits. The definition of a near miss must be specified within the occurrence definition. Here it is important to contrast as for example by multiple regression. The processor 304 is applied to allow individual and combined events, binaries, and images to be compared statistically to targets (which target may be each other). This mitigates the primary weakness of the application of multiple regressions to define relationally statistical values as a function of a plurality of different relational variables. While many reading the medical literature are compelled by the assumption laden mathematical embellishments, which commonly include many multiple regression equation based evaluations of complex relational physiologic data sets, a truly skilled mathematician is aware that the application of multiple regression equations to relational physiologic datasets will commonly produce outputs of dubious mathematical integrity and reproducibly. This is one of the advantages of statistical processing using the processor 304 which allows statistical analysis to be applied with a much wider discretion over a priori separation and combination of images.

According to one aspect of the present invention a Patient Safety Discovery Processor (PSDP) is provided at one of the levels but ideally at the level of the International Patient safety processor. Like the patient safety comparison processor, the PSDP compares (as for example by statistical analysis) occurrences such as events, binaries, images, cascades, repeating occurrences and patterned occurrences to other objects termed "highly definitive objects" such as final diagnoses, results of "highly definitive" lab tests (such as a blood culture, pregnancy test, or HIV test), length of stay, expense of care, number of care workers providing care, number of care workers providing care to others (workload of the care-workers), consensus based diagnosis, to name a few. However, in contrast to the PSCP, the PSDP applies a "bottom up" approach by performing statistical analysis on occurrences (potentially substantially all objects) in the processor 304 database to identify previously unknown relationships. These relationships may include statistically significant relationships with each other and especially with objects including at least one final result, diagnosis, and/or outcome.

In one embodiment The Patient Safety Discovery Processor may determine the probability that a first occurrence is associated with a highly definitive object and then determines the probability that a second occurrence which occurs after the first object. The processor then determines the probability that each consecutive object is associated with the highly definitive object. This generates a time series of probabilities with each probability data point being derived with each new occurrence type (which may be generated each time a new object is added inside the occurrence type definition or each time the probability of the occurrence of the highly definitive object changes as a function of a new object which is added to the definition). Here a plurality of probability time series may be derived, one or more for each highly definitive object. These time series of probabilities may be converted into objects and processed to detect and characterize events of rising or falling probability (termed probability events), by the objectification processor incorporated into the processor 304. In a presently contemplated embodiment, the baseline probability is established (pretest probability) based on non-volatile risk factors and then the occurrence type definitions are built (after the initial probability has been determined by time insensitive or pretest probability assessment) so that the slope of the probability time series is less dependent of non-volatile factors.

The patterns of the time series of Probabilities (TSP) generated from sequential occurrences within an MPPC may exhibit characteristics, which provide more information then is provided by individual probabilities alone. For example, when a rise event (along the time series of Probabilities) is detected the slope and magnitude of the rise is known. A rise event along a TSP, which is of high magnitude and exhibits a rapid slope is said to define "probabilistic momentum" (PPM) which may be positive or negative. The presence of a high positive PPM provides strong evidence of the presence or future detection of the highly definitive object (or diagnosis) under test. TSP may be generated by the processor for each diagnosis for which an increased probability is identified. Treatment of a pathophysiologic process such as sepsis (if effective) will cause the generation of positive reciprocation along the TSP indicating first a positive PPM, followed by a negative PPM. This is a desirable pattern, since if the negative PPM is maintained; this provides evidence that the catastrophic event has been aborted. Therapy, which is statistically associated with a positive probabilistic reciprocation along the TSP is identified by the International processor 304.

Figure 25:
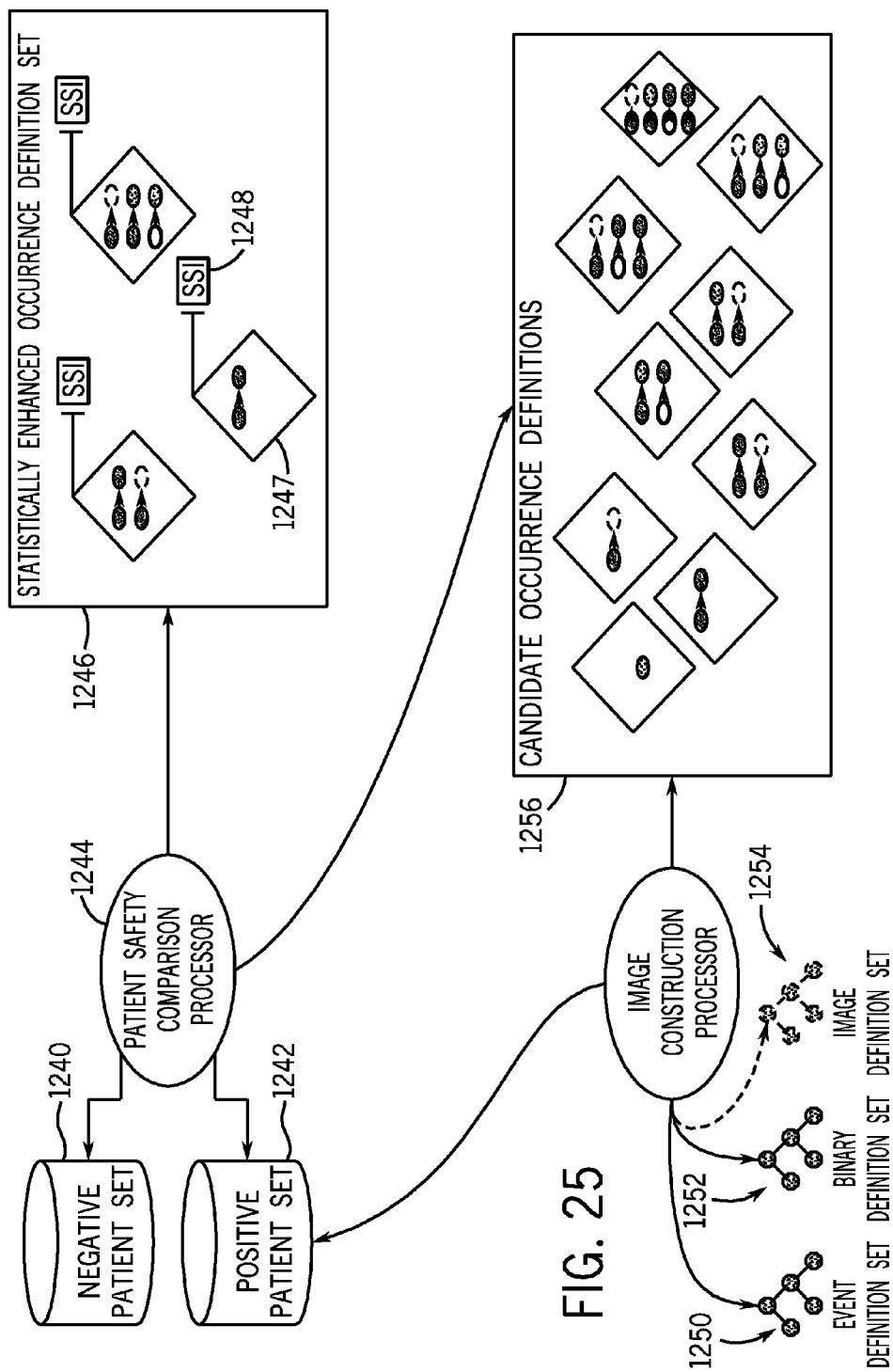
FIG. 25 is a data flow diagram illustrating guided image discovery image discovery through the use of the patient safety comparison processor and the image construction processor to produce a statistically enhanced occurrence definition set.

FIG. 25 depicts one embodiment in which the PSDP performs statistical analysis to create and/or modify an image definition set. The PSDP, provided with an event definition set 1250 and binary definition set 1252 (and optionally an image definition set 1254) as well as a domain of time series data, in association with the processor 304 and PSCP, provides an environment for guided image discovery. The output of this discovery process is a statistically enhanced occurrence definition set 1246.

The first step for the researcher using guided image discovery is to identify a domain of patients (or patient-grouped time series sets) to which discovery will be applied (The aggregate of 1240 and 1242). Next, the researcher must attach each patient with a Boolean flag indicating the presence or absence of the condition or diagnosis to which the discovered images will be related. In an example the researcher may identify a definitive object, which includes a "stand alone diagnostic meaning" (as determined by a blood culture object or pathology object for example). In one embodiment, this definitive object is used to begin the process of identification. The processor 304 marks all patients that contain this definitive object as positive (placing them logically and/or physically into the Positive Patient set 1242), but the researcher may override this designation to weed out subsequently identified false-positives. The PSDP provides tools to make individual positive or negative designation or designation by the satisfaction of a rule-set. In this way, either explicitly, by rule all patients are placed logically (and/or physically) into one of two patient sets—the Positive Patient set 1240 or the Negative Patient set 1242.

Once all patients in the domain have been designated as positive 1242 or negative 1240 then the PSDP may begin to build images correlated to the condition or diagnosis of interest. The PSDP assumes access to the results of standard processor 304 and PSCP analysis against all patients within the positive and negative groups using the supplied event 1250 and binary 1252 definition sets. An initial image definition 1254 set may be supplied as well, but is not required.

The process of building statistically enhanced occurrence definition sets 1246 depends on the ability to construct occurrence definitions using occurrences (found in the positive patient set) and finding the statistical difference between their existence in the positive 1242 and negative 1240 patient sets. (As defined above, an occurrence may be an event, relational binary, image, repeated occurrence or pattern occurrence to name a few). This process is iterative and may begin with basic occurrences (e.g. events) and then moves to more and more complex occurrences (e.g. images, repeating occurrences and pattern occurrences). Each occurrence definition created is placed into the Candidate occurrence definition cache 1256.

Figure 26:
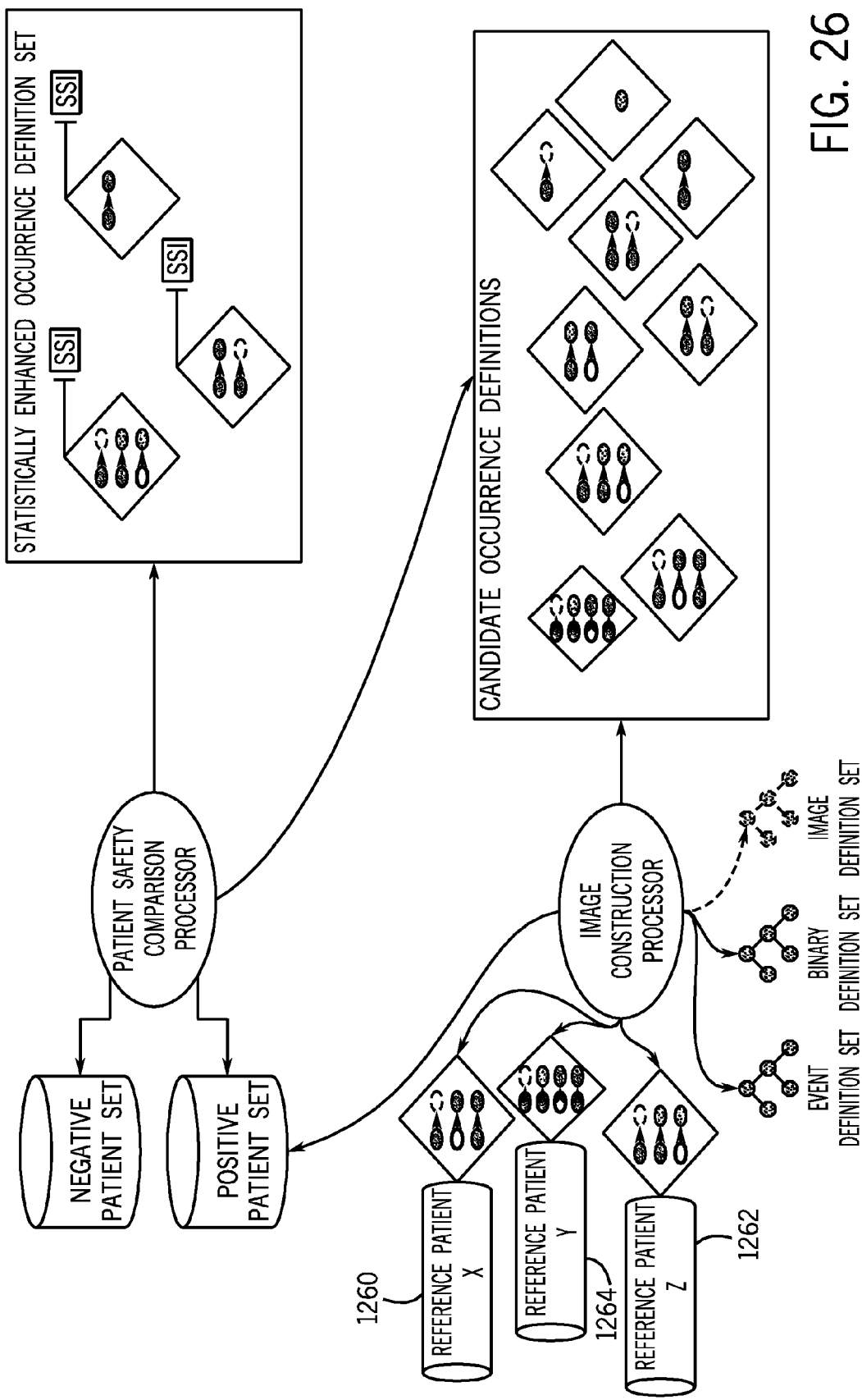
FIG. 26 is a data flow diagram illustrating guided image discovery through the use of an image patient safety comparison processor and an image construction processor with a narrowed set of reference patients to produce a statistically enhanced occurrence definition set.

In an alternative and complimentary embodiment, depicted in FIG. 26, the researcher may designate reference patients 1260, 1262, 1264 from which the candidate images must be derived (rather than from the entire Positive Patient set 1242). Further, the researcher may specify specific time series segments within the reference patients which the researcher understands to be significantly correlated to the condition being targeted. Alternatively, or in combination, the researcher may indicate certain time series segments to not be considered.

For each candidate occurrence definition created the PSCP query engine 1244 is used to execute two queries, which are identical except for the domain (one for the positive 1242 domain, and one for the negative domain 1240) to determine the percentage of identification. These queries can, as shown above, at the researcher's request (or in a way automated by the processor 304) may be limited by any number of population, risk factor, preexisting condition, or other segmentation dimensions to identify statistically significant subpopulations.

In an example, a primary element in determining correlation may be the Distinct Patient occurrences, which may be defined as the number of patients in which the occurrence was identified at least once. Multiple occurrence identification is communicated to the researcher and may be weighted as an additional factor in the inclusion of an occurrence type. As well, when recurrence of the same or similar occurrence is identified, the PSDP may attempt to add a repeated or pattern occurrence to the working occurrence type.

The difference between the percentages returned from the above queries indicates the statistical significance index (SSI) of the occurrence. The researcher will set a threshold by which the PSDP may determine whether the occurrence type is retained or discarded. If the occurrence type is retained it is stored (as depicted for example by 1247) along with its SSI 1248 with regard to the specified condition or diagnosis. At the completion of the process a set of occurrence type definitions are stored and ranked by SSI. The occurrence definition group, along with their respective SSI designation, is stored in the statistically enhanced occurrence definition set 1246 as related to the specified condition or diagnosis.

In one embodiment, the PSDP begins with basic occurrences; occurrences, for example, including a single perturbation event or single relational binary. Once these images have been analyzed the statistically significant occurrence s definitions are stored, and the PSDP begins the process of creating more complex occurrence definitions. To accomplish this process, a plurality (such as three) key time span elements may be designated. Each time series involved may be specified with an indication the maximum phase shift of their data. The maximum phase shift indicates the maximum time delay from the real-time occurrence of the data and the recording of that data. Secondly, events and binaries may be designated with an indication of their maximum span of influence. This maximum span of influence may be defined in terms of real time (e.g. 30 seconds or 2 hours) or may be a relative identification (e.g. patient stay, 3 times event duration). A hierarchy may be provided to determine the contextual maximum span of influence. For example, a time series may be designated to have a maximum span of influence and therefore, unless otherwise overridden, substantially all events that occur along the time series will inherit the maximum span of influence from their time series, binaries, which are including events from two time series, will inherit the greatest of the span of influence of the two time series (unless specifically overridden). In some cases, when fine-tuning is required, the maximum span of influence may be designated as from one specific time series of the two. Further, a maximum span of influence may be designated within the relationship between two time series. In other words, a time series may be known to have a specific span of influence on another time series. The direction of this relationship may be specified as well, since the influence from one to another time series may not be the same as the influence of the second time series to the first. Individual events and binaries may also be designated as having a specific maximum span of influence. In one embodiment, when multiple maximum spans of influence are in effect for a binary or image, the greatest maximum may be applied. Finally a third key time span may be a single tolerance element that the researcher may indicate to widen the search.

In one embodiment, specifically for the construction of occurrences (e.g. binaries and images) the PSDP uses these three time spans to determine the scope of search for elements to combine to produce the occurrence definition. In this embodiment, when the PSDP is looking for an element to combine with a given occurrence, the search looks for the overlap of the following time spans:

$(O^S-T)$ to $(O^E+T)$ $(E^S-E^{MPS})$ to $(E^E-E^{MPS})+E^{MSI}))$

Where:
$O^S$=occurrence Start time (time)
$O^E$=occurrence End time (time)
T=Tolerance (time Span)
$E^S$=Element Start time (time)
$E^E$=Element End time (time)
$E^{MPS}$=Element Maximum Phase Shift (time Span)
$E^{MSI}$=Element Maximum Span of Influence (time Span)

The PSDP uses this scope of search to identify all occurrences that should be combined with a working occurrence to determine if adding the new occurrence to the definition results in a statistically significant occurrence. In this example, the search is conducted within a single patient and only occurrences that exist within the positive patient domain are used. For efficiency, the researcher may further indicate that the occurrence must be found at least X number of times within the positive patient domain before creating a new occurrence definition to test against the negative domain. The analysis of the timing relationships among multiple variations of the image within the positive patient domain provides time interval data for determining the search windows within the occurrence definition itself, and an additional tolerance may be configured here as well. Once a new element has been chosen as providing the core for building a new occurrence definition, the occurrence definition is then used to query for SSI and to determine whether it meets threshold SSI so as to be part of the statistically enhanced occurrence definition set. Regardless of its inclusion in the statistically enhanced occurrence definition set, the new occurrence definition is stored to build additional combinations since the statistical significance of component occurrences is not always correlated with the statistical significance of a complete occurrence. In fact, a given occurrence component may predict the existence of a specific definitive object with modest probability, whereas once the complete occurrence definition has been built, the presence of the complete occurrence definition may actually predict that the definitive object will not occur and vice-versa. In this way, the PSDP continues to build more and more complex occurrence definitions to be analyzed statistically until no more combinations within the scope of search are identified.

To support the incremental creation of occurrence definitions, the processor 304 supports query capabilities to return potentially significant occurrences. This query returns a result set of components as follows: Given (occurrence definition to be Enhanced, Positive Domain); Return (Element) Where (Element is in Scope of Search) Further an aggregation query may be submitted as follows: Given (occurrence definition to be Enhanced and Positive Domain) Return (Element type, Count of occurrences Found, Count of Distinct Patient occurrences Found) Where (Element is in Scope of Search) Order By (Count of Distinct Patient occurrence)

During this analysis, the PSDP further maintains the definitions of antecedent relationships between occurrences identified. An evaluation of these antecedent relationships provides a further element in the statistical analysis. The PSDP may identify the most predictive (e.g. most statistically significant) paths of evolution of images along the timeline of the MPPC. This information will help refine protocols to be targeted not only images but image paths. The image (or other occurrence) with the maximum SSI may be designated as the primary image. Alternatively, multiple images (or occurrences) may be designated as primary the fact that they are the maximum SSI within their associated evolutionary path.

The PSDP may assist in the location of binaries, but more readily assists in the detection of certain binary types. For example, Expected and Analogous binaries may be identified with the PSDP, but Verify Non-Existence binaries require much more processor power since the PSDP uses non-existence of an event as a criteria for search, which greatly extends the scope of the search. In another instance the existence of events, which are similarly or identically, predictive may suggest the definition of an analogous binary, an analogous image, and an indication of potentially redundant or superfluous testing and the PSDP may provide this indication to the researcher.

In some cases, if a binary is identified as not predictive, an event (or both events) within that binary may be identified as predictive. Here it may be seen that one or more relationships between events may be more predictive then the presence of the events. This is one of the reasons that conventional statistical regression as applied to even a very wide range of detected events (without building the relational binaries and more complex occurrences (e.g. images) and more specifically without considering the complex relational patterns and the timing of the patterns of the events in relation to each other) is incomplete and potentially misleading.

Because the PSDP is very sensitive to event segmentation, the researcher may instruct the PSDP to break individual event definitions into a continuum of event sub types (as, for example, pertaining to slope, magnitude, threshold breach, components of the definition, to name a few). The PSDP will search both on the original event type and on each of the event subtypes to look for a threshold breaking SSI. Once this process is completed and the statistically enhanced occurrence definition set is available for use in the processor 304, the processor 304 may search for all occurrences within the statistically enhanced occurrence definition set. Once all occurrences have been identified, the processor 304 may obtain the Maximum SSI (MSSI) among all of the identified occurrences. Further, the MSSI for specific conditions and diagnoses under test then may be added as additional parallel time series and available for analysis by the processor 304 and visualization in the patient safety visualization processor. events within these MSSI time series are of particular significance. An up event in an MSSI indicates the movement of the system toward a positive predictive identification of a condition or diagnosis. From the slope of a time series of statistical values and the instantaneous statistical value of that event is derived Probabilistic Momentum within the processor 304 and patient safety visualization processor. According to an embodiment of the present invention, a high product of the positive slope, wherein the outputs of the testing used to derive the slope are time sensitive (i.e. the outputs change with time as a function of the presence or absence of the disease state or the presence of the definitive object), provides additional predictive indication beyond the that of the instantaneous predictive indication. The presence of high probabilistic momentum is highly predictive and may also provide an indicate acuity with certain disease states. The patient safety console may be configured to show the parallel time series of MSSI for the top X diagnoses or may be configured to show the MMSI with the greatest statistical momentum. Parallel probability time series may be generated by the processor for each diagnosis for which an increased or reduced probability is identified. Treatment induced reversal of a pathophysiologic process such as sepsis will cause the generation of positive reciprocation along the time series of probabilities for sepsis.

With retrospective analysis, Probabilistic Momentum toward Primary Diagnosis is a Key Performance Indicator (KPI). The increase of this KPI may be used to determine the effectiveness of a diagnostic environment. Elements (e.g. diagnostic tests) will be able to establish efficacy by demonstrating the increase Statistical Momentum toward Diagnosis. With Probabilistic Momentum toward Diagnosis and Cost added as measures in the PSCP multidimensional database the PSCP will be able to demonstrate the cost-effectiveness of diagnostic tools. In one embodiment, the PSDP utilizes the process of Retrospective Real-time analysis (RRA) to further investigate probabilistic momentum. RRA uses a time-slicing technique to examine a set of time series, and the associated object stream s, in the way they would have presented in real time. To accomplish this, the processor 304 creates a set of MPPCs, each of which represents what the MPPC would have been at a specific point in time. In other words, the processor 304 selects a point in time and truncates the MPPC to only include the data that existed at that point in time and before. In this way, and in combination with the true final MPPC, partial occurrences may be analyzed to investigate their evolution and the definitions that may be employed to identify them. The PSDP may compare a partial occurrence with the final occurrence to look for indicative elements. As well, the PSDP may compare partial occurrences across a wide range of patients and conditions. For example, the PSDP may determine partial occurrences that are very similar and that will complicate early detection and look for key elements that differentiate them.

In this manner future binaries, images, and cascades are constructed from the bottom up as more and more patient data sets are available. In essence, the entire pool of patients monitored by the processor 304, include experimental datasets whereby positive or negative statistical associations may be determined automatically and new relationships, disorders, predictive sets of testing, and superfluous testing, effective treatment, superfluous treatment, ineffective treatment and harmful treatment may all be identified from the bottom up as a function of statistical relationships.

The application of Probabilistic Momentum evaluation exploits one of the most important features of living organisms; the time dependency of pathophysiologic processes and of physiologic relationships. As previously described, perturbations and the pathologic or physiologic responses of organisms to perturbations are relationally time dependent. Each living organism is a specifically structured chemical, electrical, and mechanical entity. The relational structure of each of these components of the organism defines the timing for chemical, electrical, and mechanical action. Therefore actions, reactions, and failures of this structure will occur with order within definable limits as a function of the relational structure, which will define the temporal relationship limits of actions, reactions, and failures.

In the presence of a pathophysiologic cascade, increased probabilistic momentum may be induced by a more rapidly progressive pathophysiologic cascade but may also be induced by more rapid data sampling, broader bandwidth of testing (more testing per unit of time), and/or better focused testing. Probabilistic momentum is therefore both a function of the rate and magnitude of pathophysiologic cascade progression as well as the quality and scope of the testing applied to render the parallel time series. When the testing and expansion of the bandwidth is the same, a higher degree of probabilistic momentum suggests a greater rate of pathophysiologic cascade progression.

In one embodiment, a system and method according to the present invention is provided wherein, events, binaries, and images are defined by time aggregations wherein event aggregations are primarily (or solely) based on time (as by windowing for example). This exploits the time dependency of physiologic systems and of pathophysiologic processes and is simpler than the rendering of binaries images, and/or cascades as previously discussed. Such time aggregations may be used to complement the more complex building of the motion pictures of physiologic failure. In addition binaries, images, and/or cascades may be derived from a time based aggregation (as by combining all permutations (or specific sets of permutations) of the event objects. Alternatively, or in combination, events binaries, and images may be additionally or similarly aggregated by magnitude, slope, and/or pattern and/or type or other characteristic.

According to another aspect of the invention each time relationship may be converted to an object such that at least one portion of an event, binary, image, and/or cascade is comparable with another portion of an event, binary, image, and/or cascade. In an example, the time relationship of at least one portion of alpha event is compared to at least one portion of the beta event to derive at least one intra binary temporal relationship (which may be an object or a characteristic of the binary object). The intra binary temporal relationships (or another temporal relationship) include values, which may be converted to a time series, objectified and incorporated into the MPPC as desired. Similarly this may be performed for images and cascades. In an example, acceleration of the cascade may thereby be readily identified.

In one embodiment the processor is programmed to detect a sentinel event object (such as a rise in WBC count, a rise in respiration rate, or a rise in temperature). The processor then identifies all event objects occurring within a retrospective and prospective time window of the detection of the sentinel event. In an example, upon the detection of a rise in temperature the processor may aggregate all event objects, which occur within 48 hours after the temperature is elevated, and this aggregation may be compared to aggregations (built and/or derived from statistically derived aggregations in relation to definitive objects.) The primary relationship rendering the aggregation of these event objects is time but the event objects within the aggregation may be comprehensively compared.

With a time aggregation, upon the addition of each new event, the probability of the future occurrence of a plurality of definitive events may be determined. As discussed, Probabilistic momentum is derived when a plurality of time sensitive (volatile) events, each adding greater probability is detected and the time series of the probability of a plurality of definitive events may be plotted, objectified and analyzed.

In another embodiment, the processor repeatedly cycles (which may be a cycle of windowing) through the time series looking for (for example) objects (such as perturbation events). Each time an object is identified it is placed (for example) in a perturbation event set if this is the object type being detected. Consecutive sets are derived for each cycle. The set derived from each cycle may include no perturbation events or hundreds of perturbation events depending on the state of the organism. This approach essentially aggregates objects (events) by cycles (the cycling frequency may range for example from about 0.01 second to about 1 hour depending on the definitive object). Consecutive sets of perturbation events include objects and therefore have the characteristics of the objects, as well as the number of the objects, and the probabilities associated with the objects. These characteristics may be used to derive various time series, which may be objectified and analyzed. In an example, if along a time series of perturbation events, the number (and/or magnitude) of perturbation events shows a high positive slope, but none of the time series of the probability for any definitive process shows a high positive slope, this suggests that the processor is failing to identify (and may not timely identify) the cause of the perturbation and this may provide a warning that intensive expert physician diagnostic evaluation is timely required. The processor 304 in this case is saying, the patient's physiologic system is progressively more perturbed, and I am not identifying a likely cause at a rate matching the growth of the perturbation and the patient needs expert human brain help soon.

Perturbation object sets may be derived globally (from all available time series) or may be derived from a focused set of a particular group of time series (such as time series which relate to inflammation for example). The relative pattern of growth or decline of each different set may be compared by objectifying selected time series of characteristics of the sets. In an example, during sepsis, a set of inflammation perturbation objects may grow rapidly (with an increasing number and/or magnitude of perturbation objects and or decreasing time interval between increases in number and/or magnitude), and then this growth may be followed a rapid growth of a hemodynamic perturbation object set. The comparison of objectified time series of the sets renders parallel rise objects producing a binary with the inflammation set rise including the alpha event and the hemodynamic set rise including the beta. Upon detection, the occurrence of a respiratory set rise may then be added to produce an image (derived of time series of characteristics of sets) and finally with additional sets a motion picture of physiologic failure derived of time series of characteristics of sets (wherein the characteristics may for example include number of perturbations, magnitude of perturbations, frequency of perturbations, slope of perturbations, probability of a given definitive object to name a few).

One embodiment provides an example of the continuous derivation of specific objects (such as events, binaries and images) between two or more time series to both corroborate the significance of an object as well as to exclude perturbation due to artifact. In an example, it is well known that motion may cause artifactual desaturation events along an $SPO_2$ time series. However, motion may also occur in response to a desaturation event (particularly in response to the arousal from the desaturation). The proximate existence of arousal motion corroborates the $SPO_2$ event, binaries and images and helps to establish that the patient was sleeping or sedated at the time of the desaturation. Motion inducing artifactual desaturation and arousal motion responding to a true desaturation are generally different in relational timing, relational spatial pattern, and the relational frequency pattern and characteristics. After adjusting for any phase shift, a arousal motion object inducing artifactual desaturation object will generally early occur at the same time or precede the onset of a desaturation object. Whereas arousal motion object will occur after the onset of the desaturation object or adjacent the recovery from the desaturation object. In addition after adjusting for any phase shift, arousal motion objects commonly occur in a specific pattern, which mirrors and/or corresponds, in at least one aspect, with the pattern of $SPO_2$ objects, with the pattern of desaturation objects within the pattern of the $SPO_2$ objects preceding the pattern of motion objects. Furthermore motion arousals within a cluster are usually brief (about 2-6 seconds) and then followed by a period of little or no motion. In one embodiment the high frequency components of the frequency spectrum of the plethysmographic pulse waveform is used to indicate motion or another known method is used to either indicate threshold motion as a step function time series (as is for example outputted by the Minolta 300i pulse oximeter) or preferably a graded motion time series between the values of 1-10 is provided.

The following provides an example of an occurrence of an image of "Hypoxemia Induced Micro-arousal" (HIM), which is commonly indicative of sleep apnea induced hypoxemia. In one embodiment the HIM image is derived from a motion time series (as generated using detection of motion from the plethysmographic time series or by the use of atigraphy or another method), a $SPO_2$ time series, and a pulse time series (such as a plethysmographic pulse time series). All of these time series may be generated by a patient mounted pulse oximeter. The processor 304 detects a $SPO_2$ event, binary, or image within the span of influence of the motion event, binary, or image and the pulse event, binary, or image within the span of influence of the $SPO_2$ event, binary, or image. Together, the onset of a fall in oxygen saturation followed by the onset of a brief episode of motion (e.g. 1-6 seconds), a rise in heart rate (and/or another property of the pulse time series) and a rise in $SPO_2$ produces an occurrence of an image of HIM. In some cases the motion event, binary, or image may be indicative of pathology as a function of their characteristics alone. In an example the detection of motion occurring in a periodic cluster pattern typical of a cluster of HIM induced by a cluster of apneas as defined for example by objectification, FFT processing, by a combination of frequency domain and spatial domain processing, or another method) whereas at other times the decision to reject a given $SPO_2$ event, binary, or image may be made with consideration of the relational timing and relational pattern of the motion and the other signals. In an example the presence of a cluster of motion reciprocations in relational combination with a cluster of $SPO_2$ reciprocations provides stronger evidence of the presence of a cluster of HIM. This is further supported by the detection of a prolonged period of motion (for example 15 seconds or more at the end of a $SPO_2$ reciprocation cluster (of high $SPO_2$ desaturation magnitude). This terminal motion is typical of a hypoxia-induced awakening (HIA) induced by the cumulative effect of a cluster of severe apneas. This is dangerous image to identify in a patient being treated with patient controlled analgesia because the awakening may trigger the perception of pain causing the patient self medicate at a vulnerable time. The processor 304 may therefore be programmed to detect the combination of image of HIA in combination with PCA treatment and to send an indication to the PCA device to prevent a patient bolus from the PCA device upon the detection of HIA and during an interval (for example 30 minutes) after any image of HIA has been detected. The detection of HIA in the presence of PCA if followed closely by a self-administered bolus would provide strong evidence of overmedication (or under treatment of the sleep apnea).

One method for inclusion of a $SPO_2$ pattern as non-artifactual includes comparing the $SPO_2$ time series to a time series indicative of motion and determining the $SPO_2$ time series as non-artifactual based on both the timing and characteristics (which may be a spatial and/or frequency characteristic) of perturbations along the $SPO_2$ time series to the timing and characteristics (which may be a spatial and/or frequency characteristic) of perturbations along the motion time series. In one embodiment this may include identifying a desaturation as non artifactual by identifying that at least 4% of the desaturation occurred before the onset of threshold or trend of perturbation along the motion time series or that at least ⅓ of the desaturation magnitude occurred during a period without motion. Another method for inclusion of a cluster of desaturations as non-artifactual includes identifying a cluster pattern of desaturations, identifying a cluster pattern of brief motion events wherein the cluster patterns correspond in frequency or wherein the motion events correspond to a greater extent to the recovery than to the desaturation. Another method for identifying a desaturation or cluster as non artifactual includes transforming the plethysmographic waveform into frequency components (as for example by FFT), identifying the desaturation or cluster as non artifactual if the frequency spectrum shows a higher degree of high frequency components (or a broader bandwidth) during the recoveries from the desaturation than during the first portion of the desaturations.

In another example time series data sets of the slope of the recoveries, the magnitude of recoveries, and the recovery magnitude ratio (magnitude rise/magnitude fall of each reciprocation), duration ratio (duration rise/duration fall), area ratio (area above or below the curve rise/area above or below the curve fall), of each reciprocation) of the $SPO_2$ is generated and compared to a time series of narcotic infusion. Narcotics may both diminish the slope and magnitude of the recovery and may increase the magnitude of the fall and may reduce the recovery ratio. Therefore according to one aspect of the present invention a perturbation pattern or threshold change in one of these values (such as a 50% fall in the mean slope of the recoveries for 10 minutes may be used to trigger an indication of possible excessive narcotic treatment or to lock out the PCA.

These provide examples of relational images at the event, binary, and image level, along with specific properties and relationships which are defined in each micro domain and added to the processor 304. In this example the images of sleep apnea encapsulates the images of HIM, HIA, and motion-induced artifact, which represent a few of the basic images of the comprehensive processor 304.

In an example, the processor 304 may generate and output a cycling severity index (CSI) for the entire night) by the formula 1 and 2:

$$Ts = Tt - Tm \qquad 1.$$

Where:
Ts=study time
Tm=motion time (other than micro arousal motion)
Tt=total time $$CSI = [(Tc/Ts)/(\text{Sum } Tr)/Tc)] \text{ mean delta } SPO_2 \qquad 2.$$

Where:
Tc=cycling (cluster) time for the entire night
Tr=recovery time (between cycles within a cluster of cycles)
Ts=the study time with or without the rejected artifact time
Instead of the mean delta $SPO_2$ the greatest 10% or the greatest 10 minutes or other portion or quantification of the delta $SPO_2$ may be used.

In addition, real time (windowed) CSI (WCSI) may be given by formula 3:

$$WCSI = [(Tcw/Tw)/(\text{Sum } Tr)/Tc)] \text{ mean delta } SPO_2 \qquad 3.$$

Where
Tcw=cycling (cluster) time for the calculation window (e.g. 5 minutes)
Tw=total window time (e.g. 10-15 minutes)
Alternatively CSI may be adjusted for recovery failure to produce an RCSI with the formula 4.

$$CSI(\text{baseline } SPO_2 - \text{mean recovery } SPO_2) \qquad 4.$$

Where: all negative values for the difference are rendered equal to 1.
In the calculation of the recovery CSI, rather than the baseline $SPO_2$ a value such as 90-93 may be used or the recovery can be mathematically compared to the peak values before the falls. Further, instead of the mean recovery $SPO_2$ the lowest 10% or the lowest 10 minutes or other portion or quantification of the relative or absolute magnitude and/or slope or the recovery may be used.

In one embodiment the objects derived from narcotic and or sedative infusion is combined with the objects of recovery to produce an image indicative of drug associated recovery failure wherein, for example, the image contains an occurrence of drug infusion followed by an occurrence of a fall in recovery peak values and/or a fall in recovery slope values. The presented embodiments represent a few examples of patient safety processing technology applying the objectified time-series matrix. As noted earlier when a new micro domain is added to the matrix the question may be asked, given the addition of the new occurrences within this micro domain, does any new image within the matrix have a greater probability of being associated with a definitive object then without the addition. Many new significant relationships and measures will be identified using this method or by automating the process to provide adaptive processor 304 processing wherein the processor 304 builds and cycles though a broad range of micro domains looking for occurrences which, when added to the matrix change the probability in a significantly positive or negative way.

Figure 24:
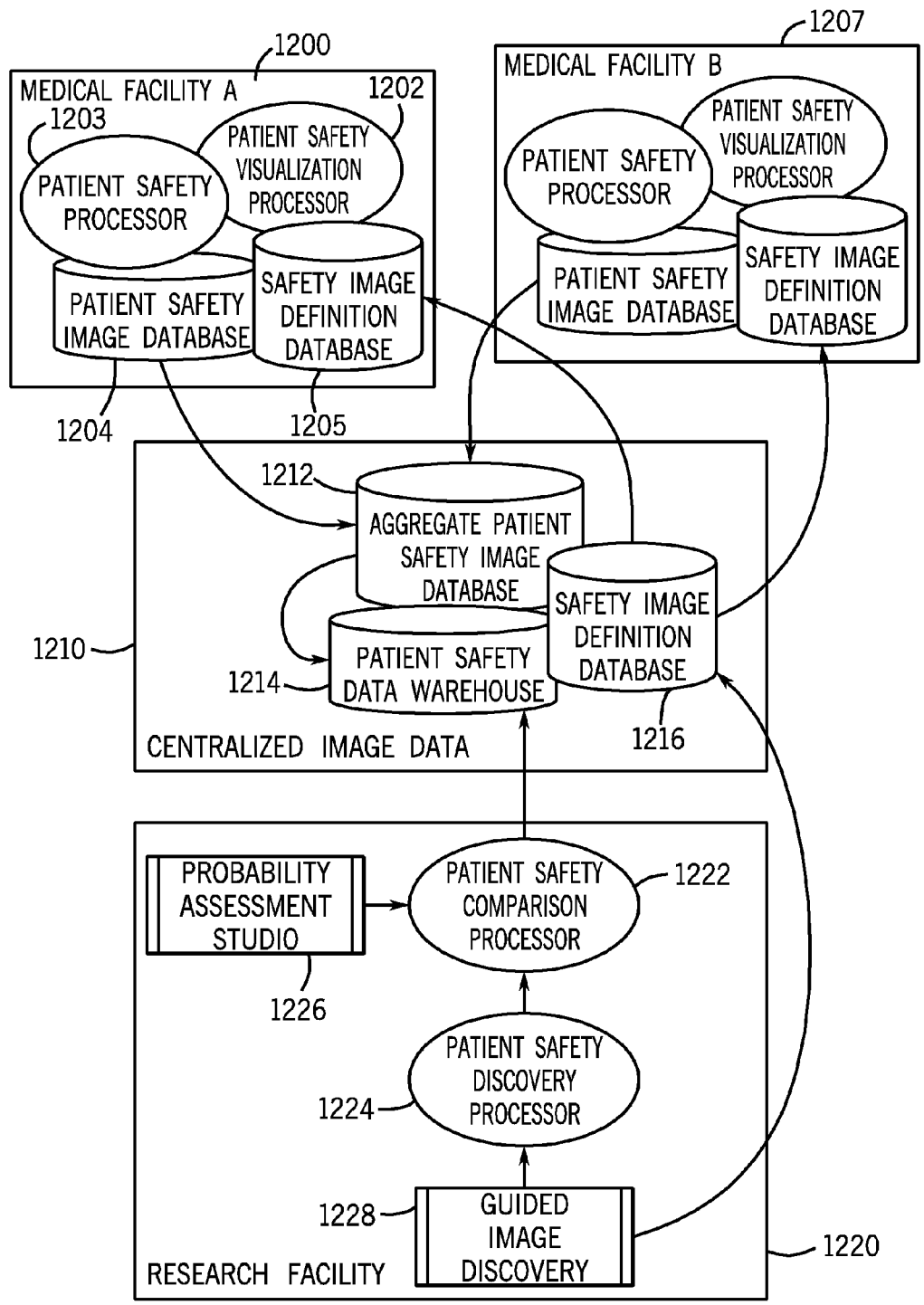
FIG. 24 is a data flow diagram of the patient safety processor network showing the input of image data into the centralized database, the use of guided image discovery to improve failure recognition and protocolization, and the distribution of safety image definitions to implement timely failure detection and intervention.

FIG. 24 is a data flow diagram of the patient safety processor network. Two active medical facilities (1200 and 1207) are connected to a centralized image data center 1210. In one embodiment, facilities would include, at minimum, two processors: the Patient safety processor 1201, and the patient safety visualization processor 1202, As well, each facility would include, at minimum, two databases: the patient safety image database 1204 containing aggregated patient data with the associated objectified time-series matrices, and the Safety image definition Database 1205 containing all of the occurrence definitions (event definitions, binary definitions, and image definitions to name a few) required to construct the Objectified time-series matrix from raw physiological signals and other inputs described above.

Patient monitoring data, including the constructed Objectified time-series Matrices flow this direction into the Aggregate patient safety image database 1212 increasing the available data against which research and other reporting activities may be conducted. This data flow may be facilitated by database synchronization, message queuing, EDI, an Enterprise Service Bus, Asynchronous Web Services, Business Process Management software or other enterprise orchestration servers to name a few. In an example of a embodiment, the Centralized image Data center 1210 contains three databases: the Aggregate patient safety image database 1212, the safety image definitions Database 1216 and the Patient Safety Data Warehouse 1214.

The Aggregate patient safety image database 1212 contains the aggregated data from the Patient Safety images Databases at any number of medical facilities. The Patient Safety Data Warehouse 1214 is a derived database generated by analysis of the Aggregate patient safety image database and is an Online Analytical Processing (OLAP) database optimized for the data mining with regard to occurrence presence and analysis within large populations.

In an example of a embodiment, the safety image definitions Database 1216 is a centralized repository of occurrence definitions (for example image definitions) that research has determined to be most accurate with respect to probabilistic momentum. These may be accessed, as described above, by any number of facilities to enhance their ability to identify and treat conditions. occurrence definitions added, changed or deleted from the Safety image definition Database 1216 may be distributed to the medical facilities by individuals or committees specializing in this distribution or by predefined transmission protocols.

The Research Facility 1220 depicted in FIG. 14 is a set of software that supports a centralized research team in creating, testing, updating and disseminating processor 304 metadata in the form of occurrence definition sets. In an example of a embodiment, the Research Facility 1220 contains the patient safety comparison processor (PSCP) 1222, the Patient Safety Discovery Processor 1224, the Probability Assessment Studio 1226 and the Guided image Discovery 1228 software. These software components, all described in detail above, facilitate discovery, verification, refinement, probability assessment and storage of occurrence definition sets.

Figure 28:
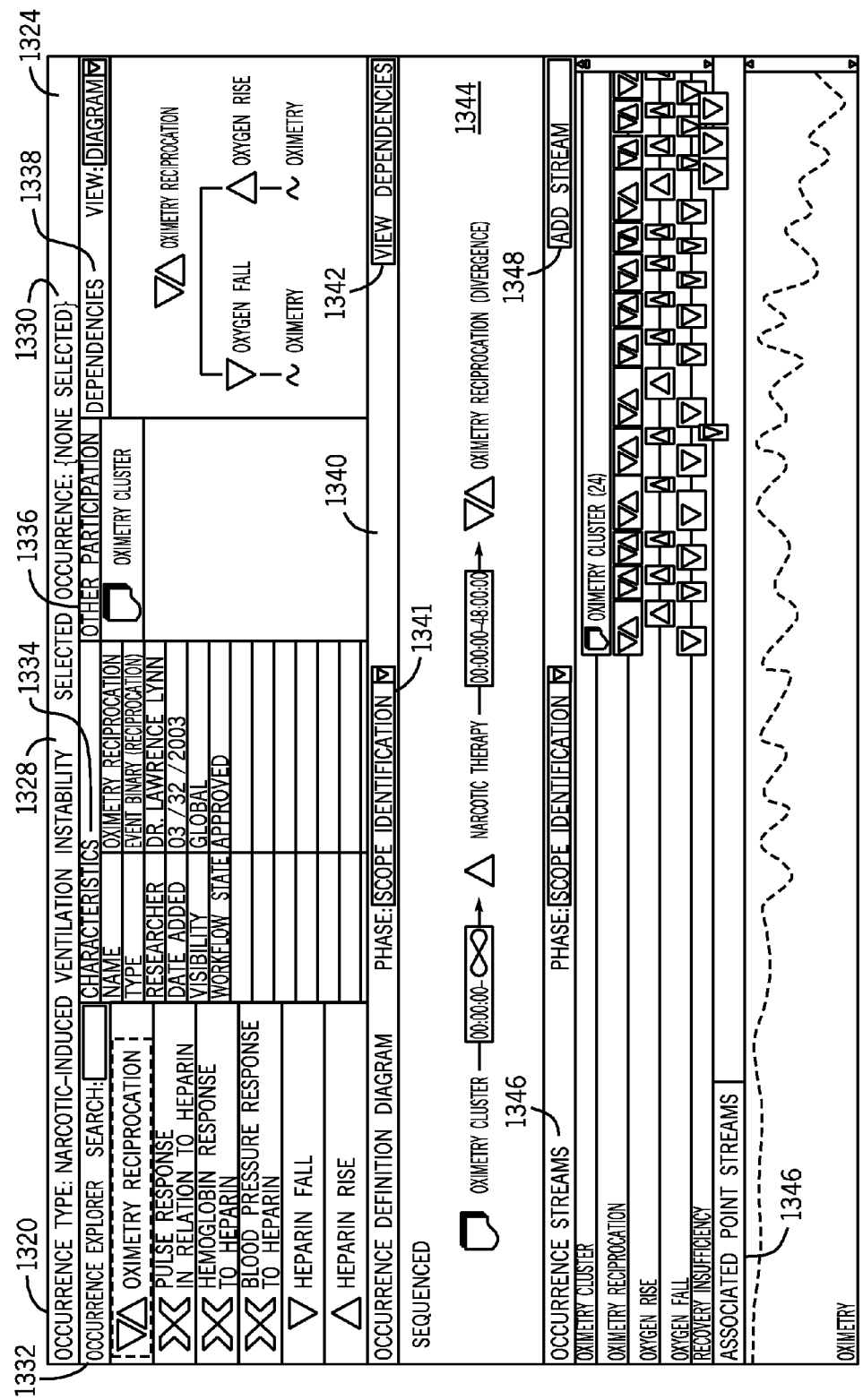
FIG. 28 is a user interface model of the occurrence definition editor depicting an image diagram within the occurrence editor that pertains to narcotic-induced ventilation instability.

FIG. 28 is a user interface model of the occurrence definition editor which, in an example of a embodiment, is a software tool used to visually construct and persist the occurrence definition set. The occurrence definition editor 1320 is a flexible environment for the investigation, identification and definition of micro-domains within a series of point and occurrence stream s. The environment may be configured to allow the researcher to locate micro-domains, to focus on particular elements within micro-domains or to create properties of a selected micro-domain. As configured in FIG. 28, the occurrence definition editor has four distinct sections.

The first section is the Selection Bar 1324 at the top of the screen. As configured this section includes the ability to select and the display of the occurrence type 1328 and Selected occurrence 1330. The selected occurrence type specifies the occurrence definition that the researcher is viewing and/or updating. This occurrence type may be one of the simpler types (event or binary) or may be a more complex type (image, repeating image or Pattern image). The occurrence type may be a candidate type which has not been persisted into the occurrence definition set. The occurrence editor also allows for the Researcher to create Derivative types in which he/she begins with the definition of a different type and makes changes to create a new type.

The Selected occurrence 1330 allows the researcher to choose an occurrence within an available occurrence stream to be a reference as he/she works on the definition of the occurrence micro-domain. Once a Selected occurrence is chosen, it may be displayed (with all or some of its constituent parts) in the bottom (fourth) section of the screen. This allows the researcher to immediately see the results of changes in the definition within a reference case. The Researcher may switch between several reference cases during the course of editing. The second section of the screen is made up of several subsections: The occurrence type Explorer 1332, the Characteristics Box 1334, the Other Participation List 1336 and the Dependency Viewer 1338. The occurrence type Explorer is the primary element of this section and all of the other subsections relate to it and to the occurrence type that is selected within it (e.g. oximetry reciprocation in FIG. 28). This section provides the ability for the researcher to search for additional occurrence types to add to the definition that is being constructed. The occurrence type Explorer 1332 lists all of the occurrence types available to the Researcher to add to the Working occurrence definition. The researcher may drag an occurrence type from the occurrence Explorer 1332 onto the Construction Surface 1344 to add an occurrence type to the Working occurrence definition. A search capability is provided to filter the list. Once the Researcher selects an occurrence type in the occurrence editor, the other three subsections within this section change to reflect information specific to the selected occurrence type.

The other three subsections provide information as follows: The Characteristics Box 1334 provides a list of characteristics of the occurrence type selected in the occurrence Explorer. These characteristics include the Name, type (i.e. is it an event, binary or image to name a few), visibility (i.e. what domain does this apply to) to name a few. This section may contain workflow details as well to allow researchers to understand the state of the occurrence definition (e.g. what researcher created it, when it was created, whether it is approved or under review etc.) The Other Participation List 1336 displays a list of occurrences in which the occurrence type selected in the occurrence Explorer is a participant. For example, as shown in FIG. 28, the oximetry reciprocation occurrence is selected in the occurrence Explorer and therefore the oximetry cluster repeating occurrence is displayed in the Other Participation List 1336. This is displayed here because the oximetry reciprocation is part of the oximetry cluster repeating occurrence. Any number of occurrence types may be listed here. The Dependency Viewer 1338 shows the dependency model of the occurrence type currently selected in the occurrence Explorer. The dependencies may be shown in various views: Dependency Tree Diagram, occurrence List, to name a few. FIG. 28 shows this section showing the dependency diagram for the oximetry reciprocation. The Dependency Viewer allows the researcher to examine all of the constituent parts of the occurrence type selected in the occurrence Explorer down to the raw signals required for the occurrence type to be constructed.

The third section of the screen is the occurrence definition Diagram 1340 where the researcher draws (e.g. through drag-and-drop) the diagram that represents the scope of the occurrence. This section may be configured using the Phase Dropdown 1341 to specify the Phase (e.g. Scope Identification, Element Construction, Scope Refinement to name a few) to which the diagram applies. The View Dependencies button 1342 allows the researcher to see the dependencies on which the displayed diagram depends. The diagram itself is displayed on the Construction Surface 1344. (The diagram shown in FIG. 28 is explained in more detail in FIG. 10.)

The fourth and final section (as configured) is the time series Section. This section contains occurrence stream s 1346 and Associated point streams 1346 (e.g. signals). These streams are added either when a specific occurrence is selected (Using the Selected occurrence functionality 1330) or individually through the Add stream button 1348. The stream s are shown parallel in time. If an occurrence stream is added, the occurrence definition editor may ask if associated occurrence streams and/or point streams should be added.

This section allows the researcher to examine real data while constructing the micro-domain that they are working on. Changes to the occurrence definition may be immediately reflected in the time series section so that the researcher may tune the definitions to reference patients. If multiple patients (or patient stays) are required the time series section may be split into multiple sub-sections to allow for groups of stream s to be coordinated in time. In this way, the researcher may want to view a positive case and a negative case (perhaps with similar, but misleading patterns) so as to refine the occurrence definition with precision.

The occurrence definition editor is built to be one part of a rich set of tools that the researcher may use to refine occurrence definitions. For example, the occurrence definition editor links to the Patient Safety Comparison processor to run statistical analysis (for example to determine SSI) on reference patient sets at the researcher's request. In this way, the researcher may immediately assess the statistical impact of changes to the definition.

Figure 29:
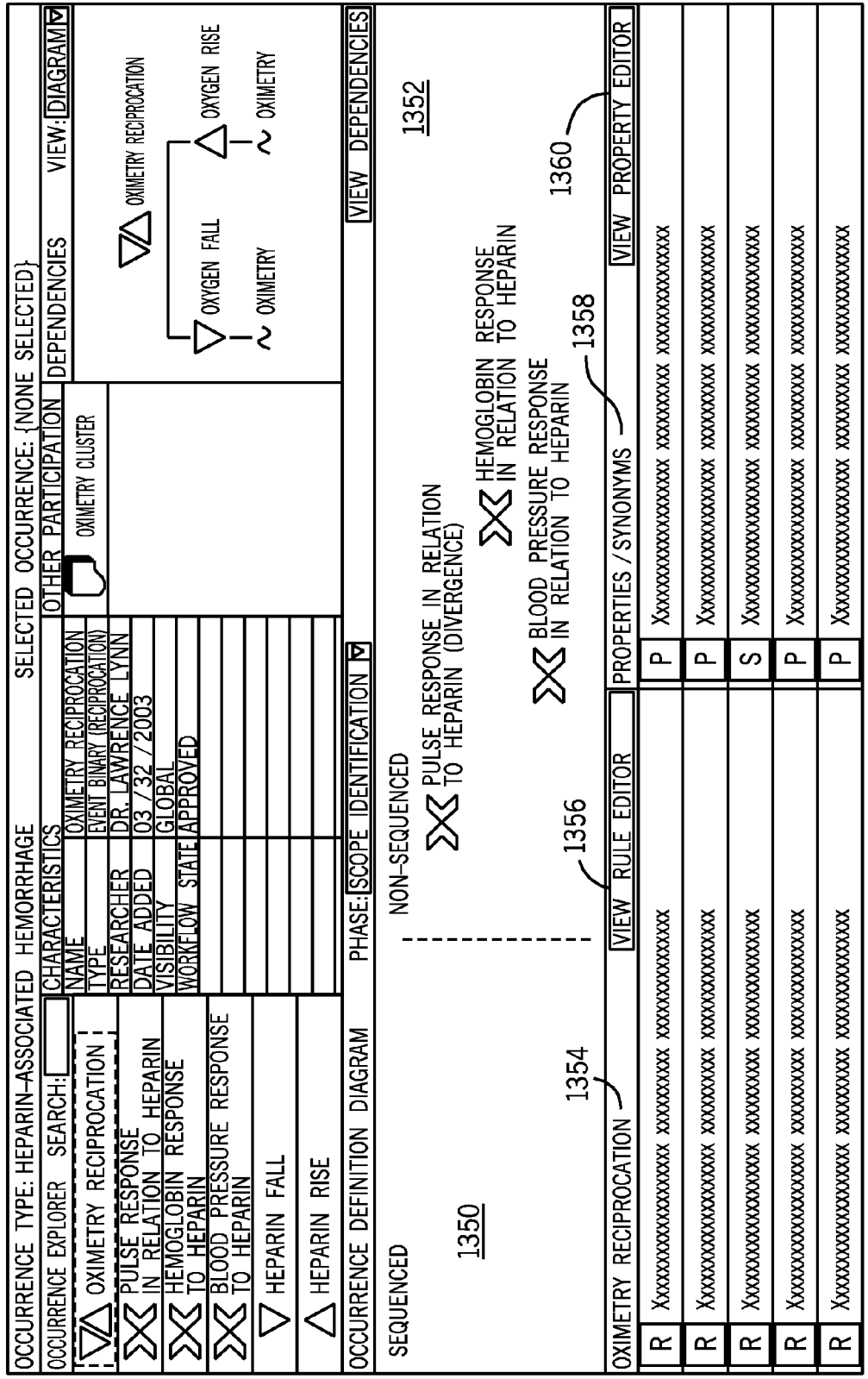
FIG. 29 is a user interface model of the occurrence definition editor depicting an image diagram within the occurrence editor that pertains to heparin-induced hemorrhage.

Further, the occurrence definition editor may be employed along with the image construction processor during guided image discovery. In this way, the automation (e.g. the location of images that may be statistically significant) provided by the processor may be directed and refined by the researcher FIG. 29 show an second exemplary depiction of the occurrence definition editor. In this case the occurrence definition editor is configured slightly different and shows the editing of the Heparin-Induced Hemorrhage image. For an overview of the occurrence definition editor user interface see FIG. 28. In FIG. 29 the Construction Surface is split into two sections—Sequenced 1350 and Non-Sequenced 1352. (The differentiation between Sequenced and Non-Sequenced elements of an image are explained in FIG. 8c.). The bottom section of the occurrence definition editor is configured differently than the one in FIG. 28. In this case, rather than viewing associated time series, the researcher has selected to see the Qualification Rules 1354 on the bottom left and the properties/Synonyms 1358 on the bottom right. These sections allow the researcher to further refine the occurrence definition. The Qualification Rules section 1354 lists the rules that must be satisfied to qualify the occurrence as a true occurrence of the Target occurrence type. These rules, as described above, may be Boolean expressions or sets of Preservation Rules to name a few. The rules are listed in this screen in a summary way (or by name) but the Researcher may edit them or get a more complete view using the View Rule editor button 1356. properties and Synonyms are listed in the property/Synonym List 1358. (properties and Synonyms are described in detail in FIG. 5 and FIG. 7a.) The properties and/or Synonyms are listed in this screen in a summary way (or by name) but the Researcher may edit them or get a more complete view using the View property editor button 1356.

Figure 30:
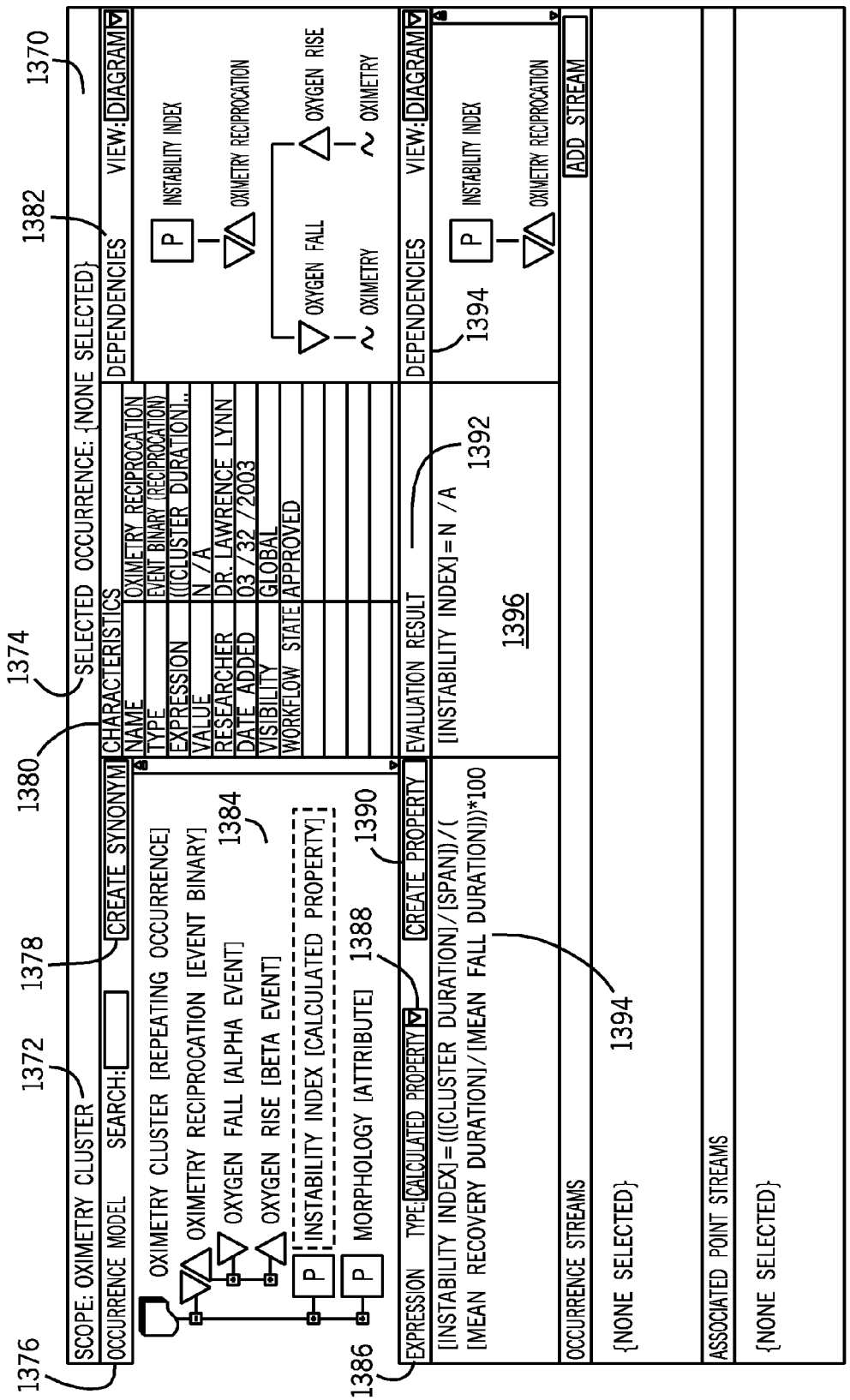
FIG. 30 is a user interface model of the occurrence property editor within the occurrence definition editor depicting the construction of an instability index within an oximetry cluster occurrence.

The property editor is described in detail in FIG. 30. If a Selected occurrence has been chosen then the evaluation result of each Qualification Rule, property and Synonym (if valid) will be displayed. Changes to the occurrence definition Diagram may affect the Qualification Rules, properties and/or Synonyms. If changes to the diagram invalidate these elements (for example, removing constituent parts that are part of a property dependency) the editor will indicate the fact with color, icons, message or all of the above (as configured by the user). Dependencies, and other characteristics, of Qualification Rules, properties and Synonyms may be viewed and/or edited within the associated editor (either Rule editor or property editor).

FIG. 30 is a user interface model of the occurrence property editor within the occurrence definition editor (described in FIG. 28 and FIG. 29) which, in an example of a embodiment, is a software tool used to visually construct and persist the occurrence properties within the occurrence definition set. The occurrence property editor may be invoked within the occurrence definition editor or may be used as a standalone tool.

As configured in FIG. 30, the occurrence property editor has four distinct sections. The first section is the Selection Bar 1370 at the top of the screen. As configured this section includes the ability to select and the display of the Scope 1372 and Selected occurrence 1374. The selected Scope 1372 specifies the occurrence definition that the researcher is viewing and/or updating. This occurrence type may be one of the simpler types (event or binary) or may be a more complex type (image, repeating image or Pattern image). In one embodiment, the Scope 1372 may include sub-elements of an occurrence type (e.g. Inflection points). If the occurrence property editor was invoked from the occurrence definition editor then the Scope 1372 is initially set as the occurrence type which the researcher was currently editing. The Selected occurrence 1374 allows the researcher to choose an occurrence within an available occurrence stream to be a reference as he/she works on the definition of the occurrence micro-domain. Once a Selected occurrence is chosen, it may be displayed (with all or some of its constituent parts) in the bottom (fourth) section of the screen. This allows the researcher to immediately see the results of changes in the definition within a reference case. The Researcher may switch between several reference cases during the course of editing.

The second section of the screen is made up of several subsections: The occurrence model View 1376, the Characteristics Box 1380, and the Dependency Viewer 1382. The occurrence model View is the primary element of this section and all of the other subsections relate to it and to the item that is selected within it (e.g. instability index Calculated property in FIG. 30). This section provides the ability for the researcher to search for items (properties, Synonyms, to name a few) within the occurrence model of the Scope to add as elements within the property definition that is being constructed. The occurrence model 1384 contains the hierarchy of all of the occurrence types within the Scope and all of their related properties, Synonyms and Rules. The researcher may drag an item (e.g. a property) from the occurrence model 1384 onto the Expression Construction Surface 1394 to add as an element in the Working property definition. A search capability is provided to filter the hierarchy. Once the Researcher selects an item in the occurrence model 1384, the other three subsections within this section change to reflect information specific to the selected item. The other three subsections provide information as follows:

The Characteristics Box 1380 provides a list of characteristics of the item selected in the occurrence model 1384. These characteristics include the Name, type (e.g. Calculated property as shown in FIG. 30), value (if a Selected occurrence is available) to name a few. This section may contain workflow details as well to allow researchers to understand the state of the occurrence definition (e.g. what researcher created it, when it was created, whether it is approved or under review etc.) The Dependency Viewer 1382 shows the dependency model of the item currently selected in the occurrence model. The dependencies may be shown in various views: Dependency Tree Diagram, occurrence List, to name a few. FIG. 30 shows this section showing the dependency diagram for the instability index Calculated property. The Dependency Viewer allows the researcher to examine all of the constituent parts of the item selected in the occurrence Explorer down to the raw signals required for the item to be constructed and/or evaluated.

The third section of the screen, in the depicted configuration, is made up of three subsections: the property Expression Box 1340, the Evaluation Result Pane 1392 and a second Dependency Viewer 1396 connected to the Working property definition. The property Expression Box 1340 and the contained property Construction Surface 1394 provides an editing space where the researcher creates the expression (either directly or through drag-and-drop) that defines the Working property. The type of the property may be selected from the type Dropdown 1388 (for example Calculated property and attribute to name a few). When the type of the property is changed, the Construction Surface 1394 is reconfigured to the property type. For example, if an attribute is selected then the Construction Surface is broken up into two parts: the Boolean condition and the Value Expression. The Dependencies View 1396 allows the researcher to see the dependencies on which the Working property depends.

The fourth and final section (as configured) is the time series Section. This section contains occurrence stream s and Associated point streams (e.g. signals) as in FIG. 28. This section allows the researcher to examine real data while constructing the property they are working on. Changes to the property definition may be immediately reflected in the time series section so that the researcher may tune the definitions to reference patients.

Figure 31:
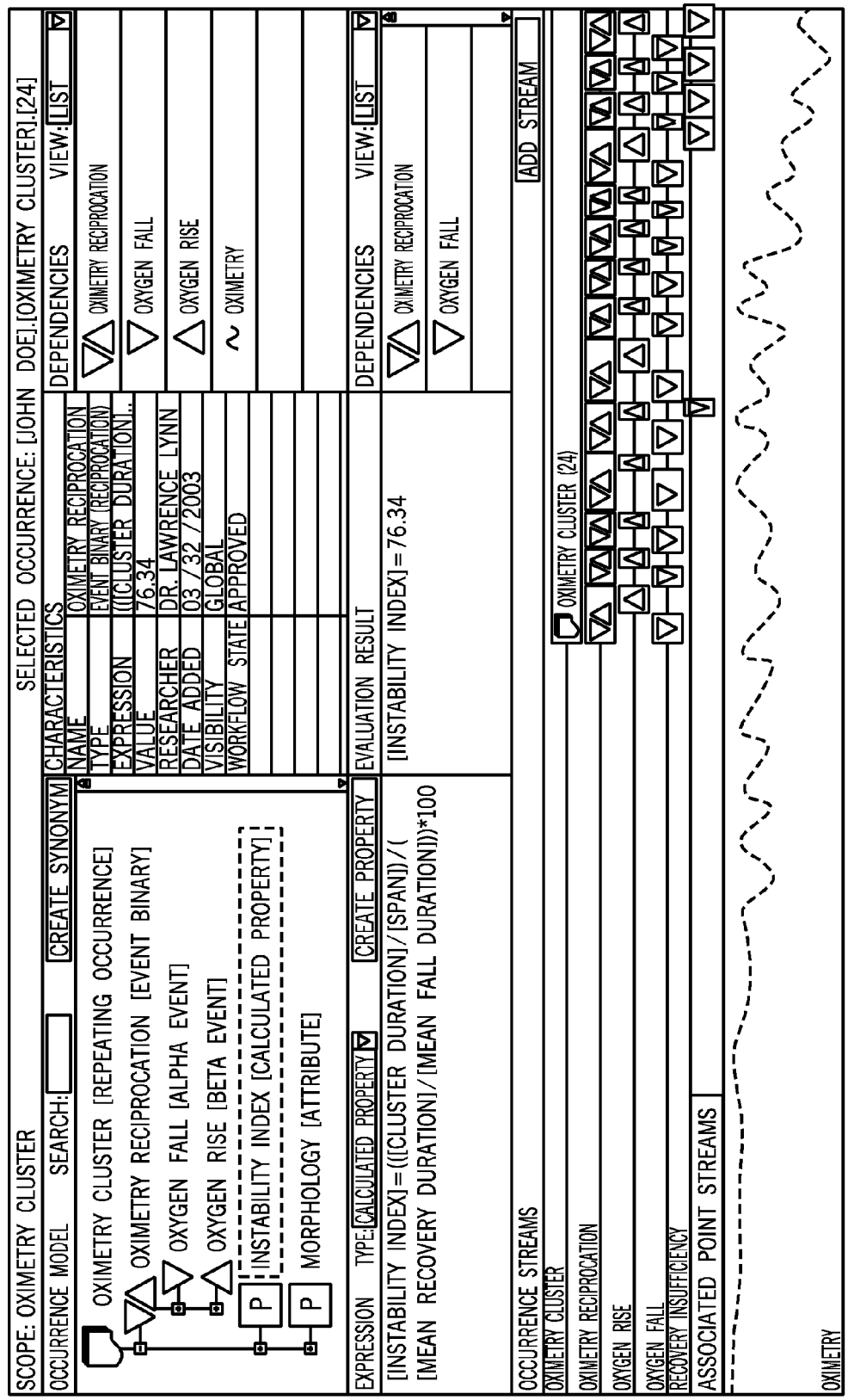
FIG. 31 is a user interface model of the occurrence property editor used with a selected reference patient and occurrence depicting the construction of an instability index within an oximetry cluster occurrence.
Figure 32:
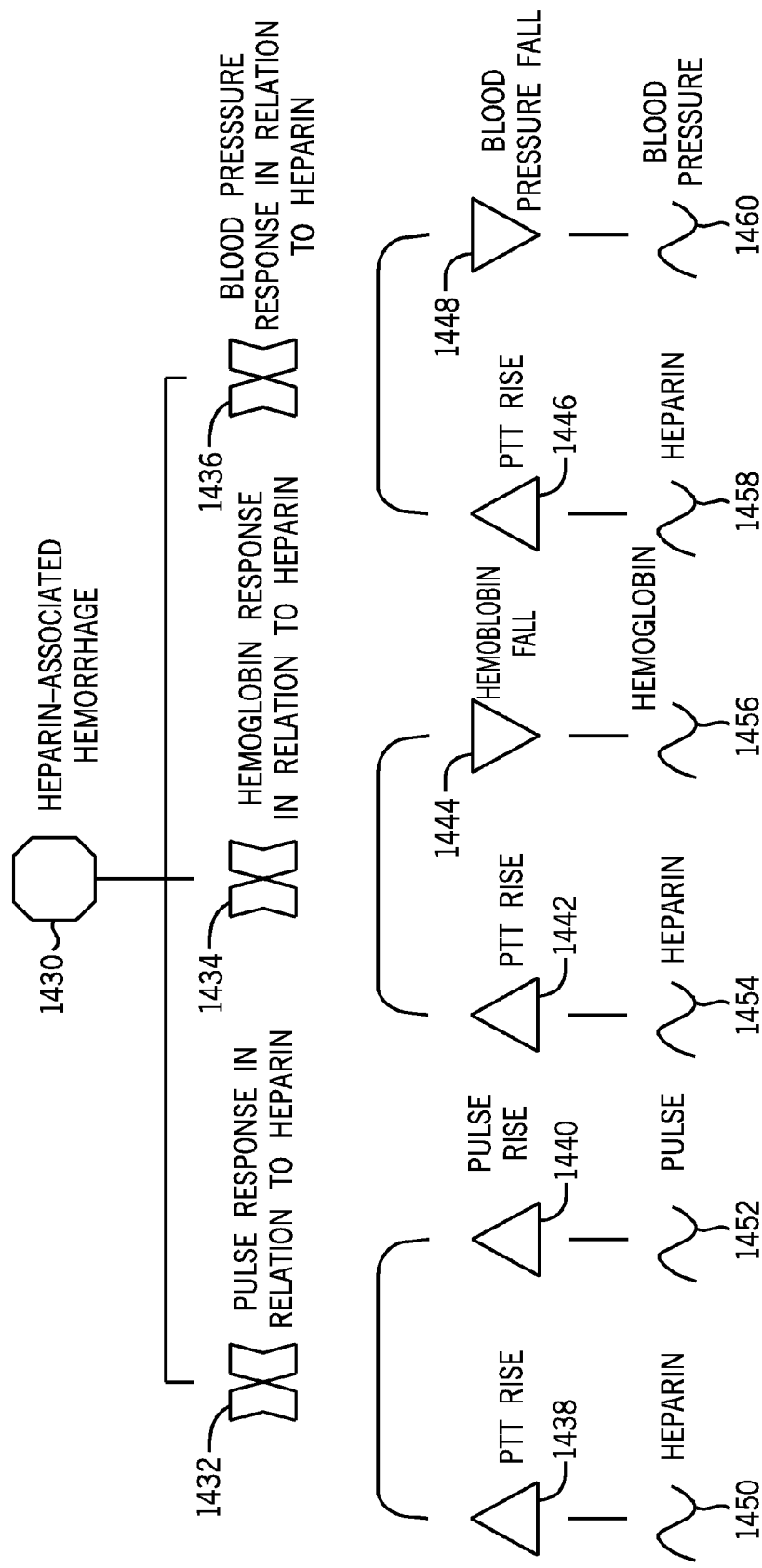
FIG. 32 is a sample dependency diagram and image dependency diagram depicting the dependencies of a heparin-induced hemorrhage image.

FIG. 31 is a user interface model of the occurrence property editor (the same as in FIG. 30) used with a selected reference patient and occurrence. FIG. 32 is a sample dependency diagram, specifically and image dependency diagram depicting the dependencies of a Heparin-Induced Hemorrhage image. dependency diagrams provide a visual view of dependency from the Root Element 1430 down to the Raw point streams (1450, 1452, 1454, 1456, 1458, and 1460).

In an example of a embodiment, a dependency diagram contains a single Root Element 1420 which is an icon representing the element which is being evaluated as regards dependency. In some cases, the Root Element 1420 may be omitted (for example, it is clearly implied within a software user interface). From the root element lines stretch downward to show dependency. In an alternative embodiment (not shown in FIG. 32) the lines may project in any direction but have an arrowhead to show the direction of dependency. Icons represent the elements of the dependency. Icons may represent occurrence types (as, for example in FIG. 32 the triangle icon 1438 represents a Heparin Rise event), point streams (as, for example in FIG. 32 the wave icon 1456 represents the Hemoglobin signal), properties, Rules, Sub-Elements to name a few. Each node within the diagram is, in itself, a dependency diagram. In an interactive environment nodes may be collapsed or expanded. Point streams are considered Leaf Nodes and have no dependencies. Other Leaf Nodes may exist. For example, if the dependency for a property is being displayed and that property is a Calculated property with the expression: Slope*0.8 then the dependency diagram would have two top-level nodes—The Slope property and the number 0.8. In this case, the number 0.8 would be a Leaf Node. Dependency diagrams may be used to show the scope dependency (as in FIG. 32) or a more detailed dependency including properties, Rules and Synonyms. This second configuration is most often used in showing the dependencies of single values, whereas the first configuration is used most often when focusing on the scope of an occurrence. The dependency diagram in FIG. 32 is symmetrical but this need not be (and often is not) the case.

A dependency diagram may be collapsed into a dependency list. A dependency list simply lists all of the dependencies, but does not show the hierarchical relationship. The diagram in FIG. 32 may be collapsed to the list:

Pulse Response in relation to Heparin or adverse PTT pattern (binary)
Hemoglobin Response in relation to Heparin or adverse PTT pattern (binary)
Blood Pressure Response in relation to Heparin or adverse PTT pattern (binary)
PTT Rise (event)
Pulse Rise (event)

Hemoglobin fall (event)
Blood Pressure fall (event)
Heparin (channel)
PTT (channel)
Pulse (channel)
Hemoglobin (channel) (as for example real-time derived by pulse oximetry)
Blood Pressure (channel)

Dependency diagrams and dependency lists may be filtered. Sample filtering include (to name a few):
Do not display point streams
Display only the top-level dependencies (i.e. within FIG. 32 Pulse Response in relation to Heparin 1432, Hemoglobin Response in relation to Heparin 1434 and Blood Pressure Response in relation to Hemoglobin 1436)
Collapse properties, Rules and Synonyms into occurrence types. In this case, only the structure is shown, not the specific sub-elements In the presence of patient data (e.g. a selected occurrence stream and occurrence) a dependency tree may be enhanced. For example, for elements that may be evaluated down to a single value (e.g. a property or Rule) may display the evaluated value. Elements that represent scope elements (e.g. an occurrence type) may provide a hyperlink into the actual occurrence that were used to meet that specific scope requirement. In some cases, such as a repeating occurrence, the dependency diagram may be expanded into an instance diagram. In this case single dependencies are expanded out to a list of all of the occurrences that were found. In this way, the instance diagram creates rapid access to the elements within the selected occurrence. This may become very useful in very complicated images, particularly when the image spans a fairly large amount of time. The selection of individual nodes within the instance diagram allows the user to navigate to the element within the occurrence and/or point streams and shifts the parallel time view to be appropriate (e.g. at the right scale and time location).

In another view, of interest to researchers, the dependency tree may be enhanced to show the statistical significance index (SSI) of each node. In this way, the researcher may recognize the statistical dependencies. If, for example, a root node has an equal or lower SSI than a child node (with reference to a specific condition) then the researcher may want to abandon the more complex image for a simpler version represented by the node.

Figure 33:
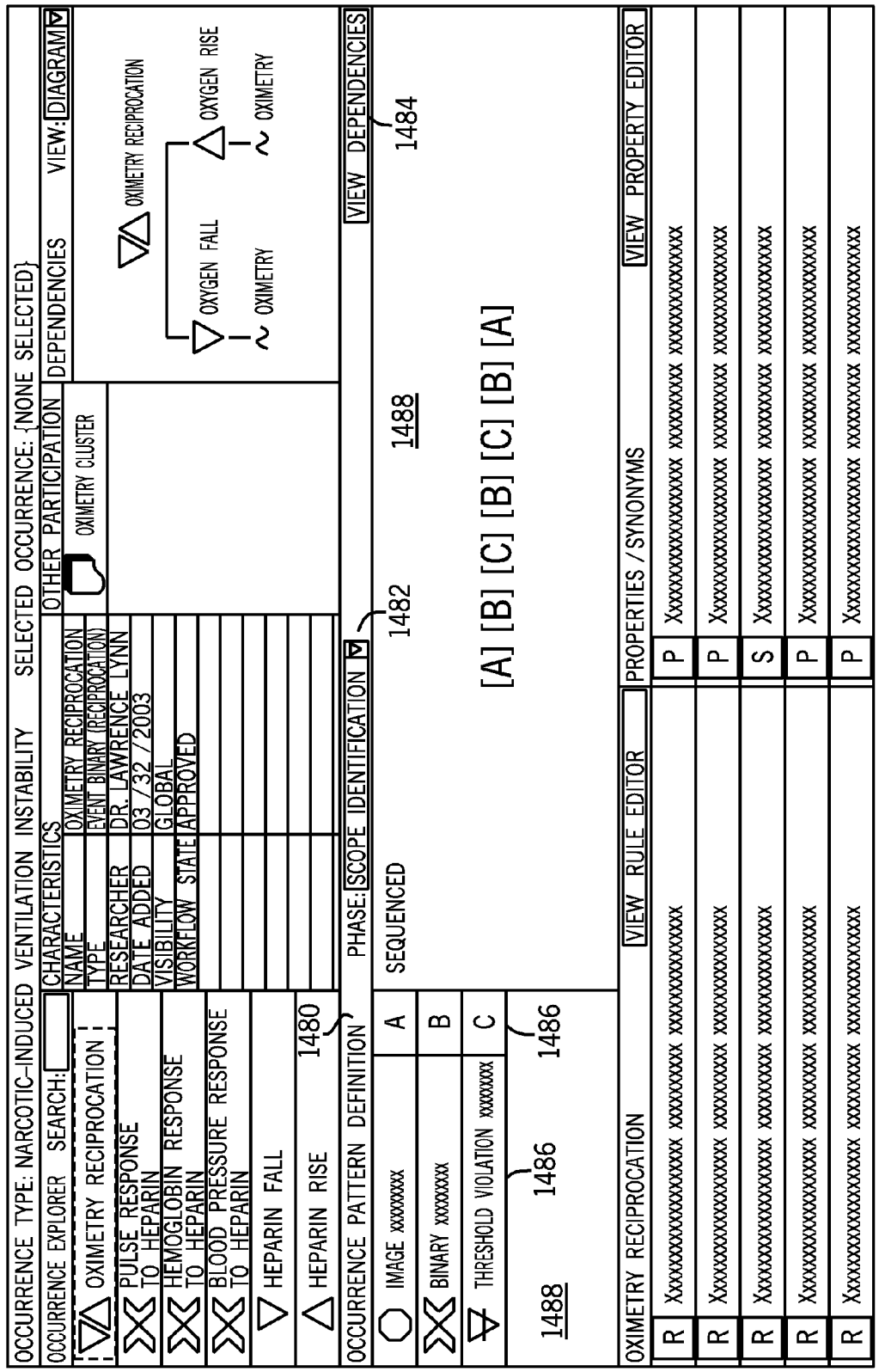
FIG. 33 is a user interface model of the occurrence editor specifically configured to define a pattern occurrence.
Figure 34:
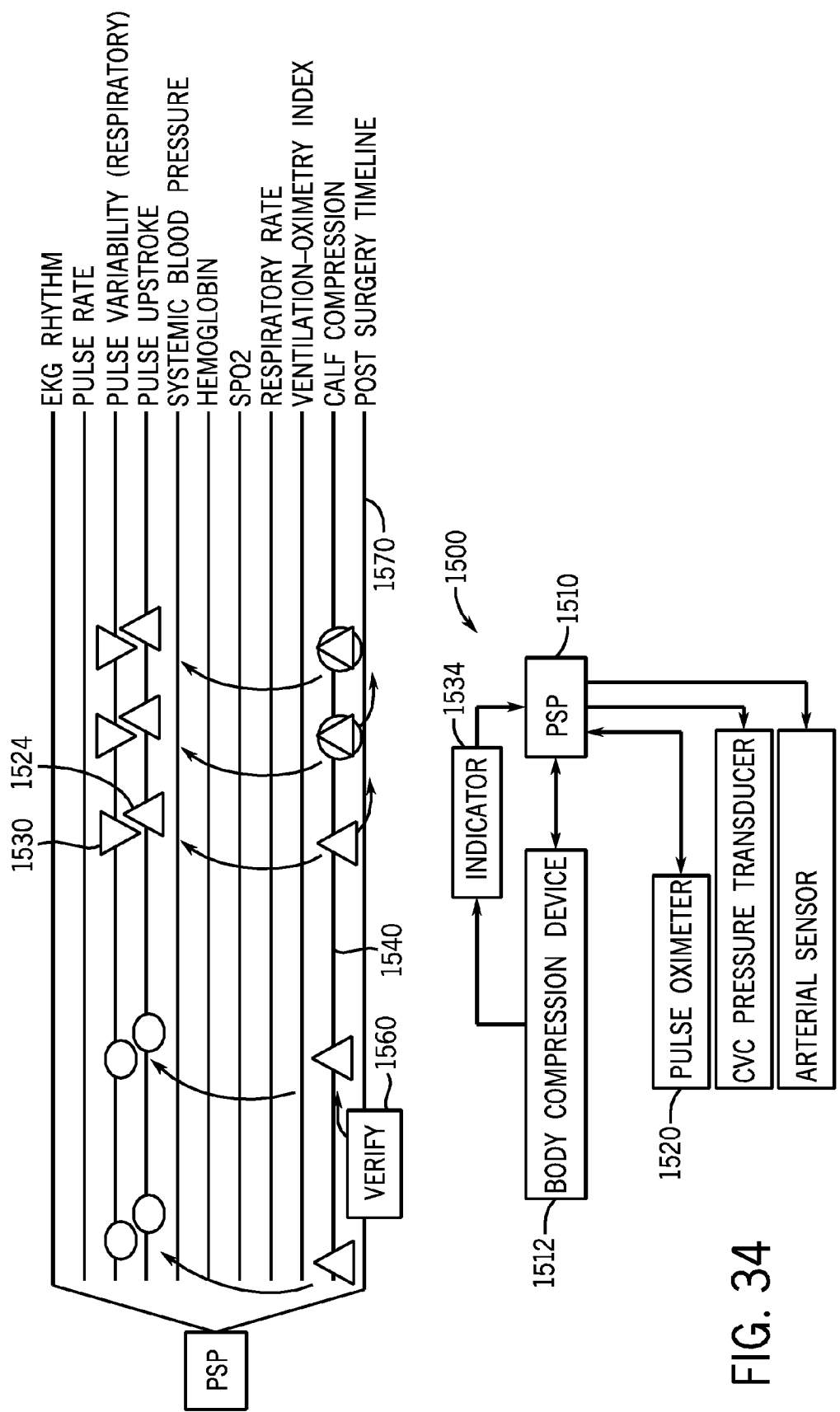
FIG. 34 is diagram of a source of time series related to a patient's intravascular volume showing the generated time series incorporated into the patient safety processor to generate an image suggestive of intravascular volume depletion.

FIG. 33 is a user interface model of the occurrence editor specifically configured to define a pattern occurrence. pattern occurrences are described in detail in FIG. 5 and FIG. 7a. The User Interface is very similar to the User Interface in FIG. 28 and FIG. 29. (See FIG. 28 and FIG. 29 for all details that are the same as in those figures.) The pattern occurrence configuration has a unique construction area. The construction area is made up of the occurrence Pattern definition bar 1480 and two subsections: the Mnemonic Representation List 1488 and the Pattern Sequence Construction Surface 1488.

The occurrence Pattern definition Bar 1480 contains a Phase dropdown 1482 and the View Dependencies button 1484 with the same role and functionality as in FIG. 28. The Mnemonic Representation List 1488 is simply a list of occurrence types selected to be part of the pattern (for example 1486) aligned with their associated Mnemonic (for example 1486). The Pattern Sequence Construction Surface 1488 allows for the arrangements of Mnemonics to represent the pattern occurrence definition. If a researcher drags an occurrence type from the occurrence Explorer onto the Mnemonic List the editor will create an entry in the list with the next Mnemonic (in, for example, alphabetical order). Mnemonics may then drag mnemonics onto the Pattern Sequence Construction Surface to be arranged to describe the pattern. Alternatively, the researcher may drag an occurrence type from the occurrence Explorer directly onto the Pattern Sequence Construction Surface. The editor will first search the Mnemonic List to see if a match is found. If a match is found then the correct Mnemonic is place onto the surface in the location indicated by the drop. If the match is not found, then the Mnemonic is added to the list and then placed onto the surface in the location of the list. One example of the basis for and the process of incorporation of a new technology into the processor 304 to optimize the efficacy and monitoring of the new technology is discussed. As an example of incorporation of new technology into the processor 304 a system and method for detecting enhanced sensitivity to augmentation of venous return is described. Although the intravascular volume status of a critically ill patient is often unknown, assessment of the intravascular volume status using pulse pressure variability, or the use of a pulse variability index has been promoted as effective in this regard however, as discussed in U.S. patent application Ser. No. 11/708,422 (the disclosure of which is incorporated by reference in its entirety for all purposes as if completely disclosed herein) this can potentially trend the wrong physiologic action increasing the pulse variability and thereby providing a false trend resulting in incorrect therapy. There is a need for continuously monitoring which provides an indication of the intravascular volume relative to the patient's needs and an embodiment of the present invention can provide that function. One embodiment of a system and method for detecting enhanced sensitivity to augmentation of venous return 1500 includes a component of the processor 304 1510 which includes a system for detecting intravascular volume status including a monitor for detecting variations in vascular pressure and/or flow (for example, a pulse oximeter, automatic blood pressure cuff, or arterial line to name a few), and a device for augmenting venous return such as a whole leg or calf compression device 1512, for compressing at least one extremity to increase venous return from the extremity, and a processor which can be the processor 304 1510 or for example a pulse oximeter 1520 for detecting and/or quantifying a measure indicative of a rise in pulse upstroke 1524 and/or arterial pressure or flow (which can for example include a reduction in pulse variability 1530 in response to spontaneous or artificial ventilation cycling). In one embodiment a conventional extremity compression device 1512 includes a sequential compression devices employed for compressing the calf(s) of a patient to prevent deep venous thrombosis which may be modified to apply progressive compression which is sustained for a brief period. (For example, the extremity compression device may have a DVT prevention mode and a venous return augmentation mode which provides a sustained compression applied from a distal to proximal direction.) For cases with greater acuity compression devices which extend to compress the thighs may be used. A compression may be timed with another mechanism for augmentation in venous return such as a fluid bolus to produce a greater effect with a smaller amount of fluid administered to the patient. Augmentation may be preceded, followed or combined with a maneuver to reduce venous return (such as a plateau at the end of inspiration or a brief period of elevated PEEP) to determine the relative sensitivity to venous return in relation to mechanical ventilation. The processor 304 can coordinate the fluid bolus and the compression to assure proper timing. An indicator 1534 may be provided which indicates when the compression device 1512 or another venous return augmenter has been activated. The indicator 1534 may for example be a pressure transducer, which can generate a time series 1540 of the pressure applied) or may be a step function or time series output from the compression device 1512 itself which indicates the occurrence and or triggering of compression of the extremity. In one embodiment the processor 304 1510 is programmed to detect a binary wherein the alpha component of the binary includes at least one event inducing augmentation of venous return (such as the compression of a body part, such as the calf, leg, abdomen, and/or upper extremity, to name a few) and the beta component includes at least one variation of a cardiovascular parameter (such as a rise in pulse upstroke 1524 or reduction of pulse variability 1530). Sequential binaries can be derived along the time series each time the compression devices acts to compress the extremity. The occurrence of a new or changing sequential beta values on the arterial side (indicative for example of increased sensitivity of cardiac output or blood pressure) to the sequential alpha augmentation events may provide indication of a decline in intravascular volume (and therefore an increased sensitivity to venous return augmentation). Alternatively the occurrence of a new or changing sequential beta values on the venous side to sequential alpha augmentation events (which may for example be a decline in the slope of decay or an increase in the area under the curve of the central venous pressure in response to leg compression) may provide indication of a excessive rise in intravascular volume producing increased sensitivity of central venous pressures and pulmonary capillary wedge (or left atrial pressures) to venous return augmentation. Using this method (which may be combined with the method of monitoring reduction of venous return in relation to ventilator changes for example as discussed in the aforementioned patent application) the processor 304 may, for example, compare relational patterns along the time series matrix from presently deployed technologies (for example pulse oximeter, central venous pressure monitor, mechanical ventilator, non invasive or invasive blood pressure monitor, pulmonary artery catheter, continuous cardiac output monitor, and the sequential calf compression devices) to provide a real-time indication of intravascular volume and of the cardiovascular sensitivity to variation of venous return reduction and augmentation. The device also provides verification 1560 of actual calf compression in relation to a time series 1570 of the post surgery timeline.

According to one embodiment for generating a more comprehensive time series matrix for analysis by the processor 304, one lumen of the double lumen cannula can be connected to an oxygen source and the other lumen connected with a pressure and/or flow sensor so that a time series of the nasal pressure can be generated along with a time series of the oxygen thereby and these can be combined with the various time series from the pulse oximeter. For ease of wearing such a cannula can be a short connected to a nasal pressure sensor and pulse oximeter worn about the neck (as for example configured like a bolero) where the cannula has a terminal is connectable to another tube providing connection to a source of oxygen. In one embodiment a single lumen catheter is used which bifurcates at the neck having a one connection for nasal pressure and one for the oxygen source. The presence of pressure induced by the continuous oxygen flow and changes in flow is detected as the DC pressure component in the tube upon which is superimposed the AC component of the nasal pressure signal.

According to another embodiment the processor 304 is applied to search for evidence of early ventilator associated pneumonia (VAP). The time series matrix of the datasets from the ventilator, for example; minute ventilation, I:E ratio, respiratory rate and effort, FIO2, oxygen consumption (if available), CO2 production, exhaled CO2, trend of triggered vs spontaneous breaths, exhaled gas components, to name a few. These may be further combined by the processor with time series of cardiovascular monitors for example heart rate, pulse pressure (and/or pleth) variability, pulse upstroke, pulse pressure, and maneuver responsive pressure variability to name a few. These may be further combined with time series of laboratory data such as Neutrophil percentage and/or count, stab (band percentage) and/or count, inflammatory markers, sputum parameters, and time series of other physiologic measures or scores such as the SPO2, temperature. These may be further combined with a time series of other vales such as sputum or BAL score or values, confusion score, and radiographic scores and/or scales. The finding of a cascade of inflammatory—respiratory—and/or cardiovascular augmentation in the absence of other sources of infection and/or in the presence of a rising sputum volume or purulence score is strongly suggestive of ventilator associated pneumonia (VAP). According to one aspect of the present invention patients managed with mechanical ventilation are monitored by a patient safety processor 304 which generates a data sets of at least respiratory data and inflammatory data and intermittently or continuously searches at least both data sets for relational patterns suggestive of VAP and provides an output upon detection of a relation pattern suggestive of VAP. The relational pattern can be a cascade comprised of linked or aggregated perturbations/trends/threshold breaches along a time series matrix.

Objectification is an example of a time series processing method which may be employed by the processor 304 to render the time series matrix freely searchable. As noted, objectification converts the time series matrix into stream s of discrete sequential and/or overlapping objects of ascending complexity, in 3 or more axes allowing each time series and the objectified matrix itself to be readily searchable in multiple dimensions. An example of the process of time series searching employing objectification is provided wherein as a first step to objectification; the processor 304 aggregates a set of time series together into a search vector. The combination of an occurrence type and a search vector defines the data from which a single occurrence stream is derived. A search vector is defined by a time window (whether explicitly or as a function of specified elements such as "patient stay" or "post-operative observation period +1 day") and a set of time series that apply, by definition or by rule, to the tracking of a phenomena within the system from which the time series are derived. For example, a search vector may be created for respiratory rate and/or amplitude for the hospital stay. The processor 304 can be directed to aggregate all signals from which respiratory rate and/or amplitude can be derived. For example, the processor 304 can use a signal from a pulse oximeter or may use the chest impedance signal as derived from an EKG signal and/or from a double lumen pressure sensing nasal cannula, and/or a sound sensor on the chest or airway, and/or another source of data.

In this way a search vector may include any number of time series. The processor 304 may be directed to "prefer" certain signals such that if a certain signal is found then other signals are ignored. Alternatively, the processor 304 may be directed to aggregate all available signals and allow them to overlap. In this way, a search vector may include overlapping time series. For example, if a patient is wearing two different oximeters, the processor 304 may be directed to include both of these into a single search vector. When there are overlapping time series within a search vector, the identification of an occurrence at the same time (or within a reasonable phase shift specified) is counted as one occurrence for the purpose of search and/or statistical analysis. In this case, both objects are stored and a relational binary is created between them (typed as, for example, "equivalent occurrence"). The processor 304 may identify one of the occurrences as "primary" and all others as secondary such that statistical analysis and search may not duplicate the multiple recording of a single event within the system being monitored. In cases where an equivalent occurrence is expected to be found, but is not, a divergent binary may be created aggregating the found occurrence and the search region in which the expected occurrence failed to be found.

In one embodiment a search vector is meant to accomplish several things including the following three things. It may allow for the aggregation of time series from the same source where there have been interruptions of the recording of data. It may allow for the aggregation of times series that are from two monitors that are of the same type or which have multiple leads. It may allow for the processor 304 to utilize different sources that represent equivalent observation of the same phenomena within the system. On the other hand, in one embodiment of the processor 304, the search vector is not used to aggregate two time series that represent distinct systemic response to phenomena within the monitored system. The identification of multiple reactions to the same phenomena may be handled by separate but parallel search vectors and allows for the identification of complex occurrence aggregations (such as images) and their evolution which will generate probabilistic momentum (explained above).

While the disclosed embodiments may be susceptible to various modifications and alternative forms, specific embodiments have been shown by way of example in the drawings and have been described in detail herein. However, it should be understood that the disclosure is not intended to be limited to the particular forms disclosed. Indeed, disclosed embodiments may not only be applied to clinical diagnosis of systems of physiological failure, but may be applied to any clinical condition that may be represented by images as provided herein. Indeed, the disclosed embodiments may be applied to monitor and/or diagnose conditions in which a patient's condition is generally improving, such as post-surgical monitoring. Rather, the disclosure is to cover all modifications, equivalents, and alternatives falling within the spirit and scope of the disclosed embodiment and as defined by the following appended claims.

What is claimed is:

1. A system for monitoring a plurality of patients in a hospital system to detect in real time the development of a sepsis condition and for identifying the patients developing the sepsis condition, the system comprising:
    a plurality of local patient safety monitors, each of the plurality of local patient safety monitors configured to receive physiological measurements from at least a pulse oximeter and a blood pressure monitor for one or more patients,
    a central patient safety monitor remote from the plurality of local patient safety monitors, the central patient safety monitor having a processor and memory storing instructions that, when executed by the processor, cause the system to:
        receive at least the physiologic measurements from the plurality of local patient safety monitors and store the physiological measurements in an electronic medical record;
        receive, from the electronic medical record, a plurality of time series associated with laboratory datasets and physiological systems of a patient;
        generate, based on the plurality of time series, a plurality of perturbed time series components including time series rise events and time series fall events;
        generate a plurality of relational binaries by associating one of the generated perturbed time series components with at least another one of the generated perturbed time series components based on a physiological relationship between the components;
        transform each of the plurality of perturbed time series components and the plurality of relational binaries into a plurality of graphical objects, wherein each of the graphical objects is configured to indicate an event of the plurality of perturbed time series components or a relationship between at least two of the perturbed time series components, and wherein each time series rise event is transformed into a first colored element, each time series fall event is transformed into a second colored element, and each relational binary is transformed into a third colored element;
        generate, from the plurality of graphical objects, a motion picture, the motion picture including an aggregate multidimensional image of the plurality of graphical objects such that the arrangement of the graphical objects in the aggregate multidimensional image indicates severity and relational progression of a sepsis condition of the patient as a progressively enlarging image as the sepsis condition progresses which displays evolving relational patterns of failure of the physiological systems of the patient; and
        generate, on a display device, a graphical display comprising viewing regions corresponding to physiological systems of the patient, wherein the viewing regions comprise at least an inflammatory region, and wherein the viewing regions are configured such that the motion picture is viewable across the viewing regions with the plurality of graphical objects displayed within the viewing region corresponding to the physiological system associated with the perturbed time series component;
        send at least one of, a notification to a patient safety console, an order for testing, or an order for therapy to at least one of the central patient safety monitor or one of the plurality of local patient safety monitors,
    wherein the notification to the patient safety console turns on a display of the motion picture of the aggregate multidimensional image of the objects.

2. The system of claim 1, wherein the memory stores additional instructions that, when executed by the processor, cause the system to:
    detect a relational pattern indicative of sepsis based on the time series rise events and the time series fall events; and
    provide an automatic alarm at one of the central patient safety monitor and at least one of the plurality of local patient safety monitors based on detecting the relational pattern indicative of sepsis.

3. The system of claim 1, wherein the memory stores additional instructions that, when executed by the processor, cause the system to determine a progression of severity of the sepsis condition of the patient by detecting changes in the perturbed time series components.

4. The system of claim 1, wherein the memory stores additional instructions that, when executed by the processor, cause the system to:
output a timeline of the motion picture of the aggregate multidimensional image of the objects to the patient safety console; and
highlight the motion picture of the aggregate multidimensional image of the objects.

5. The system of claim 1, comprising:
the patient safety console,
wherein sending at least one of, the notification to the patient safety console, the order for testing, or the order for therapy comprises sending the notification to the patient safety console.

6. The system of claim 5, wherein the patient safety console is configured to display an interactive screen comprising one or more working diagnoses, differential diagnoses, laboratory parameters, monitored parameters, or subjective parameters.

7. The system of claim 1, wherein the memory stores additional instructions that, when executed by the processor, cause the system to:
provide automated visual navigation of a portion of the aggregate multidimensional image of the objects; and
present one or more navigation movement options, the one or more navigation movement options comprising a pause option configured to pause the automated visual navigation of the portion of the aggregate multidimensional image of the objects.

8. The system of claim 7, wherein providing the automated visual navigation of the portion of the aggregate multidimensional image of the objects comprises presenting one or more audio comments or video comments provided by one or more healthcare workers.

9. The system of claim 1, comprising:
a pulse oximeter,
wherein the memory stores additional instructions that, when executed by the processor, cause the system to receive pulse oximetry data associated with the patient from the pulse oximeter, and
wherein the time lapsable motion picture of the aggregate multidimensional image of the objects is generated based on the pulse oximetry data received from the pulse oximeter.

10. A method for monitoring a plurality of patients in a hospital system to detect in real time the development of a sepsis condition and for identifying the patients developing the sepsis condition, the method comprising:
providing a plurality of local patient safety monitors, each of the plurality of local patient safety monitors configured to receive physiological measurements from at least a pulse oximeter and a blood pressure monitor for one or more patients,
providing a central patient safety monitor remote from the plurality of local patient safety monitors, the central patient safety monitor having a processor and a memory;
receiving, by the central patient safety monitor, from an electronic medical record, a plurality of time series associated with laboratory datasets and physiological systems of a patient, wherein the datasets include at least the physiological measurements received from the plurality of local patient safety monitors;
generating, by the system, based on the plurality of time series, a plurality of perturbed time series components including time series rise events and time series fall events;
generating, by the system, a plurality of relational binaries by associating one of the generated perturbed time series components with at least another one of the generated perturbed time series components based on a physiological relationship between the components;
transforming, by the system, each of the plurality of perturbed time series components and the plurality of relational binaries into a plurality of graphical objects, wherein each of the graphical objects is configured to indicate an event of the plurality of perturbed time series components or a relationship between two of the perturbed time series components;
generating, by the system, from the plurality of graphical objects, a motion picture including the plurality of graphical objects such that the arrangement of the graphical object is dynamically responsive to the time series rise events and the time series fall events and which represents a severity and progression of a sepsis condition over time as a progressively enlarging image of evolving failure of the physiological systems; and
sending, by the system, at least one of, a notification to a patient safety console, an order for testing, or an order for therapy to at least one of the central patient safety monitor or one of the local patient safety monitors,
wherein the notification to the patient safety console turns on a display of the motion picture generated by the system based on the data associated with the patient.

11. The method of claim 10, comprising:
detecting, by the system, a relational pattern indicative of sepsis based on the time series rise events and the time series fall events; and
providing, by the system, an automatic alarm based on detecting the relational pattern indicative of sepsis.

12. The method of claim 10, comprising:
determining, by the system, the severity of the sepsis condition by detecting changes in the perturbed time series components.

13. The method of claim 10, comprising:
outputting, by the system, a timeline of the motion picture; and
highlighting, by the system, the motion picture.

14. A system for monitoring a plurality of patients in a hospital system to detect in real time the development of a sepsis condition and for identifying the patients developing the sepsis condition, the system comprising:
a plurality of local patient safety monitors, each of the plurality of local patient safety monitors configured to receive physiological measurements from at least a pulse oximeter and a blood pressure monitor for one or more patients,
a central patient safety monitor remote from the plurality of local patient safety monitors, the central patient safety monitor having a processor and memory storing instructions that, when executed by the processor, cause the system to:
receive at least the physiologic measurements from the plurality of local patient safety monitors and store the physiological measurements in an electronic medical record;
receive, from the electronic medical record, a plurality of time series associated with laboratory datasets and physiological systems associated with a patient;

generate, based on the plurality of time series, a plurality of perturbed time series components including time series rise events and time series fall events;

generate, based on the plurality of perturbed time series components, a plurality of graphical objects, wherein each graphical object is configured to indicate an event of the plurality of perturbed time series components;

generate, from the plurality of graphical objects, a motion picture such that the arrangement of the graphical objects in the motion picture represents a progression and severity of a sepsis condition as a progressively enlarging image of evolving failure of the physiological systems; and send at least one of, a notification to a patient safety console, an order for testing, or an order for therapy to at least one of the central patient safety monitor or one of the plurality of local patient safety monitors, wherein the notification to the patient safety console turns on a display of the motion picture generated based on the data associated with the patient.

15. The system of claim 14, wherein the memory stores additional instructions that, when executed by the processor, cause the system to:

detect, a relational pattern indicative of sepsis based on the time series rise events and the time series fall events; and provide an automatic alarm based on detecting the relational pattern indicative of sepsis.

16. The system of claim 14, wherein the memory stores additional instructions that, when executed by the processor, cause the system to:

determine the severity of the sepsis condition by detecting changes in the perturbed time series components.

17. The system of claim 14, comprising:

the patient safety console, wherein the memory stores additional instructions that, when executed by the processor, cause the system to:

output a timeline of the motion picture to the patient safety console; and highlight the motion picture.

18. A system for monitoring a plurality of patients in a hospital system to detect in real time the development of a sepsis condition and for identifying the patients developing the sepsis condition, the system comprising:

a plurality of local patient safety monitors, each of the plurality of local patient safety monitors configured to receive physiological measurements from at least a pulse oximeter and a blood pressure monitor for one or more patients, a central patient safety monitor remote from the plurality of local patient safety monitors, the central patient safety monitor having a processor and memory storing instructions that, when executed by the processor, cause the system to:

receive at least the physiologic measurements from the plurality of local patient safety monitors and store the physiological measurements in an electronic medical record;

receive, from the electronic medical record, a plurality of time series associated with laboratory datasets and physiological systems associated with a patient;

generate, based on the plurality of time series, a plurality of perturbed time series components including time series rise events and time series fall events associated with indications of an evolving pattern of failure of the physiological systems;

transform the time series rise events and the time series fall events into a pattern of graphical objects, wherein each time series rise event is transformed into a first colored element, each time series fall event is transformed into a second colored element;

generate, from the pattern of graphical objects, a dynamic image including an aggregation of the first colored elements and the second colored elements, the dynamic image evolving to display the time series rise events and time series fall events into a representation of a progression and severity of a sepsis condition as a progressively enlarging picture indicative of the evolving pattern of failure of the physiological systems over time; and send at least one of, a notification to a patient safety console, an order for testing, or an order for therapy to at least one of the central patient safety monitor or one of the plurality of local patient safety monitors, wherein the notification to the patient safety console turns on a display of the dynamic image.

19. The system of claim 18, wherein the memory stores additional instructions that, when executed by the processor, cause the system to:

detect a relational pattern indicative of sepsis based on the time series rise events and the time series fall events; and provide an automatic alarm based on detecting the relational pattern indicative of sepsis.

20. The system of claim 18 wherein the memory stores additional instructions that, when executed by the processor, cause the system to:

determine the severity of the sepsis condition by detecting a size of the progressively enlarging picture indicative of the evolving pattern of failure of the physiological systems.

21. The system of claim 18 comprising:

the patient safety console, wherein the memory stores additional instructions that, when executed by the processor, cause the system to:

output a timeline of the dynamic image to the patient safety console; and highlight the dynamic image.

22. A system for monitoring a plurality of patients in a hospital system to detect in real time the development of a sepsis condition and for identifying the patients developing the sepsis condition, the system comprising:

a plurality of local patient safety monitors, each of the plurality of local patient safety monitors configured to receive physiological measurements from at least a pulse oximeter and a blood pressure monitor for one or more patients, a central patient safety monitor remote from the plurality of local patient safety monitors, the central patient safety monitor having a processor and memory storing instructions that, when executed by the processor, cause the system to:

receive at least the physiologic measurements from the plurality of local patient safety monitors and store the physiological measurements in an electronic medical record;

receive, from the electronic medical record, a plurality of time series associated with laboratory datasets and physiological systems associated with a patient;

generate, based on the plurality of time series, a plurality of perturbed time series components comprising time series rise events and time series fall events;

transform the plurality of perturbed time series components into one or more graphical objects, wherein each graphical object is configured to indicate an event of the plurality of perturbed time series components;

aggregate the one or more graphical objects to align each graphical object of the one or more graphical objects in temporal and spatial relation to other graphical objects of the one or more graphical objects;

generate, from the plurality of graphical objects, a motion picture, the motion picture including a multidimensional image of the one or more graphical objects such that the arrangement of the aggregated graphical objects represents a duration and relational severity of a sepsis condition as an image which changes size and shape in response to changes in severity of the sepsis condition; and send at least one of, a notification to a patient safety console, an order for testing, or an order for therapy to at least one of the central patient safety monitor or one of the plurality of local patient safety monitors, wherein the notification to the patient safety console turns on a display of the multidimensional image.

23. The system of claim 22, wherein the multidimensional image is displayed by the patient safety console as enlarging in size as the severity of the sepsis condition increases.

24. The system of claim 22, wherein indications of exogenous actions are displayed by the patient safety console on a time axis adjacent to the multidimensional image.

25. The system of claim 24, wherein the memory stores additional instructions that, when executed by the processor, cause the system to:

determine a timing of the exogenous actions in relation to the multidimensional image as a function of time; and generate output indicative of the timing of the exogenous actions.

26. The system of claim 24, wherein the memory stores additional instructions that, when executed by the processor, cause the system to:

determine a timing of the exogenous actions in relation to the multidimensional image as a function of time; and generate output indicative of a delay between the exogenous action and at least one portion of the multidimensional image and at least one portion of the exogenous actions.

27. The system of claim 22, wherein the memory stores additional instructions that, when executed by the processor, cause the system to:

output an indication of expense associated with care of the patient in timed relation to the multidimensional image.

28. The system of claim 22, wherein the multidimensional image is an animated motion picture indicative of an onset, progression, severity, and duration of the sepsis condition.

29. The system of claim 22, wherein the multidimensional image is an animated motion picture indicative of an onset, progression, severity, and duration of the sepsis condition and of exogenous actions in timed relation to the sepsis condition.

30. The system of claim 22, wherein the multidimensional image is an animated motion picture indicative of an onset, progression, severity, and duration of the sepsis condition and of antibiotic treatment in timed relation to the sepsis condition.

31. The system of claim 22, wherein the memory stores additional instructions that, when executed by the processor, cause the system to:

detect an onset of the sepsis condition.

* * * * *